(12) United States Patent
Weng

(10) Patent No.: US 7,881,872 B2
(45) Date of Patent: Feb. 1, 2011

(54) METHODS OF ANALYZING MULTI-CHANNEL PROFILES

(75) Inventor: Lee Weng, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 705 days.

(21) Appl. No.: 10/800,340

(22) Filed: Mar. 12, 2004

(65) Prior Publication Data

US 2005/0203709 A1 Sep. 15, 2005

(51) Int. Cl.
G06G 7/58 (2006.01)
G01N 33/483 (2006.01)
C12Q 1/68 (2006.01)

(52) U.S. Cl. .............................. 702/19; 703/11; 700/30; 435/6

(58) Field of Classification Search ........................ None
See application file for complete search history.

(56) References Cited

U.S. PATENT DOCUMENTS

| | | | |
|---|---|---|---|
| 5,556,752 | A | 9/1996 | Lockhart et al. |
| 5,569,588 | A | 10/1996 | Ashby et al. |
| 5,578,832 | A | 11/1996 | Trulson et al. |
| 6,040,138 | A | 3/2000 | Lockhart et al. |
| 6,218,122 | B1 | 4/2001 | Friend et al. |
| 6,324,479 | B1 | 11/2001 | Friend et al. |
| 6,351,712 | B1 | 2/2002 | Stoughton et al. |
| 6,510,270 | B1 | 1/2003 | Toth et al. |
| 6,691,042 | B2 | 2/2004 | Weng et al. |
| 6,713,257 | B2 | 3/2004 | Shoemaker et al. |
| 2003/0226098 | A1 | 12/2003 | Weng |
| 2008/0294375 | A1 | 11/2008 | Van Breemen |

FOREIGN PATENT DOCUMENTS

| | | | |
|---|---|---|---|
| WO | WO 98/38329 | | 9/1998 |
| WO | WO 98/41531 | | 9/1998 |
| WO | WO 99/58708 | | 11/1999 |
| WO | WO 99/59037 | | 11/1999 |
| WO | WO 99/66067 | | 12/1999 |
| WO | WO 00/24936 | | 5/2000 |
| WO | WO 00/39336 | | 7/2000 |
| WO | WO 01/05935 | | 1/2001 |
| WO | WO 02/16650 | | 2/2002 |
| WO | WO 03/004677 | * | 1/2003 |

OTHER PUBLICATIONS

Blanchard et al., 1996, "High-density oligonucleotide arrays" Biosensors and Bioelectronics 11:687-690.
Blanchard et al., 1996, "Sequence to array: probing the genome's secrets" Nature Biotechnology 14:1649.
Blanchard, 1998, "Synthetic DNA Arrays in Genetic Engineering" in Synthetic DNA Arrays in Genetic Engineering, vol. 20, J.K. Setlow, Ed., Plenum Press, New York at pp. 111-123.
Derisi et al., 1996, "Use of a cDNA microarray to analyse gene expression patterns in human cancer" Nature Genetics 14:457-460.
Duggan et al., 1999, "Expression profiling using cDNA microarrays" Nature Genetics Supplement 21:10-14.
Fodor et al., 1991, "Light-directed, spatially addressable parallel chemical synthesis" Science 251:767-773.
He et al., 2003, "Microarray standard data set and figures of merits for comparing data processing methods and experiment designs" Bioinformatics 19:956-965.
Lockhart et al., 1996, "Expression monitoring by hybridization to high-density oligonucleotide arrays" Nature Biotechnology 14:1675-1680.
McGall et al., 1996, "Light-directed synthesis of high-density oligonucleotide arrays using semiconductor photoresists" Proc. Natl. Acad. Sci. U.S.A. 93:13555-13560.
Pease et al., 1994, "Light-generated oligonucleotide arrays for rapid DNA sequence analysis" Proc. Natl. Acad. Sci. U.S.A. 91:5022-5026.
Roberts et al, 2000, "Signaling and circuitry of multiple MAPK pathways revealed by a matrix of global gene expression profiles" Science, 287:873-880.
Rocke et al., 2001, "A model for measurement error for gene expression arrays" J. Computational Biology 8:557-569.
Schadt et al., 2001, "Feature extraction and normalization algorithms for high-density oligonucleotide gene expression array data" J. Cell. Biochem. Supp. 37:120-125.
Schena et al., 1995, "Parallel human genome analysis: microarray-based expression monitoring of 1000 genes" Proc. Natl. Acad. Sci. U.S.A. 93:10614-10619.
Schena et al., 1995, "Quantitative monitoring of gene expression patterns with a complementary DNA microarray" Science 270:467-470.
Shalon et al., 1996, "A DNA microarray system for analyzing complex DNA samples using two- color fluorescent probe hybridization" Genome Res. 6:639-645.

* cited by examiner

*Primary Examiner*—Marjorie Moran
*Assistant Examiner*—Larry D Riggs, II
(74) *Attorney, Agent, or Firm*—Klarquist Sparkman LLP

(57) ABSTRACT

The present invention provides methods for analyzing multi-channel profiles. In the method of the invention, systematic cross-profile (cross-experiment) errors among a plurality of multi-channel profiles having a common reference channel are estimated using profiles of the common reference channel. The cross-profile errors are then removed from profiles of the experiment channels, e.g., by subtracting the error from the experiment profile. The obtained error-corrected experiment channel data can then be used in comparison with each other, e.g., in generating virtual differential profiles between pairs of experiment channels. The method of the invention is particularly useful in analyzing multi-channel expression profiles obtained in microarray measurements.

173 Claims, 54 Drawing Sheets

Y Signature = 6.23 percent
X Signature = 6.02 percent
Y Only = 1.78 percent
X Only = 1.57 percent
Signature in Both = 4.45 percent
Signature Union Correlation = 0.892

Y Signature = 7.15 percent
X Signature = 6.02 percent
Y Only = 1.77 percent
X Only = 0.641 percent
Signature in Both = 5.38 percent
Signature Union Correlation = 0.995

Y Signature = 6.49 percent
X Signature = 6.76 percent
Y Only = 1.9 percent
X Only = 2.17 percent
Signature in Both = 4.6 percent
Signature Union Correlation = 0.955

METHODS OF ANALYZING MULTI-CHANNEL PROFILES

1. FIELD OF THE INVENTION

The present invention relates to methods for analyzing multi-channel profiles, e.g., gene expression profiles. The invention also relates to methods for comparing expression profiles obtained using different microarrays.

2. BACKGROUND OF THE INVENTION

DNA array technologies have made it possible to monitor the expression level of a large number of genetic transcripts at any one time (see, e.g., Schena et al., 1995, *Science* 270:467-470; Lockhart et al., 1996, *Nature Biotechnology* 14:1675-1680; Blanchard et al., 1996, *Nature Biotechnology* 14:1649; Ashby et al., U.S. Pat. No. 5,569,588, issued Oct. 29, 1996). Of the two main formats of DNA arrays, spotted cDNA arrays are prepared by depositing PCR products of cDNA fragments with sizes ranging from about 0.6 to 2.4 kb, from full length cDNAs, ESTs, etc., onto a suitable surface (see, e.g., DeRisi et al., 1996, *Nature Genetics* 14:457-460; Shalon et al., 1996, *Genome Res.* 6:639-645; Schena et al., 1996, *Proc. Natl. Acad. Sci. U.S.A.* 93:10614-10619; and Duggan et al., *Nature Genetics Supplement* 21:10-14). Alternatively, high-density oligonucleotide arrays containing thousands of oligonucleotides complementary to defined sequences, at defined locations on a surface are synthesized in situ on the surface by, for example, photolithographic techniques (see, e.g., Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; McGall et al., 1996, *Proc. Natl. Acad. Sci. U.S.A.* 93:13555-13560; U.S. Pat. Nos. 5,578,832; 5,556,752; 5,510,270; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123). Efforts to further increase the information capacity of DNA arrays range from further reducing feature size on DNA arrays so as to further increase the number of probes in a given surface area to sensitivity- and specificity-based probe design and selection aimed at reducing the number of redundant probes needed for the detection of each target nucleic acid thereby increasing the number of target nucleic acids monitored without increasing probe density (see, e.g., Friend et al., International Publication No. WO 01/05935, published Jan. 25, 2001).

By simultaneously monitoring tens of thousands of genes, DNA array technologies have allowed, inter alia, genome-wide analysis of mRNA expression in a cell or a cell type or any biological sample. Aided by sophisticated data management and analysis methodologies, the transcriptional state of a cell or cell type as well as changes of the transcriptional state in response to external perturbations, including but not limited to drug perturbations, can be characterized on the mRNA level (see, e.g., Stoughton et al., International Publication No. WO 00/39336, published Jul. 6, 2000; Friend et al., International Publication No. WO 00/24936, published May 4, 2000). Applications of such technologies include, for example, identification of genes which are up regulated or down regulated in various physiological states, particularly diseased states. Additional exemplary uses for DNA arrays include the analyses of members of signaling pathways, and the identification of targets for various drugs. See, e.g., Friend and Hartwell, International Publication No. WO 98/38329 (published Sep. 3, 1998); Stoughton, International Publication No. WO 99/66067 (published Dec. 23, 1999); Stoughton and Friend, International Publication No. WO 99/58708 (published Nov. 18, 1999); Friend and Stoughton, International Publication No. WO 99/59037 (published Nov. 18, 1999); Friend et al., U.S. Pat. No. 6,218,122 (filed on Jun. 16, 1999).

The various characteristics of this analytic method make it particularly useful for directly comparing the abundance of mRNAs present in two cell types. For example, an array of cDNAs was hybridized with a green fluor-tagged representation of mRNAs extracted from a tumorigenic melanoma cell line (UACC-903) and a red fluor-tagged representation of mRNAs was extracted from a nontumorigenic derivative of the original cell line (UACC-903+6). Monochrome images of the fluorescent intensity observed for each of the fluors were then combined by placing each image in the appropriate color channel of a red-green-blue (RGB) image. In this composite image, one can see the differential expression of genes in the two cell lines. Intense red fluorescence at a spot indicates a high level of expression of that gene in the nontumorigenic cell line, with little expression of the same gene in the tumorigenic parent. Conversely, intense green fluorescence at a spot indicates high expression of that gene in the tumorigenic line, with little expression in the nontumorigenic daughter line. When both cell lines express a gene at similar levels, the observed array spot is yellow.

In some cases, visual inspection of such results is sufficient to identify genes which show large differential expression in the two samples. A more thorough study of the changes in expression requires the ability to discern quantitatively changes in expression levels and to determine whether observed differences are the result of random variation or whether they are likely to reflect changes in the expression levels of the genes in the samples. Assuming that DNA products from two samples have an equal probability of hybridizing to the probes, the intensity measurement is a function of the quantity of the specific DNA products available within each sample. Locally (or pixelwise), the intensity measurement is also a function of the concentration of the probe molecules. On the scanning side, the fluorescent light intensity also depends on the power and wavelength of the laser, the quantum efficiency of the photomultiplier tube, and the efficiency of other electronic devices. The resolution of a scanned image is largely determined by processing requirements and acquisition speed. The scanning stage imposes a calibration requirement, though it may be relaxed later. The image analysis task is to extract the average fluorescence intensity from each probe site (e.g., a cDNA region).

The measured fluorescence intensity for each probe site comes from various sources, e.g., background, cross-hybridization, hybridization with sample 1 or sample 2. The average intensity within a probe site can be measured by the median image value on the site. This intensity serves as a measure of the total fluors emitted from the sample mRNA targets hybridized on the probe site. The median is used as the average to mitigate the effect of outlying pixel values created by noise.

Typically, in a two-color microarray gene expression experiment, the experiment sample is labeled in one dye color (Cy5, red) and the control sample is labeled in a different color (Cy3, green). The two samples are mixed and hybridized to a micro-array slide. After hybridization, the expression intensity is measured with a laser scanner of two different colors. The experiment is conducted in a biology laboratory (wet lab). To obtain the expression profile, we compute the logarithmic ratio of the two measured intensities (red and green).

There are various types of biases (errors), e.g., inter-slide bias and color bias, which may affect the accuracy of the ratio estimation. Inter-slide bias is the difference between two separated slides. The two-color technique avoids the inter-slide error by running the experiment in a single slide. But different dyes can cause difference between the two intensity measurements, so that the ratio is biased. To overcome this color bias problem, the experiment can be run twice with reversed fluorescent dye labeling from one to the other. The two expression ratios are then combined to cancel out the color bias. A method for calculating individual errors associated with each measurement made in repeated microarray experiments was also developed. The method offers an approach for minimizing the number of times a cellular constituent quantification experiment must be repeated in order to produce data that has acceptable error levels and for combining data generated in repeats of a cellular constituent quantification experiment based on rank order of up-regulation or down-regulation. See, e.g., Stoughton et al., U.S. Pat. No. 6,351,712.

U.S. Pat. No. 6,691,042 discloses methods for generating differential profiles A vs. B, i.e., differential profiles between samples having been subject to condition A and condition B, from data obtained in separately performed experimental measurements A vs. C and B vs. D. When C and D are the same, i.e., common, the methods involve determination of systematic measurement errors or biases between measurements carried out in different experimental reactions, i.e., cross-experiment errors or biases, using data measured for samples under the common condition and for removal or reduction of such cross-experiment errors. U.S. Pat. No. 6,691,042 also provides methods for generating differential profiles A vs. B from data obtained in separately performed single-channel measurements A and B.

Discussion or citation of a reference herein shall not be construed as an admission that such reference is prior art to the present invention.

3. SUMMARY OF THE INVENTION

The invention provides a method for correcting errors in at least one of a plurality of pairs of profiles $\{A_m, C_m\}$, $A_m$ being an experiment profile, $C_m$ being a reference profile, where m=1, 2, ..., M, M is the number of pairs of profiles, said method comprising (a) calculating an average reference profile $\overline{C}$ of reference profiles $\{C_m\}$, m=1, 2, ..., M; (b) determining for at least one profile pair m∈{1, 2, ..., M} a differential reference profile of $C_m$ and $\overline{C}$; and (c) generating for said at least one profile pair m an error-adjusted experiment profile $A'_m$ by a method comprising adjusting said experimental profile $A_m$ using said differential reference profile determined for said profile pair m, thereby correcting errors in said at least one of said plurality of pairs of profiles; wherein for each m ∈{1, 2, ..., M}, said error-adjusted experiment profile $A'_m$ comprises data set $\{A'_m(k)\}$, said experiment profile $A_m$ comprises data set $\{A_m(k)\}$, said reference profile $C_m$ comprises data set $\{C_m(k)\}$, and said average reference profile $\overline{C}$ comprises data set $\{\overline{C}(k)\}$, wherein said data set $\{A_m(k)\}$ comprises measurements of a plurality of different cellular constituents measured in a sample having been subject to condition $A_m$, said data set $\{C_m(k)\}$ comprises measurements of said plurality of different cellular constituents measured in a sample having been subject to condition C, and wherein k=1, 2, ..., N is an index of measurements of cellular constituents, N being the total number of measurements. Preferably, said steps (b) and (c) are performed for each profile pair m.

The invention also provides a method for correcting errors in at least one of a plurality of pairs of profiles $\{A_m, C_m\}$, $A_m$ being an experiment profile, $C_m$ being a reference profile, where m=1, 2, ..., M, M is the number of pairs of profiles, said method comprising generating for at least one profile pair m∈{1, 2, ..., M} an error-adjusted experiment profile $A'_m$ by a method comprising adjusting said experimental profile $A_m$ using a differential reference profile generated using $C_m$ and an average reference profile $\overline{C}$ determined for said profile pair m, wherein said average reference profile $\overline{C}$ is an average of reference profiles $\{C_m\}$, m=1, 2, ..., M; wherein for each m∈{1, 2, ..., M}, said error-adjusted experiment profile A', comprises data set $\{A'_m(k)\}$, said experiment profile $A_m$ comprises data set $\{A_m(k)\}$, said reference profile $C_m$ comprises data set $\{C_m(k)\}$, and said average reference profile $\overline{C}$ comprises data set $\{\overline{C}(k)\}$, wherein said data set $\{A_m(k)\}$ comprises measurements of a plurality of different cellular constituents measured in a sample having been subject to condition $A_m$, said data set $\{C_m(k)\}$ comprises measurements of said plurality of different cellular constituents measured in a sample having been subject to condition C, and wherein k=1, 2, ..., N is an index of measurements of cellular constituents, N being the total number of measurements.

The experiment profile $A_m$ and reference profile $C_m$ are preferably measured in the same experimental reaction. In one embodiment, each said pair of profiles $A_m$ and $C_m$ is measured in a two-channel microarray experiment. In one embodiment, said reference profiles $\{C_m\}$, m=1, 2, ..., M, are measured with samples labeled with a same label. In another embodiment, at least one of said plurality of pairs of profiles $\{A_m, C_m\}$ is a virtual profile.

In a preferred embodiment, said $\overline{C}(k)$ is calculated according to equation $$\overline{C}(k) = \frac{1}{M}\sum_{m=1}^{M} C_m(k)$$

said differential reference profile is calculated according to equation $$C_{diff}(m,k) = C_m(k) - \overline{C}(k)$$

and said error-adjusted profile is calculated according to equation $$A'_m(k) = A_m - C_{diff}(m,k)$$

In another preferred embodiment, the method further comprises a step of (d) calculating for at least one, preferably each profile pair m an error-corrected experiment profile $A''_m$ comprising data set $\{A''_m(k)\}$ by combining said error-adjusted experiment profile $A'_m$ with said experiment profile $A_m$ using a weighing factor $\{w(k)\}$, k=1, 2, ..., N, wherein w(k) is a weighing factor for the k'th measurement. Preferably, said error-corrected experimental profile $A''_m$ is calculated according to equation $$A''_m(k) = (1-w(k)) \cdot A_m(k) + w(k) \cdot A'_m(k)$$

In one embodiment, said weighing factor w(k) is determining according to equation $$w(k) = 1 - e^{-0.5\left(\frac{\overline{C}(k)}{avg\_bkgstd}\right)^2}$$

where avg_bkgstd is an average background standard error. In one embodiment, said avg_bkgstd is determined according to equation $$avg\_bkgstd = \frac{1}{N}\sum_{k=1}^{N}\left(\frac{1}{M}\sum_{m=1}^{M} bkgstd(m,k)\right)$$

where bkgstd (m, k) is background standard error of $C_m(k)$.

In a preferred embodiment, the method further comprises determining errors $\{\sigma'_m\}$ of said error-adjusted experiment profiles $\{A'_m\}$. In one embodiment, said errors are determined according to equation $$\sigma'_m(k) = \sqrt{\sigma_m^2(k) + \text{mixed\_}\sigma_m^2(k) - 2 \cdot Cor(k) \cdot \sigma_m(k) \cdot \text{mixed\_}\sigma_m(k)}$$

where $\sigma_m(k)$ is the standard error of $A_m(k)$, mixed_$\sigma_m(k)$ is determined according to equation $$\text{mixed\_}\sigma_m(k) = \frac{\sigma_m(k) + (M-1) \cdot \sigma_{ref}(k)}{M}$$

where $\sigma_{ref}(k) = \sqrt{\frac{1}{M-1} \sum_m^M (C_m(k) - \overline{C}(k))^2}$ and where Cor(k) is a correlation coefficient between experiment profile and reference profile. In one embodiment, said Cor(k) is determined according to equation $$Cor(k) = Cor\text{Max} \cdot \left(1 - e^{-0.5 \cdot \left(\frac{\overline{C}(k)}{avg\_bkgstd}\right)^2}\right)$$

where CorMax is a number between 0 and 1.

In still another embodiment, the method further comprises determining errors $\{\sigma''_m\}$ of said error-corrected experiment profile $\{A''_m\}$. In one embodiment, said errors are determined according to the equation:

$$\sigma'_m(k) = \sqrt{[1-w(k)] \cdot \sigma_m^2(k) + w(k) \sigma'^2_m(k)}$$

where $\sigma_m(k)$ is the standard error of $A_m(k)$, $\sigma'_m(k)$ is determined according to the equation:

$$\sigma'_m(k) = \sqrt{\sigma_m^2(k) + \text{mixed\_}\sigma_m^2(k) - 2 \cdot Cor(k) \cdot \sigma_m(k) \cdot \text{mixed\_}\sigma_m(k)}$$

where mixed_$\sigma_m(k)$ is determined according to the equation:

$$\text{mixed\_}\sigma_m(k) = \frac{\sigma_m(k) + (M-1) \cdot \sigma_{ref}(k)}{M}$$

where $\sigma_{ref}(k) = \sqrt{\frac{1}{M-1} \sum_m^M (C_m(k) - \overline{C}(k))^2}$ and where Cor(k) is a correlation coefficient. In one embodiment, said Cor(k) is determined according to the equation:

$$Cor(k) = Cor\text{Max} \cdot \left(1 - e^{-0.5 \cdot \left(\frac{\overline{C}(k)}{avg\_bkgstd}\right)^2}\right)$$

where CorMax is a number between 0 and 1.

In another preferred embodiment, the plurality of pairs of profiles $\{A_m, C_m\}$ are transformed profiles comprising transformed measurements. In one embodiment, said transform measurements are obtained according to equations $$A_m(k) = f(x) = \frac{\ln\left(\frac{b^2 + 2 \cdot a^2 \cdot XA_m(k)}{a} + 2 \cdot \sqrt{c^2 + b^2 \cdot XA_m(k) + a^2 \cdot [XA_m(k)]^2}\right)}{a} + d,$$

for $XA_m(k) > 0$ and $$C_m(k) = f(x) = \frac{\ln\left(\frac{b^2 + 2 \cdot a^2 \cdot XC_m(k)}{a} + 2 \cdot \sqrt{c^2 + b^2 \cdot XC_m(k) + a^2 \cdot [XC_m(k)]^2}\right)}{a} + d,$$

for $XC_m(k) > 0$ where experiment profile $XA_m$ comprises measured data set $\{XA_m(k)\}$, said reference profile $XC_m$ comprises measured data set $\{XC_m(k)\}$, where d is described by equation $$d = \frac{-\ln\left(\frac{b^2}{a} + 2 \cdot c\right)}{a}$$

and where a is the fractional error coefficient of said experiment, b is the Poisson error coefficient of said experiment, and c is the standard deviation of background noise of said experiment.

In another preferred embodiment, said experiment profile $A_m$ and reference profile $C_m$ comprises measurements from which nonlinearity is removed. In one embodiment, said measurements from which nonlinearity is removed are obtained by a method comprising (i) determining an average profile of all experiment profiles $\{A_m\}$ and reference profiles $\{C_m\}$; and (ii) adjusting each $A_m$ or $C_m$ based on a difference between said $A_m$ or $C_m$ and said average profile. In one embodiment, said difference is determined using a subset of measurements in the profiles. In a preferred embodiment, said subset of measurements in the profiles consists of measurements that are ranked similarly between an experiment or reference profile and said average profile. In one embodiment, said comparing in said step (ii) is carried out by a method comprising: (ii1) binning measurements in said subset into a plurality of bins, each said bin consisting of measurements having a value in a given range; (ii2) calculating mean difference between said $A_m$ or $C_m$ and the average profile in each bin; (ii3) determining a curve of said mean difference as a function of values of measurements for said $A_m$ or $C_m$, nonlinear_$A_m$ or nonlinear_$C_m$, respectively; and (ii4) adjusting $A_m$ or $C_m$ according to equations $$A_m^{corr}(k) = A_m(k) - \text{nonlinear\_}A_m(k)$$

or $$C_m^{corr}(k) = C_m(k) - \text{nonlinear\_}C_m(k)$$

where k=1, ..., N.

In another preferred embodiment, each said experiment profile $A_m$ and reference profile $C_m$ is a normalized profile. In one embodiment, said normalized profile is obtained by a method comprising normalizing experiment profile $A_m$ and reference profile $C_m$ according to equation $$NA_m(k) = \frac{A_m(k) \cdot \overline{AC}}{\overline{A_m}} \text{ and } NC_m(k) = \frac{C_m(k) \cdot \overline{AC}}{\overline{C_m}}$$

where $\overline{A_m}$ is an average of profile $\{A_m(k)\}$, and $\overline{C_m}$ is an average of profile $\{C_m(k)\}$;

wherein $\overline{AC}$ is an average of all profiles calculated according to equation $$\overline{AC} = \frac{1}{2M} \sum_{m=1}^{M} (\overline{A_m} + \overline{C_m}).$$

The method of the invention can further comprise normalizing errors of said experiment profile $A_m$ and reference profile $C_m$ according to equation $$\sigma_m^{NA}(k) = \frac{\sigma_m^A(k) \cdot \overline{AC}}{\overline{A_m}} \text{ and } \sigma_m^{NC}(k) = \frac{\sigma_m^C(k) \cdot \overline{AC}}{\overline{C_m}}$$

where $\sigma_m^A(k)$ and $\sigma_m^C(k)$ are the standard error of $A_m(k)$ and $C_m(k)$, respectively, and $\sigma_m^{NA}(k)$ and $\sigma_m^{NC}(k)$ are normalized standard error of $NA_m(k)$ and $NC_m(k)$, respectively.

In another embodiment, the method further comprises normalizing background errors of said experiment profile $A_m$ and reference profile $C_m$ according to equation $$bkgstd_m^{NA}(k) = \frac{bkgstd_m^A(k) \cdot \overline{AC}}{\overline{A_m}} \text{ and } bkgstd_m^{NC}(k) = \frac{bkgstd_m^C(k) \cdot \overline{AC}}{\overline{C_m}}$$

where $bkgstd_m^A(k)$ and $bkgstd_m^C(k)$ are the standard background error of $A_m(k)$ and $C_m(k)$, respectively, and $bkgstd_m^{NA}(k)$ and $bkgstd_m^{NC}(k)$ are normalized standard background error of $NA_m(k)$ and $NC_m(k)$, respectively.

In a preferred embodiment, said $\overline{A_m}$ and $\overline{C_m}$ are an average of measurements in profile $\{A_m(k)\}$ and $\{C_m(k)\}$, respectively, excluding measurements having values among the highest 10%.

The invention also provides a method of correcting errors in a plurality of pairs of profiles $\{XA_m, XC_m\}$, $XA_m$ being an experiment profile, $XC_m$ being a reference profile, where m=1, 2, ..., M, M is the number of pairs of profiles, said method comprising (a) processing said profiles to obtain a plurality of pairs of processed profiles $\{A_m, C_m\}$, $A_m$ being a processed experiment profile, $C_m$ being a processed reference profile; (b) calculating an average reference profile $\overline{C}$ of reference profiles $\{C_m\}$, m=1, 2, ..., M; (c) determining for each profile pair m a differential reference profile of $C_m$ and $\overline{C}$; and (d) generating for each profile pair m an error-adjusted experiment profile $A'_m$ by a method comprising adjusting said experimental profile $A_m$ using said differential reference profile determined for said profile pair m, thereby correcting errors in said plurality of pairs of profiles; wherein for each m∈{1, 2, ..., M}, said error-adjusted experiment profile $A'_m$ comprises data set $\{A'_m(k)\}$, said processed experiment profile $A_m$ comprises data set $\{A_m(k)\}$, said processed reference profile $C_m$ comprises data set $\{C_m(k)\}$, and said average reference profile $\overline{C}$ comprises data set $\{\overline{C}(k)\}$, said experiment profile $XA_m$ comprises data set $\{XA_m(k)\}$, said reference profile $XC_m$ comprises data set $\{XC_m(k)\}$, wherein said data set $\{XA_m(k)\}$ comprises measurements of a plurality of different cellular constituents measured in a sample having been subject to condition $A_m$, said data set $\{XC_m(k)\}$ comprises measurements of said plurality of different cellular constituents measured in a sample having been subject to condition C, and where k=1, 2, ..., N is an index of measurements of cellular constituents, N being the total number of measurements. The experiment profile $XA_m$ and reference profile $XC_m$ are preferably measured in the same experimental reaction. In one embodiment, each said pair of profiles $XA_m$ and $XC_m$ is measured in a two-channel microarray experiment. Preferably, said reference profiles $\{XC_m\}$, m=1, 2, ..., M, are measured with samples labeled with a same label. In another embodiment, at least one of said pair of profiles $\{XA_m, XC_m\}$ is a virtual profile.

In one embodiment, said step (a) of the method comprises normalizing each said experiment profile $XA_m$ and reference profile $XC_m$. In a preferred embodiment, said normalizing is carried out according to equation $$A_m(k) = NA_m(k) = \frac{XA_m(k) \cdot \overline{XAC}}{\overline{XA_m}} \text{ and }$$

$$C_m(k) = NC_m(k) = \frac{XC_m(k) \cdot \overline{XAC}}{\overline{XC_m}}$$

where $NA_m$ and $NC_m$ denotes normalized experiment and normalized reference profiles, respectively, where $\overline{XA_m}$ is an average of profile $\{XA_m\}$, and $\overline{XC_m}$ is an average of profile $\{XC_m\}$; wherein $\overline{XAC}$ is an average of all profiles calculated according to equation $$\overline{XAC} = \frac{1}{2M} \sum_{m=1}^{M} (\overline{XA_m} + \overline{XC_m}).$$

In another embodiment, the method of the invention further comprises normalizing errors of said experiment profile $XA_m$ and reference profile $XC_m$ according to equation $$\sigma_m^A(k) = \frac{\sigma_m^{XA}(k) \cdot \overline{XAC}}{\overline{XA_m}} \text{ and } \sigma_m^C(k) = \frac{\sigma_m^{XC}(k) \cdot \overline{XAC}}{\overline{XC_m}}$$

where $\sigma_m^{XA}(k)$ and $\sigma_m^{XC}(k)$ are the standard error of $XA_m(k)$ and $XC_m(k)$, respectively, and $\sigma_m^A(k)$ and $\sigma_m^C(k)$ are normalized standard error of $An(k)$ and $C_m(k)$, respectively.

In still another embodiment, the method of the invention further comprises normalizing background errors of said experiment profile $XA_m$ and reference profile $XC_m$ according to equation $$bkgstd_m^A(k) = \frac{bkgstd_m^{XA}(k) \cdot \overline{XAC}}{\overline{XA_m}} \text{ and } bkgstd_m^C(k) = \frac{bkgstd_m^{XC}(k) \cdot \overline{XAC}}{\overline{XC_m}}$$

where $bkgstd_m^{XA}(k)$ and $bkgstd_m^{XC}(k)$ are the standard background error of $XA_m(k)$ and $XC_m(k)$, respectively, and $bkgstd_m^A(k)$ and $bkgstd_m^C(k)$ are normalized standard background error of $A_m(k)$ and $C_m(k)$, respectively.

Preferably, said $\overline{XA_m}$ and $\overline{XC_m}$ are an average of measurements in profile $\{XA_m\}$ and $\{XC_m\}$, respectively, excluding measurements having values among the highest 10%.

In still another embodiment, said step (a) of the invention further comprises transforming said normalized profiles to obtain transformed profiles. In one embodiment, said transforming is carried out according to equations $$TA_m(k) = f(x) = \frac{\ln\left(\frac{b^2 + 2 \cdot a^2 \cdot NA_m(k)}{a} + 2 \cdot \sqrt{\frac{c^2 + b^2 \cdot NA_m(k) + a^2 \cdot [NA_m(k)]^2}{}}\right)}{a} + d,$$

for $NA_m(k) > 0$ and $TC_m(k) =$ $$f(x) = \frac{\ln\left(\frac{b^2 + 2 \cdot a^2 \cdot NC_m(k)}{a} + 2 \cdot \sqrt{\frac{c^2 + b^2 \cdot NC_m(k) + a^2 \cdot [NC_m(k)]^2}{}}\right)}{a} + d,$$

for $NC_m(k) > 0$ where experiment profile $XA_m$ comprises measured data set $\{XA_m(k)\}$, said reference profile $XC_m$ comprises measured data set $\{XC_m(k)\}$, where d is described by equation $$d = \frac{-\ln\left(\frac{b^2}{a} + 2 \cdot c\right)}{a}$$

and where a is the fractional error coefficient of said experiment, b is the Poisson error coefficient of said experiment, and c is the standard deviation of background noise of said experiment.

In still another embodiment, said step (a) of the invention further comprises removing nonlinearity from each said transformed experiment profile $TA_m$ and transformed reference profile $TC_m$. In one embodiment, said removing nonlinearity is carried out by a method comprising (a1) determining an average transformed profile of all transformed experiment profiles $\{TA_m\}$ and transformed reference profiles $\{TC_m\}$; and (a2) adjusting each $TA_m$ or $TC_m$ using a difference between said $TA_m$ or $TC_m$ and said average transformed profile. In a preferred embodiment, said difference is determined using a subset of measurements in said transformed profiles. In one embodiment, said subset of measurements in said transformed profiles consists of measurements that are ranked similarly between an experiment or reference profile and said average profile. In one embodiment, said comparing in said step (a2) is carried out by a method comprising: (a2i) binning measurements in said subset into a plurality of bins, each said bin consisting of measurements having a value in a given range; (a2ii) calculating mean difference between said $A_m$ or $C_m$ and the average profile in each bin; (a2iii) determining a curve of said mean difference as a function of values of measurements for said $TA_m$ or $TC_m$, nonlinear_$TA_m$ or nonlinear_$TC_m$, respectively; and (a2iv) adjusting $TA_m$ or $TC_m$ according to equations $$TA_m^{corr}(k) = TA_m(k) - \text{nonlinear\_}TA_m(k)$$

or $$TC_m^{corr}(k) = TC_m(k) - \text{nonlinear\_}TC_m(k)$$

where $k = 1, \ldots, N$.

In one embodiment, said $\overline{C}(k)$ is calculated according to equation $$\overline{C}(k) = \frac{1}{M}\sum_{m=1}^{M} C_m(k)$$

wherein said differential reference profile is calculated according to equation $$C_{diff}(m,k) = C_m(k) - \overline{C}(k)$$

and wherein said error-adjusted profile is calculated according to equation $$A'_m(k) = A_m - C_{diff}(m,k).$$

In another embodiment, the method further comprises (d) calculating for at least one, preferably each profile pair m an error-corrected experiment profile $A''_m$ comprising data set $\{A''_m(k)\}$ by combining said error-adjusted experiment profile $A'_m$ with said experiment profile $A_m$ using a weighing factor $\{w(k)\}$, $k=1, 2, \ldots, N$, wherein $w(k)$ is a weighing factor for the k'th measurement.

In a preferred embodiment, said error-corrected experimental profile $A''_m$ is calculated according to equation $$A''_m(k) = (1 - w(k)) \cdot A_m(k) + w(k) A_m(k).$$

In one embodiment, said weighing factor is determining according to equation $$w(k) = 1 - e^{-0.5 \left(\frac{\overline{C}(k)}{avg\_bkgstd}\right)^2}$$

where avg_bkgstd is an average background noise. In one embodiment, said avg_bkgstd is determined according to equation $$avg\_bkgstd = \frac{1}{N}\sum_{k=1}^{N}\left(\frac{1}{M}\sum_{m=1}^{M} bkgstd(m,k)\right)$$

where bkgstd (m, k) is background standard error of $C_m(k)$.

In another embodiment, the method further comprises determining errors $\{\sigma'_m\}$ of said error-adjusted experiment profile $\{A'_m\}$. In one embodiment, said errors are determined according to equation $$\sigma'_m(k) = \sqrt{\sigma_m^2(k) + \text{mixed\_}\sigma_m^2(k) - 2 \cdot Cor(k) \cdot \sigma_m(k) \cdot \text{mixed\_}\sigma_m(k)}$$

where $\sigma_m(k)$ is the standard error of $A_m(k)$, mixed_$\sigma_m(k)$ is determined according to equation $$\text{mixed\_}\sigma_m(k) = \frac{\sigma_m(k) + (M-1) \cdot \sigma_{ref}(k)}{M}$$

where $\sigma_{ref}(k) = \sqrt{\frac{1}{M-1}\sum_{m}^{M}(C_m(k) - \overline{C}(k))^2}$ and where Cor(k) is a correlation coefficient between experiment profile $A_m$ and reference profile $C_m$. In one embodiment, said Cor(k) is determined according to equation $$Cor(k) = CorMax \cdot \left(1 - e^{-0.5 \cdot \left(\frac{\overline{C}(k)}{avg\_bkgstd}\right)^2}\right)$$

where CorMax is a number between 0 and 1.

In still another embodiment, the method further comprises determining errors $\{\sigma''_m\}$ of said error-corrected experiment profile $\{A''_m\}$. In one embodiment, said errors are determined according to the equation:

$$\sigma'_m(k) = \sqrt{[1-w(k)] \cdot \sigma_m^2(k) + w(k) \sigma'^2_m(k)}$$

where $\sigma_m(k)$ is the standard error of $A_m(k)$, $\sigma'_m(k)$ is determined according to the equation:

$$\sigma'_m(k) = \sqrt{\sigma_m^2(k) + mixed\_\sigma_m^2(k) - 2 \cdot Cor(k) \cdot \sigma_m(k) \cdot mixed\_\sigma_m(k)}$$

where $mixed\_\sigma_m(k)$ is determined according to the equation:

$$mixed\_\sigma_m(k) = \frac{\sigma_m(k) + (M-1) \cdot \sigma_{ref}(k)}{M}$$

$$\text{where } \sigma_{ref}(k) = \sqrt{\frac{1}{M-1} \sum_m^M (C_m(k) - \overline{C}(k))^2}$$

and where Cor(k) is a correlation coefficient. In one embodiment, said Cor(k) is determined according to the equation:

$$Cor(k) = CorMax \cdot \left(1 - e^{-0.5 \cdot \left(\frac{\overline{C}(k)}{avg\_bkgstd}\right)^2}\right)$$

where CorMax is a number between 0 and 1.

The invention further provides a method for generating a differential profile A vs. B from differential profiles A vs. $C_A$ and B vs. $C_B$, comprising calculating said differential profile A vs. B according to equation $$lratioAB(k) = polarityAC \cdot lratioAC(k) - polarityBC \cdot lratioBC(k)$$

where k=1, 2, ..., N, is the index of measurements in a profile, N being the total number of measurements; wherein lratioAC(k)=Log $\{A(k)/C_A(k)\}$, if PolarityAC=1, and lratioAC(k)=Log $\{C_A(k)/A(k)\}$, if PolarityAC=-1, where A(k), and $C_A(k)$ are the k'th measurement from sample A and $C_A$, respectively; wherein lratioBC(k)=Log $\{B(k)/C_B(k)\}$, if PolarityBC=1, and lratioAC(k)=Log $\{C_B(k)/B(k)\}$, if PolarityBC=-1, where B(k), and $C_B(k)$ are the k'th measurement from sample B and $C_B$, respectively; wherein $\{A(k)\}$ representing measurements of a plurality of different cellular constituents measured in a sample having been subject to condition A, $\{B(k)\}$ representing measurements of said plurality of different cellular constituents measured in a sample having been subject to condition B, and $\{C_A(k)\}$ and $\{C_B(k)\}$ each representing measurements of said plurality of different cellular constituents measured in a sample having been subject to condition C. In one embodiment, A vs. $C_A$ and B vs. $C_B$ are experimentally measured profiles. In another embodiment, at least one of A vs. $C_A$ and B vs. $C_B$ is a virtual profile.

In one embodiment, the method further comprising calculating an error of differential profile A vs. B according to equation $$\sigma_{lratioAB}(k) =$$

$$\sqrt{\sigma_{lratioAC}^2(k) + \sigma_{lratioBC}^2(k) - 2 \cdot CorMax \cdot \sigma_{lratioAC}(k) \cdot \sigma_{lratioBC}(k)}$$

wherein $\sigma_{lratioAC}(k)$ and $\sigma_{lratioBc}(k)$ are errors of lratioAC(k) and lratioBC(k), respectively, and wherein CorMax is an estimated maximum correlation coefficient between errors of A/C and B/C.

The invention also provides a computer system comprising a processor and a memory coupled to said processor and encoding one or more programs, wherein said one or more programs cause the processor to carry out any one of the methods of the invention.

The invention also provides a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out any one of the methods of the invention.

4. BRIEF DESCRIPTION OF FIGURES

Figure 4:
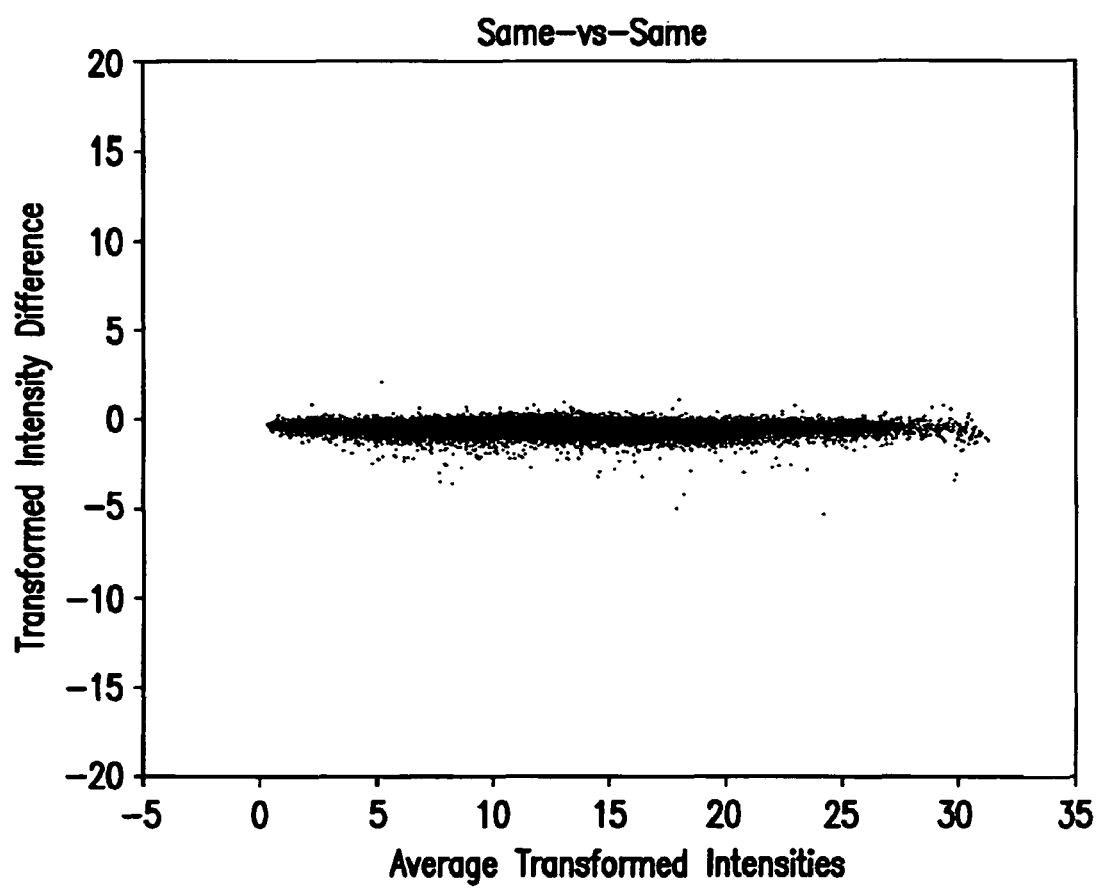

FIG. 4 shows results of a Same-vs-Same from one chip. X-axis is the average of the transformed intensities in the red and the green channels of the same chip. Y-axis is the difference of the transformed intensities in the red and the green channel.

Figure 5:
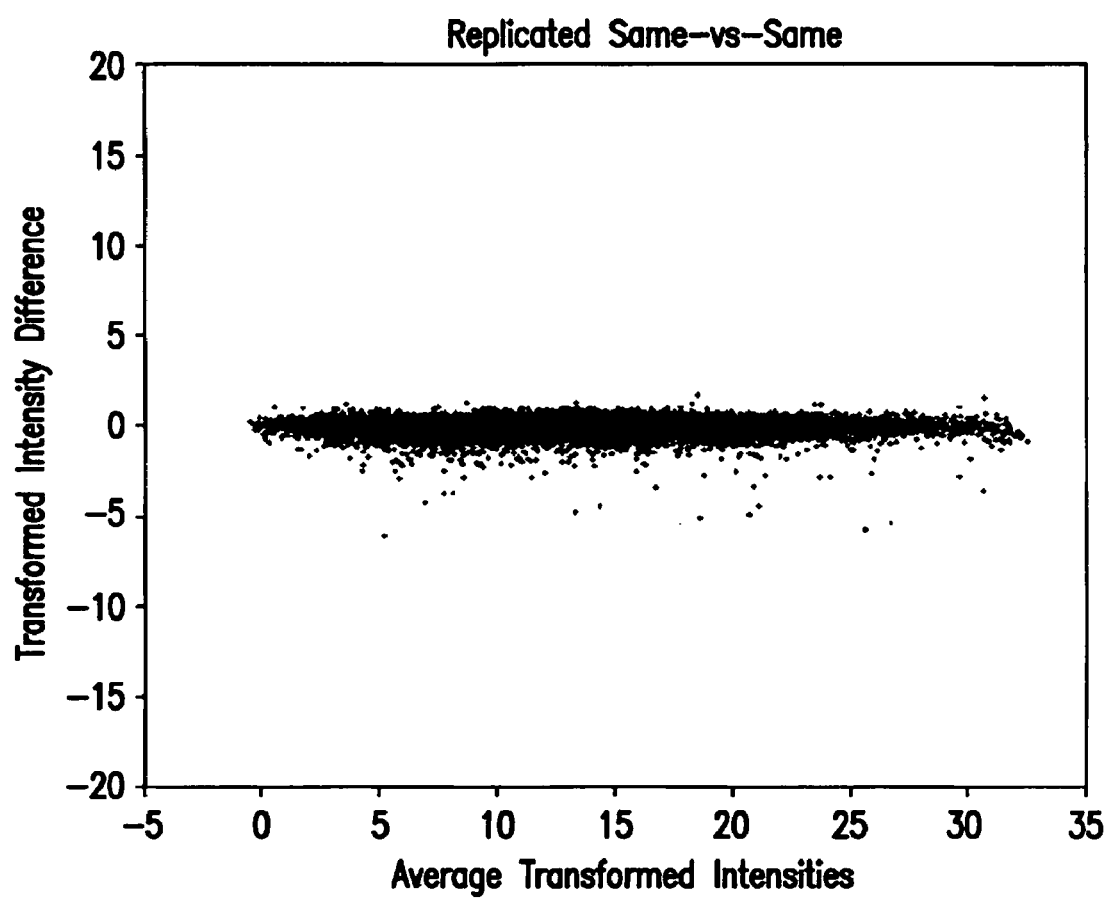

FIG. 5 shows results of a Same-vs-Same from one replicated chip. X-axis is the average of the transformed intensities in the red and the green channels of the same chip. Y-axis is the difference of the transformed intensities in the red and the green channel.

Figure 6:
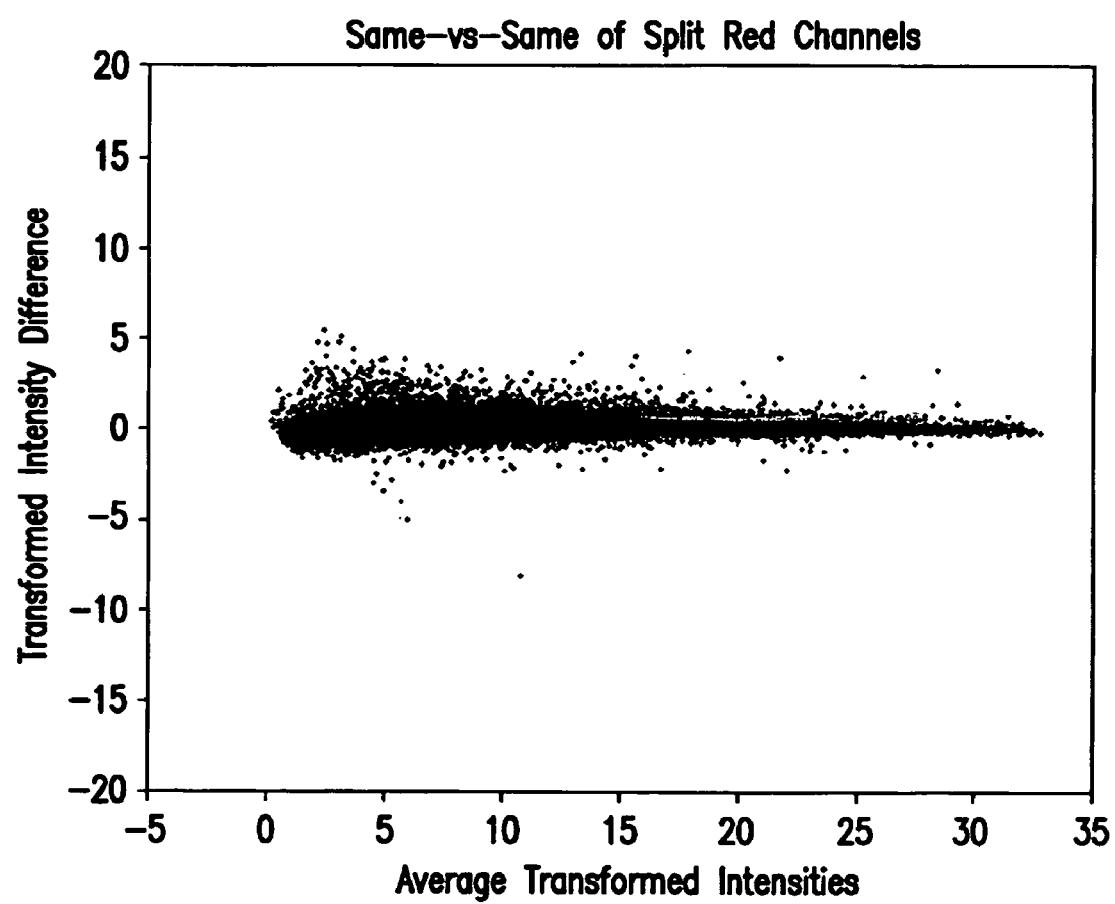

FIG. 6 shows results of a Same-vs-Same from split red channels of two chips. X-axis is the average of the transformed intensities in the red channel in one chip and the red channel in the other chip. Y-axis is the difference of the transformed intensities in the red channels.

Figure 7:
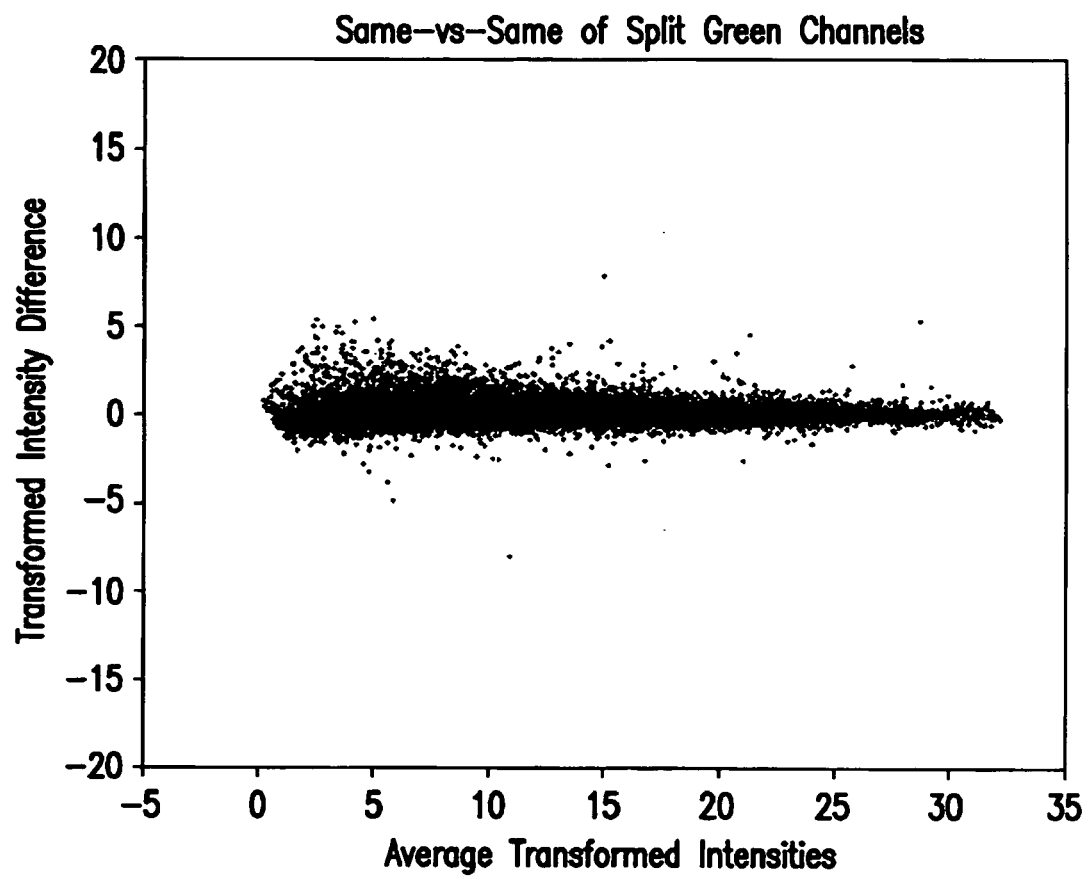

FIG. 7 shows results of a Same-vs-Same from split green channels of two chips. X-axis is the average of the transformed intensities in the green channel in one chip and the green channel in the other chip. Y-axis is the difference of the transformed intensities in the green channels.

Figure 8:
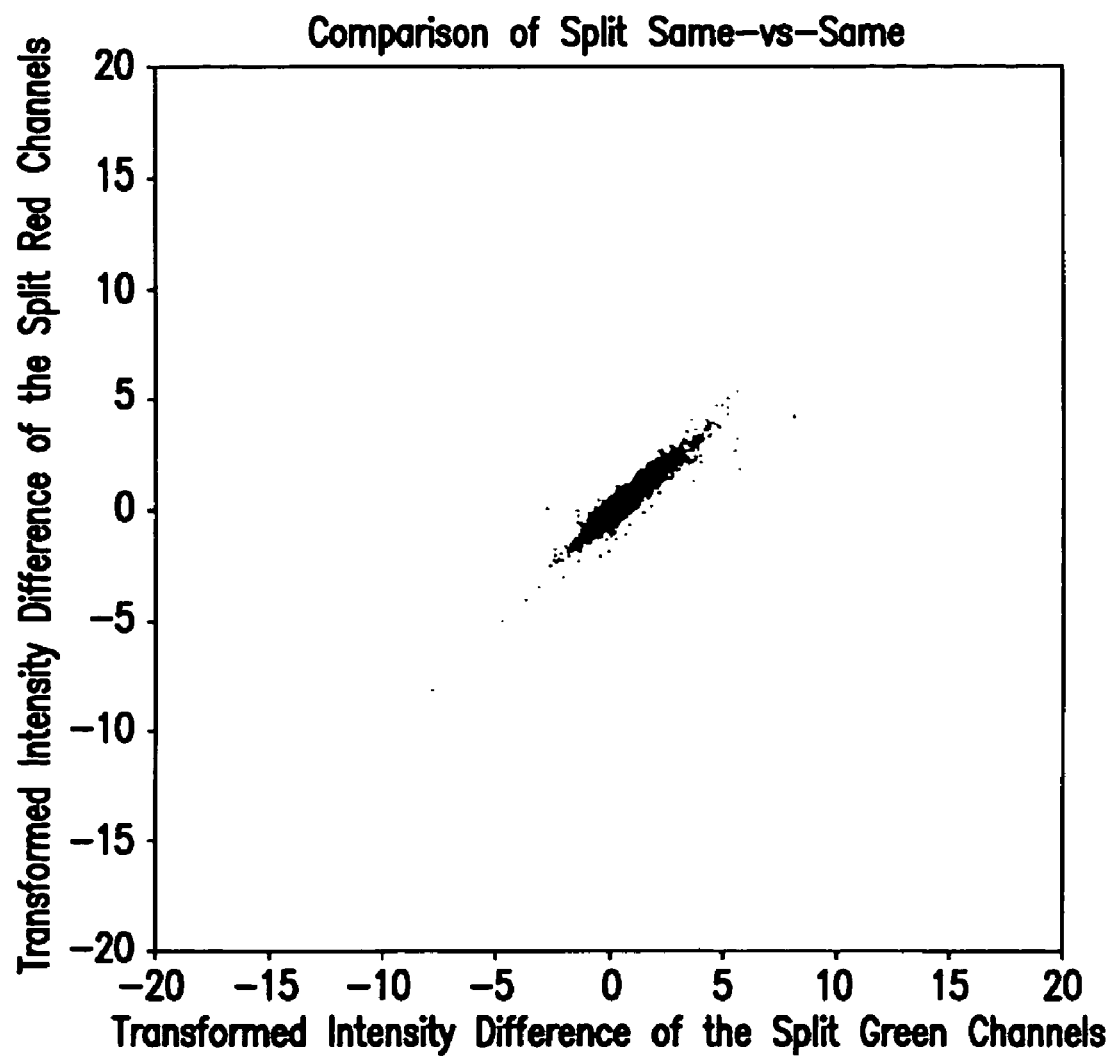

FIG. 8 shows a comparison of the intensity differences in FIG. 6 and FIG. 7. X-axis is the difference of the transformed intensities in the green channels. Y-axis is the difference of the transformed intensities in the red channels.

Figure 9:
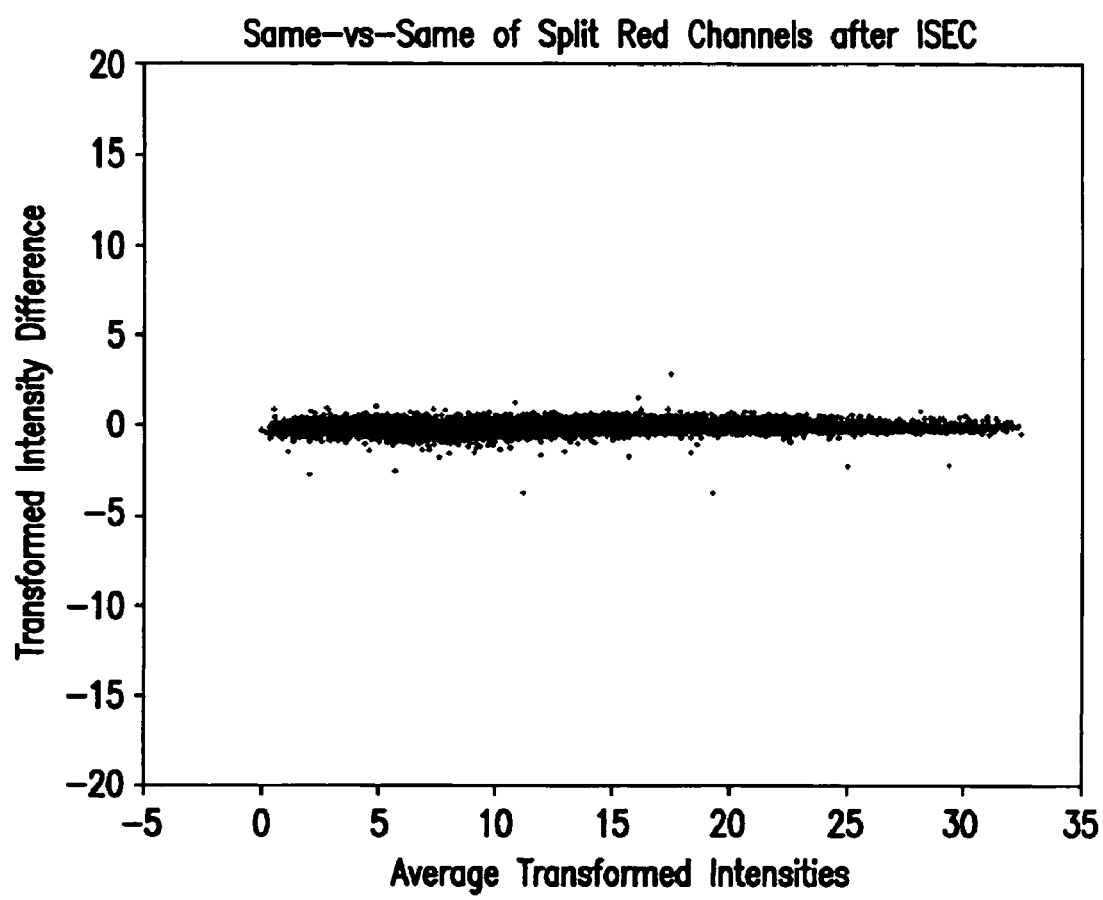

FIG. 9 shows results of a Same-vs-Same from split red channels of two chips after inter-slide error correction.

Figure 10:
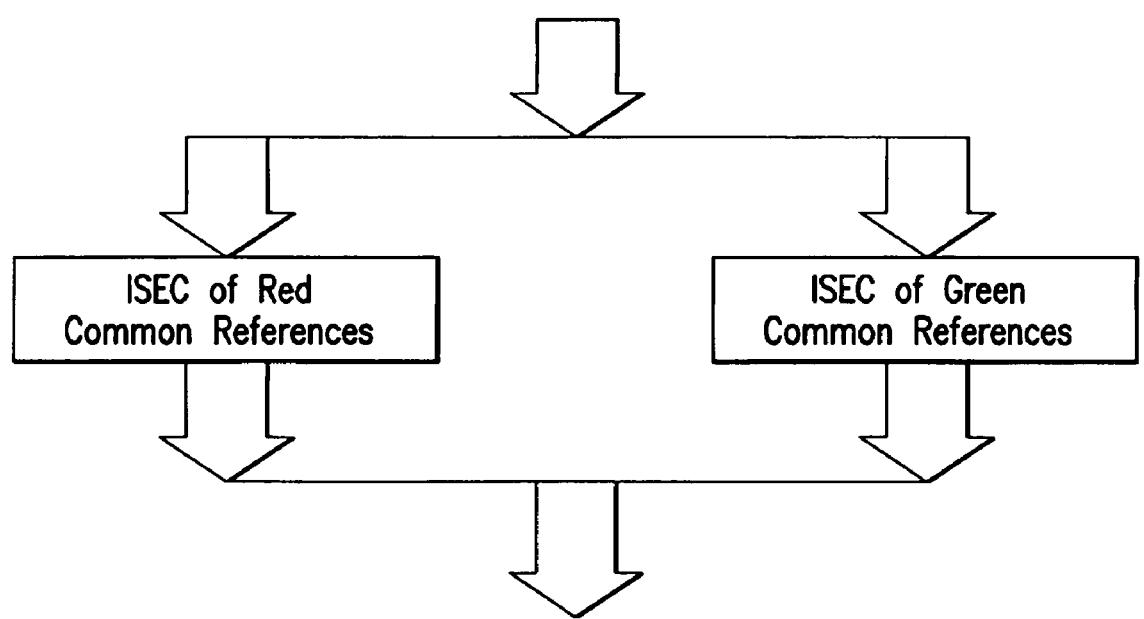

FIG. 10 illustrates that common reference controls of different fluor-colors are processed separately in ISEC.

Figure 11:
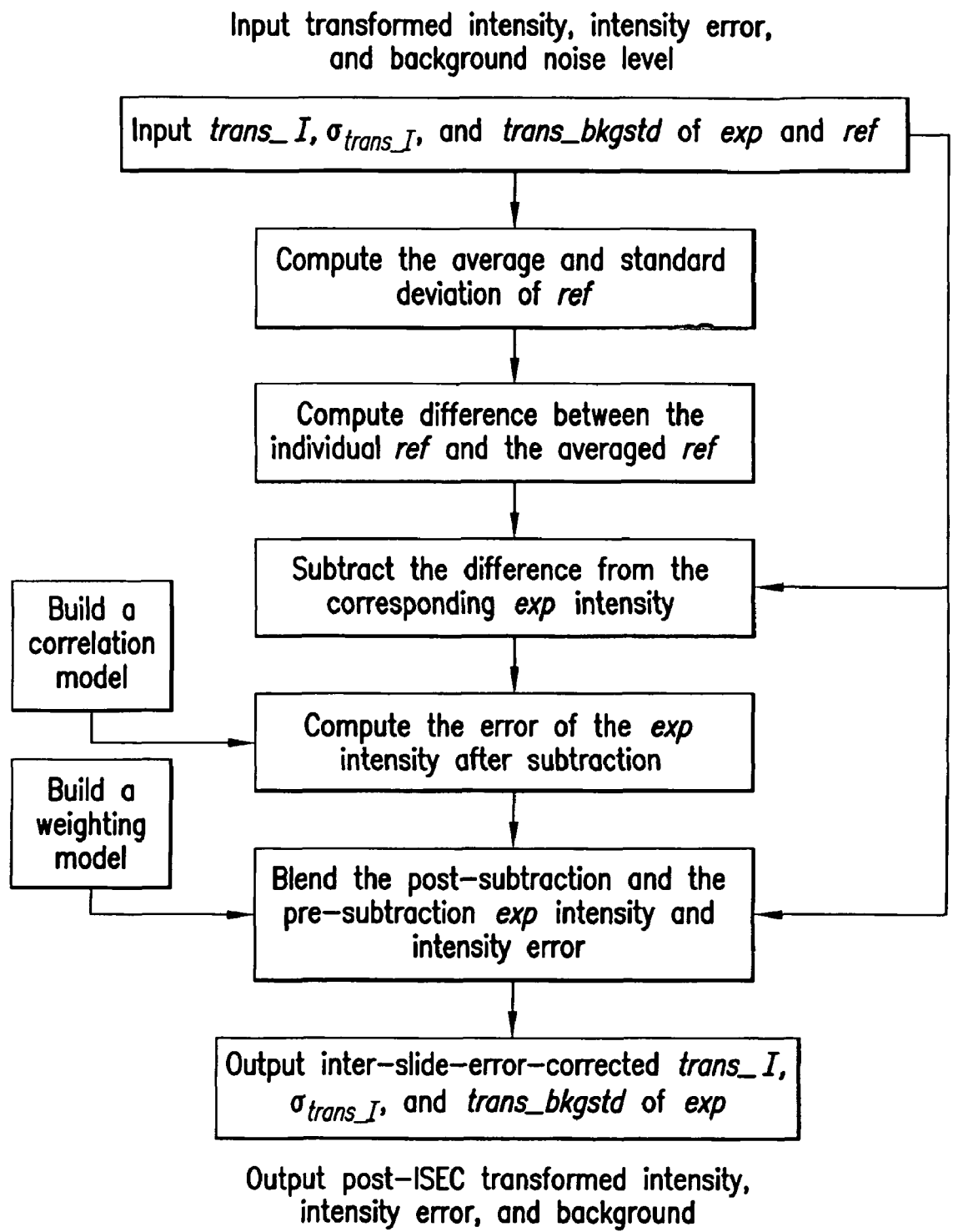

FIG. 11 shows a flowchart of an exemplary embodiment of the multi-chip ISEC algorithm.

Figure 12:
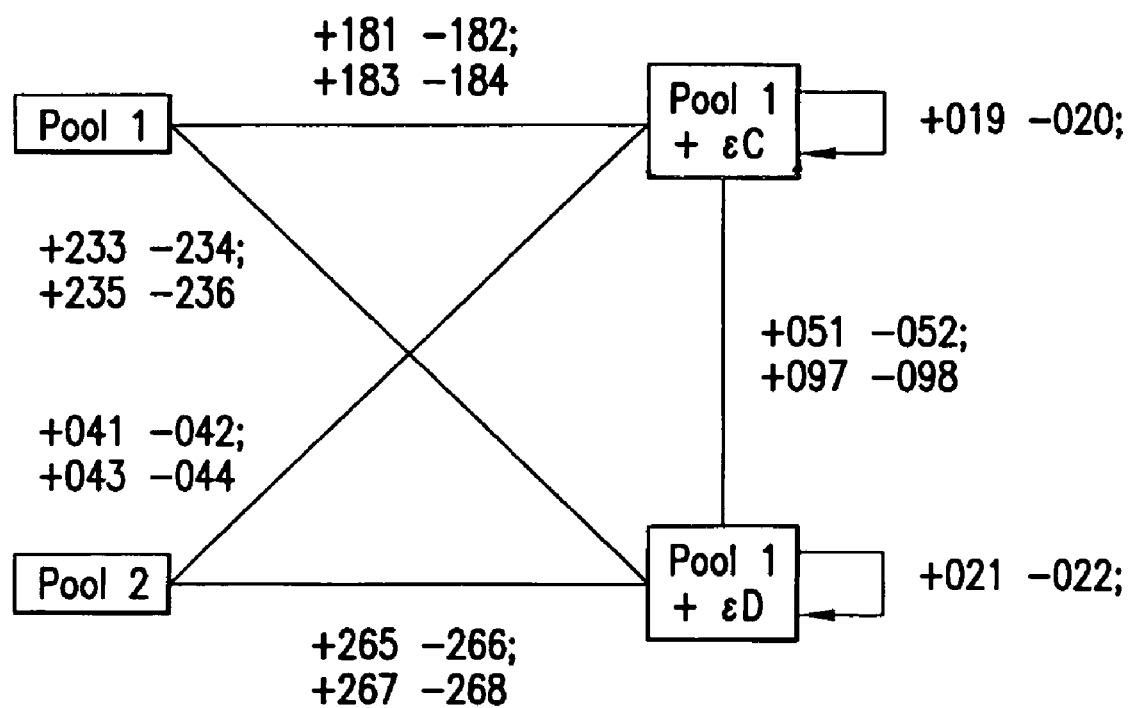

FIG. 12 shows the experiment design of the verification data. There were four samples. Pool 1 was the near common reference sample that included Tissue C (Thymus) and Tissue D (Spleen) and 8 other different tissues. Pool 2 was the distant common reference sample that did not include Tissue C and Tissue D. Pool 1+$\epsilon$6C was a sample that included an additional amount ($\epsilon$=0.3) of Tissue C in Pool 1. Pool 1+$\epsilon$D was a sample that included an additional amount of Tissue D in Pool 1. Edges between samples are two-color microarray hybridizations. Numbers on the edges are the last three digits of chip bar codes. "−" sign indicates fluor-reversal chip.

Figure 13:
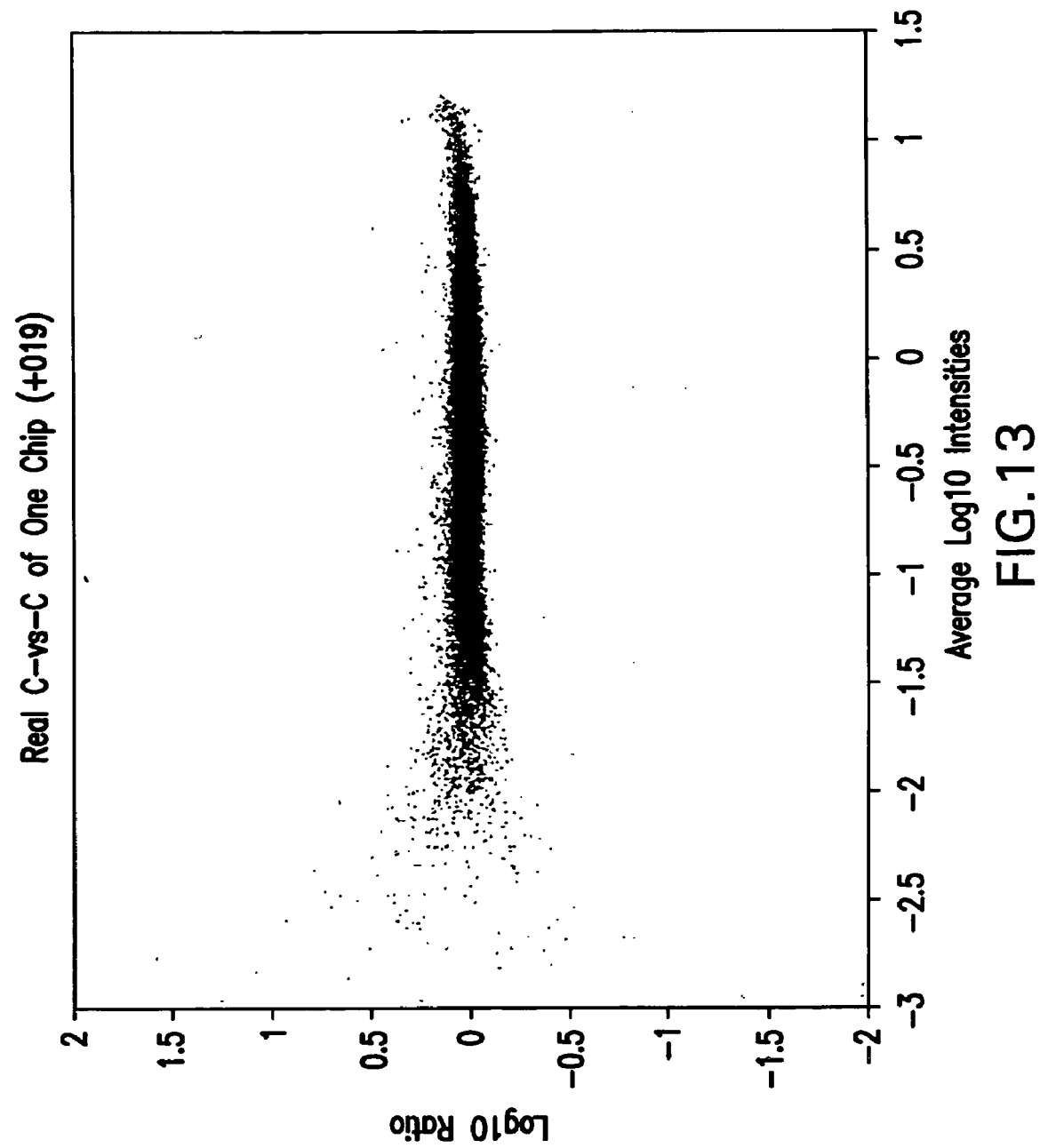

FIG. 13 is a feature-level ratio plot of a real same-vs-same profile from one C-vs-C chip (+019). X-axis is the average log 10 intensities and Y-axis is the log ratio of the experiment and the baseline intensities.

Figure 14:
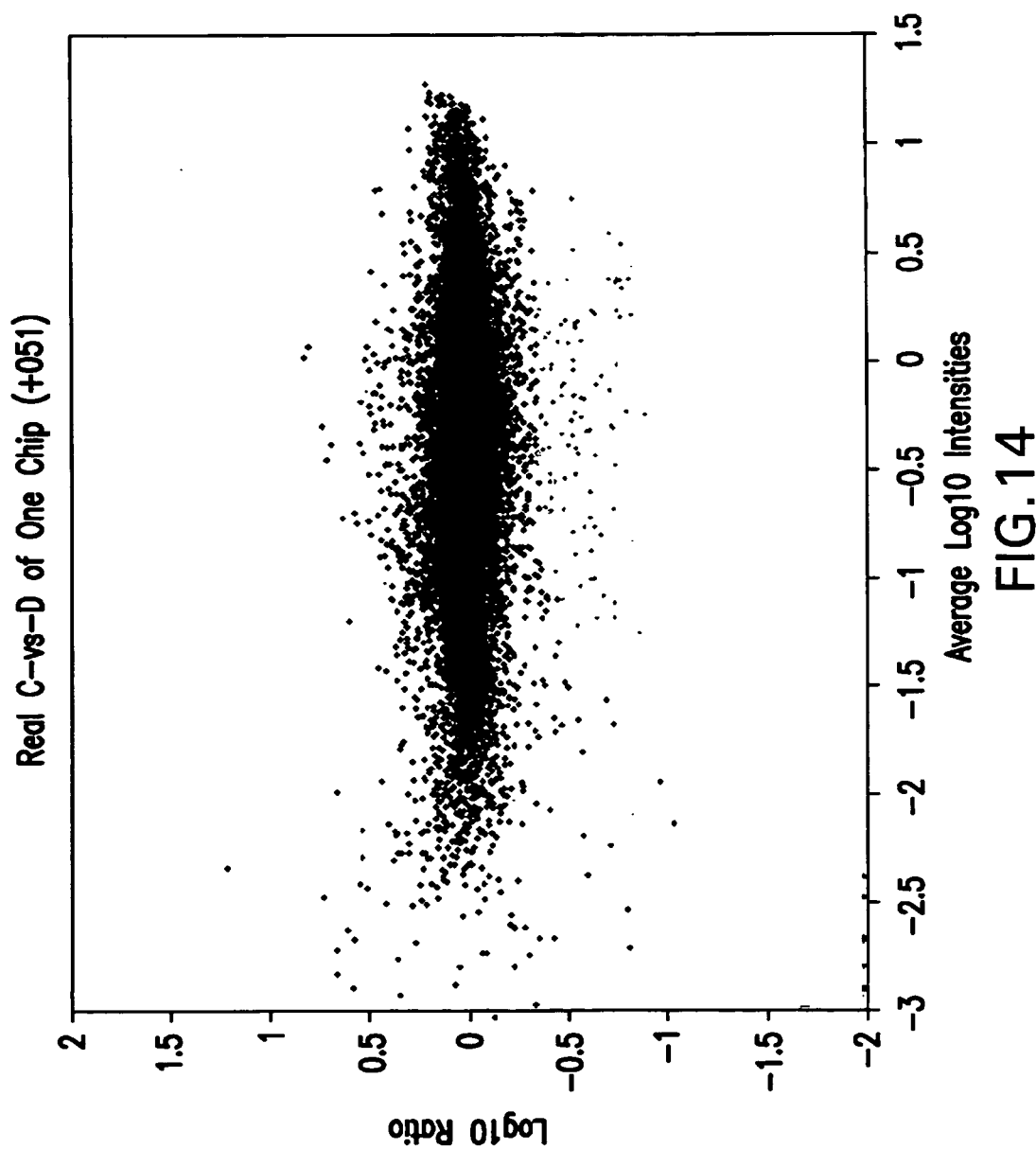

FIG. 14 is a feature-level ratio plot of a real different-vs-different profile from one C-vs-D chip (+051). X-axis is the average log 10 intensities and Y-axis is the log ratio of the experiment D and the baseline C intensities. For p-value<0.01, up-regulated features are in red, and down-regulated features are in green. Blue spots are features having p-value>0.01.

Figure 15:
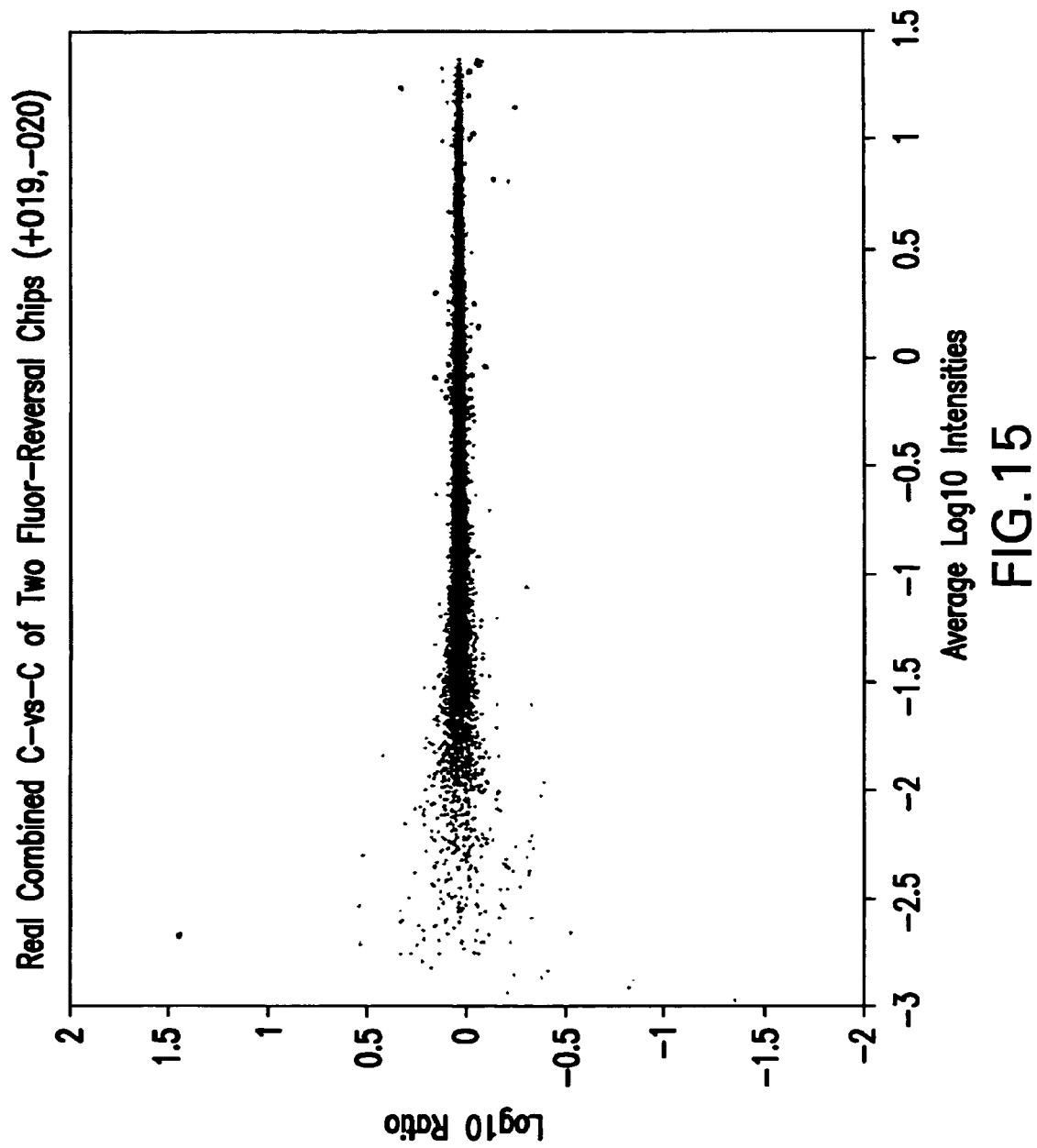

FIG. 15 is a feature-level ratio plot of a real combined same-vs-same experiment from two fluor-reversal C-vs-C chips (+019, −020). X-axis is the average log 10 intensities and Y-axis is the log ratio of the experiment and the baseline intensities.

Figure 16:
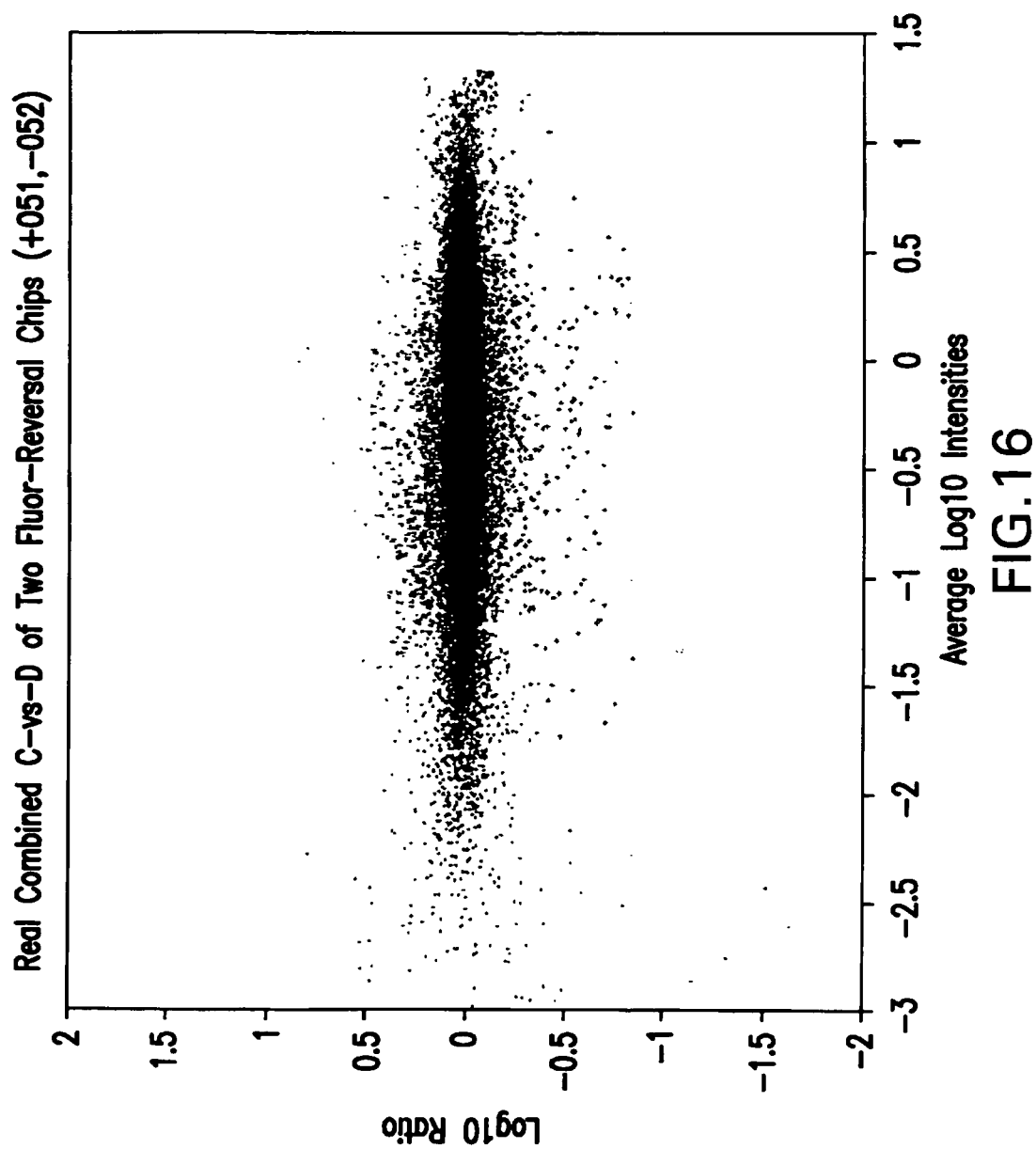

FIG. 16 is a feature-level ratio plot of a real combined different-vs-different experiment from two C-vs-D chips (+051, −052). X-axis is the average log 10 intensities and Y-axis is the log ratio of the experiment D and the baseline C intensities. For p-value<0.01, up-regulated features are in red, and down-regulated features are in green. Blue spots are features having p-value>0.01.

Figure 17:
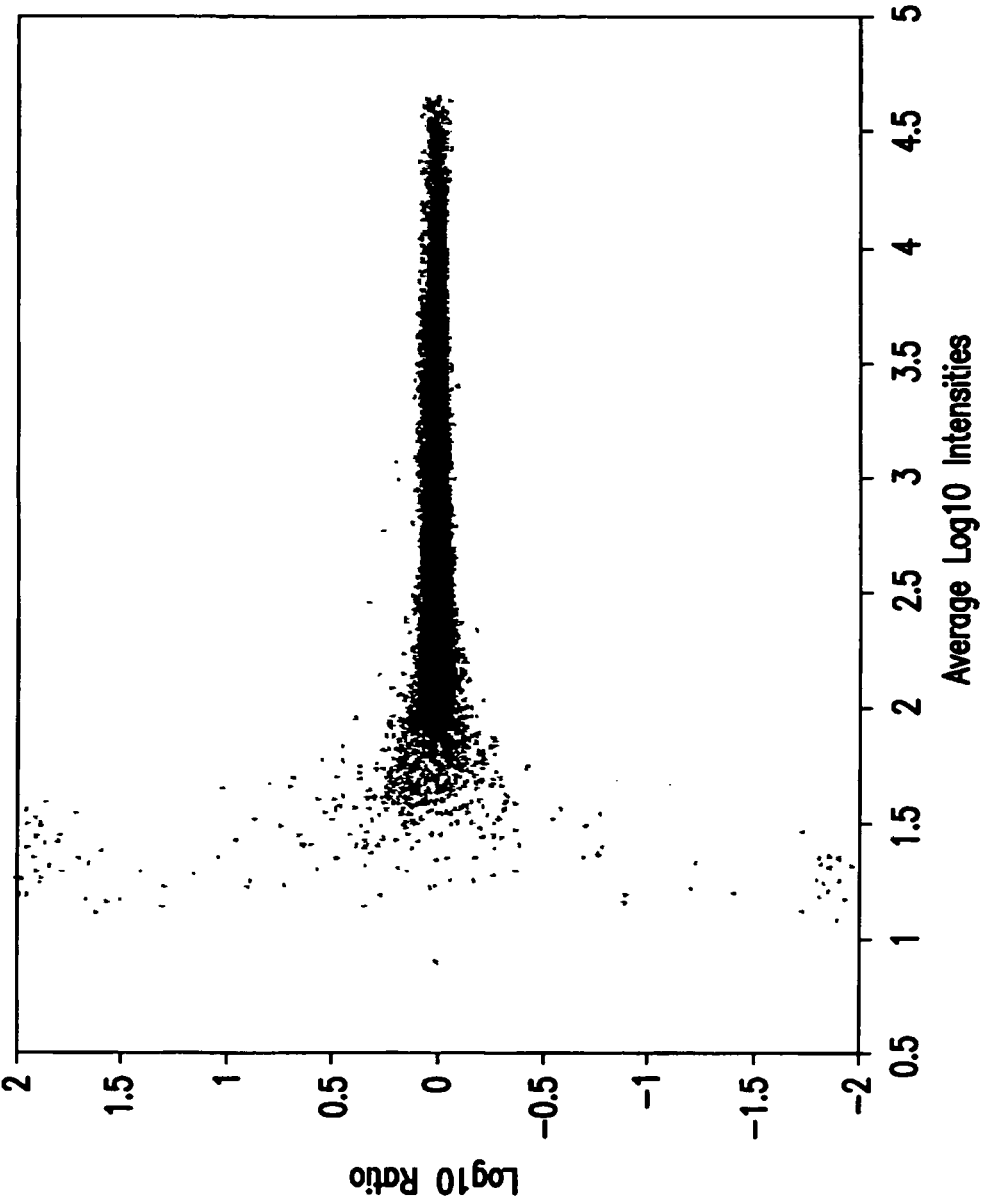

FIG. 17 is a feature-level ratio plot of a re-ratio virtual same-vs-same profile C-vs-C from two Pool1-vs-C chips (+181, +183) of the same red color. The common reference sample is the near pool (Pool 1).

Figure 18:
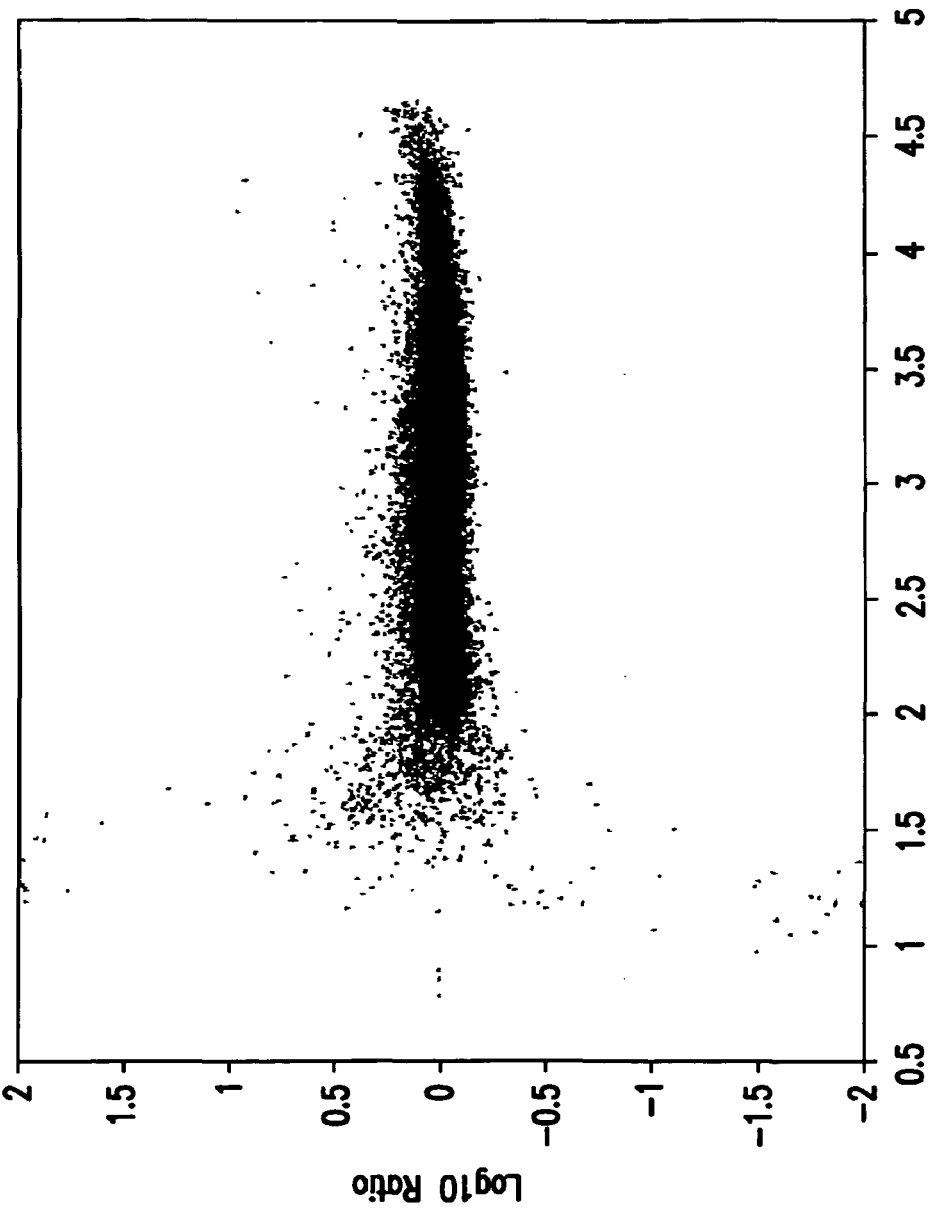

FIG. 18 is a feature-level ratio plot of a re-ratio virtual same-vs-same profile C-vs-C from two Pool1-vs-C chips (+181, −182) of different colors. The common reference sample is the near pool (Pool 1).

Figure 19:
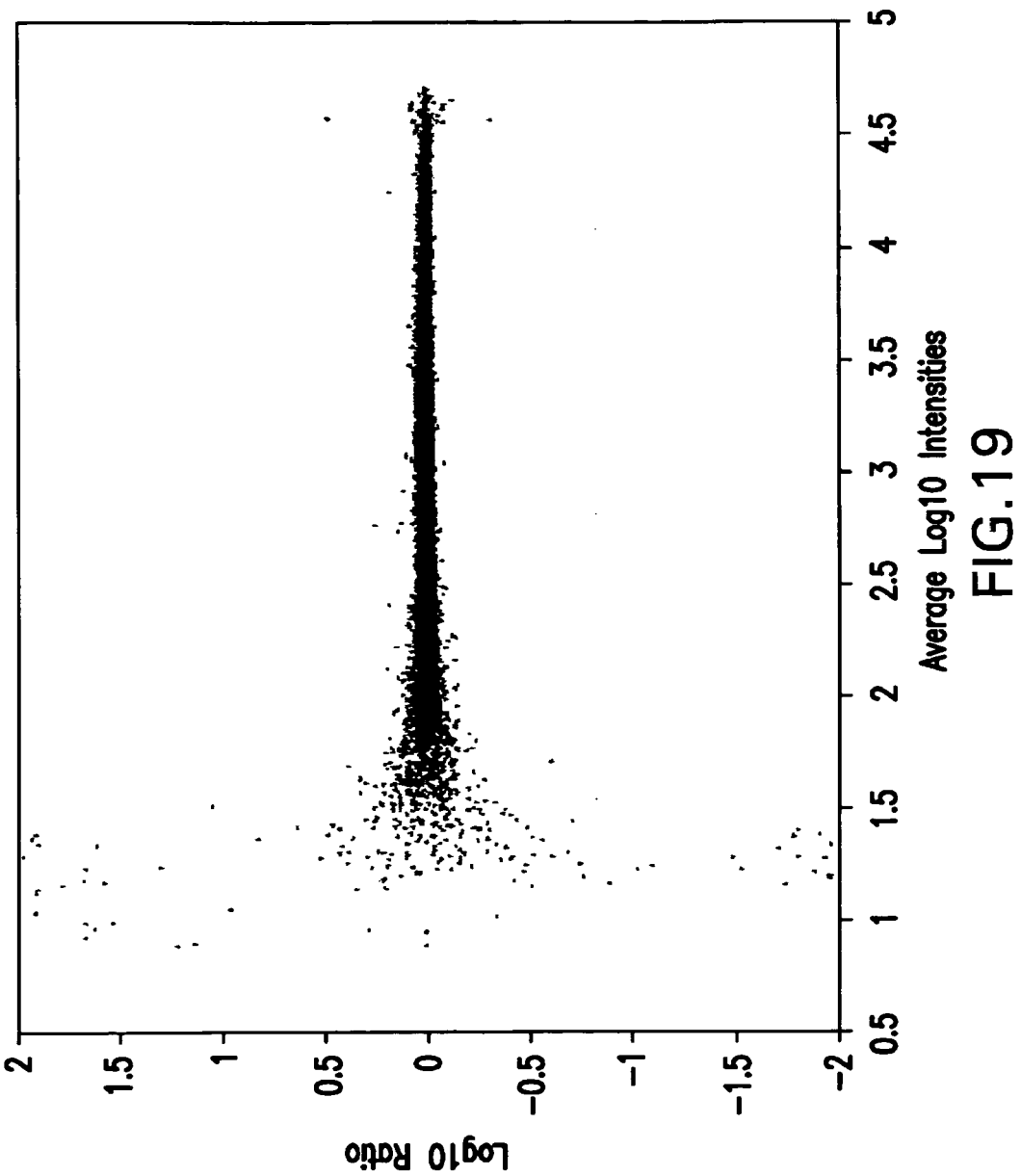

FIG. 19 is a feature-level ratio plot of a re-ratio virtual same-vs-same experiment C-vs-C from two combined fluor-reversal experiments Pool1-vs-C (+181, −182) and (+183, −184). The common reference sample is the near pool (Pool 1).

Figure 20:
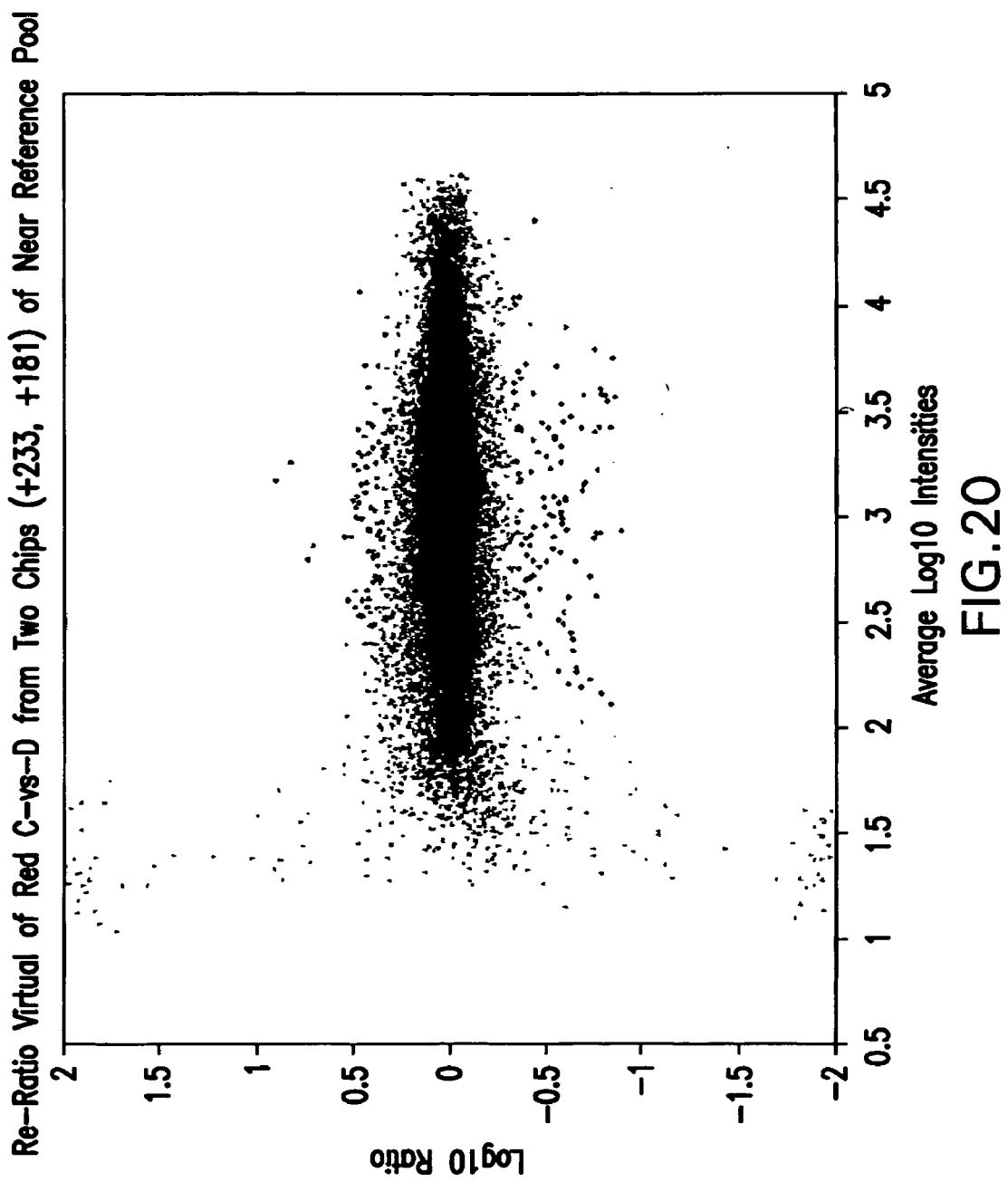

FIG. 20 is a feature-level ratio plot of a re-ratio virtual different-vs-different experiment C-vs-D from red experiment Pool1-vs-D (+233) and red baseline Pool1-vs-C (+181). The common reference sample is the near pool.

Figure 21:
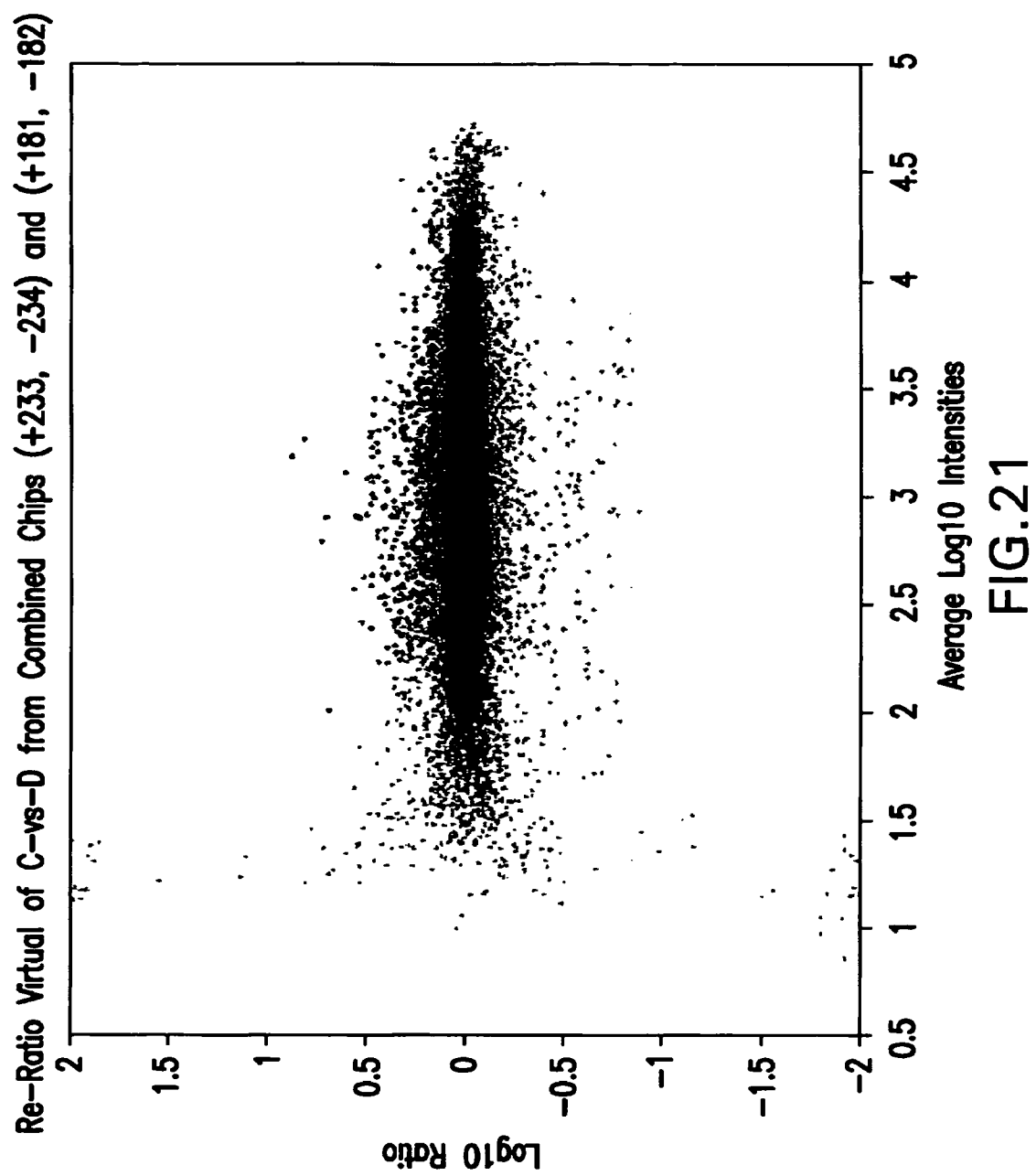

FIG. 21 is a feature-level ratio plot of a re-ratioer virtual different-vs-different experiment from two combined fluor-reversal experiments Pool1-vs-D (+233, −234) and combined baseline Pool1-vs-C (+181, −182). The common reference sample is the near pool (Pool 1).

Figure 22:
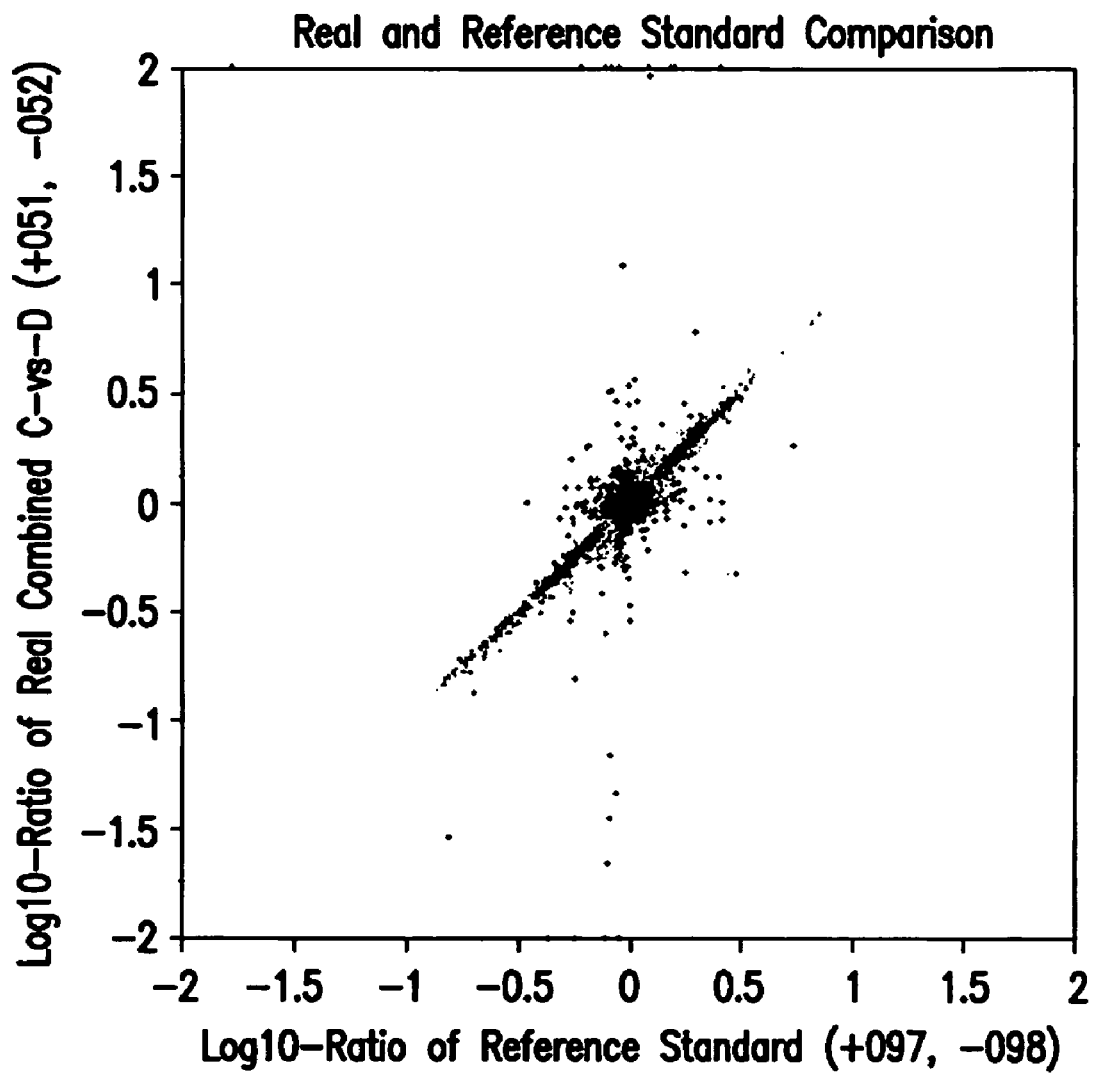

FIG. 22 shows a log-ratio comparison plot of the reference standard C-vs-D (+97, −98) in X axis vs. one real combined experiment C-vs-D (FIG. 16) (+051, −052) in Y-axis. Red dots are signature features in both X and Y. Blue dots are signature features in X only. Green dots are signature features in Y only. The detection threshold is P-value<0.01.

Figure 23:
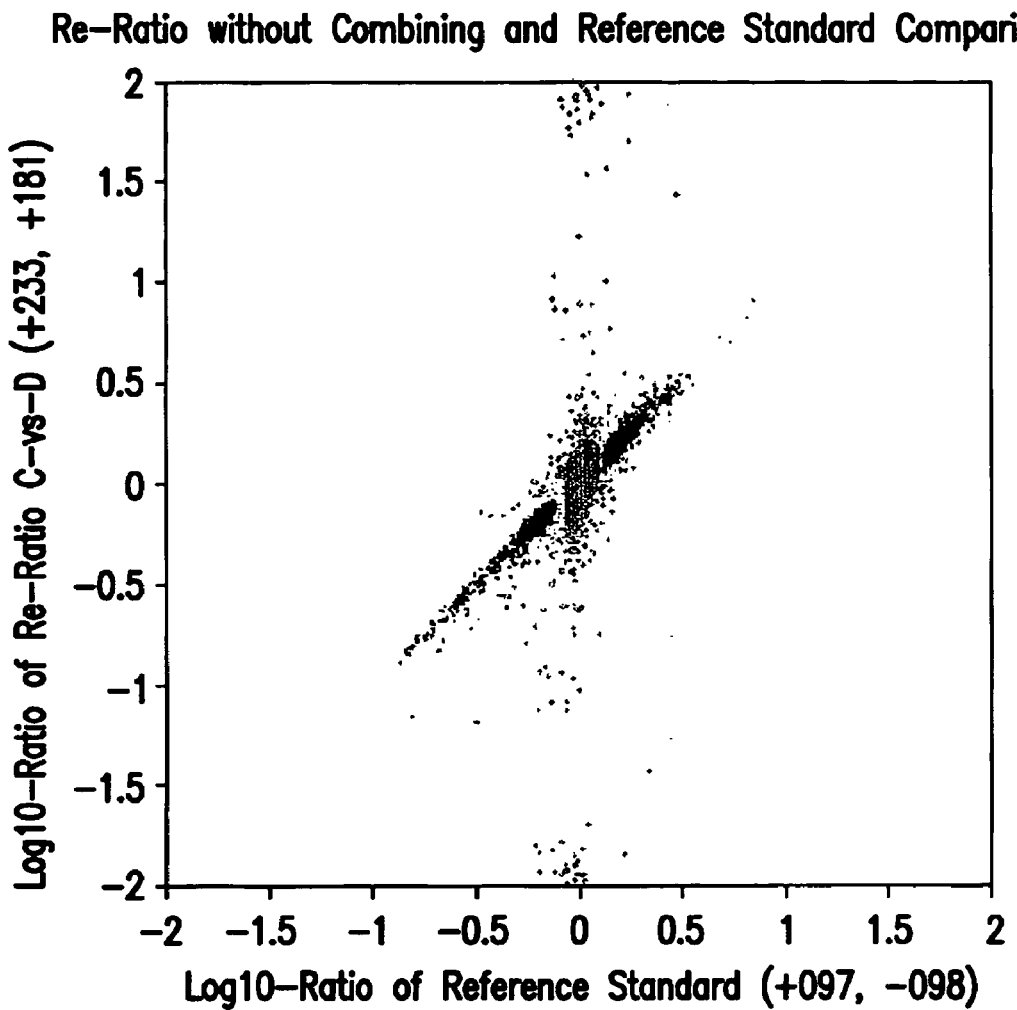

FIG. 23 shows a log-ratio comparison plot of the reference standard C-vs-D (+97, −98) in X axis vs. the re-ratio virtual experiment C-vs-D as shown in FIG. 20 (+233, +181) in Y-axis. The re-ratio data have the same near pool (Pool 1) as the common reference. Red dots are signature features in both X and Y. Blue dots are signature features in X only. Green dots are signature features in Y only. The detection threshold is P-value<0.01.

Figure 24:
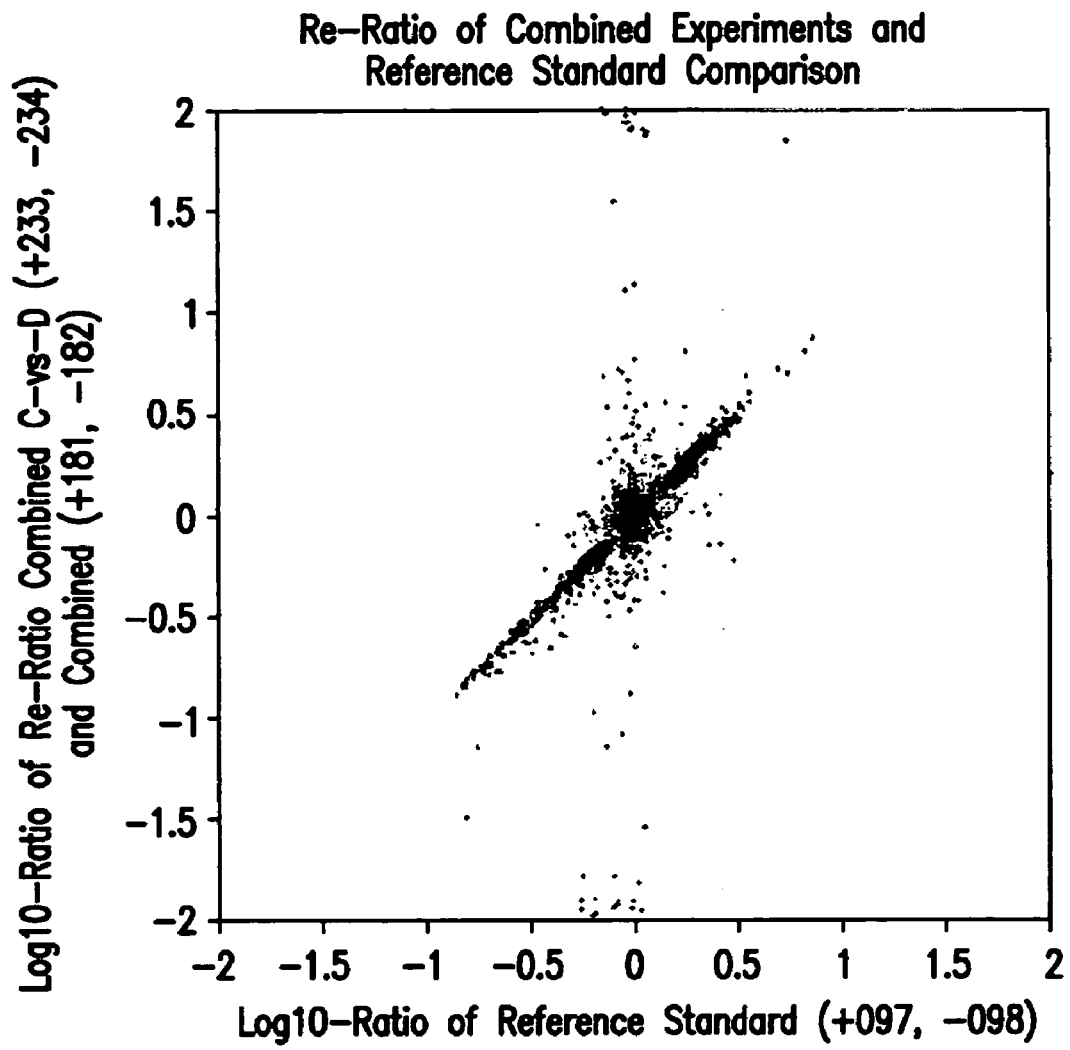

FIG. 24 shows a log-ratio comparison plot of the reference standard C-vs-D (+97, −98) in X axis vs. one re-ratio experiment C-vs-D (FIG. 21) of combined (+233, −234) and combined (+181, −182) in Y-axis. The re-ratio data have the same near pool (Pool 1) as the common reference. Red dots are signature features in both X and Y. Blue dots are signature features in X only. Green dots are signature features in Y only. The detection threshold is P-value<0.01.

Figure 25:
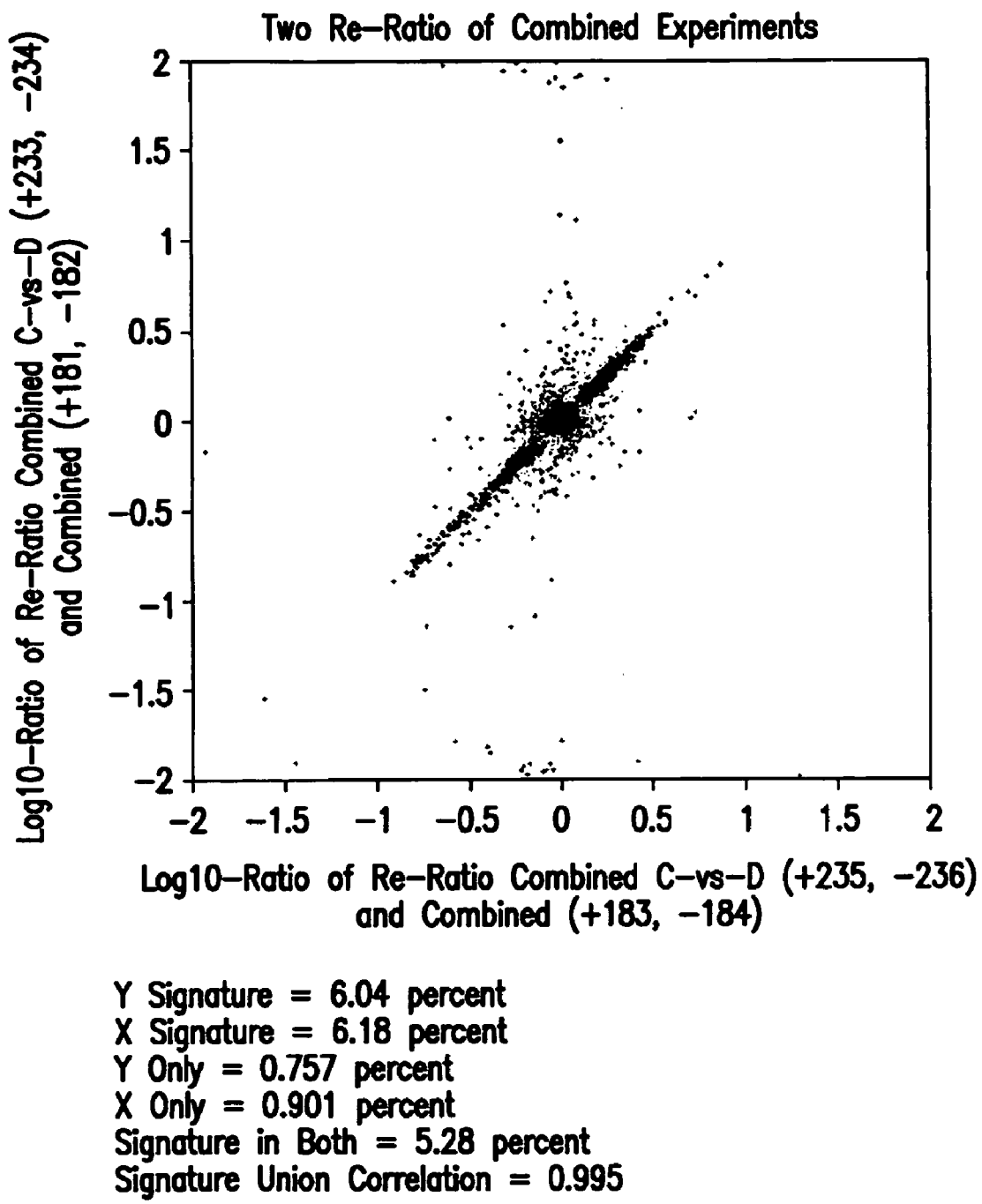

FIG. 25 shows a log-ratio comparison plot of one re-ratio experiment of C-vs-D of combined (+235, −236) and combined (+183, −184) in X axis vs. another re-ratio experiment C-vs-D (FIG. 21) of combined (+233, −234) and combined (+181, −182) in Y-axis. The re-ratio data have the same near pool (Pool 1) as the common reference. Red dots are signature features in both X and Y. Blue dots are signature features in X only. Green dots are signature features in Y only. The detection threshold is P-value<0.01.

Figure 26:
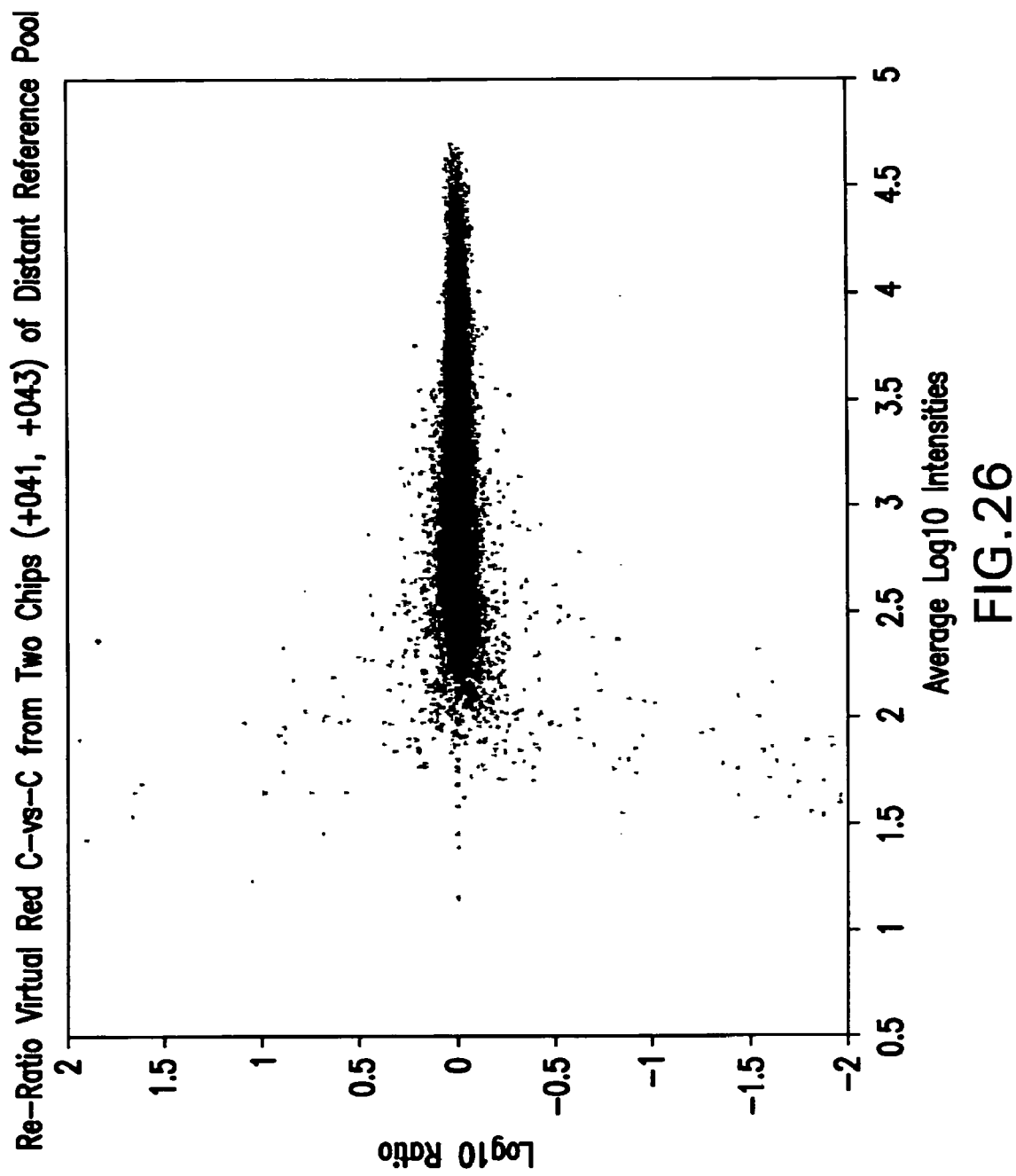

FIG. 26 is a feature-level ratio plot of a re-ratio virtual same-vs-same profile C-vs-C from two Pool2-vs-C chips (+041, +043) of the same red color. The common reference sample was the distant pool (Pool 2).

Figure 27:
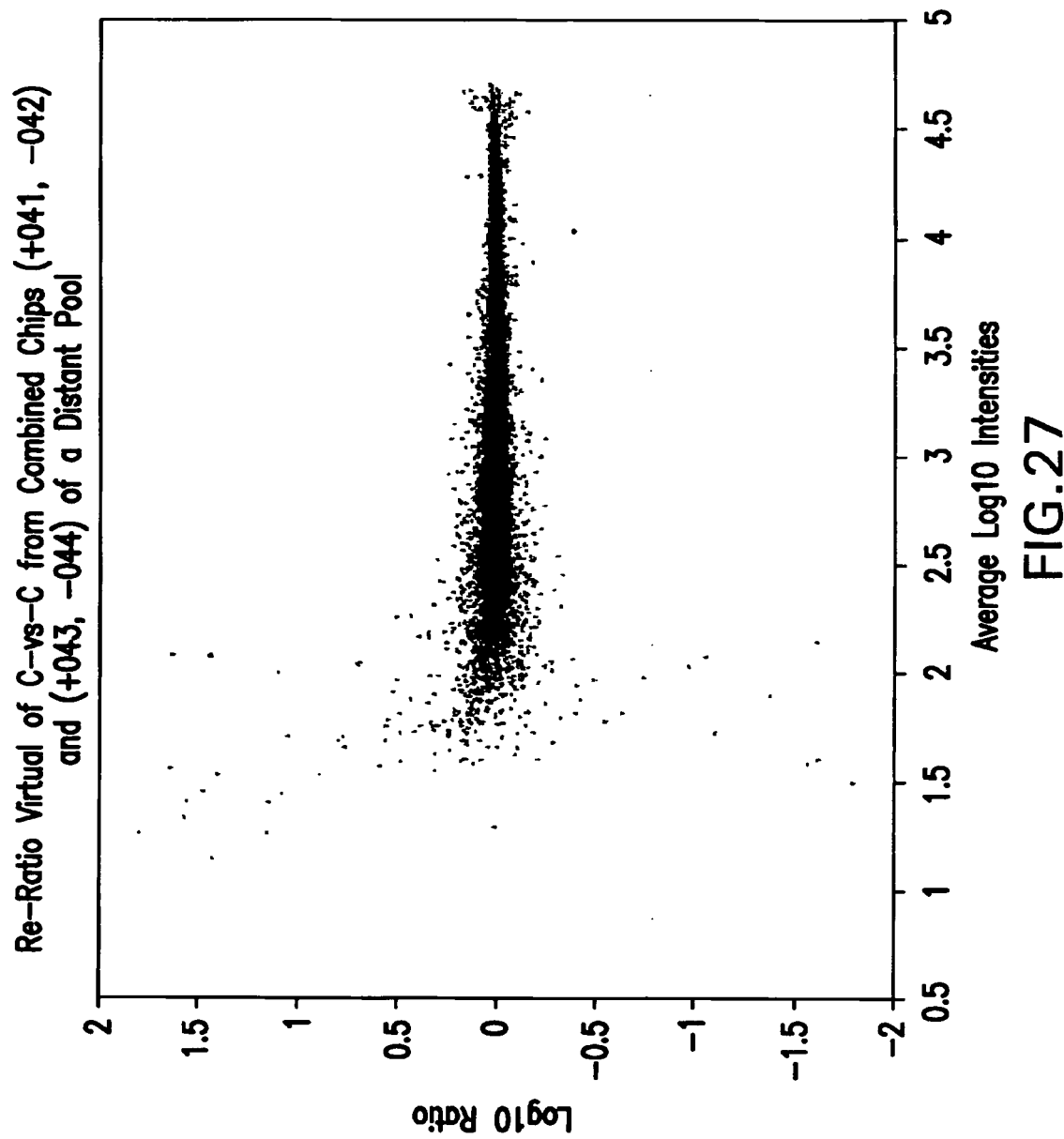

FIG. 27 is a feature-level ratio plot of a re-ratio virtual same-vs-same experiment C-vs-C from two combined fluor-reversal experiments Pool2-vs-C (+041, −042) and (+043, −044). The common reference sample was the distant pool (Pool 2).

Figure 28:
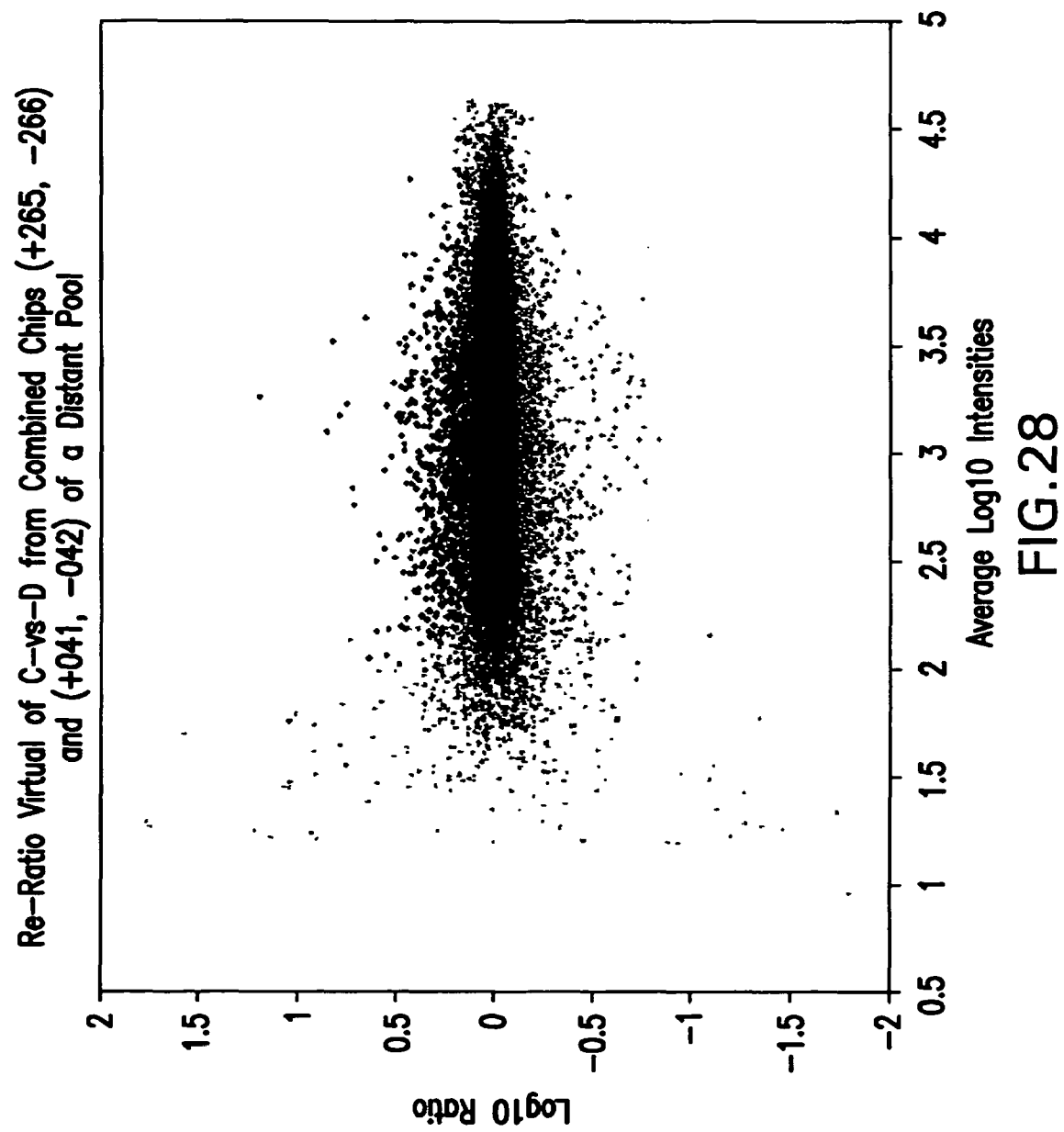

FIG. 28 is a feature-level ratio plot of a virtual different-vs-different experiment from two combined fluor-reversal experiments Pool 1-vs-D (+265, −266) and combined baseline Pool1-vs-C (+041, −042). The common reference sample is the distant pool (Pool 2).

Figure 29:
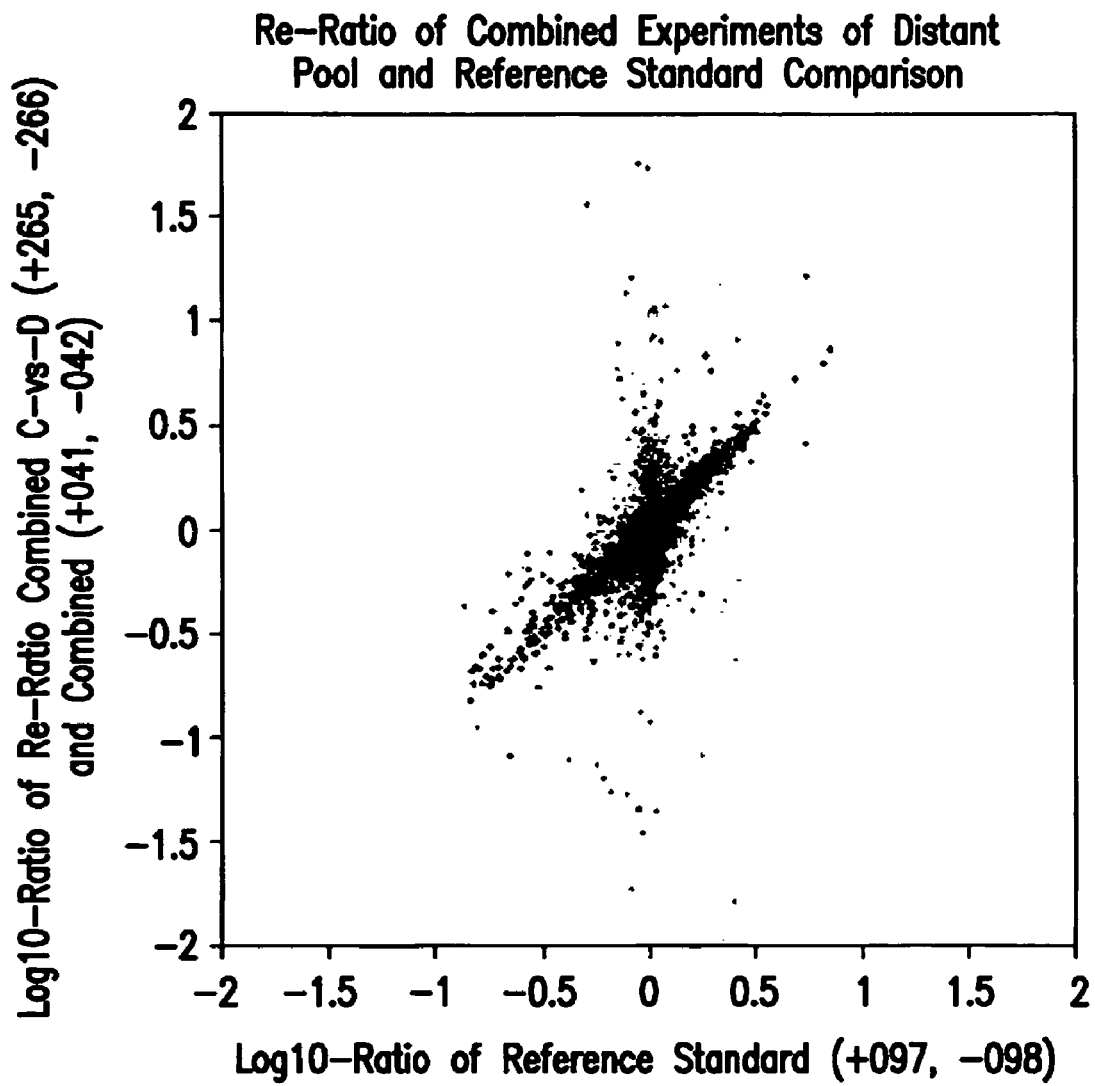

FIG. 29 is a feature-level comparison plot of the reference standard C-vs-D (+97, −98) in X axis vs. one re-ratio experiment C-vs-D (FIG. 28) of combined (+265, −266) and combined (+041, −042) in Y-axis. The re-ratio data have the same distant pool (Pool 2). Red dots are signature features in both X and Y. Blue dots are signature features in X only. Green dots are signature features in Y only. The detection threshold is P-value<0.01.

Figure 30:
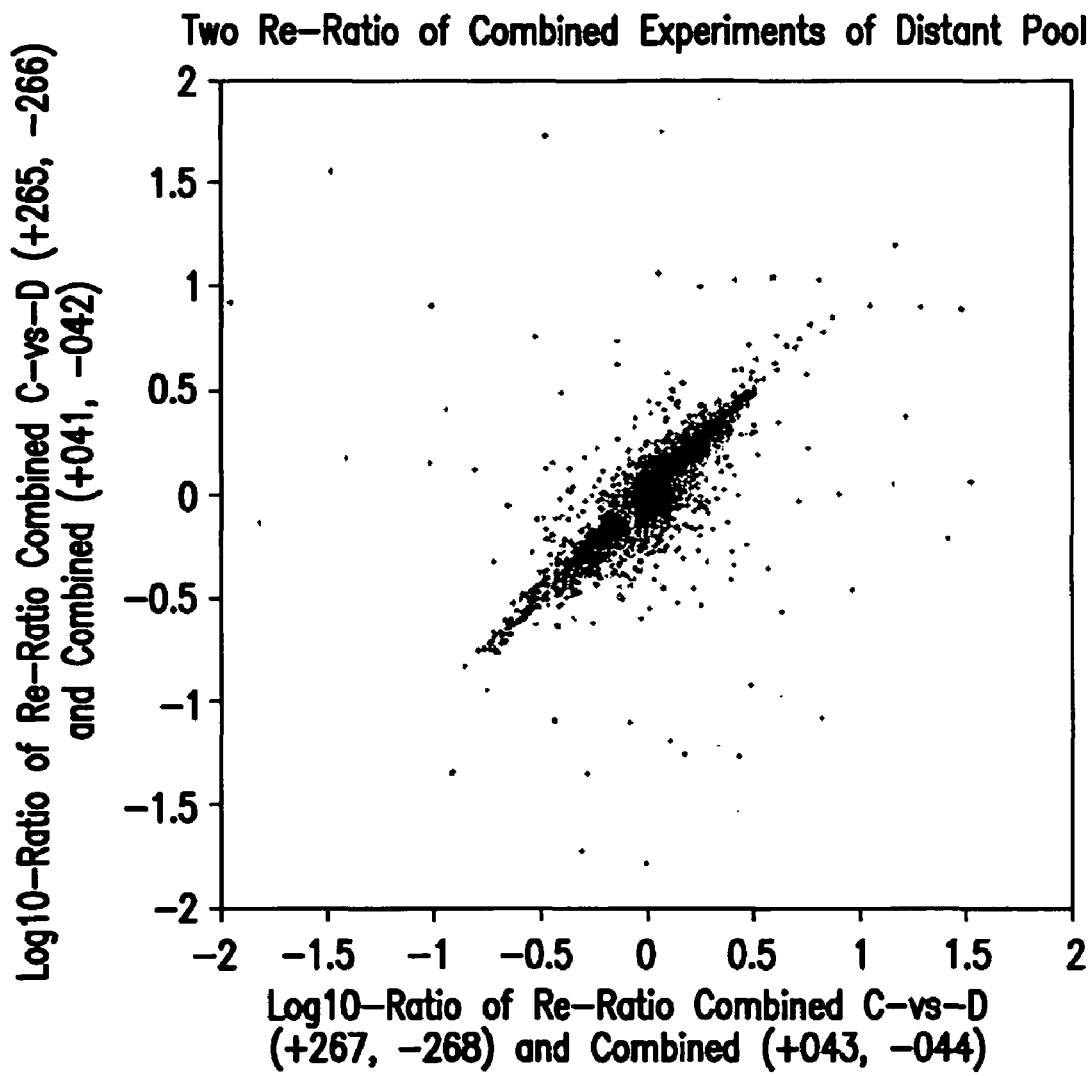

FIG. 30 shows a log-ratio comparison plot of one re-ratio experiment of C-vs-D of combined (+267, −268) and combined (+043, −044) in X axis vs. another re-ratio experiment C-vs-D (FIG. 28) of combined (+265, −266) and combined (+041, −042) in Y-axis. The re-ratio data have the same distant pool (Pool 2). Red dots are signature features in both X and Y. Blue dots are signature features in X only. Green dots are signature features in Y only. The detection threshold is P-value<0.01.

Figure 31:
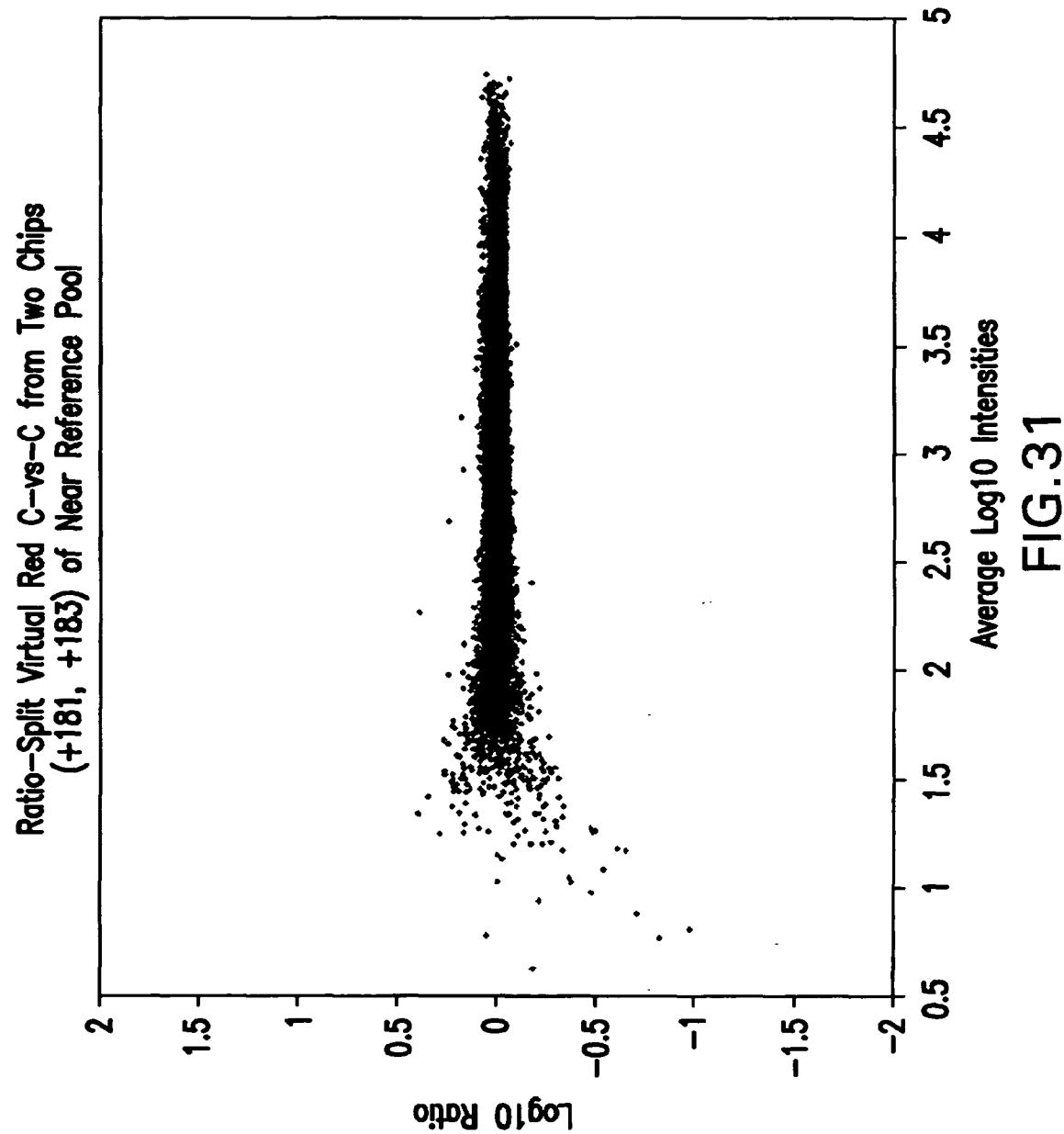

FIG. 31 is a feature-level ratio plot of a ratio-split virtual same-vs-same profile C-vs-C from two Pool1-vs-C chips (+181, +183) of the same red color. The common reference sample is the near pool (Pool 1).

Figure 32:
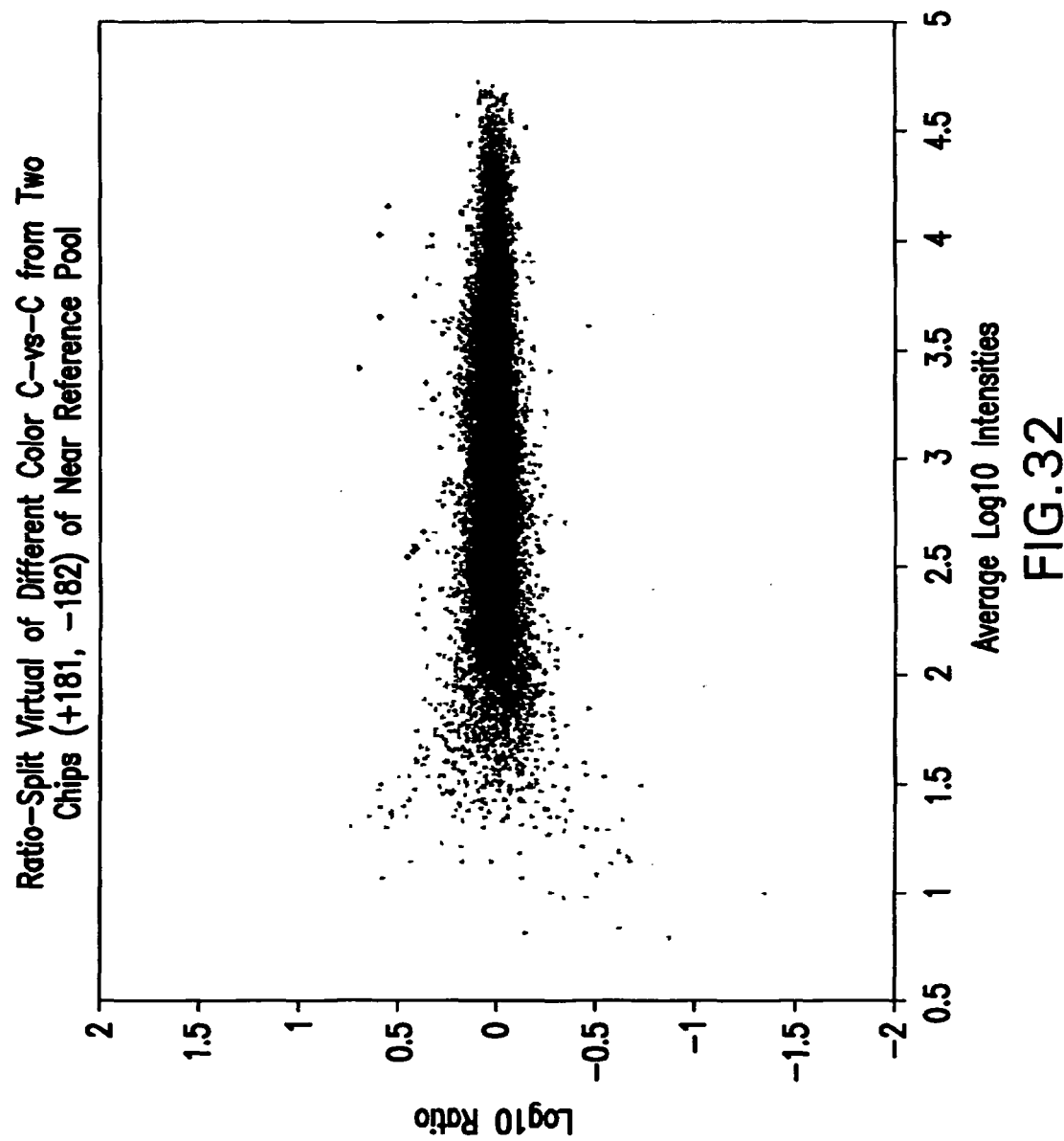

FIG. 32 is a feature-level ratio plot of a ratio-splitter virtual same-vs-same profile C-vs-C from two Pool1-vs-C chips (+181, −182) of different colors. The common reference sample is the near pool (Pool 1).

Figure 33:
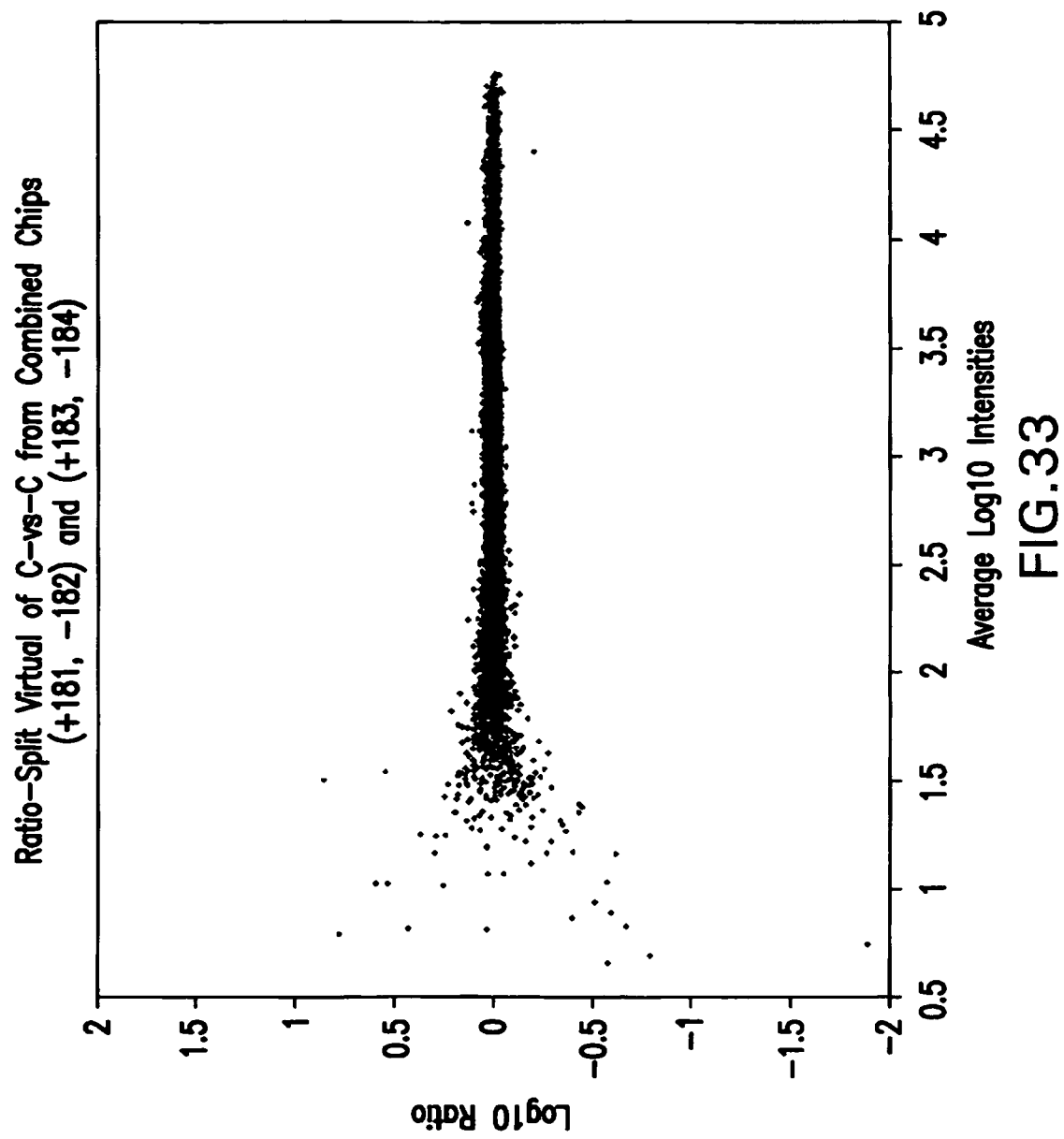

FIG. 33 is a feature-level ratio plot of a ratio-splitter virtual same-vs-same experiment C-vs-C from two combined fluor-reversal experiments Pool 1-vs-C (+181, −182) and (+183, −184). The common reference sample is the near pool (Pool 1).

Figure 34:
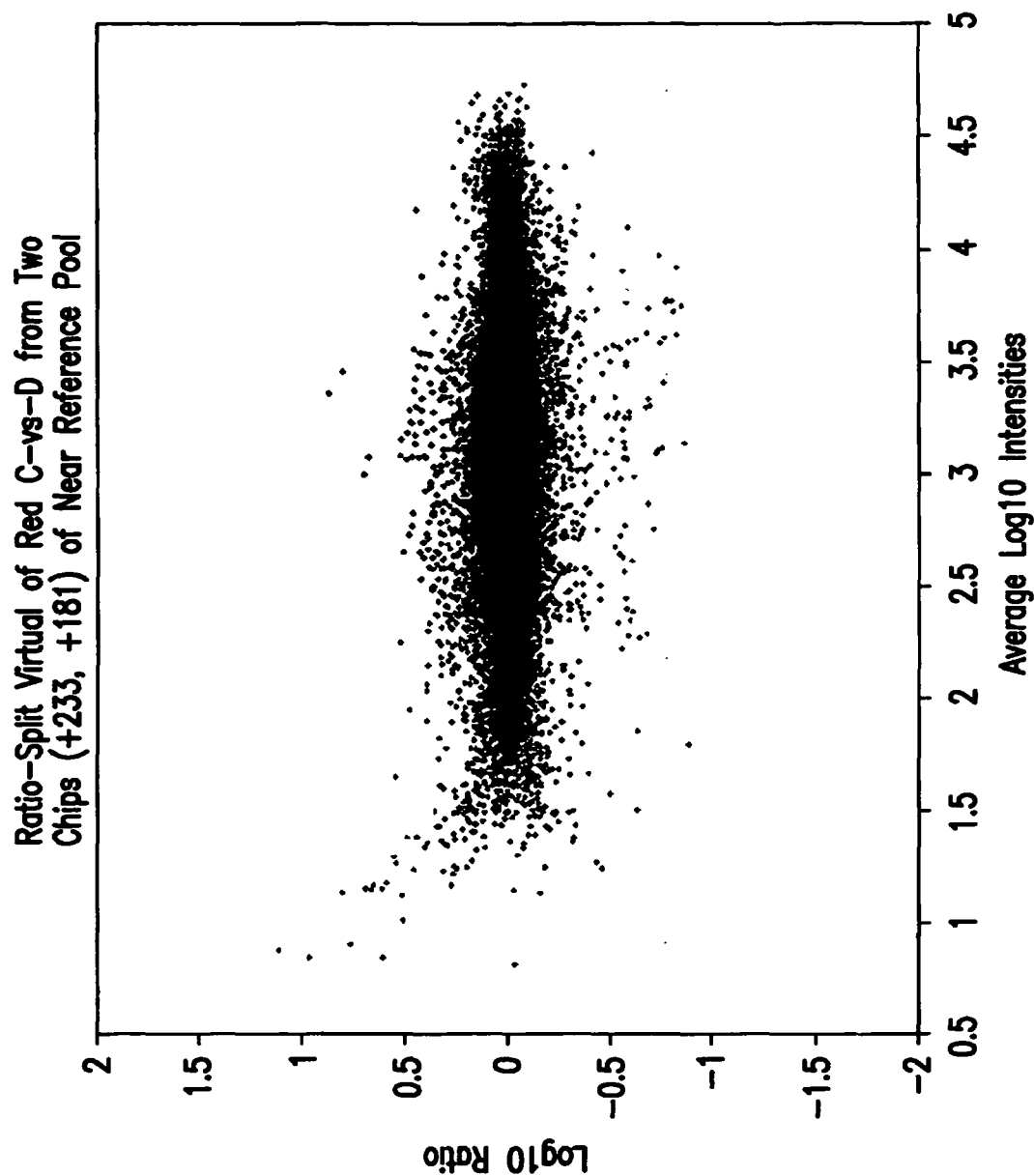

FIG. 34 is a feature-level ratio plot of a ratio-splitter virtual different-vs-different experiment C-vs-D from red experiment Pool1-vs-D (+233) and red baseline Pool1-vs-C (+181). The common reference sample is the near pool.

Figure 35:
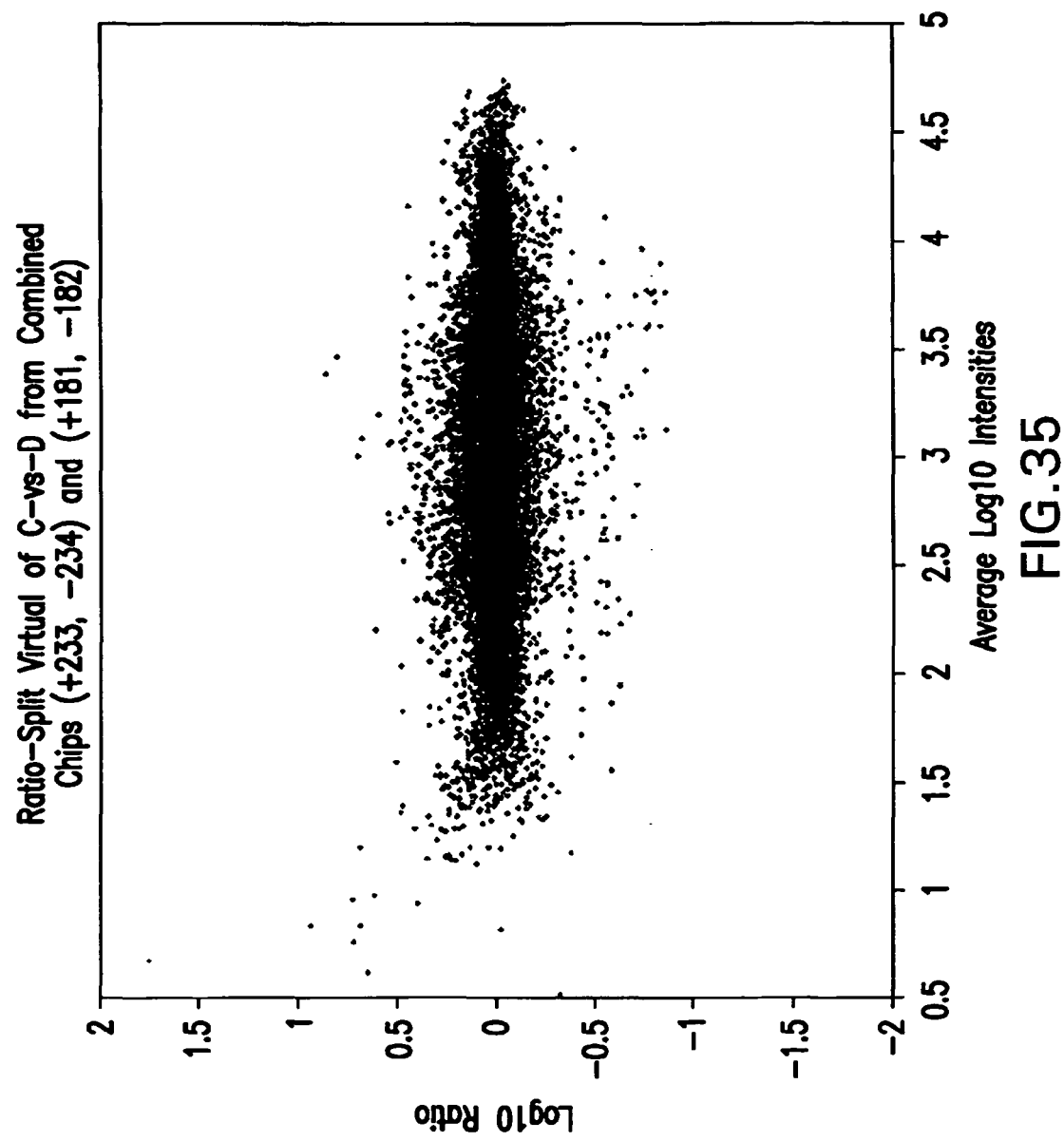

FIG. 35 is a feature-level ratio plot of a ratio-splitter virtual different-vs-different experiment from two combined fluor-reversal experiments Pool1-vs-D (+233, −234) and combined baseline Pool1-vs-C (+181, −182). The common reference sample is the near pool (Pool 1).

Figure 36:
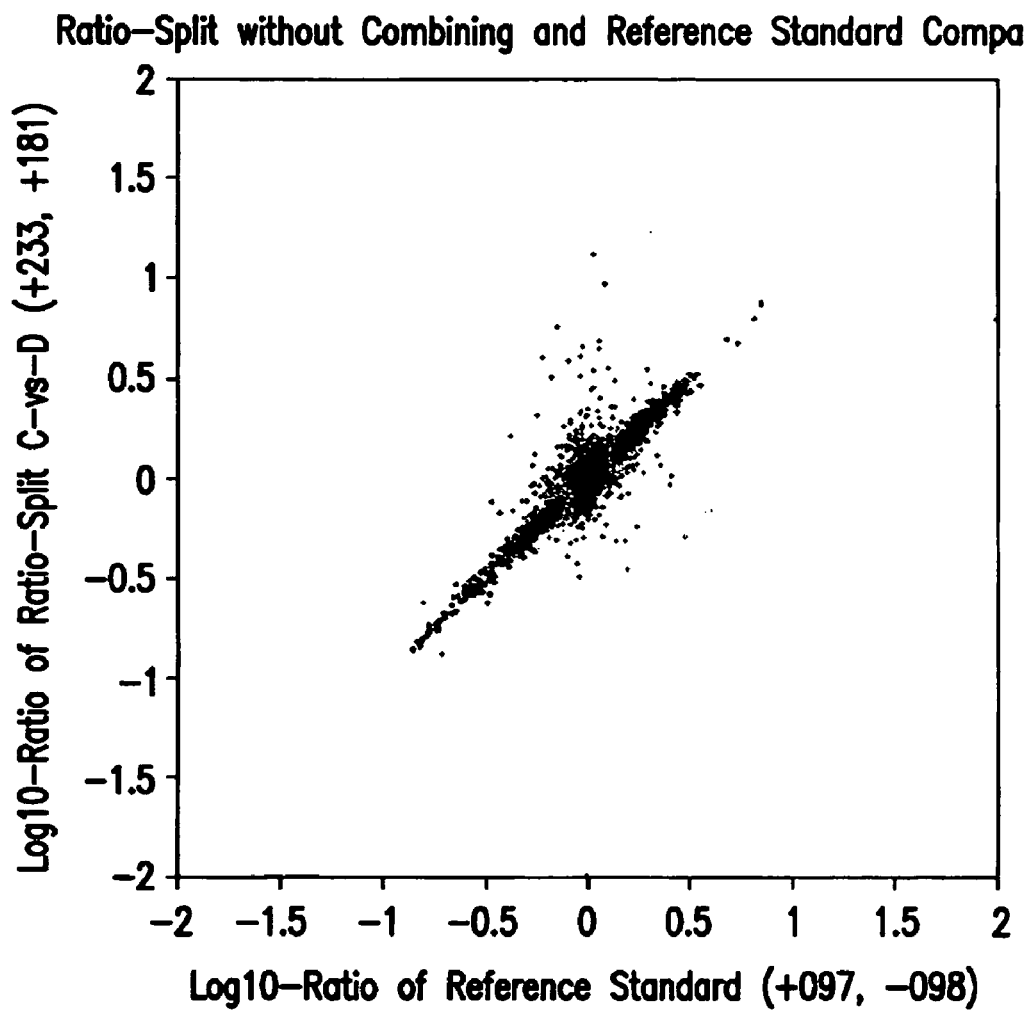

FIG. 36 shows a log-ratio comparison plot of the reference standard C-vs-D (+97, −98) in X axis vs. one ratio-splitter experiment C-vs-D (FIG. 20) (+233, +181) in Y-axis. The ratio-splitter data have the same near pool (Pool 1). Red dots are signature features in both X and Y. Blue dots are signature features in X only. Green dots are signature features in Y only. The detection threshold is P-value<0.01.

Figure 37:
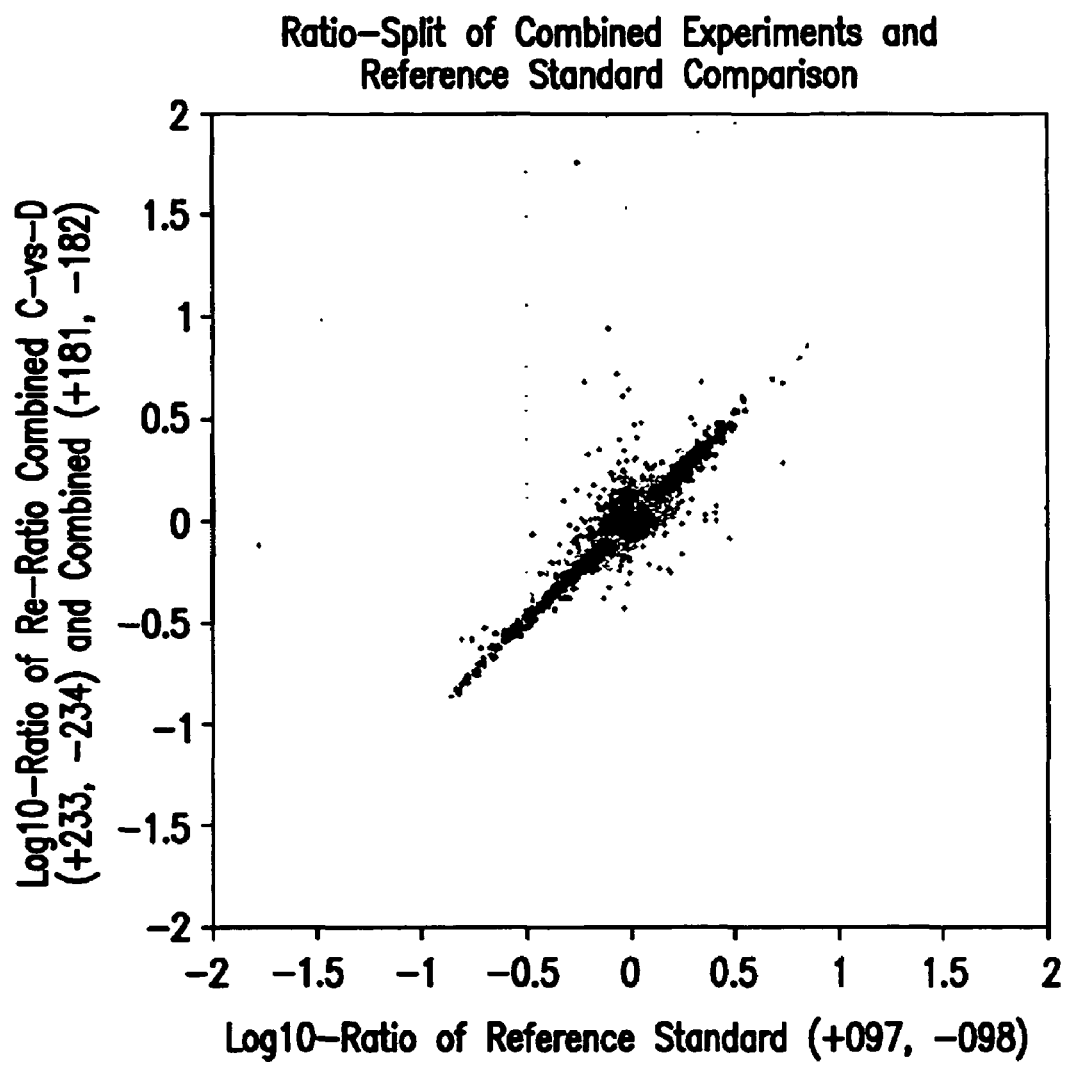

FIG. 37 shows a log-ratio comparison plot of the reference standard C-vs-D (+97, −98) in X axis vs. one ratio-splitter experiment C-vs-D (FIG. 35) of combined (+233, −234) and combined (+181, −182) in Y-axis. The ratio-splitter data have the same near pool (Pool 1). Red dots are signature features in both X and Y. Blue dots are signature features in X only. Green dots are signature features in Y only. The detection threshold is P-value<0.01.

Figure 38:
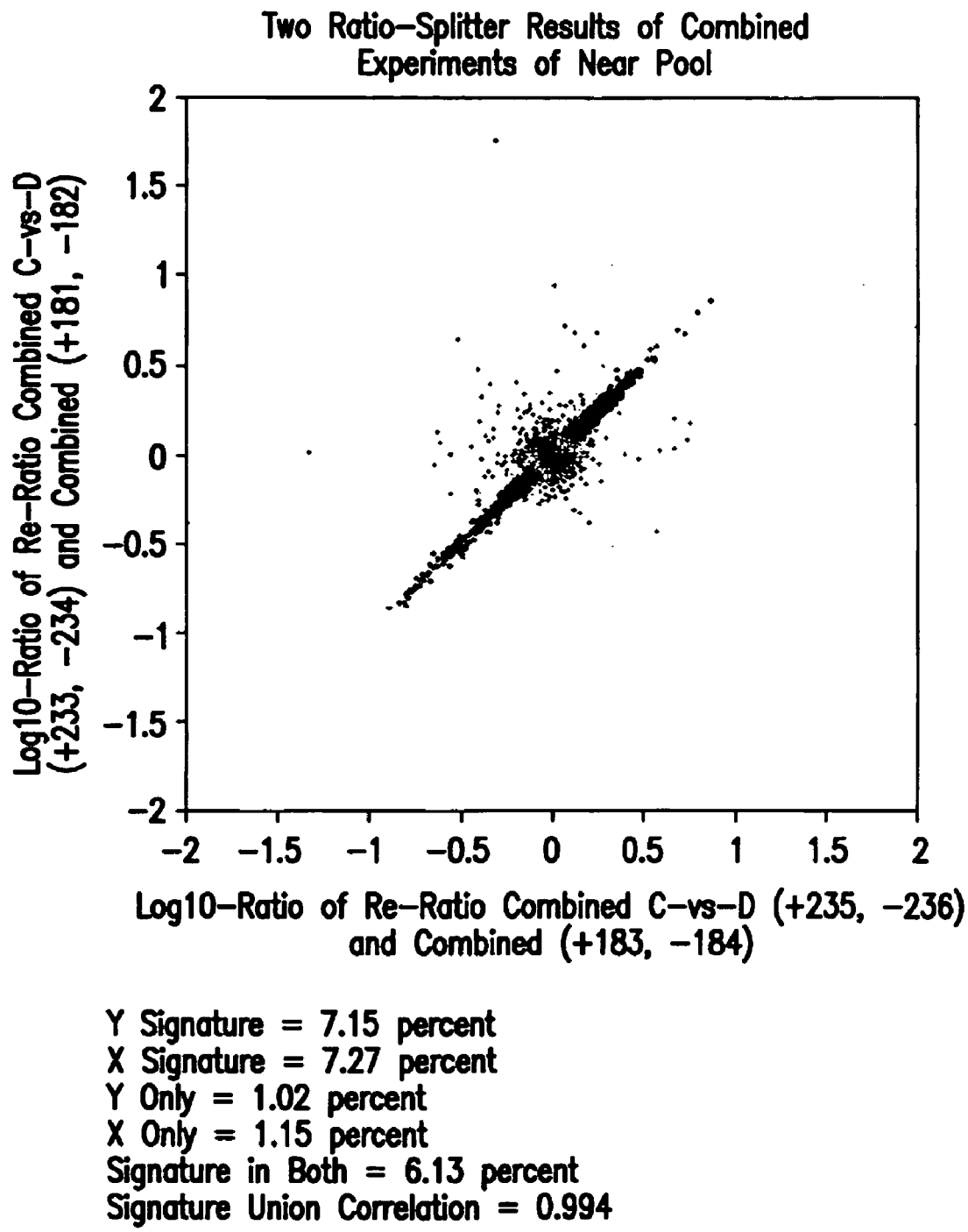

FIG. 38 shows a log-ratio comparison plot of one ratio-splitter experiment of C-vs-D of combined (+235, −236) and combined (+183, −184) in X axis vs. another ratio-splitter experiment C-vs-D (FIG. 35) of combined (+233, −234) and combined (+181, −182) in Y-axis. The ratio-splitter data have the same near pool (Pool 1). Red dots are signature features in both X and Y. Blue dots are signature features in X only. Green dots are signature features in Y only. The detection threshold is P-value<0.01.

Figure 39:
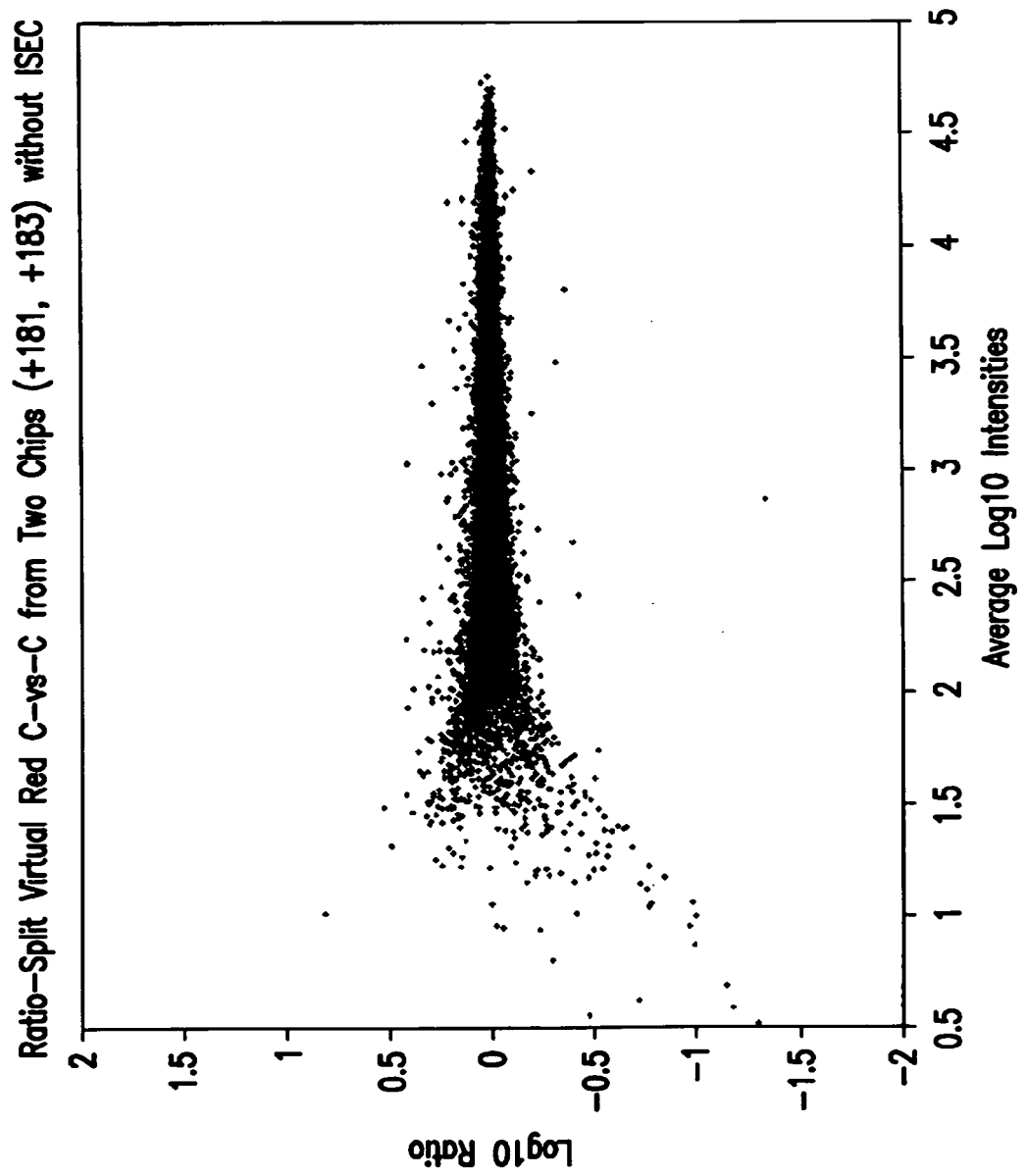

FIG. 39 is a feature-level ratio plot of a ratio-split virtual same-vs-same profile C-vs-C from two chips (+181, +183) of the same red color without using the common reference pool for ISEC.

Figure 40:
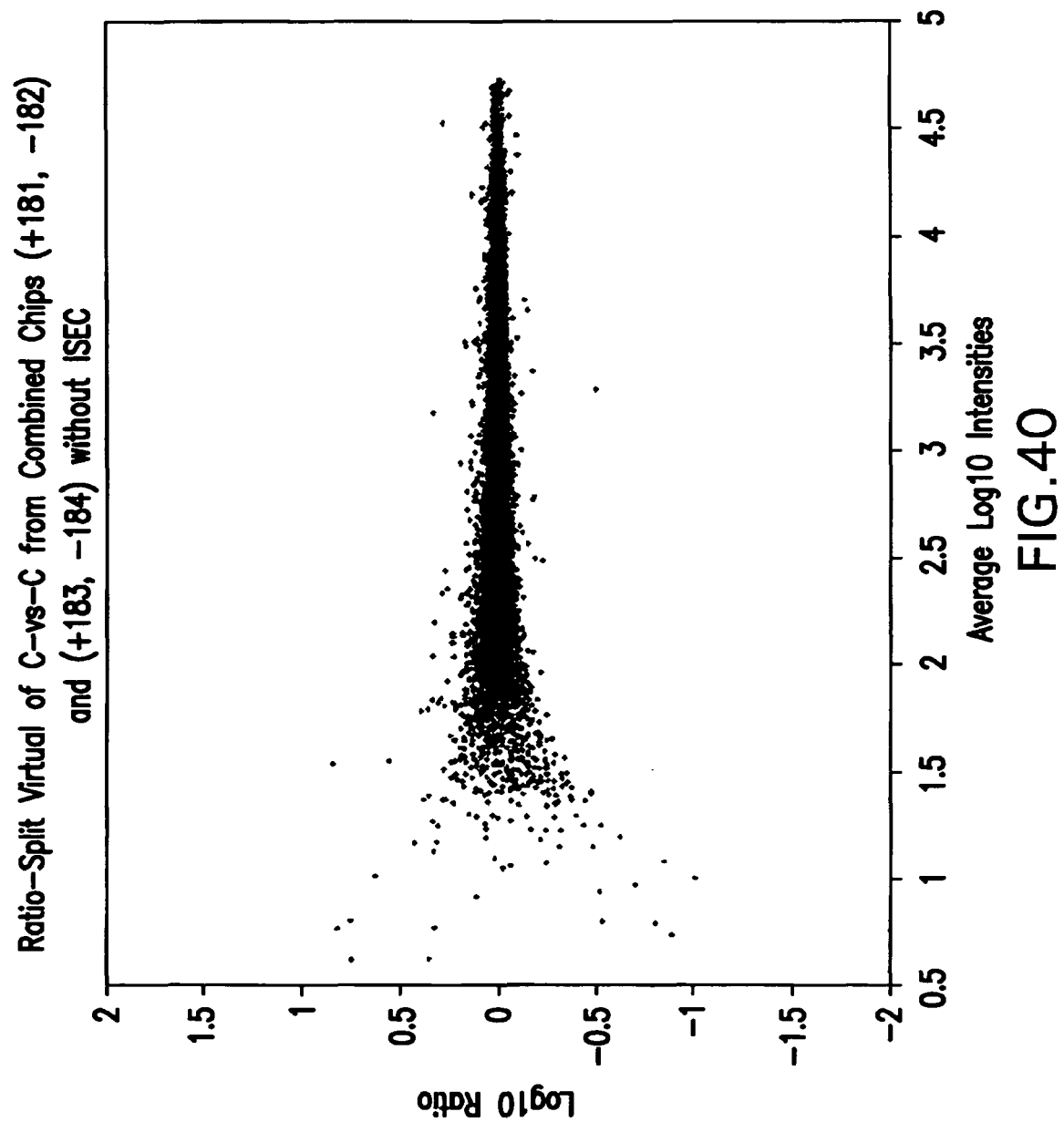

FIG. 40 is a feature-level ratio plot of a ratio-splitter virtual same-vs-same experiment C-vs-C from two combined fluor-reversal experiments (+181, −182) and (+183, −184). The common reference sample is not used for ISEC.

Figure 41:
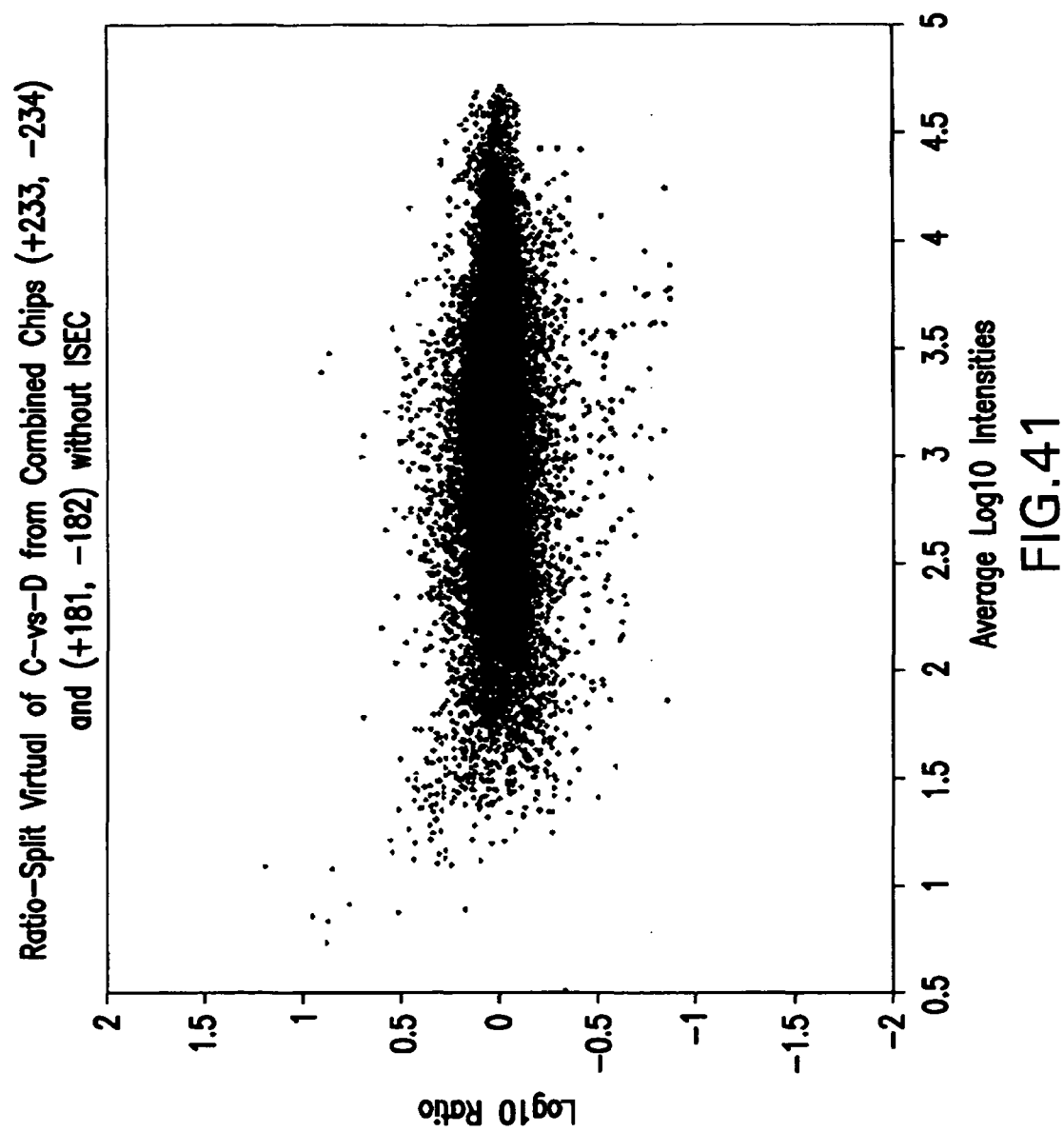

FIG. 41 is a feature-level ratio plot of a ratio-splitter virtual C-vs-D experiment from two combined fluor-reversal experiments (+233, −234) and combined baseline (+181, −182). The common reference sample is not used for ISEC.

Figure 42:
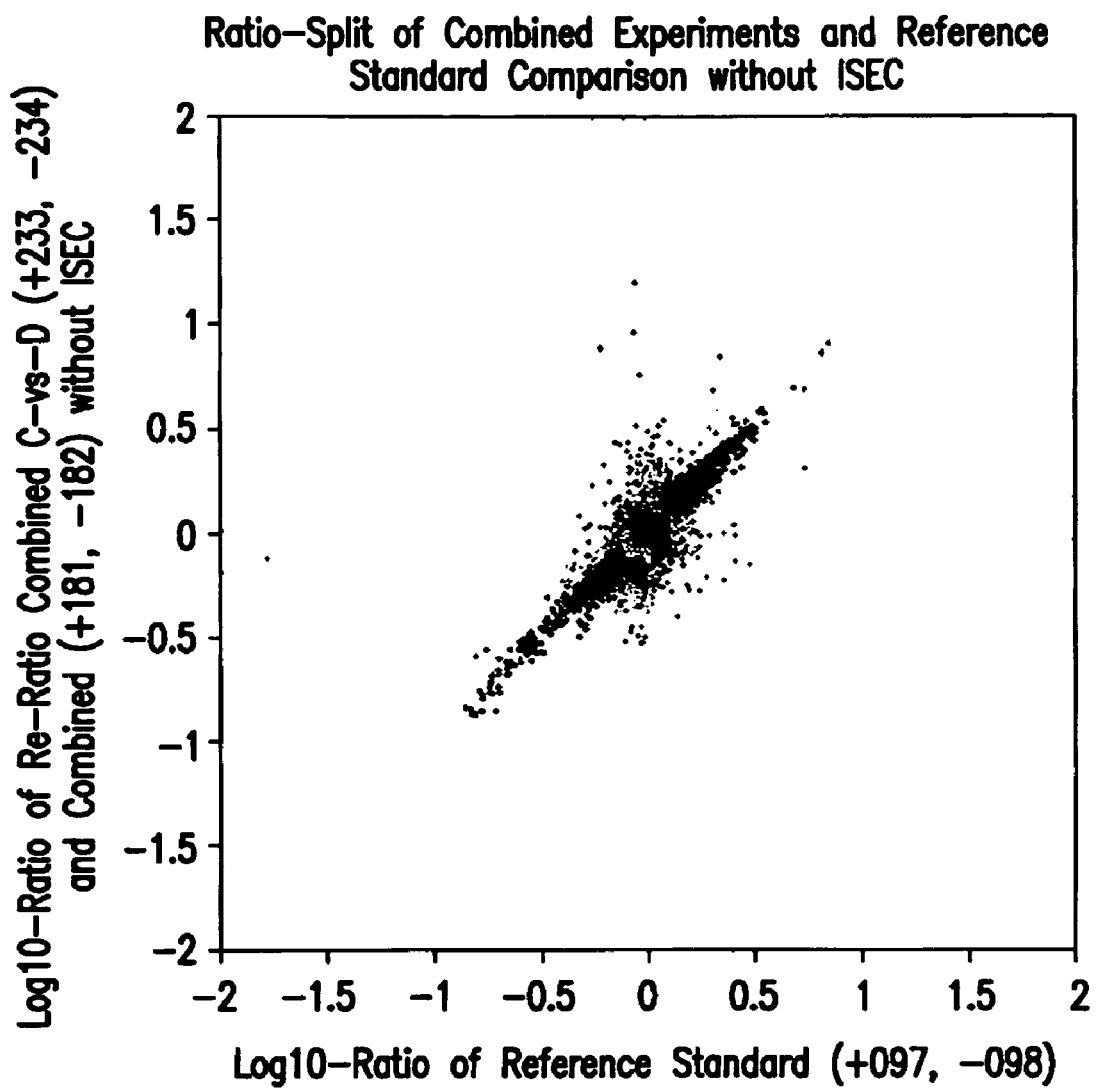

FIG. 42 is a log-ratio comparison plot of the reference standard C-vs-D (+97, −98) in X axis vs. one ratio-splitter experiment C-vs-D without ISEC (FIG. 41) of combined (+233, −234) and combined (+181, −182) in Y-axis. Red dots are signature features in both X and Y. Blue dots are signature features in X only. Green dots are signature features in Y only. The detection threshold is P-value<0.01.

Figure 43:
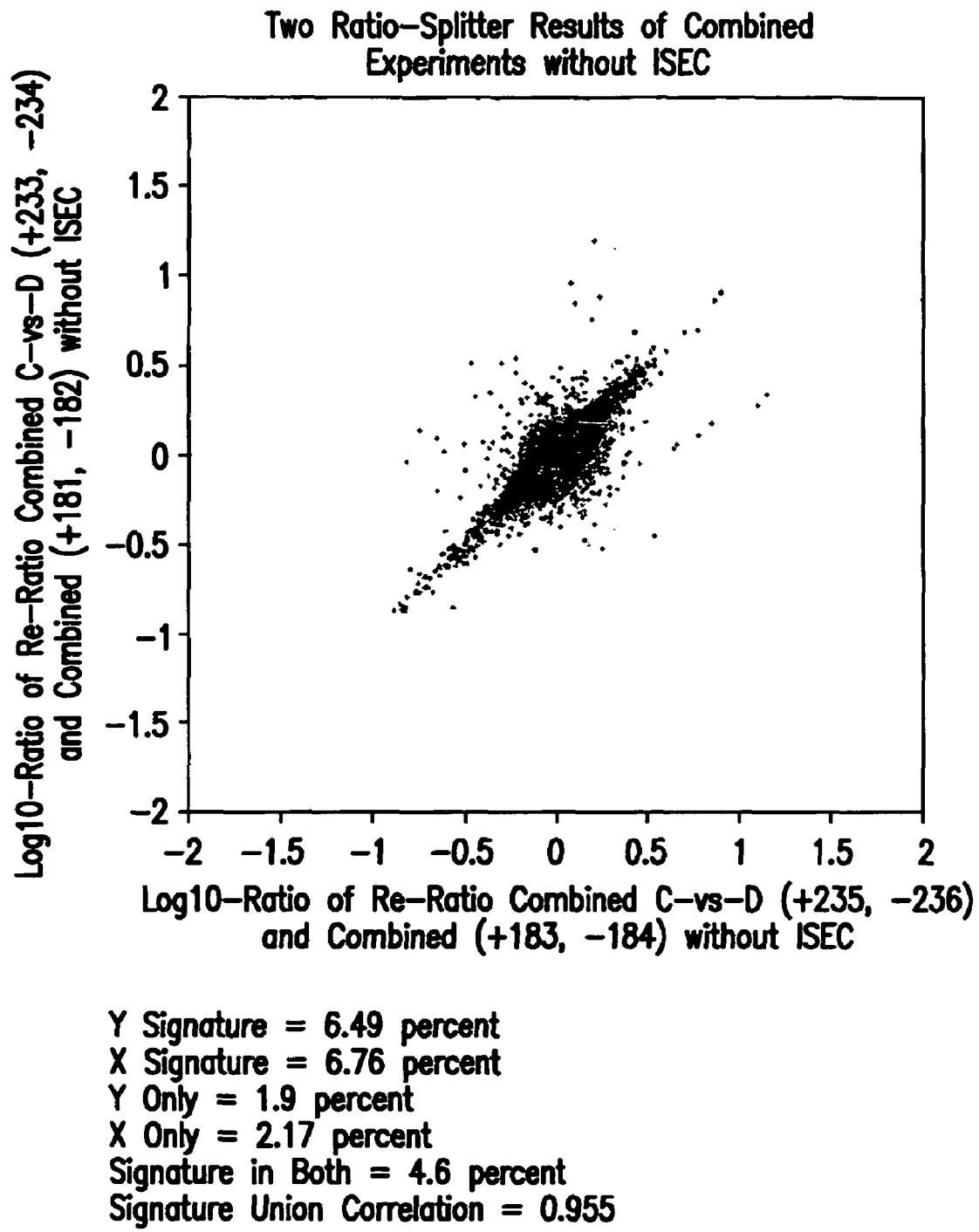

FIG. 43 shows a log-ratio comparison plot of one ratio-splitter experiment of C-vs-D without ISEC of combined (+235, −236) and combined (+183, −184) in X axis vs. another ratio-splitter experiment C-vs-D without ISEC (FIG. 41) of combined (+233, −234) and combined (+181, −182) in Y-axis. Red dots are signature features in both X and Y. Blue dots are signature features in X only. Green dots are signature features in Y only. The detection threshold is P-value<0.01.

Figure 44A:
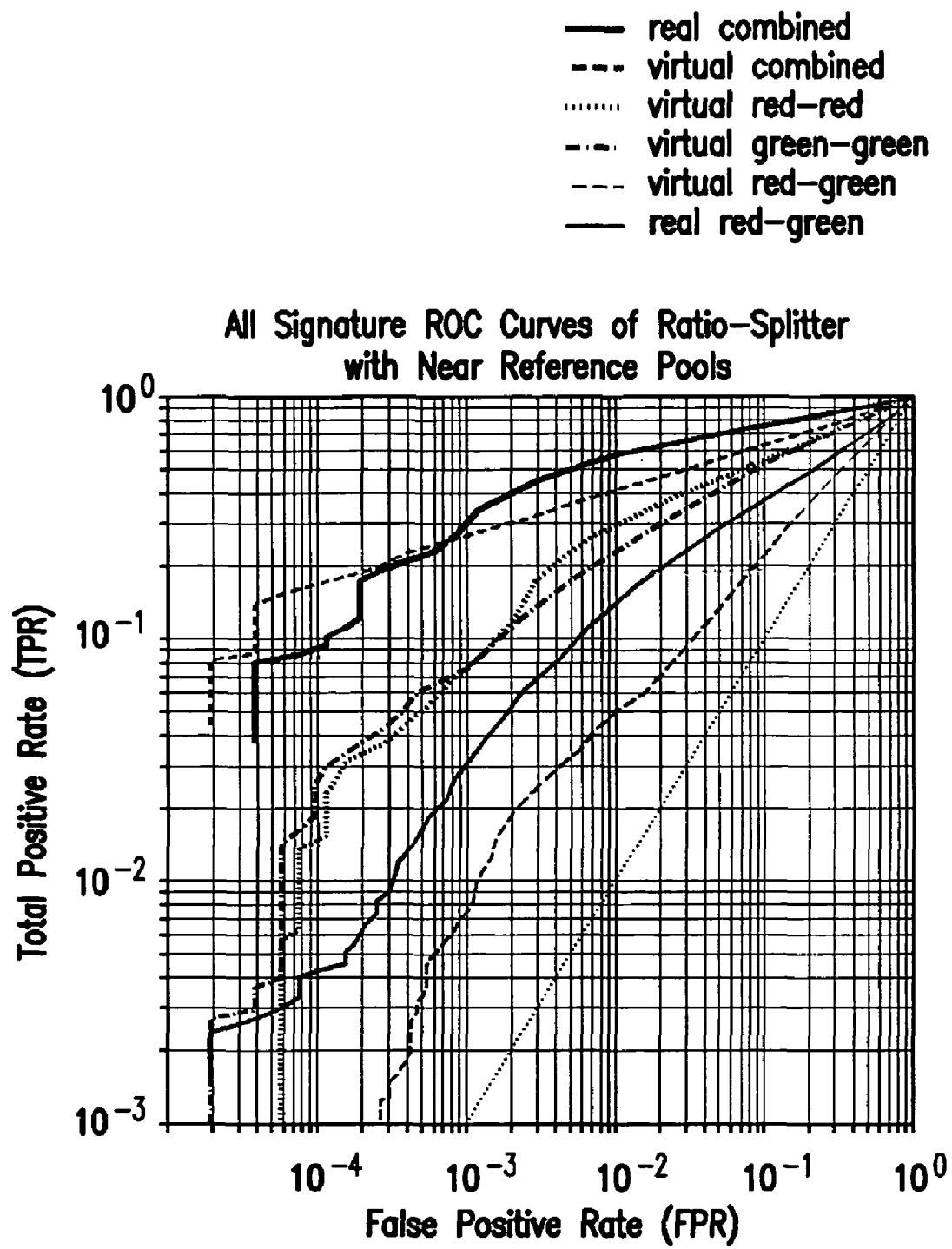
Figure 44B:
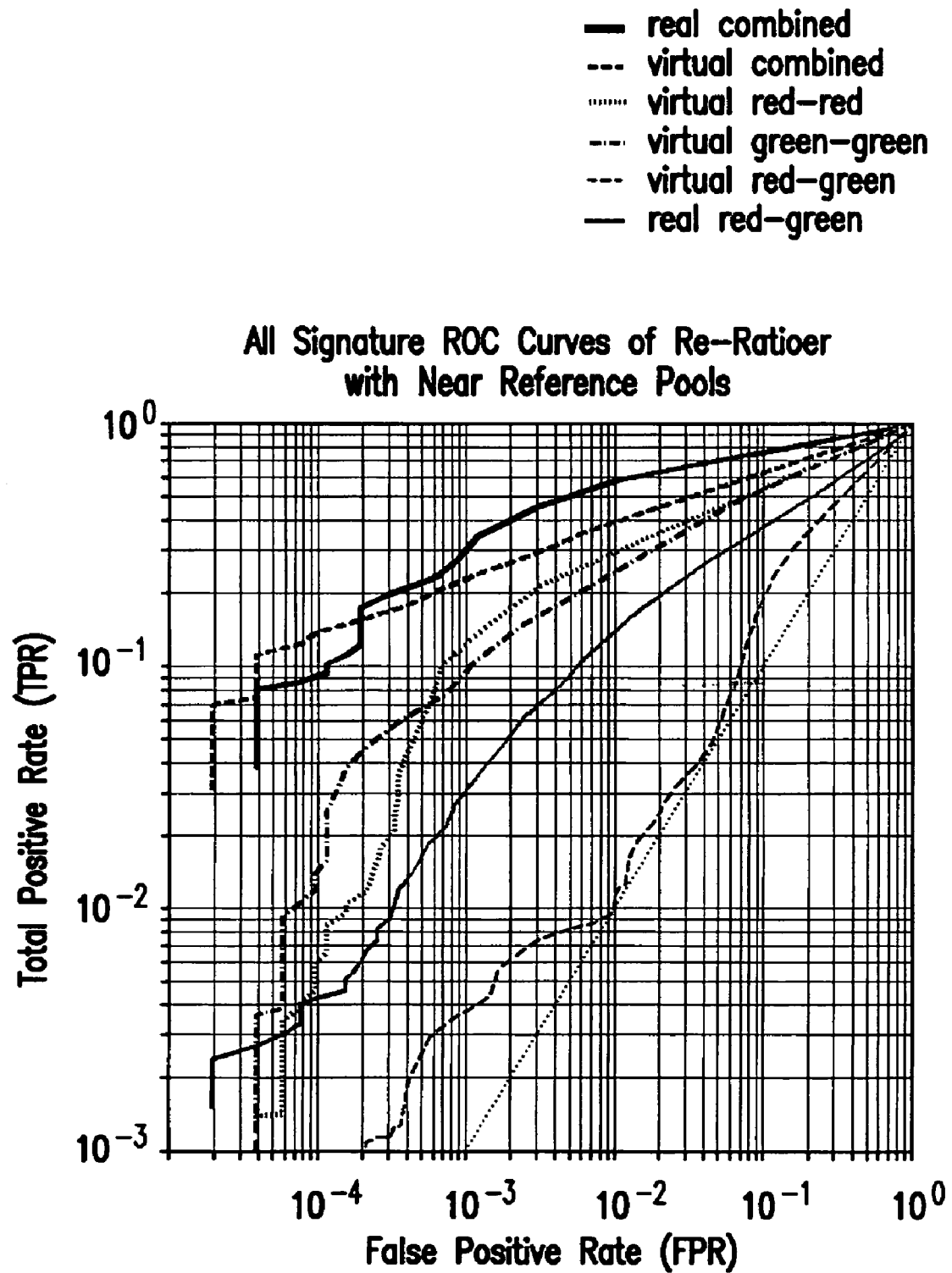

FIGS. 44A-B are all-signature-ROC plots of (A) Ratio-Splitter and (B) Re-Ratioer. All detected differentially expressed feature-level signatures are included in the study. Both of them have the near common reference pools. The thick solid black line is the ROC curve of the fluor-reversal combined real ratio experiments of the original data. The thin solid black line is the ROC curve of the real single red-vs-green experiment without fluor-reversal combination. These two lines are the same in (A) and (B). They are the reference ROC curves in the all-signature comparison. The dotted thin black straight line is the random decision ROC curve where there is no statistical power.

Figure 45A:
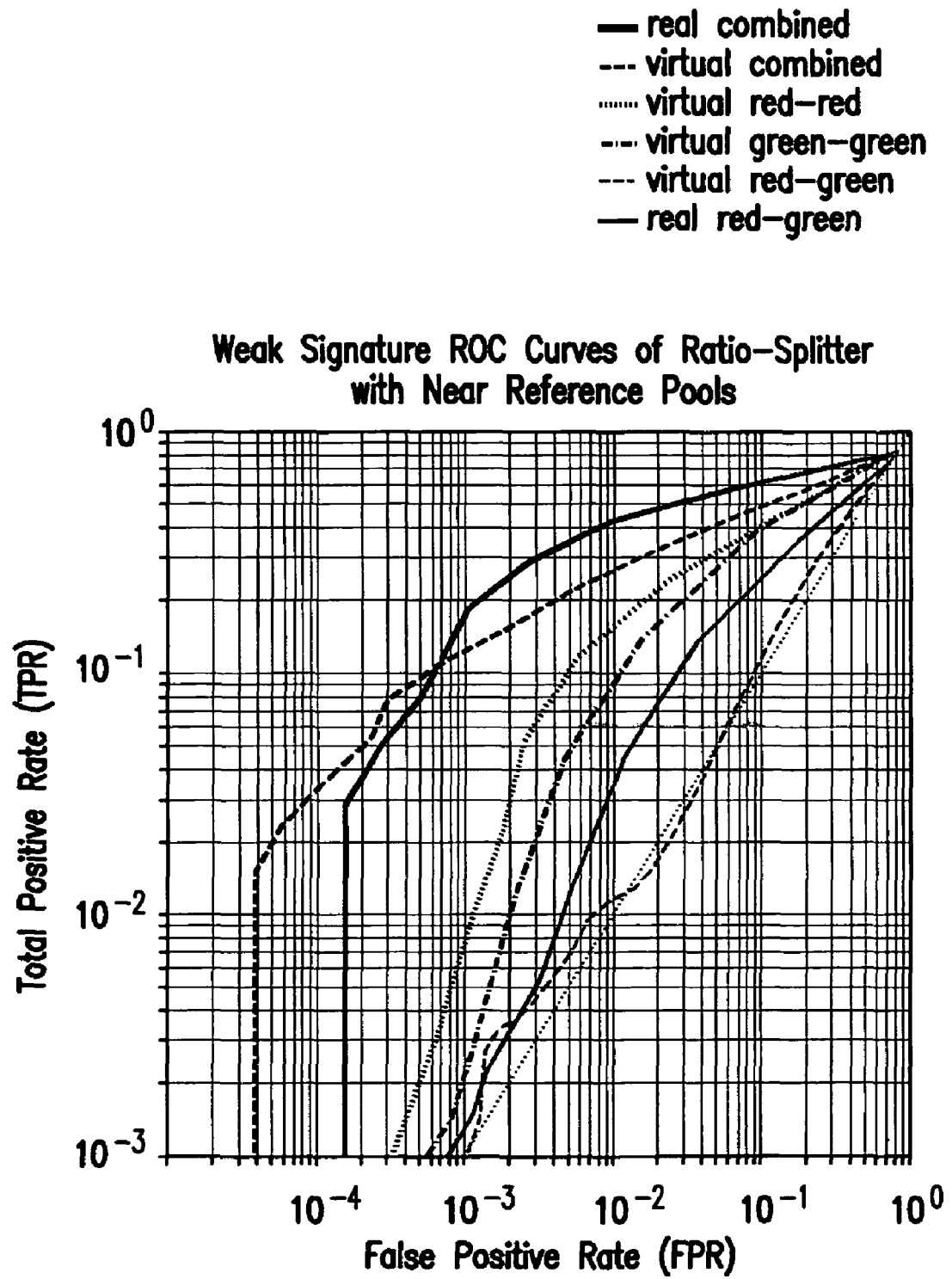
Figure 45B:
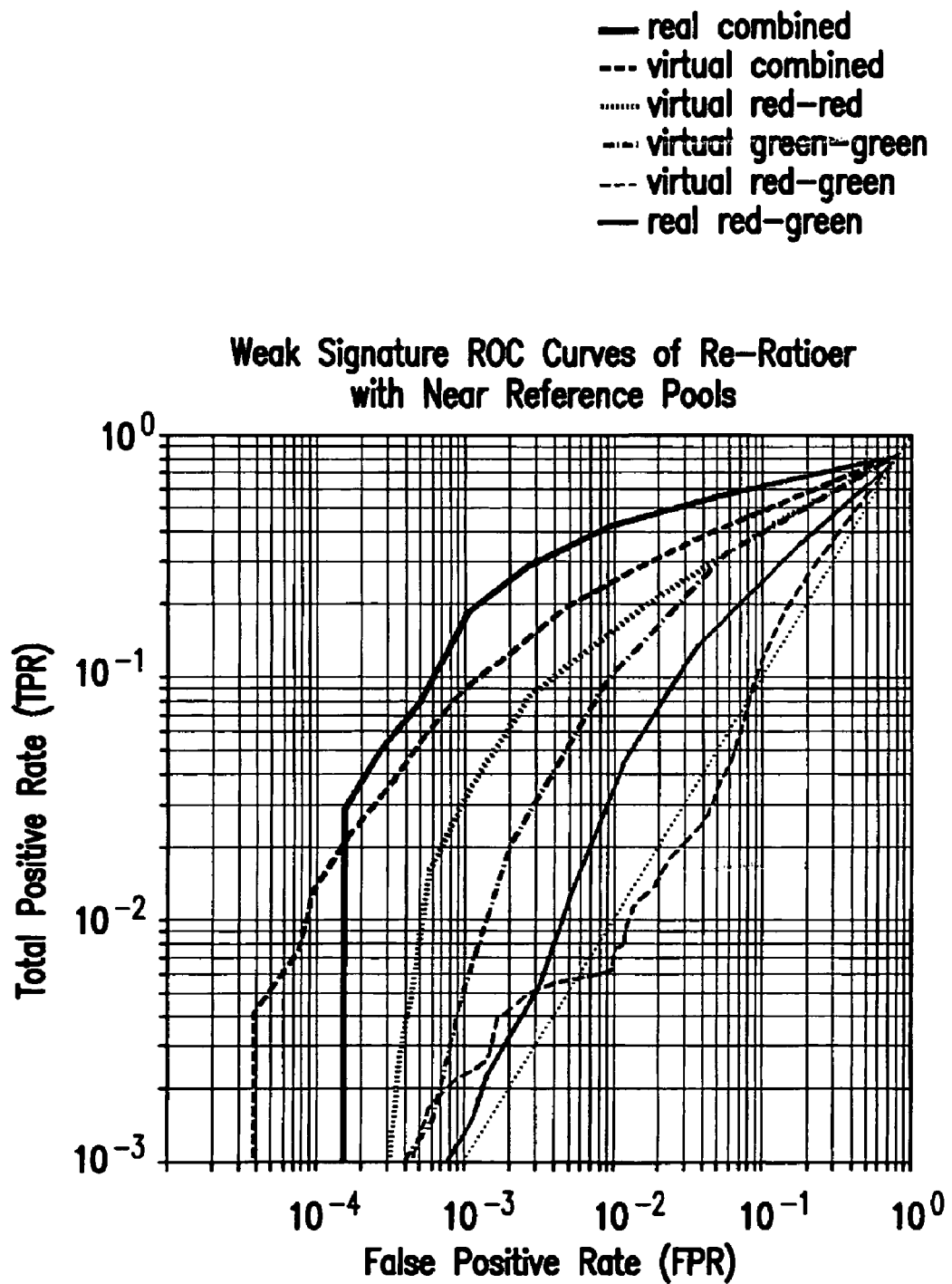

FIGS. 45A-B are weak-signature-ROC plots of (A) Ratio-Splitter and (B) Re-Ratioer. Strong signatures of more than 1.2-fold in the real combined experiments are excluded in the study. Both of them have the near common reference pools. The thick solid black line is the ROC curve of the fluor-reversal combined real ratio experiments of the original data. The thin solid black line is the ROC curve of the real single red-vs-green experiment without fluor-reversal combination. These two lines are the same in (A) and (B). They are the reference ROC curves in the weak-signature comparison.

Figure 46A:
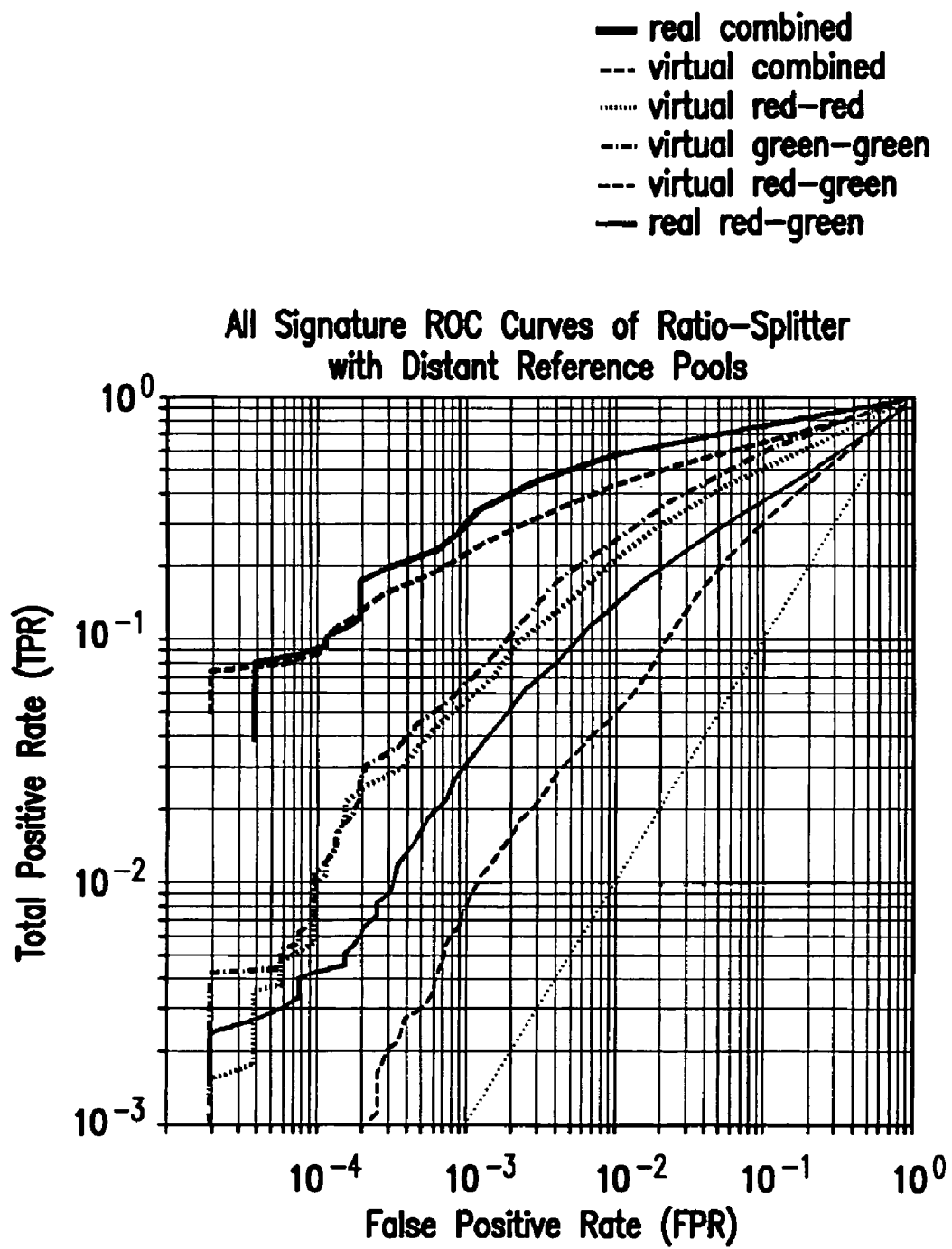
Figure 46B:
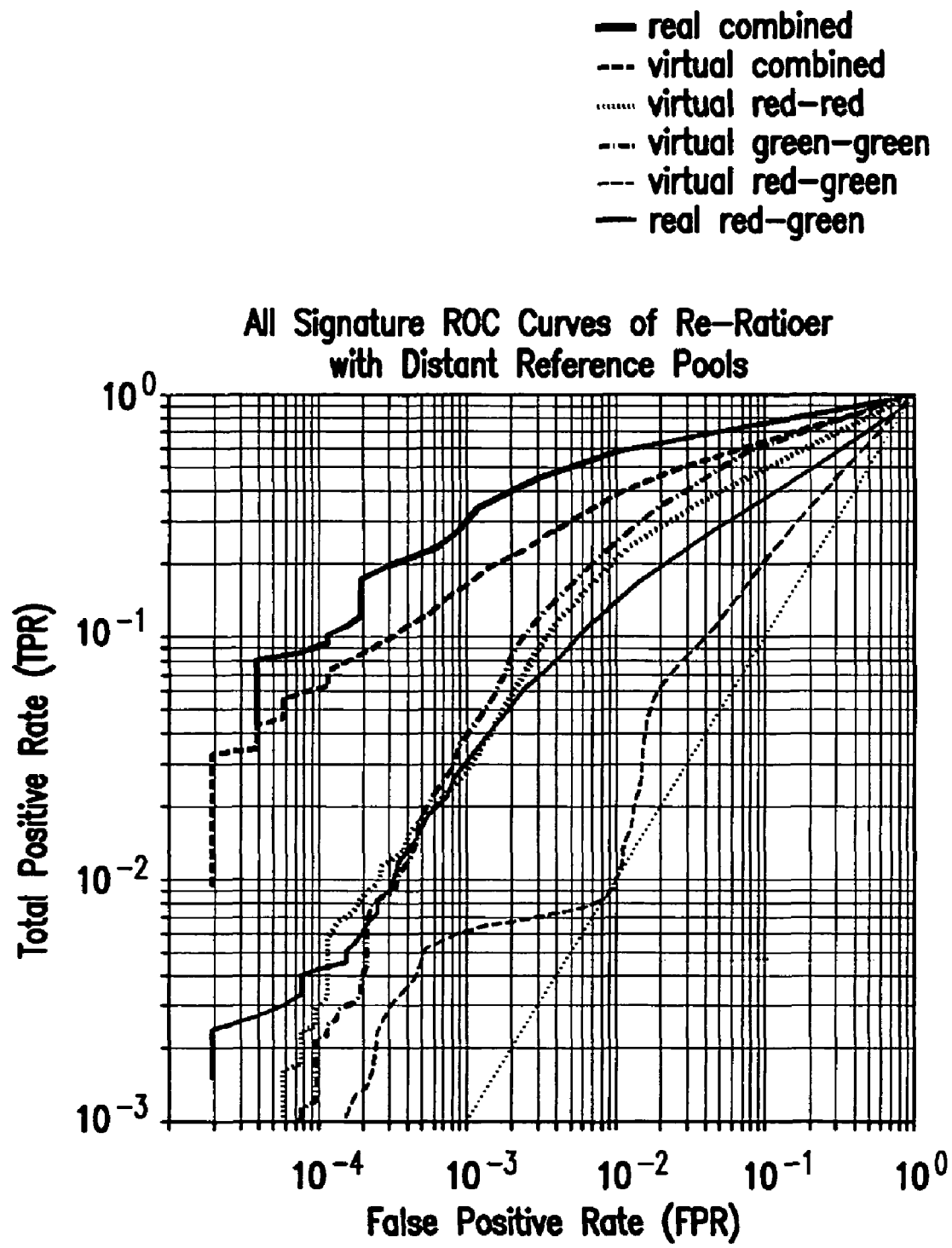

FIGS. 46A-B are all-signature-ROC plots of (A) Ratio-Splitter and (B) Re-Ratioer. Both of them have the distant common reference pools.

Figure 47A:
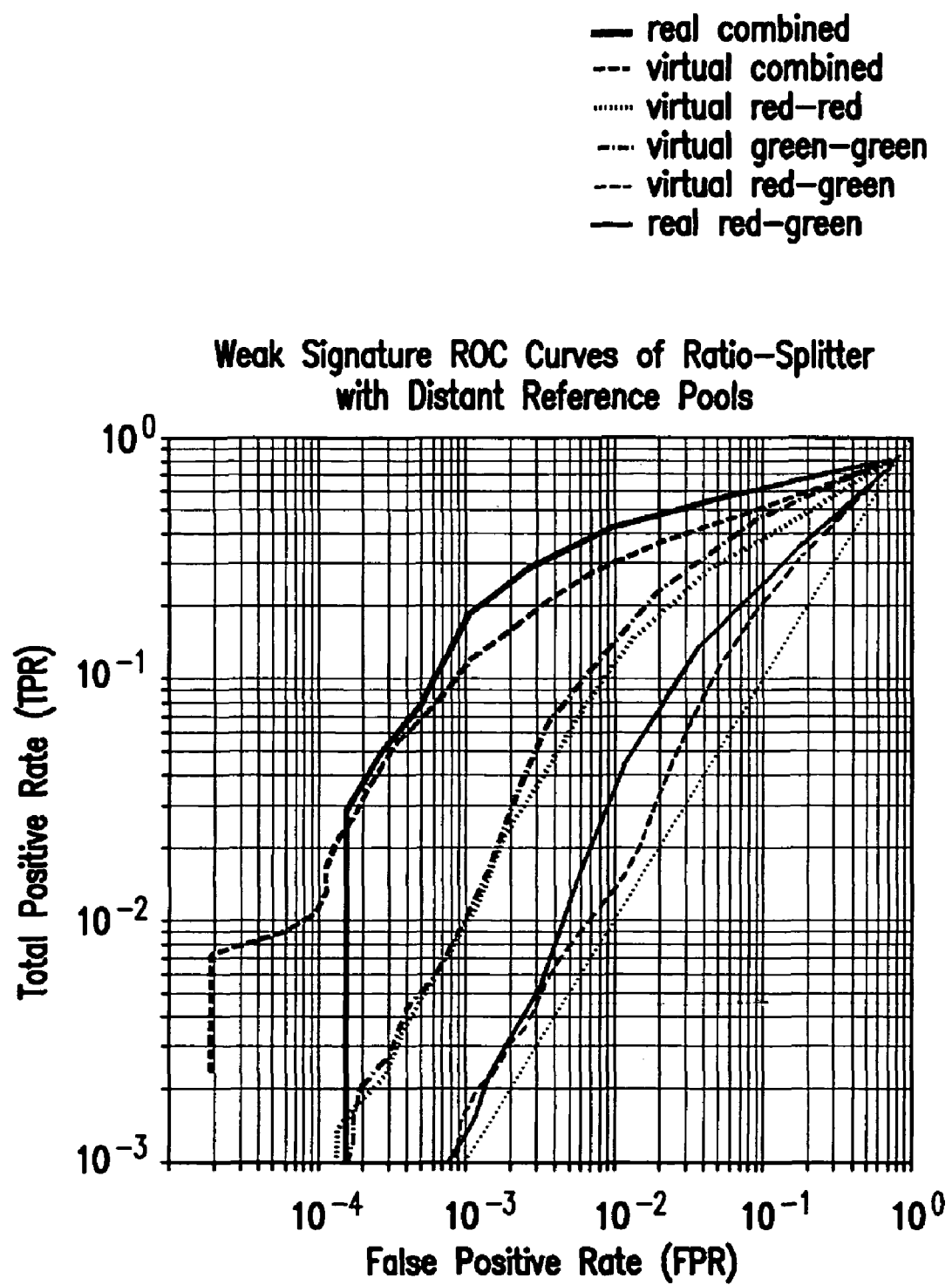
Figure 47B:
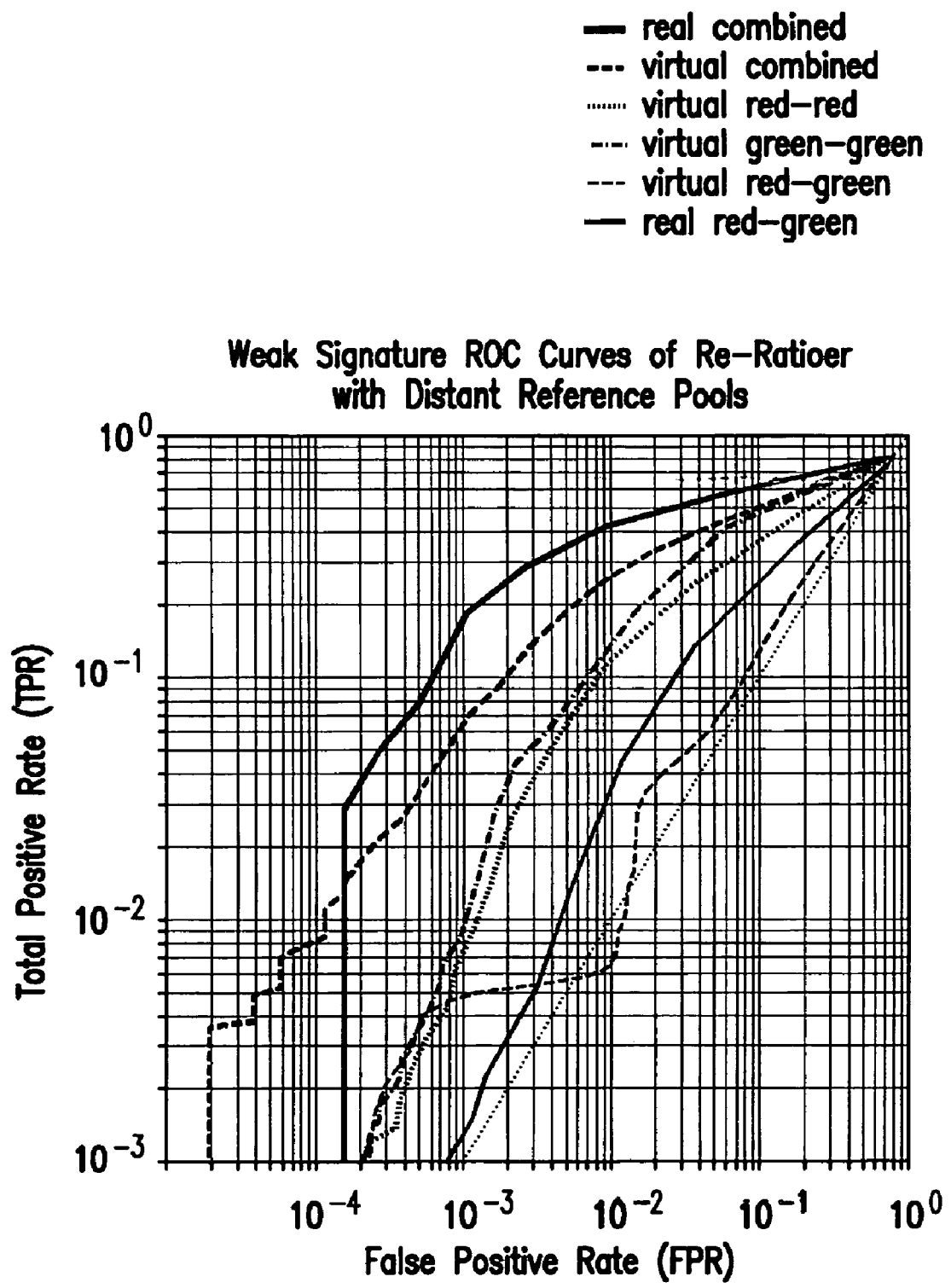

FIGS. 47A-B are weak-signature-ROC plots of (A) Ratio-Splitter and (B) Re-Ratioer. Both of them have the distant common reference pools.

Figure 48A:
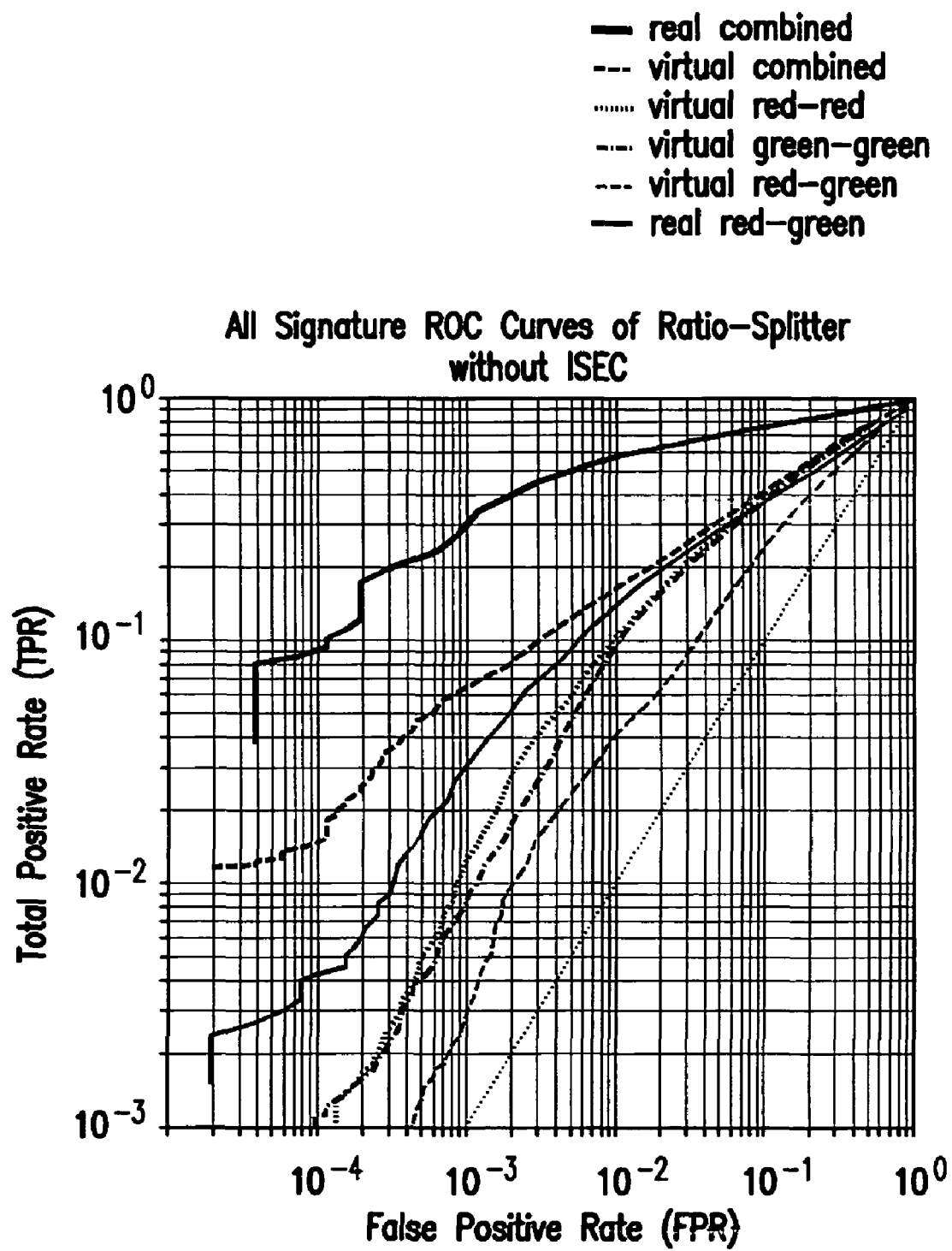
Figure 48B:
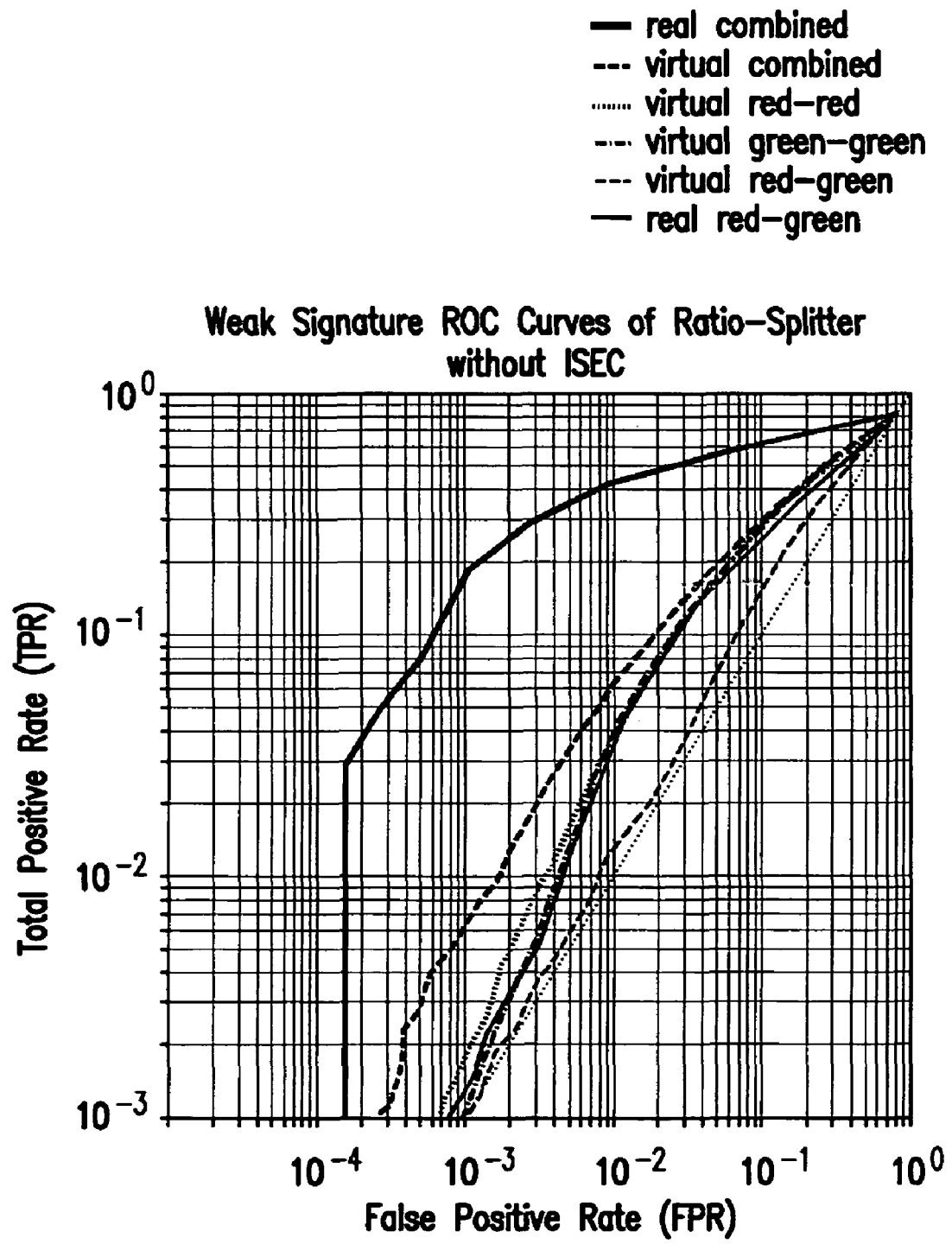

FIGS. 48A-B are (A) All-signature-ROC plot and (B) weak-signature plot of Ratio-Splitter without common reference controls. Both of them do not have ISEC applied.

Figure 49:
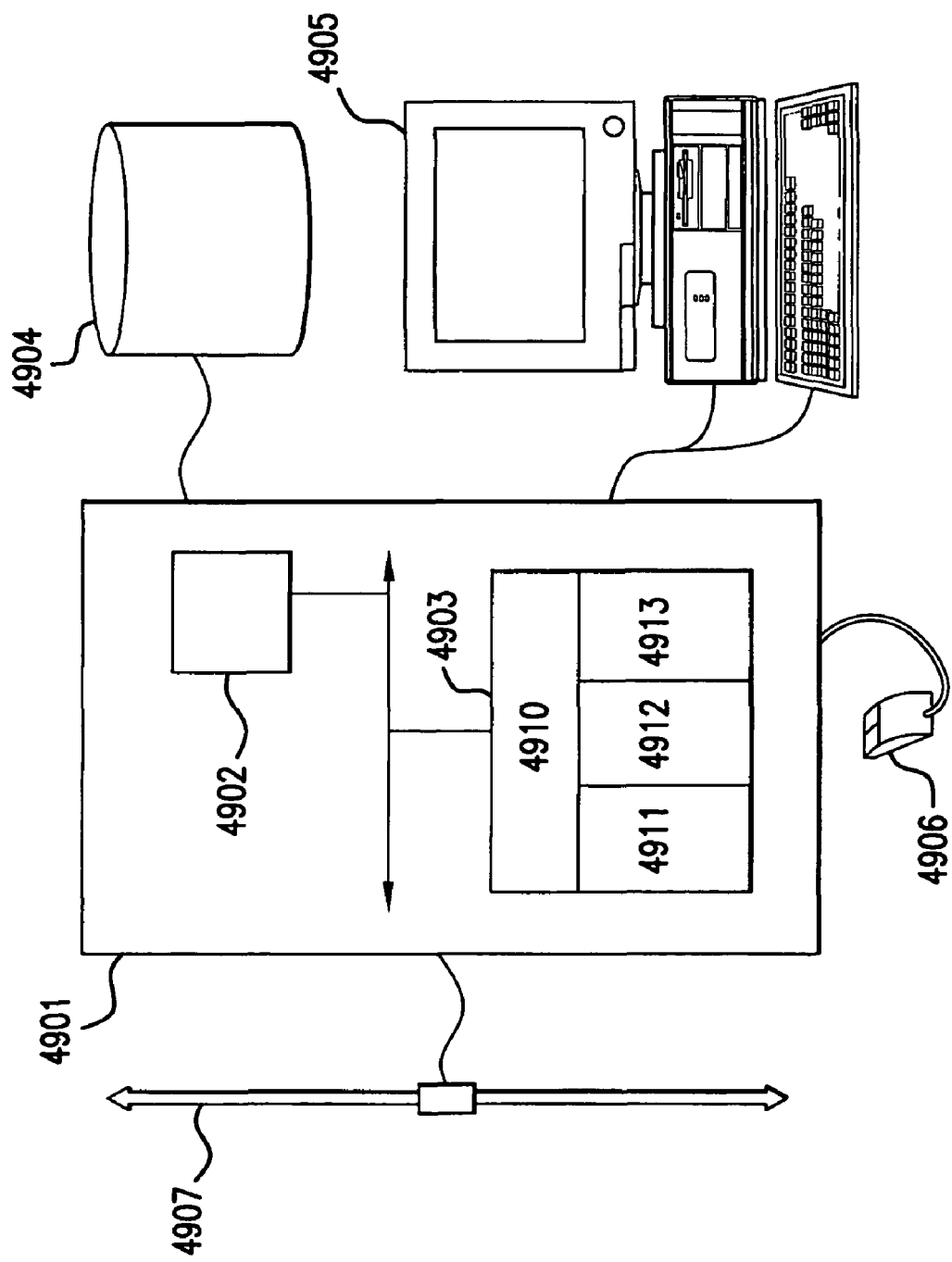

FIG. 49 illustrates an exemplary embodiment of a computer system useful for implementing the methods of this invention.

5. DETAILED DESCRIPTION OF THE INVENTION

The present invention provides methods for analyzing multi-channel profiles, e.g., two-channel profiles. For example, a R-channel profile $^1A/^2A/\ldots^{R-1}/C$ (R is an integer) comprises measurements of a plurality of samples $^1A$, $^2A$, $\ldots$ $^{R-1}A$, and C, where measurements of each sample constitute one channel. Thus, a multi-channel profile can comprise a plurality of profiles each representing measurements of one sample. A frequently encountered multi-channel profile is a two-channel profile, e.g., a two-color intensity profile. Herein, for simplicity reasons, methods for analyzing multi-channel profiles are often discussed with reference to two-channel profiles. It will be understood that such methods are readily applicable to multi-channel profiles.

A two-channel profile A vs. C comprises measurements of two samples A and C, where measurements from each sample constitute one channel. Thus, a two-channel profile can comprise a pair of profiles each representing measurements of one sample. A two-channel profile can also be a differential profile. As used herein, a differential profile refers to a collection of changes of measurements of cellular constituents, e.g., changes in expression levels of nucleic acid species or changes in abundances of proteins species, in cell samples under different conditions, e.g., under the perturbations of different drugs, under different environmental conditions, and so on. The pair of profiles may be measured concurrently in one experiment. Such a two-channel profile is also referred to as an experimental two-channel profile. A skilled person in the art will understand that a two-channel profile can be a pair of profiles selected from a multi-channel profile having additional profiles. For example, a two-channel profile consisting of a green channel profile and a red channel profile may be obtained from a three-channel profile which also comprises a blue channel. The pair of profiles may also be measured separately and combined together. Methods for combining separately measured profile date sets are described in this application and in U.S. Pat. Nos. 6,351,712 and 6,691,042, each of which is incorporated herein by reference in its entirety. A two-channel profile that comprises a pair of separately measured profiles is also referred to as a virtual two-channel profile. In preferred embodiments, C in a two-channel profile, either experimental or virtual, is a reference sample. In such cases, measurements of sample C are also referred to as the reference channel, and the corresponding measurements of sample A are also referred to as the experiment channel.

The invention provides a method for correcting systematic cross-profile (cross-experiment) errors among a plurality of multi-channel profiles having a common reference channel. A common reference channel or common reference profile refers to profiles measured using reference samples that are nominally the same, i.e., prepared the same way. The method involves estimating the cross-experiment errors using profiles in the common reference channel, and removing such cross-experimental errors from profiles in the experiment channels. In one embodiment, an average reference profile is obtained by averaging the profiles of the common reference channel. The systematic cross-experiment error in each individual multi-channel profile is then determined by comparing the reference channel profile in the multi-channel profile with the average reference profile. Such systematic cross-experiment error can be represented as an error profile. The systematic cross-experiment error can then be removed from the experiment channel, e.g., by subtracting the error profile from the experiment profile. The obtained error-corrected experiment channel data can then be used in comparison with each other, e.g., in generating virtual differential profiles between pairs of experiment channels.

Profiles of measurements of cellular constituents, e.g., measured expression levels of nucleic acid species, in a cell sample having been subject to a particular condition, e.g., conditions A, B, or C, are represented as sets of data $\{A(k)\}$, $\{B(k)\}$, and $\{C(k)\}$, respectively, in which $k=1, 2, \ldots, N$, and N is the number of measurements of cellular constituents, equivalently, the number of probes used to carry out the measurement. Herein, for convenience, such data sets are often referred to as A, B, or C. It will be understood by one of ordinary skill in the art that a profile of measurements may comprise redundant measurements. For example, the same probe may be printed at more than one location on an array. A profile obtained from such an array comprises more than one measurement of the probe, each obtained from the probe at a different probe site. Herein, each of such measurements is also referred to as a feature. The changes in measurements of cellular constituents, e.g., expression levels, can be characterized by any convenient metric, e.g., arithmetic difference, ratio, log(ratio), etc. The mathematical operation log can be any logarithm operation. Preferably, it is the natural log or log 10. As used herein, a differential profile A vs. B is defined as a profile representing changes of cellular constituents, e.g., expression levels of nucleic acid species or abundances of proteins species, from A to B, e.g., B-A, when an arithmetic difference is used, or B/A, when a ratio is used, where the difference or ratio is calculated for each feature. Differential profiles obtained from mathematical operations, e.g., arithmetic difference, ratio, log(ratio), etc., on the measured data sets, e.g., A, B, or C, are often referred to by short-hand symbols, e.g., A-B, A/B, or log(A/B). It will be understood by one skill in the art that when such short-hand symbols are used, they refer to data sets representing the differential profiles that contain data points resulting from the respective mathematical operation. For example, differential profile A-B refers to a differential profile comprising data set $\{A(k)-B(k)\}$, whereas differential profile log(B/A) refers to a differential profile comprising data set $\{\log[B(k)/A(k)]\}$. Thus, for example, a differential profile A vs. B can comprise a collection of ratios of expression levels $\{B(k)/A(k)\}$, or log(ratio)'s, i.e., $\{\log[B(k)/A(k)]\}$, and so on. It will be apparent to one skill in the art that a differential profile can be a response profile as described in Section 5.1.2, infra.

The methods of the invention are applicable to any type of multi-channel profiles, including but not limited to profiles of raw measurements, e.g., raw fluorescence intensities, or transformed profiles. Any type of suitably transformed profiles can be used in the present invention. In one embodiment, log (intensity) is used. In a preferred embodiment, transformed profiles obtained by the methods described in U.S. patent application Ser. No. 10/354,664, filed on Jan. 30, 2003, which is incorporated by reference herewith in its entirety, are used.

As used herein, a "same-type" or "same vs. same" profile or differential profile is often referred to. As used herein, a same-type profile or differential profile refers to a profile or differential profile for which the two conditions are the same, e.g., C vs. C. In a preferred embodiment, a same-type profile or differential profile contains data measured from a biological sample in a base-line state. As used herein, a "baseline state" refers to a state of a biological sample that is a reference or control state.

As used herein, a "single-channel measurement" refers broadly to any measurements of cellular constituents made on a sample having been subject to a given condition in a single experimental reaction, whereas a "two-channel measurement" refers to any measurements of cellular constituents made distinguishably and concurrently on two different samples in the same experimental reaction. The term "same experimental reaction" refers to use in the same reaction mixture, i.e., by contacting with the same reagents in the same composition at the same time (e.g., using the same microarray for nucleic acid hybridization to measure mRNA, cDNA or amplified RNA; or the same antibody array to measure protein levels). Data generated in a single-channel measurement of a sample subject to condition A are often represented as A, whereas data generated in a two-channel measurement of two samples having been subject to conditions A and B, respectively, are often represented as A vs. B. For example, measurement of the expression level of a gene in a cell sample having been subject to an environmental perturbation A obtained in a single color microarray experiment is a single-channel measurement A. On the other hand, measurement of the expression levels of the genes in two cell samples, one having been subject condition A and one having been subject to condition C, obtained in a single two-color fluorescence experiment is a two-channel measurement A vs. C. In some embodiments, a two-channel measurement such as A vs. C can be broken into two separate single-channel measurements A and C. In this invention, a pair of two-channel measurements comprising measurements of samples having been subject to a common condition in one of the two channels are often of interest. In such cases, data associated with the common condition may further be identified by their association with the other condition in each two-channel measurement, e.g., $C_A$ identifying data set measured using a sample having been subject to condition C in a two-channel measurement A vs. $C_A$ and $C_B$ identifying data set measured on a sample having been subject to condition C in a two-channel measurement B vs. $C_B$. Any types of single-channel and/or two-channel measurements known in the art can be used in the invention. Preferably, when single-channel measurements are used for generation of a differential profile, the two single-channel measurements are of the same type, e.g., both fluorescence measurements. Expression measurements made distinguishably and concurrently on more than two different samples, e.g., N-color fluorescence experiments, where N is greater than two, can also be used in generation of differential expression profiles by the methods of the present invention.

Although the methods of the present invention are often described for microarray-based expression measurements, it will be apparent to one skilled in the art that the methods of the present invention can also be adapted for generating response profiles of other types of cellular constituents.

5.1. Biological State and Expression Profile

The state of a cell or other biological sample is represented by cellular constituents (any measurable biological variables) as defined in Section 5.1.1, infra. Those cellular constituents vary in response to perturbations, or under different conditions.

5.1.1. Biological State

As used herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms.

The state of a biological sample can be measured by the content, activities or structures of its cellular constituents. The state of a biological sample, as used herein, is taken from the state of a collection of cellular constituents, which are sufficient to characterize the cell or organism for an intended purpose including, but not limited to characterizing the effects of a drug or other perturbation. The term "cellular constituent" is also broadly defined in this disclosure to encompass any kind of measurable biological variable. The measurements and/or observations made on the state of these constituents can be of their abundances (i.e., amounts or concentrations in a biological sample), or their activities, or their states of modification (e.g., phosphorylation), or other measurements relevant to the biology of a biological sample. In various embodiments, this invention includes making such measurements and/or observations on different collections of cellular constituents. These different collections of cellular constituents are also called herein aspects of the biological state of a biological sample.

One aspect of the biological state of a biological sample (e.g., a cell or cell culture) usefully measured in the present invention is its transcriptional state. In fact, the transcriptional state is the currently preferred aspect of the biological state measured in this invention. The transcriptional state of a biological sample includes the identities and abundances of the constituent RNA species, especially mRNAs, in the cell under a given set of conditions. Preferably, a substantial fraction of all constituent RNA species in the biological sample are measured, but at least a sufficient fraction is measured to characterize the action of a drug or other perturbation of interest. The transcriptional state of a biological sample can be conveniently determined by, e.g., measuring cDNA abundances by any of several existing gene expression technologies. One particularly preferred embodiment of the invention employs DNA arrays for measuring mRNA or transcript level of a large number of genes. The other preferred embodiment of the invention employs DNA arrays for measuring expression levels of a large number of exons in the genome of an organism.

Another aspect of the biological state of a biological sample usefully measured in the present invention is its translational state. The translational state of a biological sample includes the identities and abundances of the constituent protein species in the biological sample under a given set of conditions. Preferably, a substantial fraction of all constituent protein species in the biological sample is measured, but at least a sufficient fraction is measured to characterize the action of a drug of interest. As is known to those of skill in the art, the transcriptional state is often representative of the translational state.

Other aspects of the biological state of a biological sample are also of use in this invention. For example, the activity state of a biological sample, as that term is used herein, includes the activities of the constituent protein species (and also optionally catalytically active nucleic acid species) in the biological sample under a given set of conditions. As is known to those of skill in the art, the translational state is often representative of the activity state.

This invention is also adaptable, where relevant, to "mixed" aspects of the biological state of a biological sample in which measurements of different aspects of the biological state of a biological sample are combined. For example, in one mixed aspect, the abundances of certain RNA species and of certain protein species, are combined with measurements of the activities of certain other protein species. Further, it will be appreciated from the following that this invention is also adaptable to other aspects of the biological state of the biological sample that are measurable.

The biological state of a biological sample (e.g., a cell or cell culture) is represented by a profile of some number of cellular constituents. Such a profile of cellular constituents can be represented by the vector S: $S=[S_1, \ldots S_i, \ldots S_k]$, where $S_i$ is the level of the i'th cellular constituent, for example, the transcript level of gene i, or alternatively, the abundance or activity level of protein i.

In some embodiments, cellular constituents are measured as continuous variables. For example, transcriptional rates are typically measured as number of molecules synthesized per unit of time. Transcriptional rate may also be measured as percentage of a control rate. However, in some other embodiments, cellular constituents may be measured as categorical variables. For example, transcriptional rates may be measured as either "on" or "off", where the value "on" indicates a transcriptional rate above a predetermined threshold and value "off" indicates a transcriptional rate below that threshold.

5.1.2. Biological Responses and Expression Profiles

The responses of a biological sample to a perturbation, i.e., under a condition, such as the application of a drug, can be measured by observing the changes in the biological state of the biological sample. A response profile is a collection of changes of cellular constituents. In the present invention, the response profile of a biological sample (e.g., a cell or cell culture) to the perturbation m is defined as the vector $v^{(m)}$:

$$v^{(m)} = [v_1^{(m)}, \ldots v_i^{(m)}, \ldots v_k^{(m)}],$$

where $v_i^m$ is the amplitude of response of cellular constituent i under the perturbation m. In some particularly preferred embodiments of this invention, the biological response to the application of a drug, a drug candidate or any other perturbation, is measured by the induced change in the transcript level of at least 2 genes, preferably more than 10 genes, more preferably more than 100 genes and most preferably more than 1,000 genes. In another preferred embodiment of the invention, the biological response to the application of a drug, a drug candidate or any other perturbation, is measured by the induced change in the expression levels of a plurality of exons in at least 2 genes, preferably more than 10 genes, more preferably more than 100 genes and most preferably more than 1,000 genes.

In some embodiments of the invention, the response is simply the difference between biological variables before and after perturbation. In some preferred embodiments, the response is defined as the ratio of cellular constituents before and after a perturbation is applied.

In some preferred embodiments, $v_i^m$ is set to zero if the response of gene i is below some threshold amplitude or confidence level determined from knowledge of the measurement error behavior. In such embodiments, those cellular constituents whose measured responses are lower than the threshold are given the response value of zero, whereas those cellular constituents whose measured responses are greater than the threshold retain their measured response values. This truncation of the response vector is a good strategy when most of the smaller responses are expected to be greatly dominated by measurement error. After the truncation, the response vector $v^{(m)}$ also approximates a 'matched detector' (see, e.g., Van Trees, 1968, Detection, Estimation, and Modulation Theory Vol. I, Wiley & Sons) for the existence of similar perturbations. It is apparent to those skilled in the art that the truncation levels can be set based upon the purpose of detection and the measurement errors. For example, in some embodiments, genes whose transcript level changes are lower than two fold or more preferably four fold are given the value of zero.

In some preferred embodiments, perturbations are applied at several levels of strength. For example, different amounts of a drug may be applied to a biological sample to observe its response. In such embodiments, the perturbation responses may be interpolated by approximating each by a single parameterized "model" function of the perturbation strength u. An exemplary model function appropriate for approximating transcriptional state data is the Hill function, which has adjustable parameters a, $u_0$, and n:

$$H(u) = \frac{a(u/u_0)^n}{1+(u/u_0)^n}.$$

The adjustable parameters are selected independently for each cellular constituent of the perturbation response. Preferably, the adjustable parameters are selected for each cellular constituent so that the sum of the squares of the differences between the model function (e.g., the Hill function) and the corresponding experimental data at each perturbation strength is minimized. This preferable parameter adjustment method is well known in the art as a least squares fit. Other possible model functions are based on polynomial fitting, for example by various known classes of polynomials. More detailed description of model fitting and biological response has been disclosed in Friend and Stoughton, Methods of Determining Protein Activity Levels Using Gene Expression Profiles, U.S. Pat. No. 6,324,479, which is incorporated herein by reference for all purposes.

5.2. Method of Analyzing Profiles: Re-Ratioer

Figure 1:
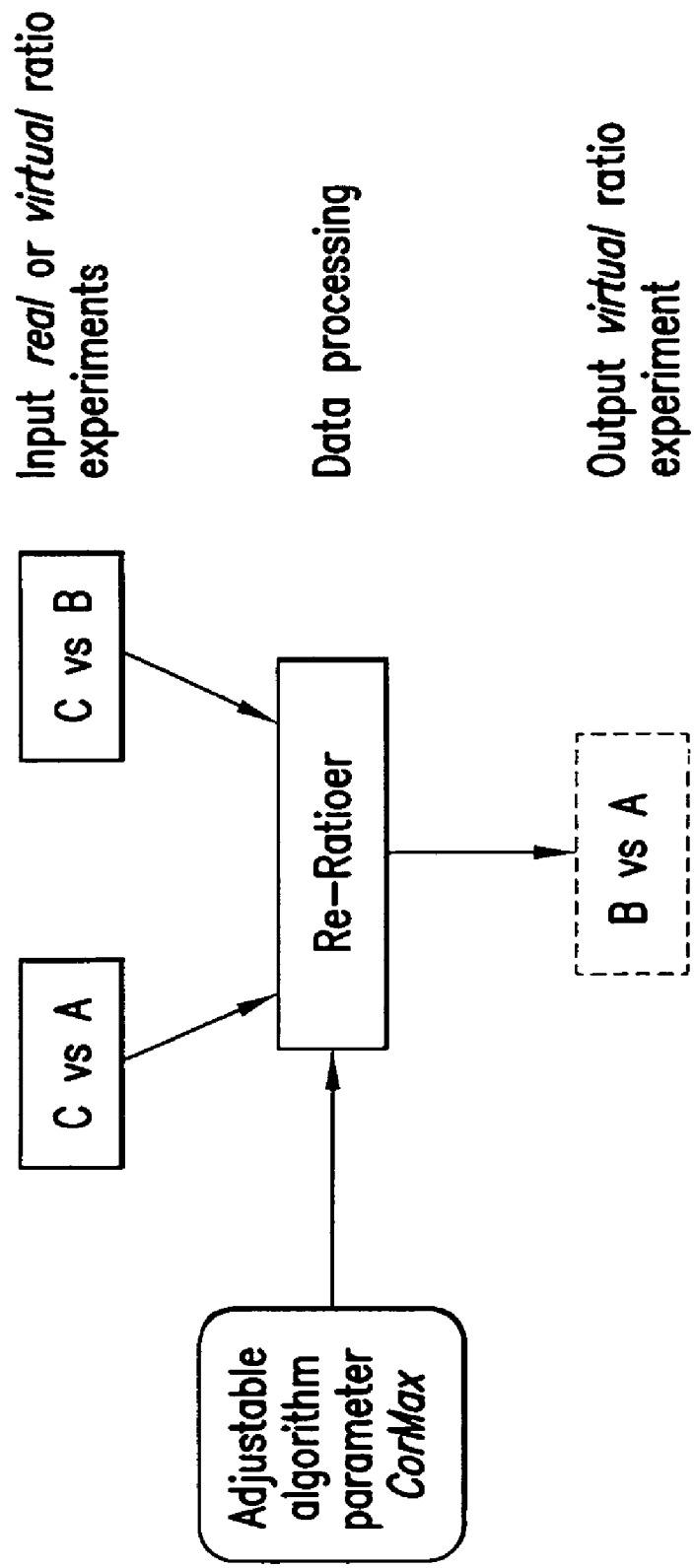
FIG. 1 shows the data flow chart of an exemplary embodiment of the re-ratioer.

The invention provides a method for generating a virtual ratio profile from two two-channel profiles. The two input two-channel profiles can be both experimental, both virtual, or one experimental and one virtual. In one embodiment, the invention provides a method termed "re-ratioer," which takes two input ratio profiles A/C and B/C and generates a new "virtual" ratio profile or experiment A/B. It does not require the raw intensity information. FIG. 1 shows a flowchart of an exemplary embodiment of the re-ratioer.

Assuming input experiment C-vs-A (A/C) has the following data fields:

lratioAC(k)— Log 10 ratio of $I_A(k)/I_C(k)$, where $I_A(k)$, and $I_C(k)$ are hybridization intensities of the k'th sequence (or reporter) of Sample A and C.

$\sigma_{lratioAC}(k)$—Error estimation of lratioAC(k).

Intensity1AC(k)—Intensity of the green (Cy3) channel. For positive polarity, it is the denominator of the ratio, $I_C(k)$ in this case.

Intensity2AC(k)—Intensity of the red (Cy5) channel. For positive polarity, it is the numerator of the ratio, $I_A(k)$ in this case.

PolarityAC—A parameter used to characterize the order of $I_A(k)$ and $I_C(k)$ in the ratio, i.e., which term is the denominator and which term is the numerator. It has a value of either +1 or −1. It can be chosen to be positive one for one order, e.g., $I_A(k)/I_C(k)$. It is then negative one for $I_C(k)/I_A(k)$. In a preferred embodiment, the order of $I_A(k)$ and $I_C(k)$ in the ratio corresponds to the labeling scheme of sample A and C. A negative value indicates the profile is reversely labeled.

Data fields for input experiment C-vs-B (B/C) are similarly defined.

The re-ratioer computes data fields of the new virtual ratio experiment B-vs-A (A/B) as following:

$$lratioAB(k) = polarityAC \cdot lratioAC(k) - polarityBC \cdot lratioBC(k) \tag{1}$$

$$\sigma_{lratioAB}(k) = \sqrt{\sigma_{lratioAC}^2(k) + \sigma_{lratioBC}^2(k) - 2 \cdot CorMax \cdot \sigma_{lratioAC}(k) \cdot \sigma_{lratioBC}(k)} \tag{2}$$

$$PolarityAB = +1 \tag{3}$$

if PolarityAC>0 and PolarityBC>0:

$$Intensity1AB(k) = \sqrt{Intensity1AC(k) \cdot Intensity2BC(k)} \tag{4}$$

$$Intensity2AB(k) = \sqrt{Intensity2AC(k) \cdot Intensity1BC(k)} \tag{5}$$

if PolarityAC<0 and PolarityBC<0:

$$Intensity1AB(k) = \sqrt{Intensity2AC(k) \cdot Intensity1BC(k)} \tag{6}$$

$$Intensity2AB(k) = \sqrt{Intensity1AC(k) \cdot Intensity2BC(k)} \tag{7}$$

if PolarityAC>0 and PolarityBC<0:

$$Intensity1AB(k) = \sqrt{Intensity1AC(k) \cdot Intensity1BC(k)} \tag{8}$$

$$Intensity2AB(k) = \sqrt{Intensity2AC(k) \cdot Intensity2BC(k)} \tag{9}$$

if PolarityAC<0 and PolarityBC>0:

$$\text{Intensity1}AB(k) = \sqrt{\text{Intensity2}AC(k) \cdot \text{Intensity2}BC(k)} \tag{10}$$

$$\text{Intensity2}AB(k) = \sqrt{\text{Intensity1}AC(k) \cdot \text{Intensity1}BC(k)} \tag{11}$$

In Equation 2, the parameter CorMax is the estimated maximum correlation coefficient between errors of A/C and B/C. CorMax has a value in the range of 0 to 1. The default value of CorMax is 0.5. It is the only adjustable parameter shown in FIG. 1. When this parameter is small, the estimated A/B error is more conservative (larger). When it is large, the estimated A/B error is more aggressive (smaller).

The re-ratioer can be applied when the end result is a ratio experiment A/B and available input ratio experiments have a common reference C. For example, in a pooled experiment design, these are real ratio experiments in compound-vs-pool and vehicle-vs-pool. Re-ratioer can be used to derive virtual ratio experiment of compound-vs-vehicle with the re-ratioer. The re-ratioer can also be used in looped designs to derive distant ratios. For example, given real profiles A/B, B/D, and D/E, virtual experiment A/D can first be obtained from A/B and B/D. Virtual A/E can then be obtained from the virtual A/D and the real D/E.

The main advantage of the re-ratioer is its simplicity. The new ratio is directly derived from two input ratios (Equation 1). There is no normalization needed. Intensities are not involved in the ratio computation. The only thing the user needs to do is to specify the two inputs. One is the numerator (experiment) of the new virtual ratio and the other is the denominator (baseline) of the new ratio. Any one of the two inputs can be real or virtual ratio profile or experiment. Pre-combined ratio experiments can be directly used as inputs.

The re-ratioer has its limitations. The two input ratio experiments must have a common reference C. The common reference itself will introduce errors. This error will accumulate when distant ratios are derived along a looped design. The output of the re-ratioer is a new ratio experiment. It does not provide individual intensity experiments A, B, etc.

When sequences in the common reference C are expressed, the two intensity measurements of C in A/C and B/C effectively serve as control references to reduce the inter-slide variation between the two inputs when the new ratio A/B is calculated using Equation 1. However, when the expression of C is very weak, the noise in C may cause the control reference to fluctuate. When intensity C is near zero, it becomes a zero/zero situation. The resulting log-ratio becomes unstable. Examples in Section 6 demonstrate the limitation.

5.3. Methods of Analyzing Profiles: Ratio-Splitter

The invention provides a method for correcting errors in a plurality of pairs of profiles $\{A_m, C_m\}$, where m=1, 2, ..., M, M is the number of pairs of profiles. Each pair of profiles consists of experiment profile $A_m$ comprising data set $\{A_m(k)\}$ and a reference profile $C_m$ comprising data set $\{C_m(k)\}$, where k=1, 2, ..., N, N is the number of measurements in each profile. In preferred embodiment, N is at least 10, at least 100, at least 1,000, or at least 10,000. Data set $\{A_m(k)\}$ comprises measurements or transformed measurements of a plurality of different cellular constituents measured in a sample having been subject to condition $A_m$, and data set $\{C_m(k)\}$ comprises measurements or transformed measurements of the plurality of different cellular constituents measured in a sample having been subject to condition C. Each pair of profiles can be a pair of profiles selected from a multi-channel profile having additional profiles. Preferably, experiment profile $A_m$ and reference profile $C_m$ are measured in the same experimental reaction. For example, the pair of profiles $\{A_m, C_m\}$ can be a two-channel profile measured in the mth experimental reaction. The profiles can be measured profiles. The profiles can also be transformed profiles. For example, each $C_m$, $m \in \{1, 2, \ldots, M\}$, can represent measurements or transformed measurements of a plurality of different cellular constituents measured in a sample having been subject to common condition C. The method of the invention involves determining a systematic error in each experiment profile $A_m$ based on the corresponding reference profile $C_m$, and removing such systematic error from the experiment profile. The obtained error-corrected experiment profiles can then be further analyzed, e.g., directly compared using a difference or ratio, as input data in ANOVA, and so on.

In one embodiment, an average reference profile $\overline{C}$ of the M reference profiles $\{C_m\}$ is first determined according to equation $$\overline{C}(k) = \frac{1}{M} \sum_{m=1}^{M} C_m(k) \tag{12}$$

This average reference profile $\overline{C}$ is then used as the common reference for the M profiles. The deviation of each reference profile $C_m$ from $\overline{C}$ is calculated as a differential reference profile $$C_{\text{diff}}(m,k) = C_m(k) - \overline{C}(k) \tag{13}$$

and is used as the systematic bias of $A_m$. This differential reference profile can be used to correct $A_m$ according to equation $$A'_m(k) = A_m(k) - C_{\text{diff}}(m,k) \tag{14}$$

The errors $\{\sigma'_m\}$ of the error-adjusted experiment profile $\{A'_m\}$ can be determined according to equation $$\sigma'_m(k) = \sqrt{\sigma_m^2(k) + \text{mixed\_}\sigma_m^2(k) - 2 \cdot Cor(k) \cdot \sigma_m(k) \cdot \text{mixed\_}\sigma_m(k)} \tag{15}$$

where $\sigma_m(k)$ is the standard error of $A_m(k)$, $\text{mixed\_}\sigma_m(k)$ is determined according to equation $$\text{mixed\_}\sigma_m(k) = \frac{\sigma_m(k) + (M-1) \cdot \sigma_{ref}(k)}{M} \tag{16}$$

where $$\sigma_{ref}(k) = \sqrt{\frac{1}{M-1} \sum_{m}^{M} (C_m(k) - \overline{C}(k))^2} \tag{17}$$

and where Cor(k) is a correlation coefficient between the experiment channel and the corresponding reference channel. This correlation may be intensity dependent. For example, when intensity is high, the correlation is strong, whereas when intensity is low and near the background noise level, the correlation is weak. In one embodiment, a simple correlation model is built to estimate Cor(k):

$$Cor(k) = CorMax \cdot \left(1 - e^{-0.5\left(\frac{\overline{C}(k)}{avg\_bkgstd}\right)^2}\right) \tag{18}$$

CorMax defines the maximum correlation. In some embodiments, CorMax is taken to be 0.5. CorMax can have value between 0 and 1. Small CorMax makes the error estimation more conservative, while large CorMax produces smaller error estimation, which is more aggressive.

In some cases, e.g., when one or more measurements in the common reference profiles, e.g., the common-reference intensity, are near or below the background noise level, the correlation between the experiment and the reference channels decreases significantly. In such cases, correction of systematic bias using the above-described differential reference profile may add noise to such measurements in the corrected $A_m$ rather than reduces it. Thus, in a preferred embodiment, a weighting model is used. The weighting model involves calculating an error-corrected experiment profile $A''_m$ comprising data set $\{A''_m(k)\}$, k=1, 2, . . . , N, by combining the error-adjusted experiment profile $A'_m$, e.g., $A'_m$ as determined by equation (14) with the experiment profile $A_m$ using a weighing factor $\{w(k)\}$ in such a manner that correction of each measurement by the corresponding difference value in the differential reference profile is smoothly phased out when the measurement in the common-reference profile is approaching or falling below the background noise level. In one embodiment, the weighting model calculates an error-corrected experimental profile $A'_m$ according to equation $$A''_m(k) = (1-w(k)) \cdot A_m(k) + w(k) \cdot A'_m(k) \tag{19}$$

where w(k) is a weighing factor. In a preferred embodiment, the weighing factor is determining according to equation $$w(k) = 1 - e^{-0.5\left(\frac{\overline{C}(k)}{avg\_bkgstd}\right)^2} \tag{20}$$

where avg_bkgstd is an average background standard error. In one embodiment, avg_bkgstd is determined according to equation $$avg\_bkgstd = \frac{1}{N}\sum_{k=1}^{N}\left(\frac{1}{M}\sum_{m=1}^{M} bkgstd(m,k)\right) \tag{21}$$

where bkgstd (m, k) is background standard error of $C_m(k)$.

The errors $\{\sigma''_m\}$ of error-corrected experiment profile $\{A''_m\}$ can be determined according to the equation:

$$\sigma''_m(k) = \sqrt{[1-w(k)] \cdot \sigma_m^2(k) + w(k)\sigma'^2_m(k)}. \tag{22}$$

The experiment and reference profiles $\{A_m, C_m\}$ can be transformed profiles. Data in such transformed profiles are transformed measurements. Any suitable type of transformed data may be used in conjunction with the present invention. In a preferred embodiment, the transformed measurements are obtained using the error model based transformation described in Section 5.4., infra.

The experiment profile $A_m$ and reference profile $C_m$ can also be normalized profiles. In one embodiment, normalized profile is obtained by normalizing data from all channels, i.e., experiment profiles $\{A_m\}$ and reference profiles $\{C_m\}$, according to equations $$NA_m(k) = \frac{A_m(k) \cdot \overline{AC}}{\overline{A_m}} \tag{23}$$

and $$NC_m(k) = \frac{C_m(k) \cdot \overline{AC}}{\overline{C_m}} \tag{24}$$

where $NA_m(k)$ and $NC_m(k)$ denotes normalized measurements in the experiment and reference channel, respectively, $\overline{A_m}$ is an average of all or a portion of measurements in profile $\{A_m(k)\}$, and $\overline{C_m}$ is an average of all or a portion of measurements in profile $\{C_m(k)\}$; $\overline{AC}$ is an average of all channels:

$$\overline{AC} = \frac{1}{2M}\sum_{m=1}^{M}(\overline{A_m} + \overline{C_m}) \tag{25}$$

The errors of the normalized experiment profile $NA_m$ and reference profile $NC_m$ can be determined according to equation $$\sigma_m^{NA}(k) = \frac{\sigma_m^A(k) \cdot \overline{AC}}{\overline{A_m}} \tag{26}$$

and $$\sigma_m^{NC}(k) = \frac{\sigma_m^C(k) \cdot \overline{AC}}{\overline{C_m}} \tag{27}$$

where $\sigma_m^A(k)$ and $\sigma_m^C(k)$ are the standard error of $A_m(k)$ and $C_m(k)$, respectively, and $\sigma_m^{NA}(k)$ and $\sigma_m^{NC}(k)$ are normalized standard error of $NA_m(k)$ and $NC_m(k)$, respectively.

The background errors of the normalized experiment profile $NA_m$ and reference profile $NC_m$ can be determined according to equation $$bkgstd_m^{NA}(k) = \frac{bkgstd_m^A(k) \cdot \overline{AC}}{\overline{A_m}} \tag{28}$$

and $$bkgstd_m^{NC}(k) = \frac{bkgstd_m^C(k) \cdot \overline{AC}}{\overline{C_m}} \tag{29}$$

where $bkgstd_m^A(k)$ and $bkgstd_m^C(k)$ are the standard background error of $A_m(k)$ and $C_m(k)$, respectively, and $bkgstd_m^{NA}(k)$ and $bkgstd_m^{NC}(k)$ are normalized standard background error of $NA_m(k)$ and $NC_m(k)$, respectively.

In a preferred embodiment, the average or median of measurements in a experiment or reference profile or channel, $\overline{A_m}$ or $\overline{C_m}$, e.g., the channel brightness, is the average of a portion of the measurements in the respective channel. In one embodiment, the portion of measurements to be used in determining the averages are obtained by eliminating measurements having values above a certain level, e.g., measurements having intensities in a chosen highest intensity range. In a preferred embodiment, measurements having values among the highest 5%, 10% or 20% are excluded from average determination.

The experiment and reference profiles $\{A_m, C_m\}$ can also be processed profiles in which nonlinearity is removed from raw or transformed experiment and reference profiles. Methods for nonlinearity removal are also called "detrending." In detrending, the measurement value, e.g., intensity-dependent non-linearity in all channels is minimized. In one embodiment, an average feature intensity profile of all channels is first calculated. This average profile is then used as the reference for correcting non-linearity. Each channel profile (experiment or reference profile) is compared to the average profile. If there is non-linearity between the two, the channel profile is adjusted to minimize the non-linearity.

In a preferred embodiment, an invariant sub-set (ISS) of features, i.e., features that are considered unchanged between an individual channel and the average profile, is identified. In one embodiment, measurements are rank ordered and compared between a channel profile and the averaged profile. Features that rank similarly within a small range are considered unchanged. In a preferred embodiment, the method described in Schadt et al., 2001, J. Cell. Biochem. Supp. 37:120-125, which is incorporated by reference herein in its entirety, is employed to find ISS.

Figure 3:
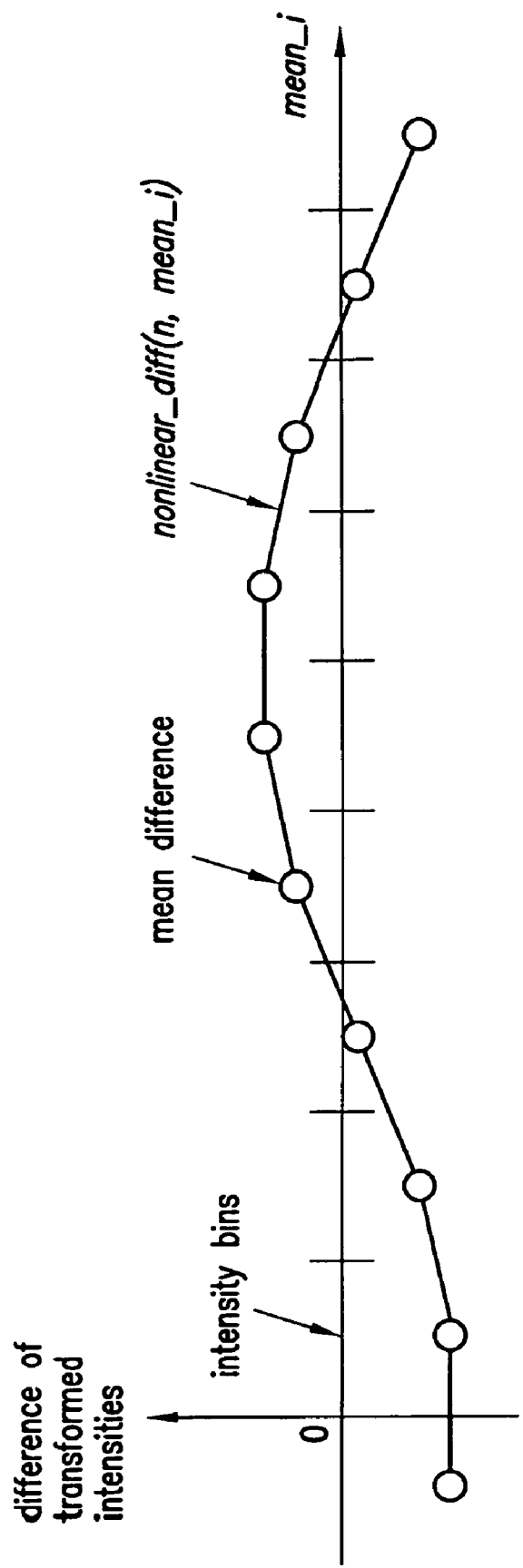
FIG. 3 illustrates a piecewise linear estimation of the non-linearity.

In a preferred embodiment, measurement values of all ISS features, both positive and negative, are cut into small range bins. The total number of bins can be defined by rounding the result of dividing the number of features by a chosen number, e.g., 1000. Preferably, the number of bins is between a minimum of about 2 for arrays with a small number of features and a maximum of about 12 for arrays with a large number of features. Mean difference between feature value in an individual channel and feature value in the average profile in each bin is calculated. The mean difference is placed as a point at the center of the bin (see, e.g., FIG. 3). In one embodiment, a smooth spline method is used to fit the non-linearity curve of the mean difference vs. mean feature value (Schadt et al., 2001, J. Cell. Biochem. Supp. 37:120-125). In another embodiment, a piece-wise linear method is used to fit the non-linearity curve. In the piece-wise linear method, straight lines connect these points from one bin to the next. The piecewise linear curve is a function of mean measurement value mean_k. This is the estimated nonlinearity function between the m'th experiment profile and the averaged profile nonlinear_$A_m$, or the m'th reference profile and the averaged profile nonlinear_$C_m$.

For all features, both invariant and variant, in each individual channel profile, the measurement values are corrected by the respective nonlinearity curve:

$$A_m^{corr}(k) = A_m(k) - \text{nonlinear}\_A_m(k) \quad (30)$$

or $$C_m^{corr}(k) = C_m(k) - \text{nonlinear}\_C_m(k) \quad (31)$$

Figure 2:
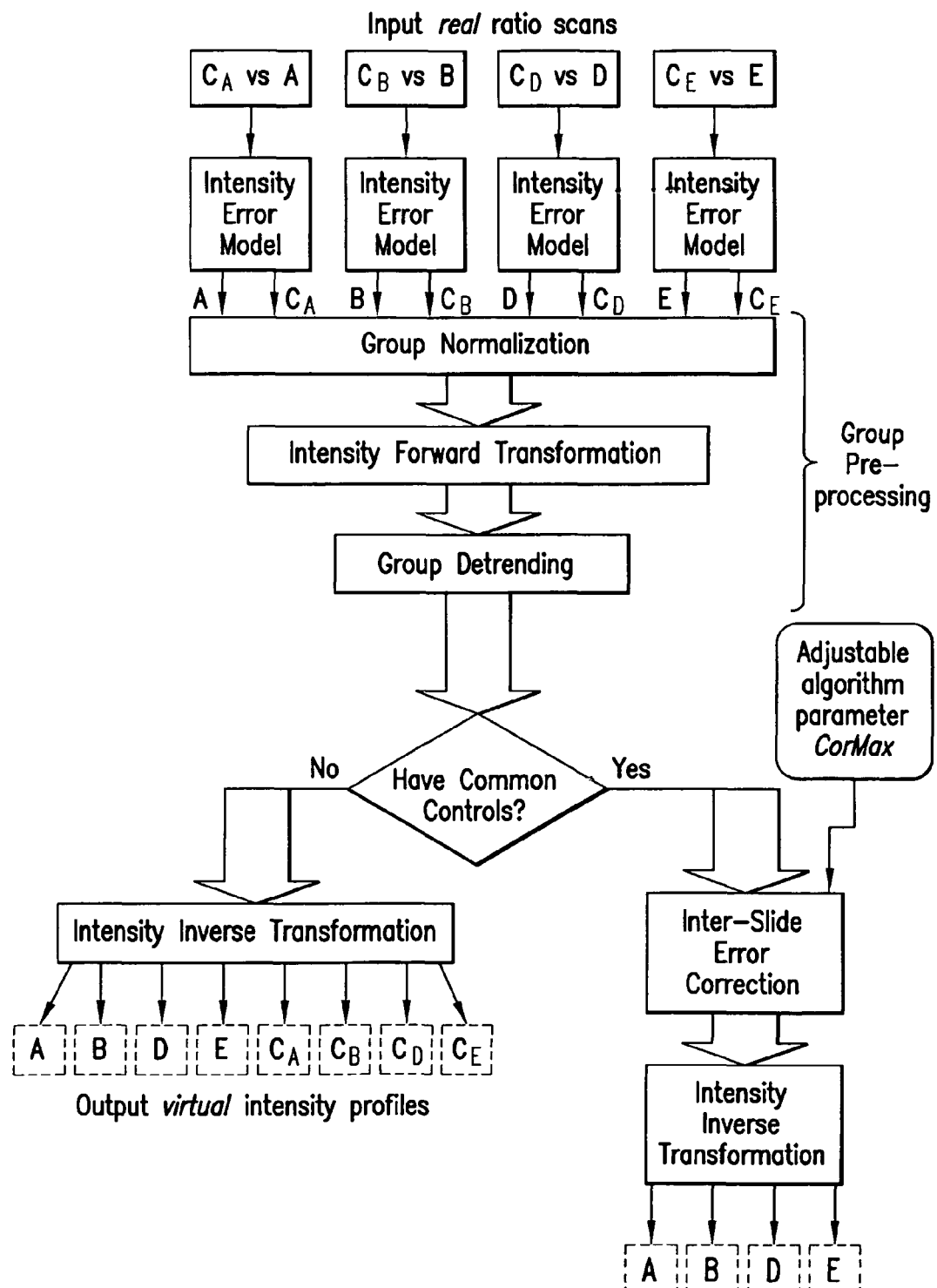
FIG. 2 shows the data flow chart of an exemplary embodiment of the ratio-splitter.

In one embodiment, the invention provides a computer program for splitting a plurality of multi-channel profiles into individual profiles. The program is also referred to as a ratio-splitter. FIG. 2 shows a flow chart of the ratio-splitter program. The ratio-splitter takes a plurality of multi-channel profiles (also termed ratio scans, e.g., the raw two-channel data, where the profile from each channel is termed a scan) and breaks them into new "virtual" intensity profiles. If all input ratio scans have a common reference channel, e.g. in a pooled design, the ratio splitter uses the data of the common reference channel to minimize the cross-experiment variations (also termed "inter-slide variation" or "inter-slide error" when the experiment is a microarray experiment) among the plurality of multi-channel profiles. In this case the ratio-splitter will produce N intensity profiles from N input ratio scans. If there is no common reference channel, the ratio-splitter will generate 2*N output intensity profiles from N input two-channel ratio scans.

As an example, the ratio scans $A/C_A$, $B/C_B$, $D/C_D$ and $E/C_E$, may or may not have common reference controls. If they do, sample $C_A$, $C_B$, $C_D$ and $C_E$ are the same. Otherwise, sample $C_A$, $C_B$, $C_D$ and $C_E$ are different. Preferably, the ratio scans are first sent to the technology-specific error-model. In one embodiment, the error-model used is the same error model for creating ratio profiles of a given microarray technology. The error model provides intensity error estimations for the red and the green channels to the ratio splitter. When creating regular ratio profiles, the error model only uses the estimated intensity errors internally. For a given scan, e.g. $C_A$-vs-A, the error model provides following quantities:

Intensity1AC(k)—Intensity of the green (Cy3) channel. For positive polarity, it is the denominator of the ratio, $I_C(k)$ in this case.

Intensity2AC(k)—Intensity of the red (Cy5) channel. For positive polarity, it is the numerator of the ratio, $I_A(k)$ in this case.

Ierr1AC(k)—Intensity error of the green (Cy3) channel.

Ierr2AC(k)—Intensity error of the red (Cy5) channel.

bkgstd1AC(k)—Background standard error of the green (Cy3) channel.

bkgstd2AC(k)—Background standard error of the red (Cy5) channel.

Intensity data from the error model are then sent to group preprocessing that includes one or more of the following: normalization, intensity transformation, and detrending. Group preprocessing reduces certain systematic biases in the data, such as gain biases and non-linearity.

If there are no common reference controls, i.e. sample $C_A$, $C_B$, $C_D$ and $C_E$ are different, the ratio-splitter inversely transforms the intensity data and output 2*N intensity profiles. If the user indicates there are common references, the ratio-splitter uses the common reference to estimate and correct inter-slide errors. Then the intensity data is inversely transformed. In this case, there are N intensity profiles from the ratio-splitter output.

There are three components in the group processing: group normalization, intensity transformation, and group detrending.

In group normalization, the average brightness of all intensity channels are made the same. In the ratio-splitter a global normalization is used. The channel brightness, Brightness(n), is the average of intensities from all positive features in the n'th channel, preferably after excluding top 10% brightest spots that are often saturated. Assuming there are N ratio scans (2*N channels), and there are K features on each chip, the intensity of the k'th feature (k: 1–K) on the n'th channel (n: 1-2*N) is normalized as $$I_{norm}(n, k) = \frac{I(n, k) \cdot \overline{\text{Brightness}}}{\text{Brightness}(n)} \quad (32)$$

$$\sigma_{I_{norm}}(k) = \frac{\sigma_I(n, k) \cdot \overline{\text{Brightness}}}{\text{Brightness}(n)} \quad (33)$$

$$bkgstd_{norm}(k) = \frac{bkgstd(n,k) \cdot \overline{\text{Brightness}}}{\text{Brightness}(n)} \quad (34)$$

where $$\overline{\text{Brightness}} = \frac{1}{2 \cdot N} \sum_{n=1}^{2 \cdot N} \text{Brightness}(n), \quad (35)$$

is the average brightness of all channels. In Eq. 34, $bkgstd_{norm}$(k) is the normalized standard background error of the k'th feature.

To simplify detrending and inter-slide error correction, an intensity forward transformation can be applied. A preferred transformation is the error-model based transformation that is described in Section 5.4., infra, and in U.S. patent application Ser. No. 10/354,664, filed on Jan. 30, 2003, which is incorporated by reference herein in its entirety. In the transformed domain, the intensity variance is more homogenous across all intensity levels.

In the detrending step, the intensity dependant non-linearity in all channels is minimized. In one embodiment, an average feature intensity profile of all intensity channels is first calculated. This average profile is then used as the reference in correcting non-linearity. Each intensity channel profile is compared to the average profile. If there is non-linearity between the two, the channel profile, but not the average profile, is adjusted to minimize the non-linearity.

In a preferred embodiment, an invariant sub-set (ISS) of features, i.e., features that are considered unchanged between the individual channel and the average profile, is identified. In one embodiment, intensities are rank ordered and compared among channel profiles and the averaged profile. Features that rank similarly within a small range are considered unchanged. In a preferred embodiment, the method described in Schadt et al., 2001, J. Cell. Biochem. Supp. 37:120-125, which is incorporated by reference herein in its entirety, can be employed to find ISS.

In one embodiment, a smoothing spline method is used to obtained the non-linearity curve of the intensity difference vs. mean intensity of the channel profile and the average profile (Schadt et al., 2001, J. Cell. Biochem. Supp. 37:120-125). In another embodiment, a piece-wise linear method is used to fit the non-linearity curve. Straight lines connect these points from one bin to the next. In a preferred embodiment, transformed intensities of all ISS features, both positive and negative, are cut into small range bins. The total number of bins can be defined by the round number of the number of features divided by a chosen number, e.g., 1000. Preferably, the number of bins is between a minimum of about 2 for arrays with a small number of features and a maximum of about 12 for arrays with a large number of features. Mean difference between an individual channel and the average profile of the transformed feature intensities in each bin is calculated. The mean difference is placed as a point at the center of the bin (see FIG. 3). The piecewise linear curve is a function of mean transformed intensity mean_i. This is the estimated nonlinearity function, nonlinear_diff(n, mean_i), between the n'th profile and the averaged profile.

For all features in each individual channel profile, their transformed intensities are corrected by the nonlinearity curve:

$$corr\_trans\_I(n,k) = trans\_I(n,k) - \text{nonlinear\_diff}(trans\_I(n,k)) \quad (36)$$

When using two-color ratio arrays to compare two samples, imperfectness in microarray slides may be corrected. For example, many unwanted microarray measurement variations come from the manufacturing quality variation and hybridization process variation. The imperfection is usually spot and chip dependent. Oftentimes, the variations have similar effects on both red and green measurements. When ratios of the red and the green intensities of the same chip are computed, the effects caused by the slide imperfection may often be canceled. As the result, the spot/chip dependent variations have relatively small effects on intra-slide differential expression measurements in ratios or log-ratios of the two-color arrays.

But when splitting the two channels and using them as individual intensity profiles together with split profiles from other two-color microarrays, the spot/chip dependent variations may not cancel out anymore. Intensity measurement errors caused by the imperfectness reduce the precision of the inter-slide intensity comparison.

When common control samples are hybridized in one channel of the two-color microarrays, such as in the pooled design, the reference channel can be used to reduce the inter-slide error significantly. An inter-slide error correction method was first introduced in U.S. Pat. No. 6,691,042 for building one virtual ratio profile from two two-channel profiles. In the ratio-splitter of this disclosure, two-channel profiles are split to provide intensity profiles instead of ratio profiles.

As an example to demonstrate the concept of inter-slide error correction, FIG. 4 is an intensity-difference plot of a same-vs-same chip in the transformed domain. FIG. 5 is a replicated chip of the one in FIG. 4. After splitting these two chips, the two profiles from the red channel are paired together and their difference is shown in FIG. 6, and the two profiles from the green channel are paired together and their difference is shown in FIG. 7. Because of the inter-slide errors, the same-vs-same differences in FIG. 6 and FIG. 7 have larger spread (Y axis) than those of the same-slide pairs as shown in FIG. 4 and FIG. 5. Large spread indicates lower precision in expression measurements when intensity data of different chips are compared.

However, when the two same-vs-same differences in FIG. 6 and FIG. 7 are compared (see FIG. 8), it can be seen that they are strongly correlated. This is surprising because the same-vs-same difference is expected to be random. The strong correlation shown in FIG. 8 indicates that the two intensity measurements from one chip in FIG. 4 or FIG. 5 have correlated variations. This correlation may come from the common-mode random error within a slide, and may be spot and slide dependent. This common-mode error does not affect the comparison between channels measured with the same slide. On the other hand, the common-mode errors in different chips are not related. When two intensity profiles from two different slides are compared, the common-mode error becomes differential-mode error that may increase the inter-slide error in the comparisons of the split intensities. Such inter-slide error is undesirable.

FIG. 8 also shows that the inter-slide error can be estimated if the two split chips have one channel in common. For example, if the sample in the green channel is the common reference control, the difference between the two green channel profiles shown in FIG. 7 provides valuable information about the inter-slide error between the two slides. This inter-slide error may be used as the error between the two red channel profiles shown in FIG. 6, because FIG. 6 and FIG. 7 are highly positively correlated (FIG. 8). The systematic inter-slide error in the red channel can be estimated by the same-vs-same comparison of the green channel. If the difference of the green common reference channel is removed from the difference of the red channel, the inter-slide variation of in the red channel is significantly reduced. This removal is termed inter-slide error correction (ISEC). FIG. 9 is the same red channel difference shown in FIG. 6 after ISEC. It can be seen that after ISEC the difference spread in the red channel is much narrower. This indicates that ISEC improves the precision of intensity measurement. The transformed intensity difference after ISEC in FIG. 9 is even tighter than those from the same chips in FIG. 4 and FIG. 5. This is because there is no fluor-bias when we use only one color in comparison.

In one embodiment, when some of the input ratio scans have common reference controls in the green channel and others have common controls in the red channel, to avoid mixing the fluor bias in inter-slide error estimation, the scans of common controls in different fluorescence colors are processed separately (FIG. 10), i.e., scans having common controls of the same color are grouped together and processed using ISEC. For simplicity reasons, the ISEC algorithm is described below without specifying the fluor-color of the common control. FIG. 11 shows a flowchart of an exemplary embodiment of the ISEC algorithm used in the ratio-splitter. The symbol "ref" denotes the data from the common reference control channel and the symbol "exp" denotes the experiment data in the other channel.

In ISEC, the mean and the standard-deviation of the reference intensity are first computed:

$$\text{avg\_ref}(k) = \frac{1}{N_{ref}} \sum_{n=1}^{N_{ref}} \text{trans\_I\_ref}(n, k) \tag{37}$$

$$\text{std\_ref}(k) = \sqrt{\frac{1}{N_{ref}-1} \sum_{n=1}^{N_{ref}} (\text{trans\_I\_ref}(n, k) - \text{avg\_ref}(k))^2} \tag{38}$$

where n is the index of chips, k is the index of features, $N_{ref}$ is the total number of reference channels in a given color.

The difference of the individual common reference intensity and the averaged reference intensity is:

$$\text{ref\_diff}(n,k) = \text{trans\_I\_ref}(n,k) - \text{avg\_ref}(k) \tag{39}$$

The adjusted experiment intensity is calculated by subtracting the difference from the original intensity:

$$\text{adj\_I}(n,k) = \text{trans\_I\_exp}(n,k) - \text{ref\_diff}(k) \tag{40}$$

The error of the adjusted experiment intensity is then determined. When $N_{ref}$ is large, std_ref(k) in Equation 38 is an unbiased estimation of the standard deviation of the common reference. However, when $N_{ref}$ is small, std_ref(k) is not reliable. In one embodiment, to stabilize the error estimation for the common reference, the scattered error std_ref(k) is combined with the error model estimated error $\sigma_{trans\_I}(n\ k)$. In a preferred embodiment, the combined error estimation is:

$$\text{mixed}\_\sigma_{trans\_I\_ref}(n, k) = \frac{\sigma_{trans\_I\_ref}(n, k) + (N_{ref} - 1) \cdot \text{std\_ref}(k)}{N_{ref}} \tag{41}$$

The error of the adjusted experiment intensity in Equation 40 can be estimated as:

$$\sigma_{adj\_I}(n, k) = \sqrt{\sigma^2_{trans\_I\_exp}(n, k) + \text{mixed}\_\sigma^2_{trans\_I\_ref}(n, k) - 2 \cdot Cor(k) \cdot \sigma_{trans\_I\_exp}(n, k) \cdot \text{mixed}\_\sigma_{trans\_I\_ref}(n, k)} \tag{42}$$

In Equation 42, Cor(k) is an estimated correlation coefficient between the experiment and the reference channels. FIG. 8 shows the inter-slide error correction. This correlation is intensity dependent. When intensity is high, the correlation is strong. When intensity is low and near the background noise level, the correlation is weak. In one embodiment, a simple correlation model is built to estimate Cor(k):

$$Cor(k) = Cor\text{Max} \cdot \left(1 - e^{-0.5 \cdot \left(\frac{\text{avg\_ref}(k)}{\text{avg\_bkgstd}}\right)^2}\right) \tag{43}$$

where the average background standard error avg_bkgstd is computed as $$\text{avg\_bkgstd} = \frac{1}{K} \sum_{k=1}^{K} \left(\frac{1}{N_{ref}} \sum_{n=1}^{N_{ref}} \text{trans\_bkgstd}(n, k)\right) \tag{44}$$

Parameter CorMax in Equation 43 defines the maximum correlation, CorMax=0.5 by default. CorMax can have value between 0 and 1. Smaller CorMax makes the error estimation more conservative. While larger CorMax produces smaller error estimation, which is more aggressive.

When the common-reference intensity is very low, e.g., near or below the background noise level, the correlation between the experiment and the reference channels decreases significantly. In this case, the ISEC method in Equation 18 may no longer be desired and may add noise in the result. Thus, it is preferable that when intensity is near zero, ISEC should be phased out. In one embodiment, a weighting model is used in the ratio splitter to smoothly phase out ISEC. In a preferred embodiment, the weighting function is:

$$\text{Weights}(k) = 1 - e^{-0.5 \cdot \left(\frac{\text{avg\_ref}(k)}{\text{avg\_bkgstd}}\right)^2} \tag{45}$$

When avg_ref(k) is large, Weights(k) is one. When avg_ref(k) is below avg_bkgstd, Weights(k) is near zero. The original transformed intensity is combined with the adjusted intensity to get the final transformed experiment intensity:

$$\text{trans\_I\_exp}(n, k) = \tag{46}$$
$$(1 - \text{Weights}(k)) \cdot \text{trans\_I\_exp}(n, k) + \text{Weights}(k) \cdot \text{adj\_I}(n, k)$$

$$\sigma_{trans\_I\_exp}(n, k) = \tag{47}$$
$$\sqrt{(1 - \text{Weights}(k)) \cdot \sigma^2_{trans\_I\_exp}(n, k) + \text{Weights}(k) \cdot \sigma^2_{adj\_I}(n, k)}$$

Ratio splitter provides users of two-color microarrays the maximum flexibility in analyzing the data. They can be compared in ANOVA, trend, and clustering methods. Profiles from the ratio-splitter output can be used in building new intensity or ratio experiments of any combinations.

It is shown in the Examples that the ISEC method makes the quality of split intensity profiles significantly better. It is preferable that common reference controls are employed whenever possible to allow achieving more accurate results in splitting the ratio data. In addition, with common references available, the commonly used fluor-reversal procedure may become unnecessary. If all experimental samples are in one color and all common reference controls in the other color, the color bias will have no effect in differential analysis of the split intensities. This may permit a saving of up to 50 percent of chips.

In the fluor-reversal case, to avoid mixing the fluorescent color bias in the ISEC process, two-channel data with red and the green references are processed in two separate groups. After ratio split, the intensity replicates of two different colors can be combined together to form an intensity experiment free of color bias. Otherwise the color bias will affect downstream analyses if different colors are not carefully separated or combined. Methods for combining fluor-reversed pair of profiles are known in the art; see, e.g., U.S. Pat. No. 6,691,042.

Preferably, the ratio splitter is used to process ratio data that have the raw scan data with an internal error model. The internal error model not only provides the intensity error estimation, but also the parameters for intensity transformation applied in the ratio splitter. It is less preferred to apply the ratio splitter to data loaded from an external error model or without an error model.

5.4. Data Transformations

The methods of the invention can be used to analyze transformed measurements. Measured data obtained in a microarray experiment often contain errors due both to the inherent stochastic nature of gene expression and to measurement errors from various external sources. The many sources of measurement error that may occur in a measured signal include those that fall into three categories—additive error, multiplicative error, and Poisson error. The signal magnitude-independent or intensity-independent additive error includes errors resulted from, e.g., background fluctuation, or spot-to-spot variations in signal intensity among negative control spots, etc. The signal magnitude-dependent or intensity-dependent multiplicative error, which is assumed to be directly proportional to the signal intensity, includes errors resulted from, e.g., the scatter observed for ratios that should be unity. The multiplicative error is also termed fractional error. The third type of error is a result of variation in number of available binding sites in a spot. This type of error depends on the square-root of the signal magnitude, e.g., measured intensity. It is also called the Poisson error, because it is believed that the number of binding sites on a microarray spot follows a Poisson distribution, and has a variance which is proportional to the average number of binding sites.

5.4.1. Error Model Based Transformations

In a preferred embodiment, measured data are first transformed by an error model based transformation before analyzed by the improved ANOVA method of the invention. The results from the ANOVA analysis can be transformed back by an appropriate inverse transformation. An error model based data transformation method is described in U.S. patent application Ser. No. 10/354,664, filed on Jan. 30, 2003, which is incorporated by reference herewith in its entirety.

5.4.1.1. Error Models

Errors in measured data can be described by error models (see, e.g., Supplementary material to Roberts et al, 2000, Science, 287:873-880; and Rocke et al., 2001, J. Computational Biology 8:557-569). In preferred embodiments, an error model (see, e.g., Supplementary material to Roberts et al, 2000, Science, 287:873-880; and Rocke et al., 2001, J. Computational Biology 8:557-569) contains two or three error terms to describe the dominant error sources. In a two-term error model, a first error term is used to describe the low-level additive error which comes from, e.g., the background of the array chip. Since this additive error has a constant variance, in this disclosure, it is also called the constant error. The constant error is independent from the hybridization levels of individual spots on a microarray. It may come from scanner electronics noise and/or fluorescence due to nonspecific binding of fluorescence molecules to the surface of the microarray. In one embodiment, this constant additive error is taken to have a normal distribution with a mean bkg and a standard deviation $\sigma_{bkg}$. After background level subtraction, which is typically applied in microarray data processing, the additive mean bkg becomes zero. In this disclosure, it is often assumed that the background intensity offset has been corrected. An ordinary skilled artisan in the art will appreciate that in cases where the background mean is not corrected, the methods of the invention can be used with an additional step of making such a correction.

The second error source is the multiplicative error that is the combined result of the speckle noise inherent in the coherent laser scanner and the fluorescence dye related noise. The multiplicative error is also called fractional error because its level is directly proportional to the magnitude of the measured signal, e.g., the measured intensity level. It is the dominant error source at high intensity levels. In one embodiment in which the measured signal is obtained from a microarray experiment, the standard deviation of the fractional error in the k'th spot can be approximated as $$\sigma_{frac}(k) \approx a \cdot x(k) \tag{48}$$

where $x(k)$ is the measured intensity in the k'th spot. The constant a in Equation 4 is termed fractional error coefficient, and describes the proportion of the fractional error to the intensity of the measured signal. In one embodiment, the constant has a value in the range of 0.1 to 0.2. This constant may vary depending on the particular microarray technology used for obtaining the measured signal and/or the particular hybridization protocol used in the measurement. In one embodiment, parameter a is determined during the error building phase by measuring the variance of the log ratio near the high intensity side in a same-vs.-same ratio experiment where the intensities in the ratio numerator and denominator come from the same sample and treatment. At high intensities, the variance of log ratio $x_1$ over $x_2$ relates to parameter a:

$$\mathrm{Var}\{\ln(x_1/x_2)\} \approx \frac{(a \cdot x_1)^2}{x_1^2} + \frac{(a \cdot x_2)^2}{x_2^2} = 2 \cdot a^2 \tag{49}$$

when $x_1$ and $x_2 \gg \sigma_{bkg}$. In one embodiment, $x_1$ and $x_2$ are at least 4, 10, 50, 100, or 200 times $\sigma_{bkg}$.

In a two-term error model, the measurement error in a measured signal, e.g., measured intensity, x(k) can be defined as $$\sigma_x(k) = \sqrt{\sigma_{bkg}(k)^2 + \sigma_{frac}(k)^2} \approx \sqrt{\sigma_{bkg}(k)^2 + a^2 \cdot x(k)^2} \quad (50)$$

In a preferred embodiment of the invention, the background noise variances in Equation 6 are taken as slightly different in different microarray spots or regions of a microarray chip. In one embodiment, the difference is less than 20%, 10%, 5%, or 1%.

In a three-term error model, an extra square-root term is included to describe measurement errors originated from variation in the number of available binding sites in a microarray spot. This term is also called the Poisson term. In one embodiment, without knowledge of actual number of binding sites in a microarray spot, the measured intensity is used to provide an estimate of the average number of binding sites. In such an embodiment, the Poisson error can be approximated as $$\sigma_{Poisson}(k) \approx b \cdot \sqrt{x(k)} \quad (51)$$

where parameter b is an overall proportional factor, termed Poisson error coefficient. In a three-term error model, the measurement error in a measured signal, e.g., a measured fluorescence intensity, x(k) can be defined as $$\sigma_x(k) = \sqrt{\sigma_{bkg}(k)^2 + \sigma_{Poisson}(k)^2 + \sigma_{frac}(k)^2} \quad (52)$$
$$\approx \sqrt{\sigma_{bkg}(k)^2 + b^2 \cdot x(k) + a^2 \cdot x(k)^2}$$

In a preferred embodiment, during error model development, when $\sigma_{bkg}$ and parameter a have been determined, parameter b in Equation 52 is determined by measuring the intensity variance in the middle intensity ranges of the same-vs.-same experiments. In one embodiment, the intensity variance is measured in the 25 to 75 percentile range, 35 to 65 percentile range, or 45 to 50 percentile range for determination of b.

In a preferred embodiment, after the error model development phase, parameters a and b are fixed for an error model under a given microarray technology and experiment protocol. The background noise $\sigma_{bkg}$ can be estimated for each particular microarray experiment. In another preferred embodiment, when a set of replicate experiments are carried out, the background noise $\sigma_{bkg}$ for the set can be obtained by averaging the background noise estimated for each of the replicate experiments.

The two-term error model as described by Equation 50 can been seen as a simplified version of the three-term error model described by Equation 52 by setting the Poisson parameter b to zero. In this disclosure, Equation 52 is used as the general mathematical description of error models. It will be apparent to an ordinarily skilled artisan that any results obtained based on Equation 52 are also applicable to a two-term error model by setting the Poisson parameter b to zero.

It will be apparent to an ordinarily skilled artisan that other methods may also be used to determine an error model (see, e.g., Rocke et al., 2001, J. Computational Biology 8:557-569).

5.4.1.2. Intensity Transformations

It is clear from Equation 8 that microarray intensity measurements do not meet the constant-variance requirement. There are different measurement errors (or variances) in different intensities. The intensity error is a function of intensity itself. To overcome this problem, a function $f()$ is needed to transform measured data, e.g. the intensity data, x to a new domain y in which the variance becomes a constant. All analysis and data processing can then be carried out in the transformed domain. In a preferred embodiment, such a transformation is described as $$y(k) = f(x(k)), \text{ for all } x \text{ and} \quad (53)$$

$$\sigma_y(k) \approx C, \text{ for all x where C is a constant.} \quad (54)$$

Preferably the transformation works for both positive and negative (e.g, negative signals obtained after background subtraction) x. More preferably the transformation meets the following additional constraints:

(i) Monotonic: If x(k1)>x(k2), then y(k1)>y(k2) for all x;
(ii) Zero intercept: $f(0)=0$; and
(iii) Smooth: The first and the second derivatives of the function f should be continuous functions.

Still more preferably, an inverse transformation function g exists so that the transformed data in the transformed domain can be transformed back to the original domain. The inverse transformation does the following operation:

$$x(k) = g(y(k)), \text{ for all } y \quad (55)$$

Preferably, the inverse transformation function g meets above four constraints as well. In one embodiment, the error in the inversely transformed intensity can be determined when the first derivative $f'()$ of the forward transformation function $f$ is available:

$$\sigma_x(k) \approx \frac{\sigma_y(k)}{df(x(k))/dx(k)} = \frac{\sigma_y(k)}{f'(x(k))} \quad (56)$$

It is most preferable that the forward transformation function $f$ its first derivatives $f'$, and the inverse transformation function g are all in analytical closed-forms.

A transformation based on an error model is provided and used to transform measured data obtained in an experiment to a transformed domain such that the measurement errors in transformed data are equal to the measurement errors in the measured data normalized by errors determined based on an error model. As used in this disclosure, such an measurement error, i.e., a measurement error which equals the measurement error in the measured signal normalized by an error determined based on an error model, is also referred to as a normalized error. Any suitable error model can be used in the invention. In a preferred embodiment, the error model is a two-term or a three-term error model described in Section 5.4.1.1. In a particularly preferred embodiment, the variance of the transformed data in the transformed domain is close to a constant. More preferably, the transformation meets all requirements discussed in Section 5.4.1.2. The basic concept of the new transformation method is to apply an error model to normalize errors in real measurements, e.g., standard deviations in measured data, such that the normalized errors are close to a constant. Then a transformation function $f()$ is found by the integration of the normalization function. The methods are applicable to any set of measured data whose errors can be described by a particular error model.

In a specific embodiment, the real measurement standard deviation Δx is for the positive intensity x>0. The real standard deviation Δx is usually known before the transformation. An error model in Equation 52 provides (x that is an estimate of the real standard deviation Δx for different intensities. In one embodiment, Δx is an error determined by the experiment. In another embodiment, Δx is calculated using an error model of the experiment. In a preferred embodiment, Δx is chosen to be the larger of an experimentally determined error or an error model-calculated error. Assuming the transformed standard deviation is Δy, the following approximation relates the two errors with the first derivative function of the transformation:

$$f'(x) = \frac{dy}{dx} \approx \frac{\Delta y}{\Delta x} \tag{57}$$

If the equation is rearranged, one obtains $$\Delta y \approx \Delta x \cdot f'(x) \tag{58}$$

Because Equation 8 is an approximation of Δx, if a normalization function y' is defined as follows:

$$y' = f'(x) = \frac{1}{\sqrt{c^2 + b^2 \cdot x + a^2 \cdot x^2}}, \text{ for } x > 0, \tag{59}$$

where a, b, and c are defined as in Section 5.4.1.1, one can expect that the variance of y is close to a constant.

Equation 15 provides an analytical form of the first derivative function of the desired transformation. To obtain the transformation function itself, both sides of Equation 15 are integrated:

$$y = f(x) = \int f'(x) \cdot dx = \int \frac{dx}{\sqrt{c^2 + b^2 \cdot x + a^2 \cdot x^2}}, \text{ for } x > 0 \tag{60}$$

The integral in Equation 60 does have an analytical solution. The solution is described by equation $$y = f(x) = \frac{\ln\left(\frac{b^2 + 2 \cdot a^2 \cdot x}{a} + 2 \cdot \sqrt{c^2 + b^2 \cdot x + a^2 \cdot x^2}\right)}{a} + d, \text{ for } x > 0 \tag{61}$$

Applying the zero intercept constraint (ii) in Section 5.4.1.2, i.e., y=0 when x=0, the constant d in Equation 61 is found to be $$d = \frac{-\ln\left(\frac{b^2}{a} + 2 \cdot c\right)}{a} \tag{62}$$

As indicated in Equation 55 in Section 5.4.1.2, preferably one finds the inverse transformation function g(y) so that the transformed intensity y can be converted back to the original x scale whenever necessary. By using linear algebra or a symbolic-solution software, such as Maple, one finds $$x = g(y) = \frac{-\left(\begin{array}{c}4 \cdot a^2 \cdot c^2 - a^2 \cdot e^{2a \cdot (y-d)} + \\ 2 \cdot a \cdot b^2 \cdot e^{a \cdot (y-d)} - b^4\end{array}\right)}{4 \cdot a^3 \cdot e^{a \cdot (y-d)}}, \text{ for } y > 0 \tag{63}$$

To complete the forward and the inverse transformation pair for both intensity and its error, the standard deviation of the inversely transformed intensity can be estimated by using Equation 56.

In a specific embodiment, the transformation function can be further defined to be symmetric to zero for all x. When x<0, the absolute value |x| is used to replace x in the forward transformation in Equation 61 and to give a negative sign to the result y. In the inverse transformation in Equation 63, when y<0, the absolute value |y| is used to replace y and to give a negative sign to the result x. Under the forward transformation, the estimated transformed error $\sigma_y$ is one over all intensity ranges of x or y, so that constant C=1 in Equation 54. The transformation also meets all other requirements and constraints described above. In addition, the transformation has several other interesting properties:

$$y = f(x) \approx \frac{\ln(4 \cdot a \cdot x)}{a}, \text{ when } x \text{ is very large} \tag{64}$$

$$y' = f'(x) \approx \frac{1}{c}, \text{ when } |x| \text{ is very small} \tag{65}$$

The transformation described in this section is applicable to any measured data in which the errors can be described by a three-term error model. In preferred embodiments, the measured data are measured in a microarray gene expression experiment. In other preferred embodiments, the measured data are measured in a protein array experiment or a 2D gel protein experiment.

In one preferred embodiment, the measured data are signal data obtained in an microarray experiment in which two spots or probes on a microarray are used for obtaining each measured signal, one comprising the targeted nucleotide sequence, i.e., the target probe (TP), e.g., a perfect-match probe, and the other comprising a reference sequence, i.e., a reference probe (RP), e.g., a mutated mismatch probe. The RP probe is used as a negative control, e.g., to remove undesired effects from non-specific hybridization. In one embodiment, the measured signal obtained in such a manner is defined as the difference between the intensities of the TP and RP, $x_{TP}-x_{RP}$. In such an embodiment, the fractional error, the Poisson error, and the background constant error $\sigma_{bkg}$ are described respectively according to equations $$\sigma_{frac}(k) \approx a \cdot x(k) = a \cdot \sqrt{x_{TP}(k)^2 + x_{RP}(k)^2} \tag{66}$$

$$\sigma_{Poisson}(k) \approx b \cdot \sqrt{x(k)} = b \cdot (x_{TP}(k)^2 + x_{RP}(k)^2)^{\frac{1}{4}} \tag{67}$$

$$\sigma_{bkg}(k) = \sqrt{\sigma_{bkg\_TP}(k)^2 + \sigma_{bkg\_RP}(k)^2} \tag{68}$$

The transformation described in this section remains applicable if Equations 66-68 are used to calculate the fractional error, the Poisson error and the background constant error, respectively. In one embodiment, the TP probe is a perfect-match probe (PM), and the RP probe is a mismatch probe (MM) (see, e.g., Lockhart et al., 1996, *Nature Biotechnology* 14: 1675). In another embodiment, the RP probe is a reverse probe of the TP probe, i.e., the RP probe has a sequence that is the reverse complement of the TP probe (see, Shoemaker et al., U.S. patent application Ser. No. 09/781,814, filed on Feb. 12, 2001; and Shoemaker et al., U.S. patent application Ser. No. 09/724,538, filed on Nov. 28, 2000).

It will be apparent to one skilled in the art that although the transformations as described by equations 61 and 63 are preferably carried out using parameters a, b, and c chosen based on a three-term error model, the transformations as described by equations 61 and 63 can also be used by replacing parameters a, b, and c with other parameters. Embodiments using such parameters are also encompassed by the present invention.

5.4.2. Other Transformations

Another transformation that can be used to transform the data before ANOVA analysis is a logarithm transformation:

$$y(k) = f(x(k)) = \ln(x(k)), \text{ for } x > 0 \tag{69}$$

In Equation 52, when intensity x is very high, the fractional error is the dominant error source. In this case, the standard deviation of y is approximately a constant:

$$\sigma_y(k) \approx \sigma_x(k) \cdot f'(x(k)) \approx \frac{a \cdot x(k)}{x(k)} = a, \text{ when } x \text{ is very large} \tag{70}$$

When intensity x is low, the standard deviation of y is inversely proportional to x, and is approaching infinity:

$$\sigma_y(k) \approx \sigma_x(k) \cdot f'(x(k)) \approx \frac{\sigma_{bkg}(k)}{x(k)}, \text{ when } x \text{ is very small} \tag{71}$$

Still another transformation that can be used to transform the data is a piecewise hybrid transformation (see, e.g., D. Holder, et al, "Quantitation of Gene Expression for High-Density Oligonucleotide Arrays: A SAFER Approach", presented in Genelogic Workshop on Low Level Analysis of Affymetrix Genechip® data, Nov. 19, 2001, Bethesda, Md., http://oz.berkeley.edu/users/terry/zarray/Affy/GL_Workshop/Holder.ppt). This hybrid transformation uses a linear function at the low intensity side and a logarithm function for high intensities. An arbitrary parameter c' defines the boundary between the linear and the logarithmic functions. Equation 72 is the mathematical definition of the hybrid transformation function.

$$y(k) = f(x(k)) = x(k), \text{ for } 0 \leq x(k) < c'$$
$$y(k) = f(x(k)) = c' \cdot \ln(x(k)/c') + c', \text{ for } x(k) > c'$$
$$y(k) = f(x(k)) = 0, \text{ for } x(k) < 0 \tag{72}$$

In one embodiment, parameter c' in Equation 72 is chosen to be 20. Errors of the hybrid-transformed intensities can be estimated as $$\sigma_y(k) \approx \sigma_x(k) \cdot f'(x(k)) = \sigma_x(k), \text{ for } 0 \leq x(k) < c'$$
$$\sigma_y(k) \approx \sigma_x(k) \cdot f'(x(k)) = c' \cdot \sigma_x(k)/x(k), \text{ for } x(k) \geq c' \tag{73}$$

5.5. Implementation Systems and Methods

The analytical methods of the present invention can preferably be implemented using a computer system, such as the computer system described in this section, according to the following programs and methods. Such a computer system can also preferably store and manipulate a compendium of the present invention which comprises a plurality of perturbation response profiles and which can be used by a computer system in implementing the analytical methods of this invention. Accordingly, such computer systems are also considered part of the present invention.

An exemplary computer system suitable from implementing the analytic methods of this invention is illustrated in FIG. 49. Computer system 4901 is illustrated here as comprising internal components and as being linked to external components. The internal components of this computer system include a processor element 4902 interconnected with a main memory 4903. For example, computer system 4901 can be an Intel Pentium®-based processor of 200 MHZ or greater clock rate and with 32 MB or more main memory. In a preferred embodiment, computer system 4901 is a cluster of a plurality of computers comprising a head "node" and eight sibling "nodes," with each node having a central processing unit ("CPU"). In addition, the cluster also comprises at least 128 MB of random access memory ("RAM") on the head node and at least 256 MB of RAM on each of the eight sibling nodes. Therefore, the computer systems of the present invention are not limited to those consisting of a single memory unit or a single processor unit.

The external components can include a mass storage 4904. This mass storage can be one or more hard disks that are typically packaged together with the processor and memory. Such hard disk are typically of 1 GB or greater storage capacity and more preferably have at least 6 GB of storage capacity. For example, in a preferred embodiment, described above, wherein a computer system of the invention comprises several nodes, each node can have its own hard drive. The head node preferably has a hard drive with at least 6 GB of storage capacity whereas each sibling node preferably has a hard drive with at least 9 GB of storage capacity. A computer system of the invention can further comprise other mass storage units including, for example, one or more floppy drives, one more CD-ROM drives, one or more DVD drives or one or more DAT drives.

Other external components typically include a user interface device 4905, which is most typically a monitor and a keyboard together with a graphical input device 4906 such as a "mouse." The computer system is also typically linked to a network link 4907 which can be, e.g., part of a local area network ("LAN") to other, local computer systems and/or part of a wide area network ("WAN"), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components that are also shown schematically in FIG. 49. The software components comprise both software components that are standard in the art and components that are special to the present invention. These software components are typically stored on mass storage such as the hard drive 4904, but can be stored on other computer readable media as well including, for example, one or more floppy disks, one or more CD-ROMs, one or more DVDs or one or more DATs. Software component 4910 represents an operating system which is responsible for managing the computer system and its network interconnections. The operating system can be, for example, of the Microsoft Windows™ family such as Windows 95, Window 98, Windows NT or Windows 2000. Alternatively, the operating software can be a Macintosh operating system, a UNIX operating system or the LINUX operating system. Software components 4911 comprises common languages and functions that are preferably present in the system to assist programs implementing methods specific to the present invention. Languages that can be used to program the analytic methods of the invention include, for example, C and C++, FORTRAN, PERL, HTML, JAVA, and any of the UNIX or LINUX shell command languages such as C shell script language. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

Software component 4912 comprises any analytic methods of the present invention described supra, preferably programmed in a procedural language or symbolic package. For example, software component 4912 preferably includes programs that cause the processor to implement steps of accepting a plurality of measured expression profiles and storing the profiles in the memory. For example, the computer system can accept exon expression profiles that are manually entered by a user (e.g., by means of the user interface). More preferably, however, the programs cause the computer system to retrieve measured expression profiles from a database. Such a database can be stored on a mass storage (e.g., a hard drive) or other computer readable medium and loaded into the memory of the computer, or the compendium can be accessed by the computer system by means of the network 4907.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

6. EXAMPLES

The following examples are presented by way of illustration of the present invention, and are not intended to limit the present invention in any way.

6.1. Verification Data

To verify the re-ratioer and the ratio splitter, the microarray data as described in He et al., 2003, Bioinformatics 19:956-965 were used. In this data set, replicated and fluor-reversed two-color Agilent microarrays were hybridized to many different tissue samples in a pooled-looped design. FIG. 12 shows part of the design that was used in the verification examples of the examples. There were four samples. Pool 1 was the near common reference sample that included Tissue C (Thymus) and Tissue D (Spleen) and 8 other different tissues. Pool 2 was the distant common reference sample that did not include Tissue C and Tissue D. Pool 1+$\epsilon$C was a sample that included an additional amount ($\epsilon$=0.3) of Tissue C in Pool 1. Pool 1+$\epsilon$D was a sample that included an additional amount of Tissue D in Pool 1. Edges between samples are two-color microarray hybridizations. Numbers on the edges are the last three digits of chip bar codes. The "−" sign indicates fluor-reversal chip. A total of 24 chips were included in the design. Most of the ratio experiments had two fluor-reversal pairs, except the same-vs-same experiment where there was one fluor-reversal pair.

In the rest of the example section, "Pool 1+$\epsilon$C" will be referred to as sample C and "Pool 1+$\epsilon$D" will be referred to as sample D. As discussed in the following examples, the "virtual D/C" from the re-ratioer or the ratio-splitter was compared to the real D/C measured from direct hybridizations. Some of the real ratio experiments that were used as verification references are shown in FIG. 13-16. The same threshold p-value<0.01 was applied to all of them in detecting differentially expressed features.

6.2. Precision and Accuracy of the Re-Ratioer

6.2.1. Results with Near Reference Pool

FIG. 17 shows the re-ratioer result of a virtual same-vs-same experiment (C-vs-C). This result came from two real chips of Pool 1 vs. C of the same color. The overall spread of log ratios is tight except at the low intensity end. The large log-ratio variation at low intensities is the major limitation of the re-ratioer. The large variation was caused by the extra noise introduced by the common reference at low intensities.

FIG. 18 is the re-ratioer result of a virtual same-vs-same experiment (C-vs-C) of the same near pool (Pool 1) but different colors. Comparing FIG. 17 and FIG. 18, it can be seen that color biases caused significant log-ratio variations when two different color-polarity chips were used in the re-ratioer.

FIG. 19 is the re-ratioer result of a virtual same-vs-same experiment (C-vs-C) from two fluor-reversally combined real ratio experiments of the same near pool. Combined fluor-reversal experiments helped to reduce the variations in the overall re-ratio result. But at the low intensity end, the wide spread still exists.

FIG. 20 is the re-ratio result of a virtual different-vs-different (C-vs-D) experiement of the same color and the same near pool. FIG. 21 is the re-ratio result of a virtual different-vs-different (C-vs-D) experiement from two combined fluor-reversal real ratio experiments. Combined real experiments had smaller measurement errors, and the resulted virtual experiment had higher sensitivity in detecting differential expressions.

In order to verify the accuracy of the re-ratioer, a reference standard is needed. A combined fluor-reversal real C-vs-D experiment (+97, −98) was used as the standard. FIG. 22 shows the comparison of log-ratios between the reference standard and one real combined experiment shown in FIG. 16. It can be seen that the reference standard and the real combined experiment of FIG. 16 show a high log-ratio correlation in their signatures. It provides an accuracy standard for re-ratioer and ratio-splitter performance evaluation.

FIG. 23 is a comparison between C-vs-D log-ratio of a re-ratio virtual experiment (shown in FIG. 20) and the log-ratio of the reference standard. FIG. 24 is a comparison between C-vs-D log-ratio of a re-ratio experiment of combined experiments (shown in FIG. 21) and the log-ratio of the reference standard. The re-ratio result of the combined experiments with the near pool shows similar accuracy as the reference standard. FIG. 25 is the comparison between two C-vs-D log-ratios of two re-ratio combined experiments. The two re-ratio results were consistent with each other, but not as good as those from real experiments in FIG. 22.

6.2.2. Results with Distant Reference Pool

Results shown in the previous section came from data of a near pool, i.e. sample C and sample D were part of the pooled sample (Pool 1). In this example results from data with a distant pool as the common reference, i.e., sample C and sample D were not included in the reference pool, are described.

FIG. 26 shows the re-ratio result of a virtual same-vs-same experiment (C-vs-C). This result came from measurements obtained using two real chips of Pool 2 vs. C of the same color. The overall spread of log ratios is larger than that from the near pool shown in FIG. 17. FIG. 27 is the re-ratio result of a virtual same-vs-same experiment (C-vs-C) from two fluor-reversally combined real ratio experiments with the same distant pool. Combined fluor-reversal experiments helped reducing the variations in the overall re-ratio result. But the result of the distant pool data also exhibits wider spread in log ratios than that of the near pool as shown in FIG. 19. FIG. 26 and FIG. 27 indicate that using a distant pool reduced the precision in re-ratio results.

FIG. 28 is the re-ratio result of a virtual different-vs-different (C-vs-D) experiment from two combined fluor-reversal real ratio experiments with the distant pool (Pool 2) as the common reference. FIG. 29 is a comparison between log-ratio of this re-ratio experiment and the log-ratio of the reference standard. Comparing to FIG. 24, it can be seen that the re-ratio result of combined experiments with the distant pool as the common reference is quite different from the reference standard. This demonstrates that the accuracy of the re-ratio result employing a distant pool was not as good as the accuracy that employing a near pool. FIG. 30 is a comparison between log-ratios of two re-ratio combined experiments C-vs-D employing the distant pool. Comparing to FIG. 25, it can be seen that the results with the distant pool had lower reproducibility than the results with the near pool.

6.3. Precision and Accuracy of the Ratio-Splitter

When a distant pool is used, the ratio-splitter may also suffer from the same proble of low precision and low accuracy as in the case of re-ratioer. In this example, the ratio-splitter is verified in data either with a common near pool or without a common pool.

6.3.1. Results with a Near Reference Pool

FIG. 31 shows the ratio-splitter result of a virtual same-vs-same experiment (C-vs-C). This result came from measured data obtained using two real chips of Pool 1 vs. C of the same color. The overall spread of log ratios is tight. Comparing to the re-ratio result in FIG. 17, the ratio-splitter did not have the problem of wide spread log-ratios at the low intensity end. This is one of the main advantages of the ratio-splitter.

FIG. 32 is the ratio-splitter result of a virtual same-vs-same experiment (C-vs-C) employing the same near pool (Pool 1) as the common reference but different colors. Similar to the re-ratio result shown in FIG. 18, color biases caused significant log-ratio variations when data measured using two chips of different color-polarity were used in the ratio-splitter.

FIG. 33 is the ratio-splitter result of a virtual same-vs-same experiment (C-vs-C) from two fluor-reversally combined real ratio experiments employing the same near pool. Combined fluor-reversal experiments reduced the variations in the overall re-ratio result.

FIG. 34 is the ratio-splitter result of a virtual different-vs-different (C-vs-D) experiement of the same color and the same near pool. FIG. 35 is the re-ratio result of a virtual different-vs-different (C-vs-D) experiment from two combined fluor-reversal real ratio experiments. Combined real experiments had smaller measurement errors, allowing the resulting virtual experiment higher sensitivity in detecting differential expressions.

FIG. 36 is a comparison between C-vs-D log-ratio of a ratio-splitter experiment (shown in FIG. 34) and the log-ratio of the reference standard. FIG. 37 is a comparison between C-vs-D log-ratio of a re-ratio experiment of combined experiments (shown in FIG. 35) and the log-ratio of the reference standard. The ratio-splitter result of combined experiments employing the near pool showed similar accuracy as the reference standard. For the same threshold p-value<0.01, the ratio-splitter detected slightly more signatures than the re-ratioer (FIG. 24). FIG. 38 is a comparison between log-ratios of two ratio-splitter combined experiments C-vs-D. The two ratio-splitter results were consistent and similar to the re-ratioer results shown in FIG. 25.

6.3.2. Results without a Reference Pool (Without ISEC)

In the re-ratioer and ratio-splitter verification examples discussed above, common reference controls were employed, i.e., there was either a near pool or a distant pool in one of the two channels. The common controls were used as references to reduce inter-slide variations. However, when the common controls are not available, the inter-slide error correction (ISEC) is preferably not used during ratio splitting. Ratio-splitter results without leveraging common reference pools are shown in this example.

FIG. 39 shows the ratio-splitter result of a virtual same-vs-same experiment (C-vs-C) without ISEC. The overall spread of log ratios was larger than that with ISEC in FIG. 31. FIG. 40 is the ratio-splitter result of a virtual same-vs-same experiment (C-vs-C) from two fluor-reversally combined real ratio experiments without ISEC. The result without ISEC showed wider spread in log ratios than that with ISEC as shown in FIG. 33. FIG. 39 and FIG. 40 indicate that ratio-splitting using ISEC without a common reference pool has lower precision than ratio-splitting using ISEC with a common reference pool.

FIG. 41 is the ratio-splitter result of a virtual different-vs-different (C-vs-D) experiment from two combined fluor-reversal real ratio experiments without ISEC. FIG. 42 is a comparison between this C-vs-D log-ratios of one ratio-splitter experiment of combined experiments and the log-ratio of the reference standard. Comparing to FIG. 37 it can be seen that the ratio-splitter result of combined experiments without leveraging common reference pool in ISEC showed larger differences than the reference standard. This demonstrates that the accuracy of the ratio-splitter without ISEC is not as good as its accuracy with ISEC. FIG. 43 is a comparison between two C-vs-D log-ratios of two ratio-splitter combined experiments without ISEC. Comparing to FIG. 38, it can be seen that the results without ISEC has lower reproducibility than the results with ISEC.

6.4. Sensitivity and Specificity

The precision and accuracy of the re-ratioer and the ratio-splitter were discussed in previous examples. In this example, the sensitivity and specificity are examined. Sensitivity is the ability to detect expression changes. Generally, the higher the sensitivity is, the better the detection method is. Specificity rate can be defined as one minus false positive rate. False positives are those features or sequences that are detected as differentially expressed but that are actually not differentially expressed. The lower the false positive rate, the better the detection method is. Sensitivity and false positive may be tradeoffs. For example, increasing sensitivity by using higher p-value thresholds may increase false positive rate. ROC (receiver operating characteristics) analysis allows consideration of both sensitivity and false positive rate when comparing different gene expression detection methods.

ROC curves are plots in which the X-axis corresponds to false positive rate and the Y-axis corresponds to sensitivity. For each p-value threshold level, e.g. p-value<0.01, the false positive rate from same-vs-same experiments, and the sensitivity from different-vs-different experiments are measured. The measured false positive rate (FPR) and total positive rate (TPR) is one point on the ROC curve. By varying the threshold from very low levels to very high levels, the entire ROC curve can be obtained. For a given test data set, a detection method having its ROC curve closer to the upper-left corner of the ROC plot has higher statistical power in differential expression analysis. In this example, the total positive rate was used instead of the true positive rate because true positive rate is hard to measure. The true positive rate is related to the total positive rate, which includes both true positives and false positives. A superior method in terms of a ROC of total-positive vs. FPR is normally also superior in terms of a ROC of true-positive vs. FPR.

In all of the following ROC plots, the ROC curves are the averaged results of two different sets of same-vs-same and different-vs-different data. The false positive rate is the number of signature features for a given p-value threshold in a same-vs-same experiment divided by the total number of features in a chip. The total positive rate is the number of signature features for a given p-value threshold in a different-vs-different experiment divided by the total number of features in a chip.

The different-vs-different data are those C-vs-D experiments shown in previous sections. Sample C and sample D had moderately strong differential expressions. In addition to including all signatures in the ROC analysis, separate ROC curves for which features of more than 1.2-fold up- or down-regulation in both real combined C-vs-D experiments were excluded are also provided in FIG. 22. The weak signature ROC curves were used for examination of the performance of the re-ratioer and ratio-splitter in handling low signal-to-noise-ratio (SNR) data.

FIGS. 44(a) and (b) compare the all-signature-ROC curves of the ratio-splitter and the re-ratioer having the near common reference pool (Pool 1) used in ISEC. These ROC curves are plotted in log-log scales to help clearly compare the differences at low FPR. ROC curves of real ratio experiments in black lines are shown as references for comparison with the results of virtual experiments from ratio-splitter and re-ratioer. At the medium FPR levels (0.001<FPR<0.1), the real combined fluor-reversal experiments have higher ROC curves than the virtual combined experiments as shown by the dark dashed lines. At low FPR levels (FPR<0.001), both ratio-splitter and re-ratioer combined experiments have similar or higher ROC curves than the real combined experiments. Using the ROC curve of the combined real (thick solid black lines) as a reference, it can be seen that the ratio-splitter had a slightly higher ROC curve than the re-ratioer in the virtual combined experiments.

With the ratio-splitter and the re-ratioer, ratio experiments of the same color (red-red or green-green) can be formed. Because there is no color bias in the same-color virtual experiments, ROC curves of the same-color without combining is significantly higher than the ROC curve from the real two-color chips in FIGS. 44(a) and (b) (thin solid black lines). The virtual two-color experiment exhibits the lowest ROC curves (thin dashed lines).

FIGS. 45(a) and (b) are ROC curves of weak signatures. When signatures of strong differential expressions were excluded, all ROC curves moved down. The real combined experiments still had the highest ROC curves in the medium FPR range. Ratio-splitter still outperformed the real in the low FPR range. At low FPR range, ROC curves of the re-ratioer at the same-color are higher than the curves of the ratio-splitter. For both re-ratioer and ratio-splitter, the ROC curves of red single-color experiments of green common controls are higher than the ROC curves of the green experiments of red common controls. This is quite interesting. It indicates that green (Cy3) fluorescence is preferably used to label the common near reference pool if fluor-reversal pairs are not to be obtained. This is particularly important when differential expressions are weak.

It was shown in the previous examples that when distant pools were used, the precision and accuracy of the ratio-splitter and re-ratioer decreased. Distant pools also decrease the sensitivity and specificity in differential expression detections by the ratio-splitter or re-ratioer. FIGS. 46(a) and (b) are the all-signature ROC curves with the distant Pool 2 as the common reference in ISEC. Comparing FIG. 46 and FIG. 44, it can be seen that the decrease in statistical power in lower ROC curvers with the distant pool is quite clear. FIGS. 47(a) and (b) are the weak-signature ROC curves. Comparing them to FIG. 45, similar decreases in the statistical power can be observed. However, the difference between the red and the green ROC curves of the distant pool are not as obvious as the separation shown in FIG. 45 where the near pool is used in the weak-signature cases.

Re-ratioer and ratio-splitter with ISEC are preferably not used if there is no common reference control in one of the two channels of the original data. In such cases, the ratio-splitter only provides intensity profiles without inter-slide error correction (see FIG. 2). It was shown in the previous examples that without ISEC the measurement precision and accuracy became worse. Similar decreases in sensitivity and specificity were also seen without ISEC. FIGS. 48(a) and (b) are ROC curves of all-signature and weak-signature from the ratio-splitter without ISEC. Comparing these figures to FIG. 44(a) and FIG. 45(b), it can be seen clearly that the drop in statistical power is very significant without a near common reference pool for ISEC. Without ISEC the ratio-splitter sensitivity and specificity are also much worse than those with a distant pool when ISEC was applied (FIG. 46(a) and FIG. 47(a)). These results suggest that it is preferable to have a near common reference pool in one of the two channels of a two-color microarray experiment whenever the re-ratioer or the ratio-splitter is to be employed to process the data. The inter-slide variation is the main error source when comparing two split intensity profiles. Even though global inter-slide difference can be reduced by normalization, the remaining spot-dependent variations cannot be easily reduced, unless both common references and ISEC are employed.

As these examples demonstrated, the re-ratioer and the ratio-splitter provide additional flexibility in analyzing two-color microarray data. Ratio-splitter allows the use of two-color microarrays to generate intensity profiles as alternatives to single-channel microarrays, such as those from Affymetrix. The inter-slide error correction method (ISEC) significantly reduces slide-to-slide variations when a common reference control sample is hybridized to one of the two channels of the two-color microarrays. The following summarizes observations from method verifications described in the Example Section:

(1) A common reference sample, in particular a near reference pool, can help significantly reduce inter-slide variations and significantly improve measurement precision, accuracy, sensitivity and specificity. Spot-dependent variations, which may be strong, were difficult to reduce without employing a common reference in one of the two channels.

(2) With a near reference pool, both re-ratioer and ratio-splitter produced good virtual measurement results in comparison to the real results obtained from direct hybridizations. But none of them is as good as real hybridization in terms of precision/accuracy and sensitivity/specificity at medium FPR. Re-ratioer and ratio-splitter showed slightly better sensitivity/specificity at very low FPR than the real experiments for the verification data.

(3) A distant pool was not as effective as the near pool in reducing inter-slide variation. Employing a distant pool or employing no pool showed similar measurement precision and accuracy. Both of them were worse than the precision and accuracy when a near pool was employed. However, using a distant pool is still better than using no common reference in terms of sensitivity and specificity of the results.

(4) Ratio splitter showed better measurement precision at the low intensity end than the re-ratioer. Re-ratioer showed larger log-ratio variations at the very low intensity end.

(5) When a common reference pool was available, the ratio-splitter did not require fluor-reversal in differential expression analysis. Without color bias, the same-color experiments with ISEC had higher sensitivity and specificity than the two-color real chips without fluor-reversal.

(6) When employing a common reference, it was observed that labeling it with the green Cy3 dye was more preferably if producing higher sensitivity and specificity for weak differential signals was desired.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed:

1. A method for generating at least one error-corrected experiment profile of at least one experiment profile in a plurality of pairs of profiles $\{A_m, C_m\}$, wherein m=1, 2, ..., M, and M is the number of the pairs of profiles; and wherein, for each m ∈ {1, 2, ..., M}, $A_m$ is an experiment profile, and $C_m$ is a reference profile; and wherein $\{A_m\}$ represents experiment profiles in said plurality of pairs of profiles $\{A_m, C_m\}$ and $\{C_m\}$ represents reference profiles in said plurality of pairs of profiles $\{A_m, C_m\}$, said method comprising:

(a) calculating, on a suitably programmed computer, an average reference profile $\overline{C}$ of said plurality of reference profiles $\{C_m\}$ where m=1, 2, ..., M;

(b) determining, on a suitably programmed computer, for at least one profile pair $\{A_m, C_m\}$ where m ∈ {1, 2, ..., M} of said plurality of pairs of profiles $\{A_m, C_m\}$ a differential reference profile, $\overline{C}_{\mathit{diff}}(m,k)$, computed between $C_m$ and $\overline{C}$, wherein said average reference profile $\overline{C}$ comprises data set $\{\overline{C}(k)\}$;

(c) via said differential reference profile determined for said profile pair, removing, on a suitably programmed computer, systematic cross-experiment error from an experiment profile $A_m$ of said at least one profile pair $\{A_m, C_m\}$ where m ∈ {1, 2, ..., M} to generate a first error-corrected experiment profile $A'_m$ for each m ∈ {1, 2, ..., M}, wherein said experiment profile $A_m$ comprises a first data set, $\{A_m(k)\}$, said reference profile $C_m$ comprises a second data set, and said first error-corrected experiment profile $A'_m$ comprises data set $\{A'_m(k)\}$; wherein said first data set comprises measurements of a plurality of different cellular constituents measured in a sample having been subject to a first condition, said second data set comprises measurements of said plurality of different cellular constituents measured in a sample having been subject to a second condition; and wherein k=1, 2, ..., N; k is an index of measurements of said plurality of different cellular constituents, N being the total number of measurements, wherein generating respective $A'_m(k)$ of said first error-corrected experiment profile $A'_m$ comprises subtracting $C_{\mathit{diff}}(m,k)$ from $A_m(k)$; and (d) outputting to a user, a user interface device, a computer readable storage medium, or a local or remote computer system; or displaying: said first error-corrected experiment profile $A'_m$ or said data set $\{A'_m(k)\}$.

2. The method of claim 1, wherein said step (b) and (c) are performed for each profile pair $\{A_m, C_m\}$ where m ∈ {1, 2, ..., M}.

3. The method of claim 2, wherein each of said experiment profile $A_m$ and said reference profile $C_m$ comprises measurements of said plurality of different cellular constituents from the same experimental reaction.

4. The method of claim 3, wherein said $\overline{C}(k)$ is calculated according to the equation $$\overline{C}(k) = \frac{1}{M}\sum_{m=1}^{M} \overline{C}_m(k)$$

wherein said differential reference profile is determined according to the equation $$C_{\mathit{diff}}(m,k) = C_m(k) - \overline{C}(k)$$

and wherein said first error-corrected experiment profile $A'_m$ is generated according to the equation $$A'_m(k) = A_m(k) - C_{\mathit{diff}}(m,k)$$

wherein $\{A_m(k)\}$ is said first data set of experiment profile $A_m$.

5. The method of claim 4, further comprising:

(e) calculating, for one or more remaining profile pairs out of said profile pairs $\{A_m, C_m\}$, a respective second error-corrected experiment profile $A''_m$; and (f) outputting to, a user interface device, a computer readable storage medium, or a local or remote computer system; or displaying; said respective second error-corrected experiment profile $A''_m$ or a data set $\{A''_m(k)\}$.

6. The method of claim 5, wherein said second error-corrected experiment profile $A''_m$ is calculated according to equation $$A''_m(k) = (1-w(k)) \cdot A_m(k) + w(k) \cdot A'_m(k).$$

7. The method of claim 6, further comprising determining a weighing factor $w(k)$ according to equation $$w(k) = 1 - e^{-0.5 \left[\frac{\overline{C}(k)}{avg\_bkgstd}\right]^2}$$

where avg_bkgstd is an average background standard error.

8. The method of claim 7, further comprising determining said avg_bkgstd according to equation $$avg\_bkgstd = \frac{1}{N} \sum_{k=1}^{N} \left[\frac{1}{M} \sum_{m=1}^{M} bkgstd(m,k)\right]$$

where bkgstd $(m,k)$ is background standard error of $C_m(k)$.

9. The method of claim 4, further comprising determining errors $\{\sigma'_m(k)\}$ of said data set $\{A'_m(k)\}$ in said first error-corrected experiment profile $A'_m$.

10. The method of claim 9, further comprising determining said errors $\{\sigma'_m(k)\}$ according to the equation $$\sigma'_m(k) = \sqrt{\sigma_m^2(k) + mixed\_\sigma_m^2(k) - 2 \cdot Cor(k) \cdot \sigma_m(k) \cdot mixed\_\sigma_m(k)}$$

where $\sigma_m(k)$ is the standard error of $A_m(k)$, the method further comprising determining mixed_$\sigma_m(k)$ according to equation $$mixed\_\sigma_m(k) = \frac{\sigma_m(k) + (M-1) \cdot \sigma_{ref}(k)}{M}$$

$$\text{where } \sigma_{ref}(k) = \sqrt{\frac{1}{M-1} \sum_{m}^{M} (C_m(k) - \overline{C}(k))^2}$$

and where $Cor(k)$ is a correlation coefficient between said experiment profile $A_m$ and said reference profile $C_m$.

11. The method of claim 10, further comprising determining said $Cor(k)$ according to the equation $$Cor(k) = CorMax \cdot \left[1 - e^{-0.5 \left[\frac{\overline{C}(k)}{avg\_bkgstd}\right]^2}\right]$$

where CorMax is a number between 0 and 1.

12. The method of claim 7, further comprising determining errors $\{\sigma''_m(k)\}$ of said data set $\{A''_m(k)\}$ in said second error-corrected experiment profile $A''_m$.

13. The method of claim 12, wherein said errors $\{\sigma''_m(k)\}$ are determined according to the equation $$\sigma''_m(k) = \sqrt{[1-w(k)] \cdot \sigma_m^2(k) + w(k)\sigma'^2_m(k)}$$

where $\sigma_m(k)$ is the standard error of $A_m(k)$, the method further comprising (i) determining $\sigma'_m(k)$ according to the equation $$\sigma'_m(k) = \sqrt{\sigma_m^2(k) mixed\_\sigma_m^2(k) - 2 \cdot Cor(k) \cdot \sigma_m(k) \cdot mixed\_\sigma_m(k)}$$

(ii) determining mixed_$\sigma_m(k)$ according to the equation $$mixed\_\sigma_m(k) = \frac{\sigma_m(k) + (M-1) \cdot \sigma_{ref}(k)}{M}$$

$$\text{where } \sigma_{ref}(k) = \sqrt{\frac{1}{M-1} \sum_{m}^{M} (C_m(k) - \overline{C}(k))^2}$$

and where $Cor(k)$ is a correlation coefficient between said experiment profile $A_m$ and said reference profile $C_m$.

14. The method of claim 13, further comprising determining said $Cor(k)$ according to the equation $$Cor(k) = CorMax \cdot \left[1 - e^{-0.5 \left[\frac{\overline{C}(k)}{avg\_bkgstd}\right]^2}\right]$$

where CorMax is a number between 0 and 1.

15. The method of claim 2, wherein said experiment profile $A_m$ and said reference profile $C_m$ of each said profile pair $\{A_m, C_m\}$ are measured in a two-channel microarray experiment.

16. The method of claim 15, wherein said reference profiles $\{\overline{C}_m\}$, where m=1, 2, . . . , M, are measured with samples labeled with a same label.

17. The method of claim 2, wherein at least one of said plurality of pairs of profiles $\{A_m, C_m\}$ is a virtual profile.

18. The method of claim 1, wherein said plurality of pairs of profiles $\{A_m, C_m\}$ are transformed profiles each comprising transformed measurements of said plurality of different cellular constituents in data set $\{A_m(k)\}$ and data set $\{C_m(k)\}$, respectively; and wherein said data set $\{A_m(k)\}$ is said first data set, and said data set $\{C_m(k)\}$ is said second data set.

19. The method of claim 1, further comprising:
(a0) removing nonlinearity, prior to said calculating step (a), from measurements of said plurality of different cellular constituents to generate said plurality of pairs of profiles $\{A_m, C_m\}$ comprising said experiment profile $A_m$ and reference profile $C_m$.

20. The method of claim 19, wherein said removing step (a0) comprises:
(a0i) calculating an average profile of pre-experiment profiles $\{A_m^{pre}\}$ and pre-reference profiles $\{C_m^{pre}\}$; wherein each of said pre-experiment profiles comprises measurements of said plurality of different cellular constituents measured in said sample having been subject to said first condition, which when nonlinearity is removed therefrom, produces each said experiment profile $A_m$; and wherein each of said pre-reference profiles comprises measurements of said plurality of different cellular constituents measured in said sample having been subject to said second condition, which when nonlinearity is removed therefrom, produces each said reference profile $C_m$; and (a0ii) calculating first differences between each of said pre-experiment profiles $\{A_m^{pre}\}$ and said average profile; calculating second differences between each of said pre-reference profiles $\{C_m^{pre}\}$ and said average profile; adjusting, wherein the adjusting comprises correcting nonlinearity, each of said pre-experiment profiles $\{A_m^{pre}\}$ based on said first differences between each of said pre-experiment profiles $\{A_m^{pre}\}$ and said average profile, thereby generating each said experiment profile $A_m$; and adjusting, wherein the adjusting comprises correcting nonlinearity, each of pre-reference profiles $\{C_m^{pre}\}$ based on said second differences between each of said pre-reference profiles $\{C_m^{pre}\}$ and said average profile, thereby generating each said reference profile $C_m$.

21. The method of claim 20, further comprising calculating said first differences based on a first subset of said measurements of said plurality of different cellular constituents in said pre-experiment profiles $\{A_m^{pre}\}$ and said average profile; and calculating said second differences based on a second subset of said measurements of said plurality of different cellular constituents in said pre-reference profiles $\{C_m^{pre}\}$ and said average profile.

22. The method of claim 21, wherein said first subset consists of measurements of said plurality of different cellular constituents that are ranked similarly between each of said pre-experiment profiles $\{A_m^{pre}\}$ and said average profile, and said second subset consists of measurements of said plurality of different cellular constituents that are ranked similarly between each of said pre-reference profiles $\{C_m^{pre}\}$ and said average profile.

23. The method of claim 22, wherein said adjusting step (a0ii) is carried out by a method comprising:

(ii1) binning said first subset into a first plurality of bins, wherein each of said first plurality of bins consists of measurements of said plurality of different cellular constituents in one of said pre-experiment profiles $\{A_m^{pre}\}$ and said average profile having a value in a given range; and binning said second subset into a second plurality of bins, wherein each of said second plurality of bins consists of measurements of said plurality of different cellular constituents in one of said pre-reference profiles $\{C_m^{pre}\}$ and said average profile having a value in a given range;

(ii2) calculating, in each bin of said first plurality of bins, a first mean difference between a feature value of measurements of said one of said pre-experiment profiles $\{A_m^{pre}\}$ and a feature value of said average profile, and calculating a second mean difference between a feature value of measurements of said one of said pre-reference profiles $\{C_m^{pre}\}$ and a feature value of said average profile;

(ii3) determining a first curve of said first mean difference as a first function of values of measurements of said plurality of different cellular constituents for said one of said pre-experiment profiles $\{A_m^{pre}\}$, wherein said first function is represented by, nonlinear_$A_m^{pre}$; and determining a second curve of said second mean difference as a second function of values of measurements of said plurality of different cellular constituents for said one of said pre-reference profiles $\{C_m^{pre}\}$, wherein said second function is represented by nonlinear_$C_m^{pre}$; and (ii4) adjusting each of said pre-experiment profiles $\{A_m^{pre}\}$ according to the equation:

$$A_m(k) = A_m^{pre}(k) - \text{nonlinear\_}A_m^{pre}(k),$$

and adjusting each of said pre-reference profiles $\{C_m^{pre}\}$ according to the equation:

$$C_m(k) = C_m^{pre}(k) - \text{nonlinear\_}C_m^{pre}(k),$$

where $k=1, \ldots, N$; and where $A_m^{pre}(k)$ and $C_m^{pre}(k)$ are data sets of each of said pre-experiment profiles $\{A_m^{pre}\}$ and each of said pre-reference profiles $\{C_m^{pre}\}$, respectively; and where $A_m(k)$ and $C_m(k)$ are said first data set and said second data set, respectively.

24. The method of claim 1, further comprising:

(a0) normalizing, prior to said calculating step (a), measurements of said plurality of different cellular constituents in a pre-experiment profile $A_m^{pre}$ and a pre-reference profile $C_m^{pre}$ to generate said experiment profile $A_m$ and said reference profile $C_m$, respectively.

25. The method of claim 24, wherein said normalizing step (a0) comprises normalizing a data set $A_m^{pre}(k)$ and a data set $C_m^{pre}(k)$, according to the equations:

$$NA_m(k) = \frac{A_m(k) \cdot \overline{AC}}{\overline{A_m}} \text{ and}$$

$$NC_m(k) = \frac{C_m(k) \cdot \overline{AC}}{\overline{C_m}}$$

wherein said data sets $A_m^{pre}(k)$ and $C_m^{pre}(k)$ each comprises measurements of said plurality of different cellular constituents, where $\overline{A_m^{pre}}$ is an average of measurements of said plurality of different cellular constituents in said $A_m^{pre}(k)$, and $\overline{C_m^{pre}}$ is an average of measurements of said plurality of different cellular constituents in said $C_m^{pre}(k)$, wherein $A_m(k)$ is said first data set, wherein $A_m(k)$ comprises normalized measurements or normalized transformed measurements of said pre-experiment profile $A_m^{pre}$; and $C_m(k)$ is said second data set wherein $A_m(k)$ comprises normalized measurements or normalized transformed measurements of said reference profile $C_m^{pre}$; and wherein $\overline{A_m^{pre}C_m^{pre}}$ is an average calculated according to the equation $$\overline{A_m^{pre}C_m^{pre}} = \frac{1}{2M}\sum_{m=1}^{M}(\overline{A_m^{pre}} + \overline{C_m^{pre}}).$$

26. The method of claim 25, further comprising normalizing errors of said data sets $\{A_m^{pre}(k)\}$ and $\{C_m^{pre}(k)\}$, respectively, according to the equations:

$$\sigma_m^{NA}(k) = \frac{\sigma_m^{preA}(k) \cdot \overline{A_m^{pre}C_C^{pre}}}{\overline{A_m^{pre}}} \text{ and}$$

$$\sigma_m^{NC}(k) = \frac{\sigma_m^{preC}(k) \cdot \overline{A_m^{pre}C_m^{pre}}}{\overline{C_m^{pre}}},$$

where $\sigma_m^{preA}(k)$ and $\sigma_m^{preC}(k)$ are the standard errors of $A_m^{pre}(k)$ and $C_m^{pre}(k)$, respectively, and $\sigma_m^{NA}(k)$ and $\sigma_m^{NC}(k)$ are normalized standard errors of $A_m(k)$ and $C_m(k)$, respectively.

27. The method of claim 26, further comprising normalizing background errors of said data sets $\{A_m^{pre}(k)\}$ and $\{C_m^{pre}(k)\}$, respectively, according to the equations:

$$bkgstd_m^{NA}(k) = \frac{bkgstd_m^{preA}(k) \cdot \overline{A_m^{pre} C_m^{pre}}}{\overline{A_m^{pre}}} \text{ and}$$

$$bkgstd_m^{NC}(k) = \frac{bkgstd_m^{preC}(k) \cdot \overline{A_m^{pre} C_m^{pre}}}{\overline{C_m^{pre}}}$$

where $bkgstd_m^{preA}(k)$ and $bkgstd_m^{preC}(k)$ are the standard background errors of $A_m^{pre}(k)$ and $C_m^{pre}(k)$, respectively, and $bkgstd_m^{NA}(k)$ and $bkgstd_m^{NC}(k)$ are normalized standard background errors of $A_m(k)$ and $C_m(k)$, respectively.

28. The method of claim 27, further comprising calculating said averages $\overline{A_m^{pre}}$ and $\overline{C_m^{pre}}$ by excluding measurements of said plurality of different cellular constituents having a value among the highest 10% of said measurements of said plurality of different cellular constituents in said data sets $\{A_m^{pre}(k)\}$ and $\{C_m^{pre}(k)\}$, respectively.

29. A method for generating at least one error-corrected experiment profile of at least one experiment profile in a plurality of pairs of profiles $\{XA_m, XC_m\}$, $XA_m$ being an experiment profile, $XC_m$ being a reference profile, where $m=1, 2, \ldots, M$, M is the number of pairs of profiles, said method comprising:

(a) processing, on a suitably programmed computer, said plurality of pairs of profiles $\{XA_m, XC_m\}$ to obtain a plurality of pairs of processed profiles $\{PA_m, PC_m\}$, $PA_m$ being a processed experiment profile, $PC_m$ being a processed reference profile, wherein said processing comprises normalizing at least one said experiment profile $XA_m$ and reference profile $XC_m$;

(b) calculating, on a suitably programmed computer, an average processed reference profile $\overline{PC}$ of processed reference profiles $(PC_m)$, wherein $m=1, 2, \ldots, M$;

(c) determining, on a suitably programmed computer, for at least one processed profile pair $\{PA_m, PC_m\}$ where $m \in \{1, 2, \ldots, M\}$ of said plurality of pairs of processed profiles $\{PA_m, PC_m\}$, wherein $m=1, 2, \ldots, M$, a differential reference profile, $PC_{diff}(m,k)$, computed between $PC_m$ and $\overline{PC}$, wherein said average processed reference profile $\overline{PC}$ comprises data set $\{\overline{PC}(k)\}$;

(d) via said differential reference profile determined for said at least one processed profile pair, removing, on a suitably programmed computer, systematic cross-experiment error from a processed experiment profile $PA_m$ of said at least one processed profile pair $\{PA_m, PC_m\}$ where $m \in \{1, 2, \ldots, M\}$ to generate a first error-corrected processed experiment profile $PA'_m$; wherein for each $m \in \{1, 2, \ldots, M\}$, said processed experiment profile $PA_m$ comprises a first processed data set, $\{PA_m(k)\}$, said processed reference profile $PC_m$ comprises a second processed data set, said first error-corrected processed experiment profile $PA'_m$ comprises dataset $\{PA'_m(k)\}$, said experiment profile $XA_m$ comprises data set $\{XA_m(k)\}$, said reference profile $XC_m$ comprises data set $\{XC_m(k)\}$, wherein said data set $\{XA_m(k)\}$ comprises measurements of a plurality of different cellular constituents measured in a sample having been subject to a first condition, said data set $\{XC_m(k)\}$ comprises measurements of said plurality of different cellular constituents measured in a sample having been subject to a second condition, and where $k=1, 2, \ldots, N$; k is an index of measurements of cellular constituents, N being the total number of measurements, wherein generating respective $PA'_m(k)$ of said first error-corrected processed experiment profile $PA'_m$ comprises subtracting $PC_{diff}(m,k)$ from $PA_m(k)$; and (e) outputting to a user, a user interface device, a computer readable storage medium, or a local or remote computer system; or displaying: said first error-corrected processed experiment profile $PA'_m$ or said data set $\{PA'_m(k)\}$.

30. The method of claim 29, wherein said normalizing is carried out according to the equations:

$$NA_m(k) = \frac{XA_m(k) \cdot \overline{XAC}}{\overline{XA_m}} \text{ and}$$

$$NC_m(k) = \frac{XC_m(k) \cdot \overline{XAC}}{\overline{XC_m}}$$

where $\{NA_m(k)\}$ is said first data set of said processed experiment profile $PA_m$, and $\{NC_m(k)\}$ is said second data set of said processed reference profile $PC_m$; where $\overline{XA_m}$ is an average of measurements of said plurality of different cellular constituents of said data set $\{XA_m(k)\}$, and $\overline{XC_m}$ is an average of measurements of said plurality of different cellular constituents of data set $\{XC_m(k)\}$; and wherein $\overline{XAC}$ is an average calculated according to the equation $$\overline{XAC} = \frac{1}{2M} \sum_{m=1}^{M} (\overline{XA_m} + \overline{XC_m}).$$

31. The method of claim 30, further comprising normalizing errors of said experiment profile $XA_m$ and reference profile $XC_m$ according to the equations:

$$\sigma_m^A(k) = \frac{\sigma_m^{XA}(k) \cdot \overline{XAC}}{\overline{XA_m}} \text{ and}$$

$$\sigma_m^C(k) = \frac{\sigma_m^{XC}(k) \cdot \overline{XAC}}{\overline{XC_m}}$$

where $\sigma_m^{XA}(k)$ and $\sigma_m^{XC}(k)$ are the standard errors of $XA_m(k)$ and $XC_m(k)$, respectively, and $\sigma_m^A(k)$ and $\sigma_m^C(k)$ are normalized standard errors of $NA_m(k)$ and $NC_m(k)$, respectively.

32. The method of claim 31, further comprising normalizing background errors of said experiment profile $XA_m$ and reference profile $XC_m$ according to the equations:

$$bkgstd_m^A(k) = \frac{bkgstd_m^{XA}(k) \cdot \overline{XAC}}{\overline{XA_m}} \text{ and}$$

$$bkgstd_m^C(k) = \frac{bkgstd_m^{XC}(k) \cdot \overline{XAC}}{\overline{XC_m}}$$

where $bkgstd_m^{XA}(k)$ and $bkgstd_m^{XC}(k)$ are the standard background errors of $XA_m(k)$ and $XC_m(k)$, respectively, and $bkgstd_m^A(k)$ and $bkgstd_m^C(k)$ are normalized standard background errors of said $NA_m(k)$ and said $NC_m(k)$, respectively.

33. The method of claim 31, further comprising determining said averages $\overline{XA_m}$ and $\overline{XC_m}$ excluding measurements of said plurality of different cellular constituents having a value among the highest 10% of said measurements of said plurality of different cellular constituents in said data sets $\{XA_m(k)\}$ and $\{XC_m(k)\}$, respectively.

34. The method of claim 29, wherein said processing step (a) comprises:
normalizing each said experiment profile $XA_m$ and reference profile $XC_m$ to generate normalized data set $\{NA_m(k)\}$ and normalized data set $\{NC_m(k)\}$, respectively;
transforming said normalized data set $\{NA_m(k)\}$ to obtain a transformed data set $\{TA_m(k)\}$, where said transformed data set $\{TA_m(k)\}$ is said first data set of said processed experiment profile $PA_m$; and
transforming said normalized data set $\{NC_m(k)\}$ to obtain a transformed data set $\{TC_m(k)\}$, where said transformed data set $\{TC_m(k)\}$ is said second data set of said processed reference profile $PC_m$;
wherein said transforming is carried out for an experiment according to equations $$TA_m(k) = f(x) = \frac{\ln\left(\frac{b^2 + 2 \cdot a^2 \cdot NA_m(k)}{a} + 2 \cdot \sqrt{c^2 + b^2 \cdot NA_m(k) + a^2 \cdot [NA_m(k)]^2}\right)}{a} + d,$$

for $NA_m(k) > 0$ and $$TC_m(k) = f(x) = \frac{\ln\left(\frac{b^2 + 2 \cdot a^2 \cdot NC_m(k)}{a} + 2 \cdot \sqrt{c^2 + b^2 \cdot NC_m(k) + a^2 \cdot [NC_m(k)]^2}\right)}{a} + d,$$

for $NC_m(k) > 0$ where d is described by equation $$d = \frac{-\ln\left[\frac{b^2}{a} + 2 \cdot c\right]}{a}$$

and wherein a is the fractional error coefficient of said experiment, b is the Poisson error coefficient of said experiment, and c is the standard deviation of background noise of said experiment.

35. The method of claim 29, wherein said processing step (a) comprises:
normalizing each said experiment profile $XA_m$ and reference profile $XC_m$ to generate normalized data set $\{NA_m(k)\}$ and normalized data set $\{NC_m(k)\}$, respectively;
transforming said normalized data set $\{NA_m(k)\}$ to a new domain in which variance becomes a constant to obtain a transformed data set $\{TA_m(k)\}$;
transforming said normalized data set $\{NC_m(k)\}$ to the new domain in which variance becomes a constant to obtain a transformed data set $\{TC_m(k)\}$; and
removing nonlinearity from each said transformed data sets $\{TA_m(k)\}$ and $\{TC_m(k)\}$, respectively.

36. The method of claim 35, wherein said removing nonlinearity is carried out by a method comprising
(a1) calculating an average transformed profile of transformed experiment profiles and transformed reference profiles, wherein each of said transformed experiment profiles contains a corresponding transformed data set $\{TA_m(k)\}$, and each of said transformed reference profiles contains a corresponding said transformed data set $\{TC_m(k)\}$; and
(a2) calculating first differences between each of said transformed experiment profiles and said average transformed profile; calculating second differences between each of said transformed reference profiles and said average transformed profile; adjusting, wherein the adjusting corrects nonlinearity, each of said transformed experiment profiles based on said first differences between each of said transformed experiment profiles and said average transformed profile, and adjusting, wherein the adjusting corrects nonlinearity, each of said transformed reference profiles based on said second differences between each of said transformed reference profiles and said average transformed profile.

37. The method of claim 36, further comprising calculating said first differences based on the differences in a first subset of transformed measurements of said plurality of different cellular constituents between each of said transformed experiment profiles and said average transformed profile, and calculating said second differences based on the differences in a second subset of transformed measurements of said plurality of different cellular constituents between each of said transformed reference profiles and said average transformed profile.

38. The method of claim 37, wherein each said first subset consists of transformed measurements that are ranked similarly between each of said transformed experiment profiles and said average transformed profile, and each said second subset consists of transformed measurements that are ranked similarly between each of said transformed reference profiles and said average transformed profile.

39. The method of claim 38, wherein said adjusting step (a2) is carried out by a method comprising:
(a2i) binning said first subset into a plurality of bins, each said bin consisting of transformed measurements of said plurality of different constituents in one of said transformed experiment profiles and said average transformed profile having a value in a given range; and binning said second subset into a plurality of bins, each said bin consisting of transformed measurements of said plurality of different cellular constituents in one of said transformed reference profiles and said average transformed profile having a value in a given range;
(a2ii) calculating, in each bin of said plurality of bins, a first mean difference between a feature value of transformed measurements of said plurality of different cellular constituents in said one of said transformed experiment profiles and a feature value of said average transformed profile, and calculating a second mean difference between a feature value of transformed measurements of said plurality of different cellular constituents in said one of said reference profiles and a feature value of the average profile;
(a2iii) determining a first curve of said first mean difference as a first function of values of transformed measurements of said plurality of different constituents for said one of said transformed experiment profiles, wherein said first function is represented by, nonlinear_$TA_m$ and determining a second curve of said second mean difference as a second function of values of transformed measurements of said plurality of different cellular constituents for said one of said transformed reference profiles, wherein said second function is represented by nonlinear_$TC_m$; and (a2iv) computing corrected transformed measurements of said plurality of different cellular constituents in each said transformed data set $\{TA_m(k)\}$, according to the equation:

$$TA_m^{corr}(k) = TA_m(k) - \text{nonlinear\_}TA_m(k),$$

and computing corrected transformed measurements of said plurality of different cellular constituents in each said transformed data set $\{TC_m(k)\}$, according to the equation:

$$TC_m^{corr}(k) = TC_m(k) - \text{nonlinear\_}TC_m(k),$$

where $k=1, \ldots, N$; and where $\{TA_m^{corr}(k)\}$ is said first processed data set of said processed experiment profile $PA_m$, and $\{TC_m^{corr}(k)\}$ is said second processed data set of said processed reference profile $PC_m$.

40. The method of claim 39, wherein said processed experiment profile $PA_m$ and said processed reference profile $PC_m$ comprise transformed measurements of said plurality of different cellular constituents from the same experimental reaction.

41. The method of claim 40, further comprising calculating $\overline{PC}(k)$ according to equation $$\overline{PC}(k) = \frac{1}{M} \sum_{m=1}^{M} PC_m(k),$$

wherein $\{PC_m(k)\}$ comprises transformed measurements from said second processed data set $\{TC_m^{corr}(k)\}$ and calculating said differential reference profile according to the equation $$PC_{diff}(m,k) = PC_m(k) - \overline{PC}(k)$$

and wherein said first error-corrected profile is calculated according to the equation $$PA'_m(k) = PA_m(k) - PC_{diff}(k),$$

wherein $\{PA_m(k)\}$ comprises transformed measurements from said first data set $\{TA_m^{corr}(k)\}$.

42. The method of claim 41, further comprising
(d) calculating for each processed profile pair $\{PA_m, PC_m\}$, where $m \in \{1, 2, \ldots, M\}$, a second error-corrected experiment profile $PA'_m$ comprising data set $\{PA'_m(k)\}$ by combining said first error-corrected experiment profile $PA'_m$ with said processed experiment profile $PA_m$ using a weighing factor $\{w(k)\}$, $k=1, 2, \ldots, N$, wherein $w(k)$ is a weighing factor for the k'th measurement.

43. The method of claim 42, wherein said second error-corrected experiment profile $PA''_m$ is calculated according to the equation $$PA''_m(k) = (1-w(k)) \cdot PA_m(k) + w(k) PA'_m(k).$$

44. The method of claim 43, further comprising determining said weighing factor according to the equation $$w(k) = 1 \cdot e^{-0.5 \left[\frac{\overline{PC}(k)}{avg\_bkgstd}\right]^2}$$

where avg_bkgstd is an average background standard error.

45. The method of claim 44, further comprising determining said avg_bkgstd according to the equation $$avg\_bkgstd = \frac{1}{N} \sum_{k=1}^{N} \left[ \frac{1}{M} \sum_{m=1}^{M} bkgstd(m,k) \right]$$

where $bkgstd(m,k)$ is background standard error of $PC_m(k)$.

46. The method of claim 41, further comprising determining errors $\{P\sigma'_m\}$ of said first error-corrected experiment profile $\{PA'_m\}$, wherein said $\{P\sigma'_m\}$ comprises error data set $\{P\sigma'_m(k)\}$.

47. The method of claim 46, further comprising determining said error data set $\{P\sigma'_m(k)\}$ according to the equation $$\sigma'_m(k) = \sqrt{P\sigma_m^2(k) = \text{mixed\_}P\sigma_m^2(k) - 2\text{Cor}(k) \cdot P\sigma_m(k) \cdot \text{mixed\_}P\sigma_m(k)}$$

where $P\sigma_m(k)$ is the standard error of $A_m(k)$, and determining $\text{mixed\_}P\sigma_m(k)$ according to the equation $$P\sigma_{ref}(k) = \sqrt{\frac{1}{M-1} \sum_{m}^{M} (PC_m(k) - \overline{PC}(k))^2}$$

and where $Cor(k)$ is a correlation coefficient between said processed experiment profile $PA_m$ and said processed reference profile $PC_m$.

48. The method of claim 47, wherein said $Cor(k)$ is determined according to the equation $$Cor(k) = CorMax \cdot \left(1 - e^{-0.5 \left(\frac{\overline{C}(k)}{avg\_bkgstd}\right)^2}\right)$$

where CorMax is a number between 0 and 1.

49. The method of claim 48, further comprising determining errors $\{P\sigma''_m\}$ of said second error-corrected experiment profile $\{PA''_m\}$ wherein said $\{P\sigma''_m\}$ comprises error data set $\{P\sigma''_m(k)\}$.

50. The method of claim 49, further comprising determining said error data set $\{P\sigma''_m(k)\}$ according to the equation $$P\sigma''_m(k) = \sqrt{[1-w(k)] \cdot P\sigma_m^2(k) + w(k) P\sigma'^2_m(k)}$$

where $P\sigma_m(k)$ is the standard error of $PA_m(k)$, and further comprising determining $P\sigma'_m(k)$ according to the equation $$P\sigma'_m(k) = \sqrt{P\sigma_m^2(k) + \text{mixed\_}P\sigma_m^2(k) - 2 \cdot Cor(k) \cdot P\sigma_m(k) \cdot \text{mixed\_}P\sigma_m(k)},$$

and
further comprising determining $\text{mixed\_}P\sigma_m(k)$ according to the equation $$\text{mixed\_}P\sigma_m(k) = \frac{P\sigma_m(k) + (M-1) \cdot P\sigma_{ref}(k)}{M} \quad \text{where}$$

-continued $$P\sigma_{ref}(k) = \sqrt{\frac{1}{M-1}\sum_{m}^{M}(PC_m(k) - \overline{PC}(k))^2}$$

and where Cor(k) is a correlation coefficient between said processed experiment profile $PA_m$ and said processed reference profile $PC_m$.

51. The method of claim 50, further comprising determining said Cor(k) according to the equation $$Cor(k) = CorMax \cdot \left[1 - \varepsilon^{-0.5\left[\frac{PC[k]}{avg\_bkgstd}\right]^2}\right]$$

where CorMax is a number between 0 and 1.

52. The method of claim 51, wherein each said pair of profiles $XA_m$ and $XC_m$ comprise measurements of said plurality of different cellular constituents from a two-channel microarray experiment.

53. The method of claim 52, wherein said reference profiles $\{XC_m\}$, m=1, 2, ..., M, are measured with samples labeled with a same label.

54. The method of claim 53, wherein at least one of said pairs of profiles $\{XA_m, XC_m\}$ is a virtual profile.

55. A method for generating at least one error-corrected experiment profile of at least one experiment profile $A_m$, where m ∈ {1, 2, ..., M} in at least one of a plurality of pairs of profiles $\{A_m, C_m\}$, $A_m$ being an experiment profile, $C_m$ being a reference profile, where m=1, 2, ..., M, M is the number of pairs of profiles, said method comprising:

via a differential reference profile $C_{diff}(m,k)$ calculated between $C_m$ and an average reference profile $\overline{C}$, wherein said average reference profile $\overline{C}$ comprises data set {$\overline{C}(k)$}, removing, on a suitably programmed computer, systematic cross-experiment error from said experiment profile $A_m$ for profile pair $\{A_m, C_m\}$ where m ∈ {1, 2, ..., M} to generate a first error-corrected experiment profile $A'_m$; wherein said average reference profile $\overline{C}$ is an average of reference profiles $\{C_m\}$, m=1, 2, ..., M; wherein for each m ∈ {1, 2, ..., M}, said first error-corrected experiment profile $A'_m$ comprises data set $\{A'_m(k)\}$, said experiment profile $A_m$ comprises data set $\{A_m(k)\}$, and said reference profile $C_m$ comprises data set $\{C_m(k)\}$, wherein said data set $\{A_m(k)\}$ comprises measurements of a plurality of different cellular constituents measured in a sample having been subject to a first condition, said data set $\{C_m(k)\}$ comprises measurements of said plurality of different cellular constituents measured in a sample having been subject to a second condition, wherein k=1, 2, ..., N; k is an index of measurements of cellular constituents, N being the total number of measurements, wherein generating respective $A'_m(k)$ of said first error-corrected experiment profile $A'_m$ comprises subtracting $C_{diff}(m,k)$ from $A_m(k)$; and outputting to a user, a user interface device, a computer readable storage medium, or a local or remote computer system; or displaying: said first error-corrected experiment profile $A'_m$ or said data set $\{A'_m(k)\}$.

56. The method of claim 18, further comprising obtaining said transformed measurements of said data set $\{A_m(k)\}$ and said data set $\{C_m(k)\}$ for an experiment according to the equations:

$$A_m(k) = f(x) = \frac{\ln\left(\frac{b^2 + 2 \cdot a^2 \cdot XA_m(k)}{a} + 2 \cdot \frac{\sqrt{c^2 + b^2 \cdot XA_m + a^2 \cdot [XA_m(k)]^2}}{a}\right)}{a} + d,$$

for $XA_m(k) > 0$ and $$C_m(k) = f(x) = \frac{\ln\left(\frac{b^2 + 2 \cdot a^2 \cdot XC_m(k)}{a} + 2 \cdot \frac{\sqrt{c^2 + b^2 \cdot XC_m(k) + a^2 \cdot [XC_m(k)]^2}}{a}\right)}{a} + d,$$

for $XC_m(k) > 0$ where $\{XA_m(k)\}$ and $\{XC_m(k)\}$ are data sets comprising measurements of said plurality of different cellular constituents that when transformed produce said transformed measurements of said plurality of different cellular constituents of said data set $A_m(k)$ and said data set $C_m(k)$, respectively, where d is described by the equation:

$$d = \frac{-\ln\left[\frac{b^2}{a} + 2 \cdot c\right]}{a}$$

and where a is the fractional error coefficient of said experiment, b is the Poisson error coefficient of said experiment, and c is the standard deviation of background noise of said experiment.

57. The method of claim 29, wherein said processing comprises:

normalizing, transforming, and/or removing nonlinearity from measurements of said plurality of cellular constituents of said data set $\{XA_m(k)\}$ of said experiment profile $XA_m$, and from measurements of said plurality of cellular constituents of said data set $\{XC_m(k)\}$ of said reference profile $XC_m$.

58. A computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out a method for generating at least one error-corrected experiment profile of at least one experiment profile in a plurality of pairs of profiles $\{A_m, C_m\}$, where m=1, 2, ..., M, and M is the number of the pairs of profiles; and wherein, for each m ∈ {1, 2, ..., M}, $A_m$ is an experiment profile, and $C_m$ is a reference profile; and wherein $\{A_m\}$ represents experiment profiles in said plurality of pairs of profiles $\{A_m, C_m\}$ and $\{C_m\}$ represents reference profiles in said plurality of pairs of profiles $\{A_m, C_m\}$, said method comprising:

(a) calculating, on a computer, an average reference profile $\overline{C}$ of said plurality of reference profiles $\{C_m\}$ where m=1, 2, ..., M;

(b) determining, on a computer, for at least one profile pair $\{A_m, C_m\}$ where m ∈ {1, 2, ..., M} of said plurality of pairs of profiles $\{A_m, C_m\}$ a differential reference profile $\overline{C}_{diff}(m,k)$ computed between $C_m$ and $\overline{C}$, wherein said average reference profile $\overline{C}$ comprises data set $\{\overline{C}(k)\}$;

(c) via said differential reference profile determined for said profile pair, removing, on a computer, systematic cross-experiment error from an experiment profile $A_m$ of said at least one profile pair $\{A_m, C_m\}$ where $m \in \{1, 2, \ldots, M\}$ to generate a first error-corrected experiment profile $A'_m$ for each $m \in \{1, 2, \ldots, M\}$, wherein said experiment profile $A_m$ comprises a first data set $\{A_m(k)\}$, said reference profile $C_m$ comprises a second data set, and said first error-corrected experiment profile $A'_m$ comprises data set $\{A'_m(k)\}$; wherein said first data set comprises measurements of a plurality of different cellular constituents measured in a sample having been subject to a first condition, said second data set comprises measurements of said plurality of different cellular constituents measured in a sample having been subject to a second condition; and wherein $k=1, 2, \ldots, N$; k is an index of measurements of said plurality of different cellular constituents, N being the total number of measurements, wherein generating respective $A'_m(k)$ of said first error-corrected experiment profile $A'_m$ comprises subtracting $C_{diff}(m,k)$ from $A_m(k)$; and (d) outputting to a user, a user interface device, a computer readable storage medium, or a local or remote computer system; or displaying: said first error-corrected experiment profile $A'_m$ or said data set $\{A'_m(k)\}$.

59. The computer program product of claim 58, wherein said steps (b) and (c) are performed for each profile pair $\{A_m, C_m\}$ where $m \in 0 \{1, 2, \ldots, M\}$.

60. The computer program product of claim 59, wherein each of said experiment profile $A_m$ and said reference profile $C_m$ comprises measurements of said plurality of different cellular constituents from the same experimental reaction.

61. The computer program product of claim 60, wherein said $\overline{C}(k)$ is calculated according to the equation $$\overline{C}(k) = \frac{1}{M} \sum_{m=1}^{M} C_m(k)$$

wherein said differential reference profile is determined according to the equation $$C_{diff}(m,k) = C_m(k) - \overline{C}(k)$$

and wherein said first error-corrected experiment profile $A'_m$ is generated according to the equation $$A'_m(k) = A_m(k) - C_{diff}(m,k)$$

wherein $\{A_m(k)\}$ is said first data set of experiment profile $A_m$.

62. The computer program product of claim 61, wherein the method further comprises:

(e) calculating, for one or more remaining profile pairs out of said profile pairs $\{A_m, C_m\}$, a respective second error-corrected experiment profile $A''_m$; and (f) outputting to, a user interface device, a computer readable storage medium, or a local or remote computer system; or displaying; said respective second error-corrected experiment profile $A''_m$ or a data set $\{A''_m(k)\}$.

63. The computer program product of claim 62, wherein said second error-corrected experiment profile $A''_m$ is calculated according to the equation $$A''_m(k) = (1 - w(k)) \cdot A_m(k) + w(k) \cdot A'_m(k).$$

64. The computer program product of claim 63, wherein the method further comprises determining a weighing factor $w(k)$ according to the equation $$w(k) = 1 - e^{-0.5 \left( \frac{\overline{C}(k)}{avg\_bkgstd} \right)^2}$$

where avg_bkgstd is an average background standard error.

65. The computer program product of claim 64, wherein the method further comprises determining said avg_bkgstd according to the equation $$avg\_bkgstd = \frac{1}{N} \sum_{k=1}^{N} \left[ \frac{1}{M} \sum_{m=1}^{M} bkgstd(m,k) \right]$$

where bkgstd(m,k) is background standard error of $C_m(k)$.

66. The computer program product of claim 61, wherein the method further comprises determining errors $\{\sigma'_m(k)\}$ of said data set $\{A'_m(k)\}$ in said first error-corrected experiment profile $A'_m$.

67. The computer program product of claim 66, wherein the method further comprises determining said errors $\{\sigma'_m(k)\}$ according to the equation $$\sigma'_m(k) = \sqrt{\sigma_m^2(k) + mixed\_\sigma_m^2(k) - 2 \cdot Cor(k) \cdot \sigma_m(k) \cdot mixed\_\sigma_m(k)}$$

where $\sigma_m(k)$ is the standard error of $A_m(k)$, the method further comprising determining mixed_$\sigma_m(k)$ according to the equation $$mixed\_\sigma_m(k) = \frac{\sigma_m(k) + (M-1) \cdot \sigma_{ref}(k)}{M}$$

$$\text{where } \sigma_{ref}(k) = \sqrt{\frac{1}{M-1} \sum_{m}^{M} (C_m(k) - \overline{C}(k))^2}$$

and where Cor(k) is a correlation coefficient between said experiment profile $A_m$ and said reference profile $C_m$.

68. The computer program product of claim 67, wherein the method further comprises determining said Cor(k) according to the equation $$mixed\_\sigma_m(k) = \frac{\sigma_m(k) + (M-1) \cdot \sigma_{ref}(k)}{M}$$

$$\text{where } \sigma_{ref}(k) = \sqrt{\frac{1}{M-1} \sum_{m}^{M} (C_m(k) - \overline{C}(k))^2}$$

where CorMax is a number between 0 and 1.

69. The computer program product of claim 64, wherein the method further comprises determining errors $\{\sigma''_m(k)\}$ of said data set $\{A''_m(k)\}$ in said second error-corrected experiment profile $A''_m$.

70. The computer program product of claim 69, wherein said errors $\{\sigma''_m(k)\}$ are determined according to the equation $$\sigma''_m(k) = \sqrt{[1 - w(k)] \cdot \sigma_m^2(k) + w(k)\sigma'^2_m(k)}$$

where $\sigma_m(k)$ is the standard error of $A_m(k)$, the method further comprising (i) determining $\sigma'_m(k)$ according to the equation $$\sigma'_m(k) = \sqrt{\sigma_m^2(k) + \text{mixed\_}\sigma_m^2(k) - 2 \cdot Cor(k) \cdot \sigma_m(k) \cdot \text{mixed\_}\sigma_m(k)}$$

(ii) determining mixed_$\sigma_m$(k) according to the equation $$Cor(k) = CorMax \cdot \left(1 - e^{-0.5 \cdot \left(\frac{\overline{C}(k)}{avg\_bkgstd}\right)^2}\right)$$

and where Cor(k) is a correlation coefficient between said experiment profile $A_m$ and said reference profile $C_m$.

71. The computer program product of claim 70, wherein the method further comprises determining said Cor(k) according to the equation $$Cor(k) = Cor\text{Max} \cdot \left[1 - e^{-0.5 \cdot \left[\frac{\overline{C}(k)}{avg\_bkgstd}\right]^2}\right]$$

where CorMax is a number between 0 and 1.

72. The computer program product of claim 59, wherein said experiment profile $A_m$ and said reference profile $C_m$ of each said profile pair $\{A_m, C_m\}$ are measured in a two-channel microarray experiment.

73. The computer program product of claim 72, wherein said reference profiles $\{C_m\}$ where m=1, 2, . . . , M, are measured with samples labeled with a same label.

74. The computer program product of claim 59, wherein at least one of said plurality of pairs of profiles $\{A_m, C_m\}$ is a virtual profile.

75. The computer program product of claim 58, wherein said plurality of pair of profiles $\{A_m, C_m\}$ are transformed profiles each comprising transformed measurements of said plurality of different cellular constituents in data set $\{A_m(k)\}$ and data set $\{C_m(k)\}$, respectively; and wherein said data set $\{A_m(k)\}$ is said first data set, and said data set $\{C_m(k)\}$ is said second data set.

76. The computer program product of claim 58, wherein the method further comprises:
   (a0) removing nonlinearity, prior to said calculating step (a), from measurements of said plurality of different cellular constituents to generate said plurality of pairs of profiles $\{A_m, C_m\}$ comprising said experiment profile $A_m$ and reference profile $C_m$.

77. The computer program product of claim 76, wherein said removing step (a0) comprises:
   (a0i) calculating an average profile of pre-experiment profiles $\{A_m^{pre}\}$ and pre-reference profiles $\{C_m^{pre}\}$; wherein each of said pre-experiment profiles comprises measurements of said plurality of different cellular constituents measured in said sample having been subject to said first condition, which when nonlinearity is removed therefrom, produces each said experiment profile $A_m$; and wherein each of said pre-reference profiles comprises measurements of said plurality of different cellular constituents measured in said sample having been subject to said second condition, which when nonlinearity is removed therefrom, produces each said reference profile $C_m$; and
   (a0ii) calculating first differences between each of said pre-experiment profiles $\{A_m^{pre}\}$ and said average profile; calculating second differences between each of said pre-reference profiles $\{C_m^{pre}\}$ and said average profile; adjusting, wherein the adjusting comprises correcting nonlinearity, each of said pre-experiment profiles $\{A_m^{pre}\}$ based on said first differences between each of said pre-experiment profiles $\{A_m^{pre}\}$ and said average profile, thereby generating each said experiment profile $A_m$; and adjusting, wherein the adjusting comprises correcting nonlinearity, each of pre-reference profiles $\{C_m^{pre}\}$ based on said second differences between each of said pre-reference profiles $\{C_m^{pre}\}$ and said average profile, thereby generating each said reference profile $C_m$.

78. The computer program product of claim 77, wherein the method further comprises calculating said first differences based on a first subset of said measurements of said plurality of different cellular constituents in said pre-experiment profiles $\{A_m^{pre}\}$ and said average profile; and calculating said second differences based on a second subset of said measurements of said plurality of different cellular constituents in said pre-reference profiles $\{C_m^{pre}\}$ and said average profile.

79. The computer program product of claim 78, wherein said first subset consists of measurements of said plurality of different cellular constituents that are ranked similarly between each of said pre-experiment profiles $\{A_m^{pre}\}$ and said average profile, and said second subset consists of measurements of said plurality of different cellular constituents that are ranked similarly between each of said pre-reference profiles $\{C_m^{pre}\}$ and said average profile.

80. The computer program product of claim 79, wherein said adjusting step (a0ii) is carried out by a method comprising:
   (ii1) binning said first subset into a first plurality of bins, wherein each of said first plurality of bins consists of measurements of said plurality of different cellular constituents in one of said pre-experiment profiles $\{A_m^{pre}\}$ and said average profile having a value in a given range; and binning said second subset into a second plurality of bins, wherein each of said second plurality of bins consists of measurements of said plurality of different cellular constituents in one of said pre-reference profiles $\{C_m^{pre}\}$ and said average profile having a value in a given range;
   (ii2) calculating, in each bin of said first plurality of bins, a first mean difference between a feature value of measurements of said one of said pre-experiment profiles $\{A_m^{pre}\}$ and a feature value of said average profile, and calculating a second mean difference between a feature value of measurements of said one of said pre-reference profiles $\{C_m^{pre}\}$ and a feature value of said average profile;
   (ii3) determining a first curve of said first mean difference as a first function of values of measurements of said plurality of different cellular constituents for said one of said pre-experiment profiles $\{A_m^{pre}\}$, wherein said first function is represented by, nonlinear_$A_m^{pre}$; and determining a second curve of said second mean difference as a second function of values of measurements of said plurality of different cellular constituents for said one of said pre-reference profiles $\{C_m^{pre}\}$, wherein said second function is represented by nonlinear_$C_m^{pre}$; and (ii4) adjusting each of said pre-experiment profiles $\{A_m^{pre}\}$ according to the equation:

$$A_m(k) = A_m^{pre}(k) - \text{nonlinear\_}A_m^{pre}(k),$$

and adjusting each of said pre-reference profiles $\{C_m^{pre}\}$ according to the equation:

$$C_m(k) = C_m^{pre}(k) - \text{nonlinear\_}C_m^{pre}(k),$$

where $k=1, \ldots, N$; and where $A_m^{pre}(k)$ and $C_m^{pre}(k)$ are data sets of each of said pre-experiment profiles $\{A_m^{pre}\}$ and each of said pre-reference profiles $\{C_m^{pre}\}$, respectively; and where $A_m(k)$ and $C_m(k)$ are said first data set and said second data set, respectively.

81. The computer program product of claim 58, wherein the method further comprises:

(a0) normalizing, prior to said calculating step (a), measurements of said plurality of different cellular constituents in a pre-experiment profile $A_m^{pre}$ and a pre-reference profile $C_m^{pre}$ to generate said experiment profile $A_m$ and said reference profile $C_m$, respectively.

82. The computer program product of claim 81, wherein said normalizing step (a0) comprises normalizing a data set $A_m^{pre}(k)$ and a data set $C_m^{pre}(k)$, according to the equations:

$$A_m(k) = \frac{A_m^{pre}(k) \cdot \overline{A_m^{pre} C_m^{pre}}}{\overline{A_m^{pre}}} \text{ and } C_m(k) = \frac{C_m^{pre}(k) \cdot \overline{A_m^{pre} C_m^{pre}}}{\overline{C_m^{pre}}},$$

wherein said data sets $A_m^{pre}(k)$ and $C_m^{pre}(k)$ each comprises measurements of said plurality of different cellular constituents, where $\overline{A_m^{pre}}$ is an average of measurements of said plurality of different cellular constituents in said $A_m^{pre}(k)$, and $\overline{C_m^{pre}}$ is an average of measurements of said plurality of different cellular constituents in said $C_m^{pre}(k)$, wherein $A_m(k)$ is said first data set, wherein $A_m(k)$ comprises normalized measurements or normalized transformed measurements of said pre-experiment profile $A_m^{pre}$; and $C_m(k)$ is said second data set wherein $A_m(k)$ comprises normalized measurements or normalized transformed measurements of said reference profile $C_m^{pre}$; and wherein $\overline{A_m^{pre} C_m^{pre}}$ is an average calculated according to the equation $$\overline{A_m^{pre} C_m^{pre}} = \frac{1}{2M} \sum_{m=1}^{M} (\overline{A_m^{pre}} + \overline{C_m^{pre}}).$$

83. The computer program product of claim 82, wherein the method further comprises normalizing errors of said data sets $\{A_m^{pre}(k)\}$ and $\{C_m^{pre}(k)\}$, respectively, according to the equations:

$$\sigma_m^{NA}(k) = \frac{\sigma_m^{preA}(k) \cdot \overline{A_m^{pre} C_m^{pre}}}{\overline{A_m^{pre}}} \text{ and } \sigma_m^{NC}(k) = \frac{\sigma_m^{preC}(k) \cdot \overline{A_m^{pre} C_m^{pre}}}{\overline{C_m^{pre}}},$$

where $\sigma_m^{preA}(k)$ and $\sigma_m^{preC}(k)$ are the standard errors of $A_m^{pre}(k)$ and $C_m^{pre}(k)$, respectively, and $\sigma_m^{NA}(k)$ and $\sigma_m^{NC}(k)$ are normalized standard errors of $A_m(k)$ and $C_m(k)$, respectively.

84. The computer program product of claim 83, wherein the method further comprises normalizing background errors of said data sets $\{A_m^{pre}(k)\}$ and $\{C_m^{pre}(k)\}$, respectively, according to the equations:

$$bkgstd_m^{NA}(k) = \frac{bkgstd_m^{preA}(k) \cdot \overline{A_m^{pre} C_m^{pre}}}{\overline{A_m^{pre}}} \text{ and } bkgstd_m^{NC}(k) = \frac{bkgstd_m^{preC}(k) \cdot \overline{A_m^{pre} C_m^{pre}}}{\overline{C_m^{pre}}}$$

where $bkgstd_m^{preA}(k)$ and $bkgstd_m^{preC}(k)$ are the standard background errors of $A_m^{pre}(k)$ and $C_m^{pre}(k)$, respectively, and $bkgstd_m^{NA}(k)$ and $bkgstd_m^{NC}(k)$ are normalized standard background errors of $A_m(k)$ and $C_m(k)$, respectively.

85. The computer program product of claim 84, wherein the method further comprises calculating said averages $\overline{A_m^{pre}}$ and $\overline{C_m^{pre}}$ by excluding measurements of said plurality of different cellular constituents having a value among the highest 10% of said measurements of said plurality of different cellular constituents in said data sets $\{A_m^{pre}(k)\}$ and $\{C_m^{pre}(k)\}$, respectively.

86. A computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out a method for generating at least one error-corrected experiment profile of at least one experiment profile in a plurality of pairs of profiles $\{XA_m, XC_m\}$, $XA_m$ being an experiment profile, $XC_m$ being a reference profile, where $m=1, 2, \ldots, M$, $M$ is the number of pairs of profiles, said method comprising:

(a) processing, on a computer, said plurality of pairs of profiles $\{XA_m, XC_m\}$ to obtain a plurality of pairs of processed profiles $\{PA_m, PC_m\}$, $PA_m$ being a processed experiment profile, $PC_m$ being a processed reference profile, wherein said processing comprises normalizing at least one said experiment profile $XA_m$ and reference profile $XC_m$;

(b) calculating, on a computer, an average processed reference profile $\overline{PC}$ of processed reference profiles $\{PC_m\}$, where $m=1, 2, \ldots, M$;

(c) determining, on a computer, for at least one processed profile pair $\{PA_m, PC_m\}$ where $m \in \{1, 2, \ldots, M\}$ of said plurality of pairs of processed profiles $\{PA_m, PC_m\}$, where $m=1, 2, \ldots, M$, a differential reference profile $PC_m(m,k)$ computed between $PC_m$ and $\overline{PC}$ wherein said average processed reference profile $\overline{PC}$ comprises data set $\{\overline{PC}(k)\}$;

(d) via said differential reference profile determined for said at least one processed profile pair, removing, on a suitably programmed computer, systematic cross-experiment error from a processed experiment profile $PA_m$ of said at least one processed profile pair $\{PA_m, PC_m\}$ where $m \in \{1, 2, \ldots, M\}$ to generate a first error-corrected processed experiment profile $PA'_m$; wherein for each $m \in \{1, 2, \ldots, M\}$, said processed experiment profile $PA_m$ comprises a first processed data set, $\{PA_m(k)\}$, said processed reference profile $PC_m$ comprises a second processed data set, said first error-corrected processed experiment profile $PA'_m$ comprises dataset $\{PA'_m(k)\}$, said experiment profile $XA_m$ comprises data set $\{XA_m(k)\}$, said reference profile $XC_m$ comprises data set $\{XC_m(k)\}$, wherein said data set $\{XA_m(k)\}$ comprises measurements of a plurality of different cellular constituents measured in a sample having been subject to a first condition, said data set $\{XC_m(k)\}$ comprises measurements of said plurality of different cellular constituents measured in a sample having been subject to a second condition, and where k=1, 2, ..., N; k is an index of measurements of cellular constituents, N being the total number of measurements, wherein generating respective $PA'_m(k)$ of said first error-corrected processed experiment profile $PA'_m$ comprises subtracting $PC_{diff}(m, k)$ from $PA_m(k)$; and (e) outputting to a user, a user interface device, a computer readable storage medium, or a local or remote computer system; or displaying: said first error-corrected processed experiment profile $PA'_m$ or said data set $\{PA'_m(k)\}$.

87. The computer program product of claim 86, wherein said processing step (a) comprises normalizing each said experiment profile $XA_m$ and reference profile $XC_m$.

88. The computer program product of claim 87, wherein said normalizing is carried out according to the equations:

$$NA_m(k) = \frac{XA_m(k) \cdot \overline{XAC}}{\overline{XA_m}} \text{ and } NC_m(k) = \frac{XC_m(k) \cdot \overline{XAC}}{\overline{XC_m}}$$

where $\{NA_m(K)\}$ is said first data set of said processed experiment profile $PA_m$, and $\{NC_m(k)\}$ is said second data set of said processed reference profile $PC_m$; where $\overline{XA_m}$ is an average of measurements of said plurality of different cellular constituents of said data set $\{XA_m(k)\}$, and $\overline{XC_m}$ is an average of measurements of said plurality of different cellular constituents of data set $\{XC_m(k)\}$; and wherein $\overline{XAC}$ is an average calculated according to the equation $$\overline{XAC} = \frac{1}{2M}\sum_{m=1}^{M}(\overline{XA_m} + \overline{XC_m}).$$

89. The computer program product of claim 88, wherein the method further comprises normalizing errors of said experiment profile $XA_m$ and reference profile $XC_m$ according to the equations:

$$\sigma_m^A(k) = \frac{\sigma_m^{XA}(k) \cdot \overline{XAC}}{\overline{XA_m}} \text{ and}$$

$$\sigma_m^C(k) = \frac{\sigma_m^{XC}(k) \cdot \overline{XAC}}{\overline{XC_m}}$$

where $\sigma_m^{XA}(k)$ and $\sigma_m^{XC}(k)$ are the standard errors of $XA_m(k)$ and $XC_m(k)$, respectively, and $\sigma_m^A(k)$ and $\sigma_m^C(k)$ are normalized standard errors of $NA_m(k)$ and $NC_m(k)$, respectively.

90. The computer program product of claim 89, wherein the method further comprises normalizing background errors of said experiment profile $XA_m$ and reference profile $XC_m$ according to the equations:

$$bkgstd_m^A(k) = \frac{bkgstd_m^{XA}(k) \cdot \overline{XAC}}{\overline{XA_m}} \text{ and}$$

-continued $$bkgstd_m^C(k) = \frac{bkgstd_m^{XC}(k) \cdot \overline{XAC}}{\overline{XC_m}}$$

where $bkgstd_m^{XA}(k)$ and $bkgstd_m^{XC}(k)$ are the standard background errors of $XA_m(k)$ and $XC_m(k)$, respectively, and $bkgstd_m^A(k)$ and $bkgstd_m^C(k)$ are normalized standard background errors of said $NA_m(k)$ and said $NC_m(k)$, respectively.

91. The computer program product of claim 89, wherein the method further comprises determining said averages $\overline{XA_m}$ and $\overline{XC_m}$ excluding measurements of said plurality of different cellular constituents having a value among the highest 10% of said measurements of said plurality of different cellular constituents in said data sets $\{XA_m(k)\}$ and $\{XC_m(k)\}$, respectively.

92. The computer program product of claim 86, wherein said processing step (a) comprises:

normalizing each said experiment profile $XA_m$ and reference profile $XC_m$ to generate normalized data set $\{NA_m(k)\}$ and normalized data set $\{NC_m(k)\}$, respectively;

transforming said normalized data set $\{NA_m(k)\}$ to obtain a transformed data set $\{TA_m(k)\}$, where said transformed data set $\{TA_m(k)\}$ is said first data set of said processed experiment profile $PA_m$; and transforming said normalized data set $\{NC_m(k)\}$ to obtain a transformed data set $\{TC_m(k)\}$, where said transformed data set $\{TC_m(k)\}$ is said second data set of said processed reference profile $PC_m$;

wherein said transforming is carried out for an experiment according to equations $$TA_m(k) = f(x) = \frac{\ln\left[\frac{b^2 + 2 \cdot a^2 \cdot NA_m(k)}{a} + 2 \cdot \sqrt{c^2 + b^2 \cdot NA_m(k) + a^2 \cdot [NA_m(k)]^2}\right]}{a} + d,$$

for $NA_m(k) > 0$ and $$TC_m(k) = f(x) = \frac{\ln\left[\frac{b^2 + 2 \cdot a^2 \cdot NC_m(k)}{a} + 2 \cdot \sqrt{c^2 + b^2 \cdot NC_m(k) + a^2 \cdot [NC_m(k)]^2}\right]}{a} + d,$$

for $NC_m(k) > 0$ where d is described by equation $$d = \frac{-\ln\left[\frac{b^2}{a} + 2 \cdot c\right]}{a}$$

and where a is the fractional error coefficient of said experiment, b is the Poisson error coefficient of said experiment, and c is the standard deviation of background noise of said experiment.

93. The computer program product of claim 86, wherein said processing step (a) comprises:

normalizing each said experiment profile $XA_m$ and reference profile $XC_m$ to generate normalized data set $\{NA_m(k)\}$ and normalized data set $\{NC_m(k)\}$, respectively;

transforming said normalized data set $\{NA_m(k)\}$ to a new domain in which variance becomes a constant to obtain a transformed data set $\{TA_m(k)\}$;

transforming said normalized data set $\{NC_m(k)\}$ to the new domain in which variance becomes a constant to obtain a transformed data set $\{TC_m(k)\}$; and removing nonlinearity from each said transformed data sets $\{TA_m(k)\}$ and $\{TC_m(k)\}$, respectively.

94. The computer program product of claim 93, wherein said removing nonlinearity is carried out by a method comprising (a1) calculating an average transformed profile of transformed experiment profiles and transformed reference profiles, wherein each of said transformed experiment profiles contains a corresponding transformed data set $\{TA_m(k)\}$, and each of said transformed reference profiles contains a corresponding transformed data set $\{TC_m(k)\}$; and (a2) calculating first differences between each of said transformed experiment profiles and said average transformed profile; calculating second differences between each of said transformed reference profiles and said average transformed profile; adjusting, wherein the adjusting comprises correcting nonlinearity each of said transformed experiment profiles based on said first differences between each of said transformed experiment profiles and said average transformed profile, and adjusting, wherein the adjusting comprises correcting nonlinearity each of said transformed reference profiles based on said second differences between each of said transformed reference profiles and said average transformed profile.

95. The computer program product of claim 94, wherein the method further comprises calculating said first differences based on the differences in a first subset of transformed measurements of said plurality of different cellular constituents between each of said transformed experiment profiles and said average transformed profile, and calculating said second differences based on the differences in a second subset of transformed measurements of said plurality of different cellular constituents between each of said transformed reference profiles and said average transformed profile.

96. The computer program product of claim 95, wherein each said first subset consists of transformed measurements that are ranked similarly between each of said transformed experiment profiles and said average transformed profile, and each said second subset consists of transformed measurements that are ranked similarly between each of said transformed reference profiles and said average transformed profile.

97. The computer program product of claim 96, wherein said adjusting step (a2) is carried out by a method comprising:

(a2i) binning said first subset into a plurality of bins, each said bin consisting of transformed measurements of said plurality of different constituents in one of said transformed experiment profiles and said average transformed profile having a value in a given range; and binning said second subset into a plurality of bins, each said bin consisting of transformed measurements of said plurality of different cellular constituents in one of said transformed reference profiles and said average transformed profile having a value in a given range;

and computing corrected transformed measurements of said plurality of different cellular constituents in each said transformed data set $\{TC_m(k)\}$, according to the equation:

$$TC_m^{corr}(k) = TC_m(k) - \text{nonlinear}\_TC_m(k),$$

where $k=1, \ldots, N$; and where $\{TA_m^{corr}(k)\}$ is said first processed data set of said processed experiment profile $PA_m$, and $\{TC_m^{corr}(k)\}$ is said second processed data set of said processed reference profile $PC_m$.

98. The computer program product of claim 97, wherein said processed experiment profile $PA_m$ and said processed reference profile $PC_m$ comprise transformed measurements of said plurality of different cellular constituents from the same experiment reaction.

99. The computer program product of claim 98, wherein the method further comprises calculating $\overline{PC}(k)$ according to the equation $$\overline{PC}(k) = \frac{1}{M}\sum_{m=1}^{M} PC_m(K),$$

wherein $\{PC_m(k)\}$ comprises transformed measurements from said second processed data set $\{TC_m^{corr}(k)\}$ and calculating said differential reference profile according to the equation $$PC_{diff}(m,k) = PC_m(k) - \overline{PC}(k)$$

and wherein said first error-corrected profile is calculated according to the equation $$PA'_m(k) = PA_m(k) - PC_{diff}(m,k),$$

wherein $\{PA_m(k)\}$ comprises transformed measurements from said first data set $\{TA_m^{corr}(k)\}$.

100. The computer program product of claim 99, where the method further comprises (d) calculating for each processed profile pair $\{PA_m, PC_m\}$, where $m \in \{1, 2, \ldots, M\}$, a second error-corrected experiment profile $PA''_m$ comprising data set $\{PA''_m(k)\}$ by combining said first error-corrected experiment profile $PA'_m$ with said processed experiment profile $PA_m$ using a weighing factor $\{w(k)\}, k=1, 2, \ldots, N$, wherein $w(k)$ is a weighing factor for the k'th measurement.

101. The computer program product of claim 100, wherein said second error-corrected experiment profile $PA''_m$ is calculated according to the equation $$PA''_m(k) = (1-w(k)) \cdot PA_m(k) + w(k) PA'_m(k).$$

102. The computer program product of claim 101, wherein the method further comprises determining said weighing factor according to the equation $$w(k) = 1 - e^{-0.5\left[\frac{\overline{PC}(k)}{avg\_bkgstd}\right]^2}$$

where avg_bkgstd is an average background standard error.

103. The computer program product of claim 102, wherein the method further comprises determining said avg_bkgstd according to the equation $$avg\_bkgstd = \frac{1}{N}\sum_{k=1}^{N}\left[\frac{1}{M}\sum_{m=1}^{M} bkgstd(m,k)\right]$$

where $bkgstd(m,k)$ is background standard error of $PC_m(k)$.

104. The computer program product of claim 99, wherein the method further comprises determining errors $\{P\sigma'_m\}$ of said first error-corrected experiment profile {PA'$_m$}, wherein said {Pσ'$_m$} comprises error data set {Pσ'$_m$(k)}.

105. The computer program product of claim 104, wherein the method further comprises determining said error data set {Pσ'$_m$(k)} according to the equation $$\sigma'_m(k) = \sqrt{P\sigma_m^2(k) = \text{mixed\_P}\sigma_m^2(k) - 2Cor(k) \cdot P\sigma_m(k) \cdot \text{mixed\_P}\sigma_m(k)}$$

where Pσ$_m$(k) is the standard error of A$_m$(k), and determining mixed_Pσ$_m$(k) according to the equation $$\text{mixed\_P}\sigma_m(k) = \frac{P\sigma_m(k) + (M-1) \cdot P\sigma_{ref}(k)}{M} \text{ where}$$

$$P\sigma_{ref}(k) = \sqrt{\frac{1}{M-1} \sum_m^M (PC_m(k) - \overline{PC}(k))^2}$$

and where Cor(k) is a correlation coefficient between said processed experiment profile PA$_m$ and said processed reference profile PC$_m$.

106. The computer program product of claim 105, wherein said Cor(k) is determined according to the equation $$Cor(k) = Cor\text{Max} \cdot \left[1 - e^{-0.5\left[\frac{PC(k)}{avg\_bkgstd}\right]^2}\right]$$

where CorMax is a number between 0 and 1.

107. The computer program product of claim 106, wherein the method further comprises determining errors {Pσ"$_m$} of said second error-corrected experiment profile {PA"$_m$} where said {Pσ"$_m$} comprises error data set {Pσ"$_m$(k)}.

108. The computer program product of claim 107, wherein the method further comprises determining said error data set {Pσ"$_m$(k)} according to the equation $$P\sigma''_m(k) = \sqrt{[1-w(k)] \cdot P\sigma_m^2(k) + w(k) P\sigma_m'^2(k)}$$

where Pσ$_m$(k) is the standard error of PA$_m$(k), and the methods further comprises determining Pσ'$_m$(k) according to the equation $$P\sigma'_m(k) = \sqrt{P\sigma_m^2(k) + \text{mixed\_P}\sigma_m^2(k) - 2 \cdot Cor(k) \cdot P\sigma_m(k) \cdot \text{mixed\_P}\sigma_m(k)},$$

and
the method further comprises determining mixed_Pσ$_m$(k) according to the equation $$\text{mixed\_P}\sigma_m(k) = \frac{P\sigma_m(k) + (M-1) \cdot P\sigma_{ref}(k)}{M} \text{ where}$$

$$P\sigma_{ref}(k) = \sqrt{\frac{1}{M-1} \sum_m^M (PC_m(k) - PC(k))^2}$$

and where Cor(k) is a correlation coefficient between said processed experiment profile PA$_m$ and said processed reference profile PC$_m$.

109. The computer program product of claim 108, wherein the method further comprises determining said Cor(k) according to the equation $$Cor(k) = Cor\text{Max} \cdot \left[1 - e^{-0.5\left[\frac{PC(k)}{avg\_bkgstd}\right]^2}\right]$$

where CorMax is a number between 0 and 1.

110. The computer program product of claim 109, wherein each said pair of profiles XA$_m$ and XC$_m$ comprise measurements of said plurality of different cellular constituents from a two-channel microarray experiment.

111. The computer program product of claim 110, wherein said reference profiles {XC$_m$}, m=1, 2, . . . , M, are measured with samples labeled with a same label.

112. The computer program product of claim 111, wherein at least one of said pairs of profiles {XA$_m$, XC$_m$} is a virtual profile.

113. A computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out a method for generating at least one error-corrected experiment profile of at least one experiment profile A$_m$, where m ∈ {1, 2, . . . , M} in at least one of a plurality of pairs of profiles {A$_m$, C$_m$}, A$_m$ being an experiment profile, C$_m$ being a reference profile, where m=1, 2, . . . , M, M is the number of pairs of profiles, said method comprising:

via a differential reference profile C$_{diff}$(m,k) calculated between C$_m$ and an average reference profile $\overline{C}$ determined for profile pair {A$_m$, C$_m$} where m ∈{1, 2, . . . , M}, wherein said average reference profile $\overline{C}$ comprises data set {$\overline{C}$(k)}, removing, on a computer, systematic cross-experiment error from said experiment profile A$_m$ to generate a first error-corrected experiment profile A'$_m$; wherein said average reference profile $\overline{C}$ is an average of reference profiles {C$_m$}, m=1, 2, . . . , M; wherein for each m ∈ {1, 2, . . . , M}, said first error-corrected experiment profile A'$_m$ comprises data set {A'$_m$(k)}, said experiment profile A$_m$ comprises data set {A$_m$(k)}, and said reference profile C$_m$ comprises data set {C$_m$(k)}, wherein said data set {A$_m$(k)} comprises measurements of a plurality of different cellular constituents measured in a sample having been subject to a first condition, said data set {C$_m$(k)} comprises measurements of said plurality of different cellular constituents measured in a sample having been subject to a second condition, wherein k=1, 2, . . . , N; k is an index of measurements of cellular constituents, N being the total number of measurements, wherein generating respective A'$_m$(k) of said first error-corrected experiment profile A'$_m$ comprises subtracting C$_{diff}$(m,k) from A$_m$(k); and outputting to a user, a user interface device, a computer readable storage medium, or a local or remote computer system; or displaying: said first error-corrected experiment profile A'$_m$ or said data set {A'$_m$(k)}.

114. The computer program product of claim 75, wherein the method further comprises obtaining said transformed measurements of said data set $\{A_m(k)\}$ and said data set $\{C_m(k)\}$ for an experiment according to the equations:

$$A_m(k) = f(x) = \frac{\ln\left(\frac{b^2 + 2 \cdot a^2 \cdot XA_m(k)}{a} + 2 \cdot \sqrt{c^2 + b^2 \cdot XA_m + a^2 \cdot [XA_m(k)]^2}\right)}{a} + d,$$

for $XA_m(k) > 0$ and $$C_m(k) = f(x) = \frac{\ln\left(\frac{b^2 + 2 \cdot a^2 \cdot XC_m(k)}{a} + 2 \cdot \sqrt{c^2 + b^2 \cdot XC_m(k) + a^2 \cdot [XC_m(k)]^2}\right)}{a} + d,$$

for $XC_m(k) > 0$ where $\{XA_m(k)\}$ and $\{XC_m(k)\}$ are data sets comprising measurements of said plurality of different cellular constituents that when transformed produce said transformed measurements of said plurality of different cellular constituents of said data set $A_m(k)$ and said data set $C_m(k)$, respectively, where d is described by the equation:

$$d = \frac{-\ln\left[\frac{b^2}{a} + 2 \cdot c\right]}{a}$$

and where a is the fractional error coefficient of said experiment, b is the Poisson error coefficient of said experiment, and c is the standard deviation of background noise of said experiment.

115. The computer program product of claim 86, wherein said processing comprises:
  normalizing, transforming, and/or removing nonlinearity from measurements of said plurality of cellular constituents of said data set $\{XA_m(k)\}$ of said experiment profile $XA_m$, and from measurements of said plurality of cellular constituents of said data set $\{XC_m(k)\}$ of said reference profile $XC_m$.

116. A computer system comprising:
  a processor; and
  a memory coupled to said processor and encoding one or more programs;
  wherein said one or more programs cause the processor to carry out a method for generating at least one error-corrected experiment profile of at least one experiment profile in a plurality of pairs of profiles $\{A_m, C_m\}$, where m=1, 2, ..., M, and M is the number of the pairs of profiles; and wherein, for each m ∈ $\{1, 2, ..., M\}$, $A_m$ is an experiment profile, and $C_m$ is a reference profile; and wherein $\{A_m\}$ represents experiment profiles in said plurality of pairs of profiles $\{A_m, C_m\}$ and $\{C_m\}$ represents reference profiles in said plurality of pairs of profiles $\{A_m, C_m\}$, said method comprising:
  (a) calculating, on a computer, an average reference profile $\overline{C}$ of said plurality of reference profiles $\{C_m\}$ where m=1, 2, ..., M;
  (b) determining, on a computer, for at least one profile pair $\{A_m, C_m\}$ where m ∈ $\{1, 2, ..., M\}$ of said plurality of pairs of profiles $\{A_m, C_m\}$ a differential reference profile $\overline{C}_{diff}(m,k)$ computed between $C_m$ and $\overline{C}$, wherein said average reference profile $\overline{C}$ comprises data set $\{\overline{C}(k)\}$;
  (c) via said differential reference profile determined for said profile pair, removing, on a computer, systematic cross-experiment error from an experiment profile $A_m$ of said at least one profile pair $\{A_m, C_m\}$ where m ∈ $\{1, 2, ..., M\}$ to generate a first error-corrected experiment profile $A'_m$ for each m ∈ $\{1, 2, ..., M\}$, wherein said experiment profile $A_m$ comprises a first data set $\{A_m(k)\}$, said reference profile $C_m$ comprises a second data set, and said first error-corrected experiment profile $A'_m$ comprises data set $\{A'_m(k)\}$; wherein said first data set comprises measurements of a plurality of different cellular constituents measured in a sample having been subject to a first condition, said second data set comprises measurements of said plurality of different cellular constituents measured in a sample having been subject to a second condition; and wherein k=1, 2, ..., N; k is an index of measurements of said plurality of different cellular constituents, N being the total number of measurements, wherein said first error-corrected experiment profile $A'_m$ is generated according to the equation $A'_m(k) = A_m(k) - \overline{C}_{diff}(m,k)$; and
  (d) outputting to a user, a user interface device, a computer readable storage medium, or a local or remote computer system; or displaying: said first error-corrected experiment profile $A'_m$ or said data set $\{A'_m(k)\}$.

117. The computer system of claim 116, wherein said steps (b) and (c) are performed for each profile pair $\{A_m, C_m\}$ where m ∈ $\{1, 2, ..., M\}$.

118. The computer system of claim 117, wherein each of said experiment profile $A_m$ and said reference profile $C_m$ comprises measurements of said plurality of different cellular constituents from the same experimental reaction.

119. The computer system of claim 118, wherein said $\overline{C}(k)$ is calculated according to the equation $$\overline{C}(k) = \frac{1}{M}\sum_{m=1}^{M} \overline{C}_m(k)$$

wherein said differential reference profile is determined according to the equation $$\overline{C}_{diff}(m,k) = \overline{C}_m(k) - \overline{C}(k)$$

and wherein said first error-corrected experiment profile $A'_m$ is generated according to the equation $$A'_m(k) = A_m(k) - \overline{C}_{diff}(m,k)$$

wherein $\{A_m(k)\}$ is said first data set of experiment profile $A_m$.

120. The computer system of claim 119, wherein the method further comprises:
  (e) calculating, for one or more remaining profile pairs out of said profile pairs $\{A_m, C_m\}$, a respective second error-corrected experiment profile $A''_m$; and
  (f) outputting to, a user interface device, a computer readable storage medium, or a local or remote computer system; or displaying; said respective second error-corrected experiment profile $A''_m$ or a data set $\{A''_m(k)\}$.

121. The computer system of claim 120, wherein said second error-corrected experiment profile $A''_m$ is calculated according to the equation $$A''_m(k) = (1 - w(k)) \cdot A_m(k) + w(k) \cdot A'_m(k).$$

122. The computer system of claim 121, wherein the method further comprises determining a weighing factor w(k) according to the equation $$w(k) = 1 - e^{-0.5\left[\frac{\overline{C}(k)}{avg\_bkgstd}\right]^2}$$

where avg_bkgstd is an average background standard error.

123. The computer system of claim 122, wherein the method further comprises determining said avg_bkgstd according to the equation $$avg\_bkgstd = \frac{1}{N}\sum_{k=1}^{N}\left[\frac{1}{M}\sum_{m=1}^{M}bkgstd(m,k)\right]$$

where bkgstd(m,k) is background standard error of $C_m(k)$.

124. The computer system of claim 119, wherein the method further comprises determining errors $\{\sigma'_m(k)\}$ of said data set $\{A'_m(k)\}$ in said first error-corrected experiment profile $A'_m$.

125. The computer system of claim 124, wherein the method further comprises determining said errors $\{\sigma'_m(k)\}$ according to the equation $$\sigma'_m(k) = \sqrt{\sigma_m^2(k) + mixed\_\sigma_m^2(k) - 2\cdot Cor(k)\cdot\sigma_m(k)\cdot mixed\_\sigma_m(k)}$$

where $\sigma_m(k)$ is the standard error of $A_m(k)$, the method further comprising determining mixed_$\sigma_m(k)$ according to the equation $$mixed\_\sigma_m(k) = \frac{\sigma_m(k) + (M-1)\cdot\sigma_{ref}(k)}{M} \text{ where}$$

$$\sigma_{ref}(k) = \sqrt{\frac{1}{M-1}\sum_{m}^{M}(C_m(k) - \overline{C}(k))^2}$$

and where Cor(k) is a correlation coefficient between said experiment profile $A_m$ and said reference profile $C_m$.

126. The computer system of claim 125, wherein the method further comprises determining said Cor(k) according to the equation $$Cor(k) = CorMax\cdot\left[1 - e^{-0.5\left[\frac{\overline{C}(k)}{avg\_bkgstd}\right]^2}\right]$$

where CorMax is a number between 0 and 1.

127. The computer system of claim 122, wherein the method further comprises determining errors $\{\sigma''_m(k)\}$ of said data set $\{A''_m(k)\}$ in said second error-corrected experiment profile $A''_m$.

128. The computer system of claim 127, wherein said errors $\{\sigma''_m(k)\}$ are determined according to the equation $$\sigma''_m(k) = \sqrt{[1 - w(k)]\cdot\sigma_m^2(k) + w(k)\sigma'^2_m(k)}$$

where $\sigma_m(k)$ is the standard error of $A_m(k)$, the method further comprising (i) determining $\sigma'_m(k)$ according to the equation $$\sigma'_m(k) = \sqrt{\sigma_m^2(k) + mixed\_\sigma_m^2(k) - 2\cdot Cor(k)\cdot\sigma_m(k)\cdot mixed\_\sigma_m(k)},$$

(ii) determining mixed_$\sigma_m(k)$ according to the equation $$mixed\_\sigma_m(k) = \frac{\sigma_m(k) + (M-1)\cdot\sigma_{ref}(k)}{M} \text{ where}$$

$$\sigma_{ref}(k) = \sqrt{\frac{1}{M-1}\sum_{m}^{M}(C_m(k) - \overline{C}(k))^2}$$

and where Cor(k) is a correlation coefficient between said experiment profile $A_m$ and said reference profile $C_m$.

129. The computer system of claim 128, wherein the method further comprises determining said Cor(k) according to the equation $$Cor(k) = CorMax\cdot\left[1 - e^{-0.5\left[\frac{\overline{C}(k)}{avg\_bkgstd}\right]^2}\right]$$

where CorMax is a number between 0 and 1.

130. The computer system of claim 117, wherein said experiment profile $A_m$ and said reference profile $C_m$ of each said profile pair $\{A_m, C_m\}$ are measured in a two-channel microassay experiment.

131. The computer system of claim 130, wherein said reference profiles $\{C_m\}$, where m=1, 2, ..., M, are measured with samples labeled with a same label.

132. The computer system of claim 117, wherein at least one of said plurality of pairs of profiles $\{A_m, C_m\}$ is a virtual profile.

133. The computer system of claim 116, wherein said plurality of pairs of profiles $\{A_m, C_m\}$ are transformed profiles each comprising transformed measurements of said plurality of different cellular constituents in data set $\{A_m(k)\}$ and data set $\{C_m(k)\}$, respectively; and wherein said data set $\{A_m(k)\}$ is said first data set, and said data set $\{C_m(k)\}$ is said second data set.

134. The computer system of claim 116, wherein the method further comprises:
 (a0) removing nonlinearity, prior to said calculating step (a), from measurements of said plurality of different cellular constituents to generate said plurality of pairs of profiles $\{A_m, C_m\}$ comprising said experiment profile $A_m$ and reference profile $C_m$.

135. The computer system of claim 134, wherein said removing step (a0) comprises:
 (a0i) calculating an average profile of pre-experiment profiles $\{A_m^{pre}\}$ and pre-reference profiles $\{C_m^{pre}\}$; wherein each of said pre-experiment profiles comprises measurements of said plurality of different cellular constituents measured in said sample having been subject to said first condition, which when nonlinearity is removed therefrom, produces each said experiment profile $A_m$; and wherein each of said pre-reference profiles comprises measurements of said plurality of different cellular constituents measured in said sample having been subject to said second condition, which when nonlinearity is removed therefrom, produces each said reference profile $C_m$; and (a0ii) calculating first differences between each of said pre-experiment profiles $\{A_m^{pre}\}$ and said average profile; calculating second differences between each of said pre-reference profiles $\{C_m^{pre}\}$ and said average profile; adjusting, wherein the adjusting comprises correcting nonlinearity, each of said pre-experiment profiles $\{A_m^{pre}\}$ based on said first differences between each of said pre-experiment profiles $\{A_m^{pre}\}$ and said average profile, thereby generating each said experiment profile $A_m$; and adjusting, wherein the adjusting comprises correcting nonlinearity, each of pre-reference profiles $\{C_m^{pre}\}$ based on said second differences between each of said pre-reference profiles $\{C_m^{pre}\}$ and said average profile, thereby generating each said reference profile $C_m$.

136. The computer system of claim 135, wherein the method further comprises calculating said first differences based on a first subset of said measurements of said plurality of different cellular constituents in said pre-experiment profiles $\{A_m^{pre}\}$ and said average profile; and calculating said second differences based on a second subset of said measurements of said plurality of different cellular constituents in said pre-reference profiles $\{C_m^{pre}\}$ and said average profile.

137. The computer system of claim 136, wherein said first subset consists of measurements of said plurality of different cellular constituents that are ranked similarly between each of said pre-experiment profiles $\{A_m^{pre}\}$ and said average profile, and said second subset consists of measurements of said plurality of different cellular constituents that are ranked similarly between each of said pre-reference profiles $\{C_m^{pre}\}$ and said average profile.

138. The computer system of claim 137, wherein said adjusting step (a0ii) is carried out by a method comprising:
(ii1) binning said first subset into a first plurality of bins, wherein each of said first plurality of bins consists of measurements of said plurality of different cellular constituents in one of said pre-experiment profiles $\{A_m^{pre}\}$ and said average profile having a value in a given range; and binning said second subset into a second plurality of bins, wherein each of said second plurality of bins consists of measurements of said plurality of different cellular constituents in one of said pre-reference profiles $\{C_m^{pre}\}$ and said average profile having a value in a given range;
(ii2) calculating, in each bin of said first plurality of bins, a first mean difference between a feature value of measurements of said one of said pre-experiment profiles $\{A_m^{pre}\}$ and a feature value of said average profile, and calculating a second mean difference between a feature value of measurements of said one of said pre-reference profiles $\{C_m^{pre}\}$ and a feature value of said average profile;
(ii3) determining a first curve of said first mean difference as a first function of values of measurements of said plurality of different cellular constituents for said one of said pre-experiment profiles $\{A_m^{pre}\}$, wherein said first function is represented by, nonlinear_$A_m^{pre}$; and determining a second curve of said second mean difference as a second function of values of measurements of said plurality of different cellular constituents for said one of said pre-reference profiles $\{C_m^{pre}\}$, wherein said second function is represented by nonlinear_$C_m^{pre}$; and
(ii4) adjusting each of said pre-experiment profiles $\{A_m^{pre}\}$ according to the equation:

$$A_m(k) = A_m^{pre}(k) - \text{nonlinear}\_A_m^{pre}(k),$$

and adjusting each of said pre-reference profiles $\{C_m^{pre}\}$ according to the equation:

$$C_m(k) = C_m^{pre}(k) - \text{nonlinear}\_C_m^{pre}(k),$$

where $k=1, \ldots, N$; and where $A_m^{pre}(k)$ and $C_m^{pre}(k)$ are data sets of each of said pre-experiment profiles $\{A_m^{pre}\}$ and each of said pre-reference profiles $\{C_m^{pre}\}$, respectively; and where $A_m(k)$ and $C_m(k)$ are said first data set and said second data set, respectively.

139. The computer system of claim 116, wherein the method further comprises:
(a0) normalizing, prior to said calculating step (a), measurements of said plurality of different cellular constituents in a pre-experiment profile $A_m^{pre}$ and a pre-reference profile $C_m^{pre}$ to generate said experiment profile $A_m$ and said reference profile $C_m$, respectively.

140. The computer system of claim 139, wherein said normalizing step (a0) comprises normalizing a data set $A_m^{pre}(k)$ and a data set $C_m^{pre}(k)$, according to the equations:

$$A_m(k) = \frac{A_m^{pre}(k) \cdot \overline{A_m^{pre} C_m^{pre}}}{\overline{A_m^{pre}}} \text{ and}$$

$$C_m(k) = \frac{C_m^{pre}(k) \cdot \overline{A_m^{pre} C_m^{pre}}}{\overline{C_m^{pre}}},$$

wherein said data sets $A_m^{pre}(k)$ and $C_m^{pre}(k)$ each comprises measurements of said plurality of different cellular constituents, where $\overline{A_m^{pre}}$ is an average of measurements of said plurality of different cellular constituents in said $A_m^{pre}(k)$, and $\overline{C_m^{pre}}$ is an average of measurements of said plurality of different cellular constituents in said $C_m^{pre}(k)$, wherein $A_m(k)$ is said first data set, wherein $A_m(k)$ comprises normalized measurements of said pre-experiment profile $A_m^{pre}$; and $C_m(k)$ is said second data set wherein $A_m(k)$ comprises normalized measurements of said reference profile $C_m^{pre}$; and wherein $\overline{A_m^{pre} C_m^{pre}}$ is an average calculated according to the equation $$\overline{A_m^{pre} C_m^{pre}} = \frac{1}{2M} \sum_{m=1}^{M} (\overline{A_m^{pre}} + \overline{C_m^{pre}}).$$

141. The computer system of claim 140, wherein the method further comprises normalizing errors of said data sets $\{A_m^{pre}(k)\}$ and $\{C_m^{pre}(k)\}$, respectively, according to the equations:

$$\sigma_m^{NA}(k) = \frac{\sigma_m^{preA}(k) \cdot \overline{A_m^{pre} C_m^{pre}}}{\overline{A_m^{pre}}} \text{ and}$$

$$\sigma_m^{NC}(k) = \frac{\sigma_m^{preC}(k) \cdot \overline{A_m^{pre} C_m^{pre}}}{\overline{C_m^{pre}}},$$

where $\sigma_m^{preA}(k)$ and $\sigma_m^{preC}(k)$ are the standard errors of $A_m^{pre}(k)$ and $C_m^{pre}(k)$, respectively, and $\sigma_m^{NA}(k)$ and $\sigma_m^{NC}(k)$ are normalized standard errors of $A_m(k)$ and $C_m(k)$, respectively.

142. The computer system of claim 141, wherein the method further comprises normalizing background errors of said data sets $\{A_m^{pre}(k)\}$ and $\{C_m^{pre}(k)\}$, respectively, according to the equations:

$$bkgstd_m^{NA}(k) = \frac{bkgstd_m^{preA}(k) \cdot \overline{A_m^{pre} C_m^{pre}}}{A_m^{pre}} \text{ and}$$

$$bkgstd_m^{NC}(k) = \frac{bkgstd_m^{preC}(k) \cdot \overline{A_m^{pre} C_m^{pre}}}{C_m^{pre}}$$

where $bkgstd_m^{preA}(k)$ and $bkgstd_m^{preC}(k)$ are the standard background errors of $A_m^{pre}(k)$ and $C_m^{pre}(k)$, respectively, and $bkgstd_m^{NA}(k)$ and $bkgstd_m^{NC}(k)$ are normalized standard background errors of $A_m(k)$ and $C_m(k)$, respectively.

143. The computer system of claim 142, wherein the method further comprises calculating said averages $\overline{A_m^{pre}}$ and $\overline{C_m^{pre}}$ by excluding measurements of said plurality of different cellular constituents having a value among the highest 10% of said measurements of said plurality of different cellular constituents in said data sets $\{A_m^{pre}(k)\}$ and $\{C_m^{pre}(k)\}$, respectively.

144. A computer system comprising:
   a processor; and
   a memory coupled to said processor and encoding one or more programs; wherein said one or more programs cause the processor to carry out a method for generating at least one error-corrected experiment profile of at least one experiment profile in a plurality of pairs of profiles $\{XA_m, XC_m\}$, $XA_m$ being an experiment profile, $XC_m$ being a reference profile, wherein m=1, 2, ..., M, M is the number of pairs of profiles, said method comprising:
   (a) processing, on a computer, said plurality of pairs of profiles $\{XA_m, XC_m\}$ to obtain a plurality of pairs of processed profiles $\{PA_m, PC_m\}$, $PA_m$ being a processed experiment profile, $PC_m$ being a processed reference profile, wherein said processing comprises normalizing at least one said experiment profile $XA_m$ and reference profile $XC_m$;
   (b) calculating, on a computer, an average processed reference profile $\overline{PC}$ of processed reference profiles $\{PC_m\}$, where m=1, 2, ..., M;
   (c) determining, on a computer, for at least one processed profile pair $\{PA_m, PC_m\}$ where m ∈ $\{1, 2, ..., M\}$ of said plurality of pairs of processed profiles $\{PA_m, PC_m\}$, where m=1, 2, ..., M, a differential reference profile $PC_{diff}(m,k)$ computed between $PC_m$ and $\overline{PC}$ wherein said average processed reference profile $\overline{PC}$ comprises data set $\{\overline{PC}(k)\}$;
   (d) via said differential reference profile determined for said at least one processed profile pair, removing, on a computer, systematic cross-experiment error from a processed experiment profile $PA_m$ of said at least one processed profile pair $\{PA_m, PC_m\}$ where m ∈ $\{1, 2, ..., M\}$ to generate a first error-corrected processed experiment profile $PA'_m$; wherein for each m ∈ $\{1, 2, ..., M\}$, said processed experiment profile $PA_m$ comprises a first processed data set $\{PA_m(k)\}$, said processed reference profile $PC_m$ comprises a second processed data set, said first error-corrected processed experiment profile $PA'_m$ comprises dataset $\{PA'_m(k)\}$, said experiment profile $XA_m$ comprises data set $\{XA_m(k)\}$, said reference profile $XC_m$ comprises data set $\{XC_m(k)\}$, wherein said data set $\{XA_m(k)\}$ comprises measurements of a plurality of different cellular constituents measured in a sample having been subject to a first condition, said data set $\{XC_m(k)\}$ comprises measurements of said plurality of different cellular constituents measured in a sample having been subject to a second condition, and where k=1, 2, ..., N; k is an index of measurements of cellular constituents, N being the total number of measurements, wherein said first error-corrected processed experiment profile $PA'_m$ is generated according to the equation $PA'_m(k) = PA_m(k) - PC_{diff}(m,k)$; and
   (e) outputting to a user, a user interface device, a computer readable storage medium, or a local or remote computer system; or displaying: said first error-corrected processed experiment profile $PA'_m$ or said data set $\{PA'_m(k)\}$.

145. The computer system of claim 144, wherein said processing step (a) comprises normalizing each said experiment profile $XA_m$ and reference profile $XC_m$.

146. The computer system of claim 145, wherein said normalizing is carried out according to the equations:

$$NA_m(k) = \frac{XA_m(k) \cdot \overline{XAC}}{\overline{XA_m}} \text{ and}$$

$$NC_m(k) = \frac{XC_m(k) \cdot \overline{XAC}}{\overline{XC_m}}$$

where $\{NA_m(k)\}$ is said first data set of said processed experiment profile $PA_m$, and $\{NC_m(k)\}$ is said second data set of said processed reference profile $PC_m$; wherein $\overline{XA_m}$ is an average of measurements of said plurality of different cellular constituents of said data set $\{XA_m(k)\}$, and $\overline{XC_m}$ is an average of measurements of said plurality of different cellular constituents of data set $\{XC_m(k)\}$; and wherein $\overline{XAC}$ is an average calculated according to the equation $$\overline{XAC} = \frac{1}{2M} \sum_{m=1}^{M} (\overline{XA_m} + \overline{XC_m}).$$

147. The computer system of claim 146, wherein the method further comprises normalizing errors of said experiment profile $XA_m$ and reference profile $XC_m$ according to the equations:

$$\sigma_m^A(k) = \frac{\sigma_m^{XA}(k) \cdot \overline{XAC}}{\overline{XA_m}} \text{ and}$$

$$\sigma_m^C(k) = \frac{\sigma_m^{XC}(k) \cdot \overline{XAC}}{\overline{XC_m}}$$

where $\sigma_m^{XA}(k)$ and $\sigma_m^{XC}(k)$ are the standard errors of $XA_m(k)$ and $XC_m(k)$, respectively, and $\sigma_m^A(k)$ and $\sigma_m^C(k)$ are normalized standard errors of $NA_m(k)$ and $NC_m(k)$, respectively.

148. The computer system of claim 147, wherein the method further comprises normalizing background errors of said experiment profile $XA_m$ and reference profile $XC_m$ according to the equations:

$$bkgstd_m^A(k) = \frac{bkgstd_m^{XA}(k) \cdot \overline{XAC}}{\overline{XA_m}} \text{ and}$$

$$bkgstd_m^C(k) = \frac{bkgstd_m^{XC}(k) \cdot \overline{XAC}}{\overline{XC_m}}$$

where $bkgstd_m^{XA}(k)$ and $bkgstd_m^{XC}(k)$ are the standard background errors of $XA_m(k)$ and $XC_m(k)$, respectively, and $bkgstd_m^A(k)$ and $bkgstd_m^C(k)$ are normalized standard background errors of said $NA_m(k)$ and said $NC_m(k)$, respectively.

149. The computer system of claim 147, wherein the method further comprises determining said averages $\overline{XA_m}$ and $\overline{XC_m}$ excluding measurements of said plurality of different cellular constituents having a value among the highest 10% of said measurements of said plurality of different cellular constituents in said data sets $\{XA_m(k)\}$ and $\{XC_m(k)\}$, respectively.

150. The computer system of claim 144, wherein said processing step (a) comprises:
normalizing each said experiment profile $XA_m$ and reference profile $XC_m$ to generate normalized data set $\{NA_m(k)\}$ and normalized data set $\{NC_m(k)\}$, respectively;
transforming said normalized data set $\{NA_m(k)\}$ to obtain a transformed data set $\{TA_m(k)\}$, where said transformed data set $\{TA_m(k)\}$ is said first data set of said processed experiment profile $PA_m$; and
transforming said normalized data set $\{NC_m(k)\}$ to obtain a transformed data set $\{TC_m(k)\}$, where said transformed data set $\{TC_m(k)\}$ is said second data set of said processed reference profile $PC_m$;
wherein said transforming is carried out for an experiment according to equations $$TA_m(k) = f(x) = \frac{\ln\left[\frac{b^2 + 2 \cdot a^2 \cdot NA_m(k)}{a} + 2 \cdot \sqrt{c^2 + b^2 \cdot NA_m(k) + a^2 \cdot [NA_m(k)]^2}\right]}{a} +$$

$$d, \text{ for } NA_m(k) > 0 \text{ and}$$

$$TC_m(k) = f(x) = \frac{\ln\left[\frac{b^2 + 2 \cdot a^2 \cdot NC_m(k)}{a} + 2 \cdot \sqrt{c^2 + b^2 \cdot NC_m(k) + a^2 \cdot [NC_m(k)]^2}\right]}{a} +$$

$$d, \text{ for } NC_m(k) > 0$$

where d is described by equation $$d = \frac{-\ln\left[\frac{b^2}{a} + 2 \cdot c\right]}{a}$$

and wherein a is the fractional error coefficient of said experiment, b is the Poisson error coefficient of said experiment, and c is the standard deviation of background noise of said experiment.

151. The computer system of claim 144, wherein said processing step (a) comprises:
normalizing each said experiment profile $XA_m$ and reference profile $XC_m$ to generate normalized data set $\{NA_m(k)\}$ and normalized data set $\{NC_m(k)\}$, respectively;
transforming said normalized data set $\{NA_m(k)\}$ to obtain a transformed data set $\{TA_m(k)\}$;
transforming said normalized data set $\{NC_m(k)\}$ to obtain a transformed data set $\{TC_m(k)\}$; and
wherein said transforming is carried out for an experiment according to equations $$TA_m(k) = f(x) = \frac{\ln\left[\frac{b^2 + 2 \cdot a^2 \cdot NA_m(k)}{a} + 2 \cdot \sqrt{c^2 + b^2 \cdot NA_m(k) + a^2 \cdot [NA_m(k)]^2}\right]}{a} +$$

$$d, \text{ for } NA_m(k) > 0 \text{ and}$$

$$TC_m(k) = f(x) = \frac{\ln\left[\frac{b^2 + 2 \cdot a^2 \cdot NC_m(k)}{a} + 2 \cdot \sqrt{c^2 + b^2 \cdot NC_m(k) + a^2 \cdot [NC_m(k)]^2}\right]}{a} +$$

$$d, \text{ for } NC_m(k) > 0$$

where d is described by equation $$d = \frac{-\ln\left[\frac{b^2}{a} + 2 \cdot c\right]}{a}$$

and wherein a is the fractional error coefficient of said experiment, b is the Poisson error coefficient of said experiment, and c is the standard deviation of background noise of said experiment.

152. The computer system of claim 151, wherein said removing nonlinearity is carried out by a method comprising:
(a1) calculating an average transformed profile of transformed experiment profiles and transformed reference profiles, wherein each of said transformed experiment profiles contains a corresponding transformed data set $\{TA_m(k)\}$, and each of said transformed reference profiles contains a corresponding transformed data set $\{TC_m(k)\}$; and
(a2) calculating first differences between each of said transformed experiment profiles and said average transformed profile; calculating second differences between each of said transformed reference profiles and said average transformed profile; adjusting, wherein the adjusting comprises correcting nonlinearity each of said transformed experiment profiles based on said first differences between each of said transformed experiment profiles and said average transformed profile, and adjusting, wherein the adjusting comprises correcting nonlinearity each of said transformed reference profiles based on said second differences between each of said transformed reference profiles and said average transformed profile.

153. The computer system of claim 152, wherein the method further comprises calculating said first differences based on the differences in a first subset of transformed measurements of said plurality of different cellular constituents between each of said transformed experiment profiles and said average transformed profile, and calculating said second differences based on the differences in a second subset of transformed measurements of said plurality of different cellular constituents between each of said transformed reference profiles and said average transformed profile.

154. The computer system of claim 153, wherein each said first subset consists of transformed measurements that are ranked similarly between each of said transformed experiment profiles and said average transformed profile, and each said second subset consists of transformed measurements that are ranked similarly between each of said transformed reference profiles and said average transformed profile.

155. The computer system of claim 154, wherein said adjusting step (a2) is carried out by a method comprising:
  (a2i) binning said first subset into a plurality of bins, each said bin consisting of transformed measurements of said plurality of different constituents in one of said transformed experiment profiles and said average transformed profile having a value in a given range; and binning said second subset into a plurality of bins, each said bin consisting of transformed measurements of said plurality of different cellular constituents in one of said transformed reference profiles and said average transformed profile having a value in a given range;
  (a2ii) calculating, in each bin of said plurality of bins, a first mean difference between a feature value of transformed measurements of said plurality of different cellular constituents in said one of said transformed experiment profiles and a feature value of said average transformed profile, and calculating a second mean difference between a feature value of transformed measurements of said plurality of different cellular constituents in said one of said reference profiles and a feature value of the average profile;
  (a2iii) determining a first curve of said first mean difference as a first function of values of transformed measurements of said plurality of different constituents for said one of said transformed experiment profiles, wherein said first function is represented by, nonlinear_$TA_m$ and determining a second curve of said second mean difference as a second function of values of transformed measurements of said plurality of different cellular constituents for said one of said transformed reference profiles, wherein said second function is represented by nonlinear_$TC_m$; and
  (a2iv) computing corrected transformed measurements of said plurality of different cellular constituents in each said transformed data set $\{TA_m(k)\}$, according to the equation:

$$TA_m^{corr}(k) = TA_m(k) - \text{nonlinear\_}TA_m(k),$$

and computing corrected transformed measurements of said plurality of different cellular constituents in each said transformed data set $\{TC_m(k)\}$, according to the equation:

$$TC_m^{corr}(k) = TC_m(k) - \text{nonlinear\_}TC_m(k),$$

where k=1, ..., N; and where $\{TA_m^{corr}(k)\}$ is said first processed data set of said processed experiment profile $PA_m$, and $\{TC_m^{corr}(k)\}$ is said second processed data set of said processed reference profile $PC_m$.

156. The computer system of claim 155, wherein said processed experiment profile $PA_m$ and said processed reference profile $PC_m$ comprise transformed measurements of said plurality of different cellular constituents from the same experimental reaction.

157. The computer system of claim 156, wherein the method further comprises calculating $\overline{PC}(k)$ according to equation $$\overline{PC}(k) = \frac{1}{M} \sum_{m=1}^{M} PC_m(k),$$

wherein $\{PC_m(k)\}$ comprises transformed measurements from said second processed data set $\{TC_m^{corr}(k)\}$ and calculating said differential reference profile according to the equation $$PC_{diff}(m,k) = PC_m(k) - \overline{PC}(k)$$

and wherein said first error-corrected profile is calculated according to the equation $$PA'_m(k) = PA_m(k) - PC_{diff}(k),$$

wherein $\{PA_m(k)\}$ comprises transformed measurements from said first data set $\{TA_m^{corr}(k)\}$.

158. The computer system of claim 157, wherein the method further comprises
  (d) calculating for each processed profile pair $\{PA_m, PC_m\}$, where $m \in \{1, 2, \ldots, M\}$, a second error-corrected experiment profile $PA''_m$ comprising data set $\{PA''_m(k)\}$ by combining said first error-corrected experiment profile $PA'_m$ with said processed experiment profile $PA_m$ using a weighing factor $\{w(k)\}$, k=1, 2, ..., N, wherein w(k) is a weighing factor for the k'th measurement.

159. The computer system of claim 158, wherein said second error-corrected experiment profile $PA''_m$ is calculated according to the equation $$PA''_m(k) = (1-w(k)) \cdot PA_m(k) + w(k) PA'_m(k).$$

160. The computer system of claim 159, wherein the method further comprises determining said weighing factor according to the equation $$w(k) = 1 - e^{-0.5 \left[\frac{\overline{PC}(k)}{avg\_bkgstd}\right]^2}$$

where avg_bkgstd is an average background standard error.

161. The computer system of claim 160, wherein the method further comprises determining said avg_bkgstd according to the equation $$avg\_bkgstd = \frac{1}{N} \sum_{k=1}^{N} \left[\frac{1}{M} \sum_{m=1}^{M} bkgstd(m,k)\right]$$

where bkgstd(m,k) is background standard error of $PC_m(k)$.

162. The computer system of claim 157, wherein the method further comprises determining errors $\{P\sigma'_m\}$ of said first error-corrected experiment profile $\{PA'_m\}$, wherein said $\{P\sigma'_m\}$ comprises error data set $\{P\sigma'_m(k)\}$.

163. The computer system of claim 162, wherein the method further comprises determining said error data set $\{P\sigma'_m(k)\}$ according to the equation $$\sigma'_m(k) = \sqrt{P\sigma_m^2(k) = \text{mixed\_}P\sigma_m^2(k) - 2Cor(k) \cdot P\sigma_m(k) \cdot \text{mixed\_}P\sigma_m(k)}$$

where $P\sigma_m(k)$ is the standard error of $A_m(k)$, and determining mixed_$P\sigma_m(k)$ according to the equation $$\text{mixed\_}P\sigma_m(k) = \frac{P\sigma_m(k) + (M-1)\cdot F\sigma_{ref}(k)}{M}$$ where $$P\sigma_{ref}(k) = \sqrt{\frac{1}{M-1}\sum_m^M (PC_m(k) - \overline{PC}(k))^2}$$

and where Cor(k) is a correlation coefficient between said processed experiment profile $PA_m$ and said processed reference profile $PC_m$.

164. The computer system of claim 163, wherein said Cor(k) is determined according to the equation $$\text{Cor}(k) = \text{CorMax} \cdot \left[ 1 - e^{-0.5\left[\frac{PC(k)}{avg\_bkstd}\right]^2} \right]$$

where CorMax is a number between 0 and 1.

165. The computer system of claim 164, wherein the method further comprises determining errors $\{P\sigma''_m\}$ of said second error-corrected experiment profile $\{PA''_m\}$ wherein said $\{P\sigma''_m\}$ comprises error data set $\{P\sigma''_m(k)\}$.

166. The computer system of claim 165, wherein the method further comprises determining said error data set $\{P\sigma''_m(k)\}$ according to the equation $$P\sigma''_m(k) = \sqrt{[1 - w(k)]\cdot P\sigma_m^2(k) + w(k)P\sigma_m'^2(k)}$$

where $P\sigma_m(k)$ is the standard error of $PA_m(k)$, and the method further comprises determining $P\sigma'_m(k)$ according to the equation $$P\sigma'_m(k) = \sqrt{P\sigma_m^2(k) + \text{mixed\_}P\sigma_m^2(k) - 2\cdot \text{Cor}(k)\cdot P\sigma_m(k)\cdot \text{mixed\_}P\sigma_m(k)},$$

and the method further comprises determining mixed_$P\sigma_m(k)$ according to the equation $$\text{mixed\_}P\sigma_m(k) = \frac{P\sigma_m(k) + (M-1)\cdot P\sigma_{ref}(k)}{M}$$

where $$P\sigma_{ref}(k) = \sqrt{\frac{1}{M-1}\sum_m^M (PC_m(k) - \overline{PC}(k))^2}$$

and where Cor(k) is a correlation coefficient between said processed experiment profile $PA_m$ and said processed reference profile $PC_m$.

167. The computer system of claim 166, wherein the method further comprises determining said Cor(k) according to the equation $$\text{Cor}(k) = \text{CorMax} \cdot \left[ 1 - e^{-0.5\left[\frac{PC(k)}{avg\_bkstd}\right]^2} \right]$$

where CorMax is a number between 0 and 1.

168. The computer system of claim 167, wherein each said pair of profiles $XA_m$ and $XC_m$ comprise measurements of said plurality of different cellular constituents from a two-channel microarray experiment.

169. The computer system of claim 168, wherein said reference profiles $\{XC_m\}$, m=1, 2, ..., M, are measured with samples labeled with a same label.

170. The computer system of claim 169, wherein at least one of said pairs of profiles $\{XA_m, XC_m\}$ is a virtual profile.

171. A computer system comprising:
a processor; and
a memory coupled to said processor and encoding one or more programs;
wherein said one or more programs cause the processor to carry out a method for generating at least one error-corrected experiment profile of at least one experiment profile $A_m$, where m ∈ $\{1, 2, ..., M\}$ in at least one of a plurality of pairs of profiles $\{A_m, C_m\}$, $A_m$ being an experiment profile, $C_m$ being a reference profile, where m=1, 2, ..., M, M is the number of pairs of profiles, said method comprising:
via a differential reference profile $C_{diff}(m,k)$ calculated between $C_m$ and an average reference profile $\overline{C}$ determined for profile pair $\{A_m, C_m\}$ where m ∈ $\{1, 2, ..., M\}$, wherein said average reference profile $\overline{C}$ comprises data set $\{\overline{C}(k)\}$, removing, on a computer, systematic cross-experiment error from said experiment profile $A_m$ to generate a first error-corrected experiment profile $A'_m$; wherein said average reference profile $\overline{C}$ is an average of reference profiles $\{C_m\}$, m=1, 2, ..., M; wherein for each m ∈ $\{1, 2, ..., M\}$, said first error-corrected experiment profile $A'_m$ comprises data set $\{A'_m(k)\}$, said experiment profile $A_m$ comprises data set $\{A_m(k)\}$, and said reference profile $C_m$ comprises data set $\{C_m(k)\}$, wherein said data set $\{A_m(k)\}$ comprises measurements of a plurality of different cellular constituents measured in a sample having been subject to a first condition, said data set $\{C_m(k)\}$ comprises measurements of said plurality of different cellular constituents measured in a sample having been subject to a second condition, wherein k=1, 2, ..., N; k is an index of measurements of cellular constituents, N being the total number of measurements, wherein said first error-corrected experiment profile $A'_m$ is generated according to the equation $A'_m(k) = A_m(k) - C_{diff}(m,k)$; and
outputting to a user, a user interface device, a computer readable storage medium, or a local or remote computer system; or displaying: said first error-corrected experiment profile $A'_m$ or said data set $\{A'_m(k)\}$.

172. The computer system of claim 133, wherein the method further comprises obtaining said error-model-based transformed measurements of said data set $\{A_m(k)\}$ and said data set $\{C_m(k)\}$ for an experiment according to the equations:

$$A_m(k) = f(x) = \frac{\ln\left[\frac{b^2 + 2 \cdot a^2 \cdot XA_m(k)}{a} + 2 \cdot \sqrt{c^2 + b^2 \cdot XA_m(k) + a^2 \cdot [XA_m(k)]^2}\right]}{\alpha} + d,$$

for $XA_m(k) > 0$ and $$C_m(k) = f(x) = \frac{\ln\left[\frac{b^2 + 2 \cdot a^2 \cdot XC_m(k)}{a} + 2 \cdot \sqrt{c^2 + b^2 \cdot XC_m(k) + a^2 \cdot [XC_m(k)]^2}\right]}{\alpha} + d,$$

for $XC_m(k) > 0$ where $\{XA_m(k)\}$ and $\{XC_m(k)\}$ are data sets comprising measurements of said plurality of different cellular constituents that when transformed produce said error-model-based transformed measurements of said plurality of different cellular constituents of said data set $A_m(k)$ and said data set $C_m(k)$, respectively, where d is described by the equation:

$$d = \frac{-\ln\left[\frac{b^2}{a} + 3 \cdot c\right]}{\alpha}$$

and where a is the fractional error coefficient of said experiment, b is the Poisson error coefficient of said experiment, and c is the standard deviation of background noise of said experiment.

173. The computer system of claim 144, wherein said processing comprises:

normalizing, transforming, and/or removing nonlinearity from measurements of said plurality of cellular constituents of said data set $\{XA_m(k)\}$ of said experiment profile $XA_m$, and from measurements of said plurality of cellular constituents of said data set $\{XC_m(k)\}$ of said reference profile $XC_m$.

* * * * *